US009067951B2

(12) United States Patent
Ebel et al.

(10) Patent No.: US 9,067,951 B2
(45) Date of Patent: Jun. 30, 2015

(54) PROCESS AND INTERMEDIATES FOR THE PRODUCTION OF CCR2 ANTAGONISTS

(71) Applicants: Heiner Ebel, Biderach an der Riss (DE); Sara Frattini, Castelleone (IT); Riccardo Giovannini, Verona (IT); Christoph Hoenke, Biberach an der Riss (DE); Thomas Trieselmann, Mettenberg (DE); Patrick Tielmann, Bad Soden am Taunus (DE)

(72) Inventors: Heiner Ebel, Biderach an der Riss (DE); Sara Frattini, Castelleone (IT); Riccardo Giovannini, Verona (IT); Christoph Hoenke, Biberach an der Riss (DE); Thomas Trieselmann, Mettenberg (DE); Patrick Tielmann, Bad Soden am Taunus (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/445,137

(22) Filed: Jul. 29, 2014

(65) Prior Publication Data
US 2014/0336374 A1    Nov. 13, 2014

Related U.S. Application Data

(63) Continuation of application No. 13/949,696, filed on Jul. 24, 2013, now Pat. No. 8,835,440, which is a continuation of application No. 13/140,591, filed as application No. PCT/EP2009/067378 on Dec. 17, 2009, now abandoned.

(30) Foreign Application Priority Data

Dec. 19, 2008  (EP) ..................... 08172336
May 15, 2009  (EP) ..................... 09160416

(51) Int. Cl.
| *C07D 498/10* | (2006.01) |
| *A61K 31/506* | (2006.01) |
| *C07D 401/06* | (2006.01) |
| *C07D 401/14* | (2006.01) |
| *C07D 403/06* | (2006.01) |
| *C07D 407/14* | (2006.01) |
| *C07D 413/14* | (2006.01) |
| *C07D 471/10* | (2006.01) |
| *A61K 31/5377* | (2006.01) |
| *A61K 31/55* | (2006.01) |
| *A61K 31/551* | (2006.01) |
| *A61K 31/553* | (2006.01) |
| *C07D 403/14* | (2006.01) |
| *C07D 405/14* | (2006.01) |
| *C07D 417/14* | (2006.01) |
| *C07D 451/02* | (2006.01) |
| *C07D 471/04* | (2006.01) |
| *C07D 491/052* | (2006.01) |

(52) U.S. Cl.
CPC ............ *C07D 498/10* (2013.01); *A61K 31/506* (2013.01); *C07D 401/06* (2013.01); *C07D 401/14* (2013.01); *C07D 403/06* (2013.01); *C07D 407/14* (2013.01); *C07D 413/14* (2013.01); *C07D 471/10* (2013.01); *A61K 31/5377* (2013.01); *A61K 31/55* (2013.01); *A61K 31/551* (2013.01); *A61K 31/553* (2013.01); *C07D 403/14* (2013.01); *C07D 405/14* (2013.01); *C07D 417/14* (2013.01); *C07D 451/02* (2013.01); *C07D 471/04* (2013.01); *C07D 491/052* (2013.01)

(58) Field of Classification Search
CPC .. C07D 401/00; C07D 403/00; C07D 401/14; C07D 498/10; C07D 405/14; C07D 401/06; C07D 403/06; C07D 451/02; C07D 471/10; C07D 417/14
USPC ........................................ 544/295, 334, 329
See application file for complete search history.

(56) References Cited

U.S. PATENT DOCUMENTS

| 4,032,526 | A | 6/1977 | Cross et al. |
| 5,629,325 | A | 5/1997 | Lin et al. |
| 5,631,269 | A | 5/1997 | Broughton et al. |
| 6,127,386 | A | 10/2000 | Lin et al. |
| 6,143,892 | A | 11/2000 | Graneto et al. |
| 6,423,713 | B1 | 7/2002 | Anantanarayan et al. |
| 6,437,138 | B1 | 8/2002 | Lin et al. |
| 6,514,977 | B1 | 2/2003 | Anantanarayan et al. |
| 6,806,279 | B2 | 10/2004 | Arkin et al. |
| 6,979,686 | B1 | 12/2005 | Naraian et al. |
| 7,504,511 | B2 | 3/2009 | Carayon et al. |
| 7,507,740 | B2 | 3/2009 | Ishikawa et al. |
| 7,612,201 | B2 | 11/2009 | Beswick et al. |
| 7,777,041 | B2 | 8/2010 | Carayon et al. |
| 7,807,671 | B2 | 10/2010 | Wang et al. |
| 7,891,384 | B2 | 2/2011 | Binet et al. |
| 7,915,261 | B2 | 3/2011 | Ishii et al. |
| 7,919,494 | B2 | 4/2011 | Ishii et al. |

(Continued)

FOREIGN PATENT DOCUMENTS

| CA | 2687931 A1 | 12/2008 |
| CA | 2704883 A1 | 5/2009 |

(Continued)

OTHER PUBLICATIONS

March, Advanced Organic Chemistry Reactions, Mechanisms and Structure 641-678 (4th ed., 1992).*

(Continued)

*Primary Examiner* — Alexander R Pagano
(74) *Attorney, Agent, or Firm* — Michael P. Morris; Edward S. Lazer

(57) ABSTRACT

The present invention relates to a process for the production of novel antagonists for CCR2 (CC chemokine receptor 2) and intermediates thereof.

9 Claims, No Drawings

(56) References Cited

U.S. PATENT DOCUMENTS

| | | |
|---|---|---|
| 7,919,495 B2 | 4/2011 | Ishii et al. |
| 8,110,575 B2 | 2/2012 | Gottschling et al. |
| 8,288,540 B2 | 10/2012 | Chianelli et al. |
| 2003/0195195 A1 | 10/2003 | Haviv et al. |
| 2004/0014744 A1 | 1/2004 | Haviv et al. |
| 2004/0147561 A1 | 7/2004 | Zhong et al. |
| 2004/0167156 A1 | 8/2004 | Jiao et al. |
| 2004/0220171 A1 | 11/2004 | Pauls et al. |
| 2005/0192302 A1 | 9/2005 | Xue et al. |
| 2005/0222151 A1 | 10/2005 | Carruthers et al. |
| 2005/0245537 A1 | 11/2005 | Tsuchimori et al. |
| 2006/0004049 A1 | 1/2006 | Yao et al. |
| 2006/0030557 A1 | 2/2006 | Haviv et al. |
| 2006/0173012 A1 | 8/2006 | Hohlweg |
| 2007/0032475 A1 | 2/2007 | Ye et al. |
| 2007/0032489 A1 | 2/2007 | Weintraub et al. |
| 2007/0244132 A1 | 10/2007 | Ishikawa et al. |
| 2007/0281936 A1 | 12/2007 | Gillespie et al. |
| 2008/0161280 A1 | 7/2008 | Gandhi et al. |
| 2008/0306046 A1 | 12/2008 | Ishii et al. |
| 2009/0048238 A1 | 2/2009 | Aebi et al. |
| 2009/0131417 A1 | 5/2009 | Letavic et al. |
| 2009/0318467 A1 | 12/2009 | Adam et al. |
| 2010/0009971 A1 | 1/2010 | Ishii et al. |
| 2010/0009972 A1 | 1/2010 | Ishii et al. |
| 2010/0204209 A1 | 8/2010 | Ebel et al. |
| 2010/0204230 A1 | 8/2010 | Blurton et al. |
| 2011/0021500 A1 | 1/2011 | Gottschling et al. |
| 2011/0183957 A1 | 7/2011 | Wityak et al. |
| 2011/0195954 A1 | 8/2011 | Gottschling et al. |
| 2011/0301143 A1 | 12/2011 | Isabel et al. |
| 2012/0004252 A1 | 1/2012 | Ebel et al. |
| 2012/0053164 A1 | 3/2012 | Ebel et al. |
| 2012/0088754 A1 | 4/2012 | Van Emelen et al. |
| 2012/0108572 A1 | 5/2012 | Wagner et al. |
| 2013/0090338 A1 | 4/2013 | Ebel et al. |
| 2013/0123241 A1 | 5/2013 | Ebel et al. |
| 2013/0150354 A1 | 6/2013 | Ebel et al. |
| 2013/0172348 A1 | 7/2013 | Ebel et al. |
| 2013/0184299 A1 | 7/2013 | Ebel et al. |
| 2013/0217728 A1 | 8/2013 | Ebel et al. |
| 2013/0324517 A1 | 12/2013 | Ebel et al. |

FOREIGN PATENT DOCUMENTS

| | | | |
|---|---|---|---|
| CA | 2705405 A1 | 5/2009 | |
| EP | 175457 A1 | 2/2007 | |
| EP | 1849773 A1 | 10/2007 | |
| FR | 2854158 A1 | 10/2004 | |
| GB | 2068961 A | 8/1981 | |
| JP | 6229575 | 8/1994 | |
| JP | 03240776 | 8/2003 | |
| JP | 2008239617 A | 10/2008 | |
| JP | 2007500135 | 1/2011 | |
| WO | 8606719 A1 | 11/1986 | |
| WO | WO 9724324 A1 * | 7/1997 | |
| WO | 9921834 A1 | 5/1999 | |
| WO | 0059502 A1 | 10/2000 | |
| WO | 0066558 A1 | 11/2000 | |
| WO | 0190101 A1 | 11/2001 | |
| WO | 03037271 A2 | 5/2003 | |
| WO | 03051797 A2 | 6/2003 | |
| WO | 03066604 A2 | 8/2003 | |
| WO | 03074390 A2 | 9/2003 | |
| WO | 03092586 | 11/2003 | |
| WO | 03104223 A1 | 12/2003 | |
| WO | 2004024710 A1 | 3/2004 | |
| WO | 2004074438 A2 | 9/2004 | |
| WO | 2004080976 A1 | 9/2004 | |
| WO | 2004101546 A1 | 11/2004 | |
| WO | 2005009976 A1 | 2/2005 | |
| WO | 2005014571 A1 | 2/2005 | |
| WO | 2005060665 A2 | 7/2005 | |
| WO | 2005084667 A1 | 9/2005 | |
| WO | 2005097751 A2 | 10/2005 | |
| WO | 2005117909 A2 | 12/2005 | |
| WO | 2005118588 A1 | 12/2005 | |
| WO | 2006001958 A2 | 1/2006 | |
| WO | 2006003277 A1 | 1/2006 | |
| WO | 2006004741 A2 | 1/2006 | |
| WO | 2006012135 A1 | 2/2006 | |
| WO | 2006021801 A1 | 3/2006 | |
| WO | 2006029906 A1 | 3/2006 | |
| WO | 2006034440 A2 | 3/2006 | |
| WO | 2006034833 A1 | 4/2006 | |
| WO | 2006038734 A1 | 4/2006 | |
| WO | 2006050389 A2 | 5/2006 | |
| WO | 2006072350 A1 | 7/2006 | |
| WO | 2006073592 A2 | 7/2006 | |
| WO | 2006088075 A1 | 8/2006 | |
| WO | 2006113261 | 10/2006 | |
| WO | 2006113704 A2 | 10/2006 | |
| WO | 2007003604 A2 | 1/2007 | |
| WO | 2007016496 A2 | 2/2007 | |
| WO | 2007022937 A1 | 3/2007 | |
| WO | 2007026959 A2 | 3/2007 | |
| WO | 2007030061 A1 | 3/2007 | |
| WO | 2007038669 A2 | 4/2007 | |
| WO | 2007048779 A1 | 5/2007 | |
| WO | 2007053495 A2 | 5/2007 | |
| WO | 2007053498 A1 | 5/2007 | |
| WO | WO 2007071358 A1 * | 6/2007 | |
| WO | 2007084786 A1 | 7/2007 | |
| WO | 2007084868 A2 | 7/2007 | |
| WO | 2007092065 A2 | 8/2007 | |
| WO | 2007100851 A1 | 9/2007 | |
| WO | 2007105058 A2 | 9/2007 | |
| WO | 2007120574 A2 | 10/2007 | |
| WO | 2007127448 A2 | 11/2007 | |
| WO | 2007147874 A1 | 12/2007 | |
| WO | 2008029084 A1 | 3/2008 | |
| WO | 2008060621 A2 | 5/2008 | |
| WO | 2008083027 A1 | 7/2008 | |
| WO | 2008145681 A2 | 12/2008 | |
| WO | 2008145861 A2 | 12/2008 | |
| WO | 2009003861 A1 | 1/2009 | |
| WO | 2009013211 A2 | 1/2009 | |
| WO | 2009026204 A1 | 2/2009 | |
| WO | 2009043747 A2 | 4/2009 | |
| WO | 2009048238 A2 | 4/2009 | |
| WO | 2009065919 A2 | 5/2009 | |
| WO | 2009065920 A2 | 5/2009 | |
| WO | 2009153182 A1 | 12/2009 | |
| WO | 2010017179 A1 | 2/2010 | |
| WO | 2010020432 A2 | 2/2010 | |
| WO | 2010070032 A1 | 6/2010 | |
| WO | 2011073154 A1 | 6/2011 | |
| WO | 2011073155 A1 | 6/2011 | |
| WO | 2011141474 A1 | 11/2011 | |
| WO | 2011141477 A1 | 11/2011 | |
| WO | 2011144501 A1 | 11/2011 | |
| WO | 2011147772 A1 | 12/2011 | |
| WO | 2011151251 A1 | 12/2011 | |
| WO | 2012171863 A1 | 12/2012 | |
| WO | 2013010839 A1 | 1/2013 | |

OTHER PUBLICATIONS

Barril, Xavier, et al; 4-Amino Derivates of the Hsp90 Inhibitor CCT018159; Bioorganic & Medicinal Chemistry Letters (2006) vol. 16 p. 2543-2548.

Carter, Percy, H., et al; Advances in the Discovery of CC Chemokine Receptor 2 Antagonists; Annual Reports in Medicinal Chemistry (2007) vol. 42 pp. 211-228.

Chabner, Bruce, A., et al; Chemotherapy of Neoplastic Diseases: Antineoplastic Agents: Goodman & Gilman's: The Pharmacological Basis of Therapeutics by Laurence L. Brunton et al (2006) 11th Ed. pp. 1315-1403.

Chemical Abstracts Service, Columbus, OH, US, STN Database, accession No. 837395-83-2, compounds 837395-83-2, date Feb. 25, 2005.

(56) References Cited

OTHER PUBLICATIONS

Chemical Abstracts Service, Columbus, OH, US, STN Database, accession No. 837396-471 compounds 837396-471, dated Feb. 25, 2005.
Chemical Abstracts Service, Columbus, OH, US, Yamashita, Hiroshi et al: "Preparation of benzothiophenylpiperazine derivatives for treatment of central nervous system diseases", XP002528684 retrieved from STN. Database accession No. 2008:1217060, Compound RN: 928251-63-2 *abstract* & JP 2008 239617 A (Ohtsuka Pharmaceutical Co., LTD, Japan) Oct. 9, 2008.
Chemical Abstracts Service, Columbus, OH; US; Ledeboer; Mark W. et al: "Pyrrolopyridines useful as inhibitors of protein kinase and their prepration, pharmaceutical compositions, and use in the treatment of various diseases", XP002528685 retrieved from STN, Database accession No. 2006:1252802 Compounds RN: 916172-93-5, 916172-95-7 *abstract* & WO 2006/127587 A1 (Vertex Pharmaceuticals Incorporated; USA) Nov. 30, 2006.
Cuzzocrea, Salvstore; Shock, Inflammation and PARP; Pharmacological Research (2005) vol. 52 pp. 72-82.
Donnelly, Louise, E., et al; Chemokine Receptors as Therapeutic Targets in Chronic Obstructive Pulmonary Disease; Trends in Pharmacological Sciences (2006) vol. 27, No. 10 pp. 546-553.
Hu, Wenhui, et al; Development of a Novel Therapeutic Suppressor of Brain Proinflammatory Cytokine Up-Regulation that Attenuates Synaptic Dysfunction and Behavioral Deficits; Science Direct; Bioorganic & Medicinal Chemistry Letters (2007) vol. 17 pp. 414-418.
International Preliminary Report on Patentability for PCT/EP2009/067378 Issued Jun. 21, 2011.
International Preliminary Report on Patentability for PCT/EP2010/069549 Issued Jun. 19, 2012.
International Search Report for PCT/EP2008/056573 mailed Jan. 14, 2009.
International Search Report for PCT/EP2009/067378 mailed Apr. 16, 2010.
International Search Report for PCT/EP2010/069549 mailed Feb. 23, 2011.
International Search Report for PCT/EP2010/069550 mailed Feb. 23, 2010.
International Search Report for PCT/EP2011/057539 mailed Jul. 20, 2011.
International Search Report for PCT/EP2011/057545 mailed Jul. 4, 2011.
International Search Report for PCT/EP2011/057550 mailed Jun. 28, 2011.
International Search Report for PCT/EP2011/058355 mailed Aug. 9, 2011.
International Search Report for PCT/EP2011/058668 mailed Jun. 28, 2011.
Kuettel, Sabine, et al; Synthesis and Evaluation of Antiparasitic Activities of New 4-[5-(4-Phenoxyphenyl)-2H-pyrazol-3-yl]norpholine Derivatives; Journal Med. Chem. (2007) vol. 50 pp. 5833-5839.
Lagu, Bharat, et al; Potent and Selective CC-Chemokine Receptor-2 (CCR2) Antagonists as a Potential Treatment for Asthma; Bioorganic and Medicinal Chemistry Letters (2007) vol. 17 pp. 4382-4386.
Poupaert, Jacques, H; Drug Design: Basic Principles and Applications; Encyclopedia of Pharmaceutical Technology (2007) 3rd edition pp. 1362-1369.
Rowley, M., et al; 4-Heterocyclylpiperidines as Selective High-Affinity Ligands at the Human Dopamine D4 Receptor; J. Med. Chem (1997) vol. 40 pp. 2374-2385.
U.S. Appl. No. 13/523,220, filed Jun. 14, 2012.
U.S. Appl. No. 13/548,321, filed Jul. 13, 2012.
U.S. Appl. No. 13/696,859, filed Nov. 8, 2012.
U.S. Appl. No. 13/696,860, filed Nov. 8, 2012.
U.S. Appl. No. 13/698,065, filed Nov. 15, 2012.
U.S. Appl. No. 13/699,325, filed Nov. 21, 2012.
U.S. Appl. No. 13/700,752, filed Nov. 29, 2012.
Xu, Ping, et al; Synthesis and Anticonvulsant Activity of 3-(substituted piperazino)-6-(substituted phenyl) pyridazines; Chemical Abstracts Service (1991) vol. 23, No. 6, pp. 477-480.
U.S. Appl. No. 13/949,696, filed Jul. 24, 2013, Inventor: Heiner Ebel.
Notice of Abandonment mailed Aug. 16, 2013, for U.S. Appl. No. 13/140,591, filed Aug. 10, 2011. Inventor: Heiner Ebel.
Cannon, J.G., et al., Chapter Nineteen in Burger's Medicinal Chemistry and Drug Discovery, Fifth Edition, vol. 1., Principals and Practice, Wiley-Interscience 1995, p. 783-802, 784.
Sheridan, R.P., et al., "The Most Common Chemical Replacements in drug-like compounds", J. Chem. Inf. Comp. Sci., 2002, V. 42, p. 103-108.
Rival, Y. et al., "5-HT3 Antagonists Derived from Aminopyridazine-type Muscarinic M1 Agonists", Journal of Medicinal Chemistry, 1998, V.41, p. 311-317.
Wenhui, Hu. et al., "Development of a novel therapeutic suppressor of brain proinflammatory cytokine up-regulation that attenuates synaptic dysfunction and behavioural deficits", Bioorg. Medicine Chem. Letter, 2007, v. 17, p. 414-418.
Castro, ME, et al., "Prridazine derivatives XII. Synthesis and antipsychotic-antidepressant activity of some butyrophenone derivatives of 6-phenylpyridazine", European Journal of Medicinal Chemistry, 1994, v. 29, p. 831-839.
E.A. Steck et al., "Some 6-Aryl-3-(basically-substituted) Pyridazines", Journal of Heterocyclic Chemistry, 1975, v. 12, No. 5, p. 1009-1013.
Refaat, Hanan, et al., "Bulletin of the Faculty of Pharmacy", (Cair University) Database Caplus on STN, Entered STN 2005, vol. 42, No. 2, p. 415-423.
Hiroshi, et. al., "Preparation of benzothiophenylpiperazine derivatives for treatment of central nervous system diseases", 2008, Chemical Abstracts Service, retrieved from STN database succession No. 2008:1217060, Compound RN:92851-63-2.
Mark, W. et al., "Pyrrolopyridines useful as inhibitors of protein kinase and their preparation, pharmaceutical compositions, and use in the treatment of various diseases", Chemical Abstracts Service, 2006.
Cuzzocrea, "Shock, Inflammation and PARP", Pharmacology Res. Acad. Press, 2005, vol. 52, No. 1, p. 72-82.
Ledeboer, Mark W. et al., "Pyrrolopypyridines useful as inhibitors of protein kinase and their preparation, pharmaceutical compositions, and use in the treatment of various diseases", 2006, Chemical Abstracts Service.
Hiroshi, et al., "Preparation of benzothiophenylpiperazine derivatives for treatment of central nervous system diseases", Chemical Abstracts Service, 2008.
Hawtin, et al., AGly/Ala switch contributes to high affinity bonding of benzoxazinone-based non-peptide oxytocin receptor antagonists, 2005, FEBS letters, vol. 579, p. 349-356.
Xia, et al., Johnson and Johnson Pharmaceutical Research, "Recent Developments in CCR2 antagonists", 2009, p. 295-303.
Abbadie, et al., 100 PNAS "Impaired neuropathic pain responses in mice lacking the chemokine receptor CCR2", p. 7947-7952 (2003).
Barnes, Nature Reviews Drug Study, "New Treatments for COPD", 2003, p. 437-446.
Havlioglu, et al., "Slit Proteins Potential Endogenous Modulators of Information", Neurovirology, 8, p. 786-495, 2002.

* cited by examiner

PROCESS AND INTERMEDIATES FOR THE PRODUCTION OF CCR2 ANTAGONISTS

FIELD OF INVENTION

The present invention relates to novel antagonists for CCR2 (CC chemokine receptor 2) and their use for providing medicaments for treating conditions and diseases where activation of CCR2 plays a causative role, especially pulmonary diseases like asthma and COPD, neurologic disease, especially of pain diseases, immune related diseases, especially diabetes mellitus including diabetes nephropathy, and cardiovascular diseases, especially atherosclerotic disease.

BACKGROUND OF THE INVENTION

The chemokines are a family of small, proinflammatory cytokines, with potent chemotactic activities. Chemokines are chemotactic cytokines that are released by a wide variety of cells to attract various cells, such as monocytes, macrophages, T cells, eosinophils, basophils and neutrophils to sites of inflammation.

Chemokine receptors, such as CCR2 or CCR5 have been implicated as being important mediators of inflammatory and immunoregulatory disorders and diseases as well as autoimmune pathologies such as rheumatoid arthritis and atherosclerosis. Accordingly, agents which modulate chemokine receptors such as the CCR2 and CCR5 receptor would be useful in such disorders and diseases.

In particular it is widely accepted that numerous conditions and diseases involve inflammatory processes. Such inflammations are critically triggered and/or promoted by the activity of macrophages, which are formed by differentiation out of monocytes. It has further been found that monocytes are characterized by, e.g., a high expression of membrane-resident CCR2, whereas the CCR2 expression in macrophages is lower. CCR2 is a critical regulator of monocytes trafficking, which can be described as the movement of the monocytes towards an inflammation along a gradient of monocyte chemoattractant proteins (MCP-1, MCP-2, MCP-3, MCP-4).

Therefore, in order to reduce macrophage-induced inflammation, it would be desirable to block the monocyte CCR2 by an antagonist, so that the monocytes can be less triggered to move towards an inflammation area for conversion into macrophages.

Based on the aforesaid there is a need for providing effective antagonists for CCR2, which are pharmacologically acceptable.

DESCRIPTION OF THE INVENTION

It has now been found that such effective CCR2 inhibitors can be provided by compounds according to general formula (I),

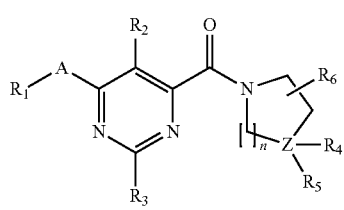

wherein $R_1$ is $-L_1-R_7$, wherein $L_1$ is a linker selected from a bond or a group selected from —$C_1$-$C_2$-alkylene, and —$C_1$-$C_2$-alkenylene which optionally comprises one or more groups selected from —O—, —C(O)—, and —NH— in the chain and which is optionally substituted by a group selected from among —OH, —$NH_2$, —$C_1$-$C_3$-alkyl, O—$C_1$-$C_6$-alkyl, and —CN, wherein $R_7$ is a ring selected from among —$C_3$-$C_8$-cycloalkyl, —$C_3$-$C_8$-heterocyclyl, —$C_5$-$C_{10}$-aryl, and —$C_5$-$C_{10}$-heteroaryl, wherein the ring $R_7$ is optionally substituted with one or more groups selected from among —$CF_3$, —O—$CF_3$, —CN, and -halogen, or wherein the ring $R_7$ is optionally substituted with one or more groups selected from among —$C_1$-$C_6$-alkyl, —O—$C_1$-$C_6$-alkyl, —$C_5$-$C_{10}$-aryl, —$C_5$-$C_{10}$-heteroaryl, —$C_3$-$C_8$-cycloalkyl, —$C_3$-$C_8$-heterocyclyl, —$C_1$-$C_6$-alkenyl, and —$C_1$-$C_6$-alkynyl, optionally being further substituted by one or more groups selected from —OH, —$NH_2$, —$C_1$-$C_3$-alkyl, —O—$C_1$-$C_6$-alkyl, —CN, —$CF_3$, —$OCF_3$, halogen, and =O, or wherein the ring $R_7$ is optionally further bi-valently substituted on two neighbouring ring atoms, such that an annellated ring is formed by one or more groups selected from among —$C_1$-$C_6$-alkylene, —$C_2$-$C_6$-alkenylene and —$C_4$-$C_6$-alkynylene, in which one or two carbon centers may optionally by replaced by 1 or 2 hetero atoms selected from N, O and S, the bivalent group being optionally substituted by one or more groups selected from —OH, —$NH_2$, —$C_1$-$C_3$-alkyl, —O—$C_1$-$C_6$-alkyl, —CN, —$CF_3$, —$OCF_3$, halogen, and =O;

$R_2$ is selected from among —H, -halogen, —CN, —O—$C_1$-$C_4$-alkyl, —$C_1$-$C_4$-alkyl, —CH=$CH_2$, —C≡CH, —$CF_3$, —$OCF_3$, —$OCF_2$H, and —$OCFH_2$;

$R_3$ is selected from among —H, -methyl, -ethyl, -propyl, -i-propyl, -cyclopropyl, —$OCH_3$, and —CN;

$R_4$ and $R_5$ are independently selected from among an electron pair, —H, —$C_1$-$C_6$-alkyl, —$NH_2$, —$C_3$-$C_8$-cycloalkyl, —$C_3$-$C_8$-heterocyclyl, —$C_5$-$C_{10}$-aryl, —$C_5$-$C_{10}$-heteroaryl, and —C(O)—N($R_8$,$R_{8'}$), with $R_8$ and $R_{8'}$ independently being selected from among —H and —$C_1$-$C_6$-alkyl, wherein $R_4$ and $R_5$ if different from an electron pair or —H are optionally independently substituted with one or more groups selected from among -halogen, —OH, —$CF_3$, —CN, —$C_1$-$C_6$-alkyl, —O—$C_1$-$C_6$-alkyl, —O—$C_3$-$C_8$-cycloalkyl, —O—$C_3$-$C_8$-heterocyclyl, —O—$C_5$-$C_{10}$-aryl, —O—$C_5$-$C_{10}$-heteroaryl, —$C_0$-$C_6$-alkylene-CN, —$C_0$-$C_4$-alkylene-O—$C_1$-$C_4$-alkyl, —$C_0$-$C_4$-alkylene-O—$C_3$-$C_8$-cycloalkyl, —$C_0$-$C_4$-alkylene-O—$C_3$-$C_8$-heterocyclyl, —$C_0$-$C_4$-alkylene-O—$C_5$-$C_{10}$-aryl, —$C_0$-$C_4$-alkylene-O—$C_5$-$C_{10}$-heteroaryl, —$C_0$-$C_4$-alkylene-Q-$C_0$-$C_4$-alkyl-N($R_9$,$R_{9'}$), —$C_0$-$C_4$-alkylene-N($R_{10}$)-Q-$C_1$-$C_4$-alkyl, —$C_0$-$C_4$-alkylene-N($R_{10}$)-Q-$C_3$-$C_8$-cycloalkyl, —$C_0$-$C_4$-alkylene-N($R_{10}$)-Q-$C_3$-$C_8$-heterocyclyl, —$C_0$-$C_4$-alkylene-N($R_{10}$)-Q-$C_5$-$C_{10}$-aryl, —$C_0$-$C_4$-alkylene-N($R_{10}$)-Q-$C_5$-$C_{10}$-heteroaryl, —$C_0$-$C_4$-alkylene-Q-N($R_{11}$,$R_{11'}$), —$C_0$-$C_4$-alkylen-N($R_{12}$)-Q-N($R_{13}$,$R_{13'}$), —$C_0$-$C_4$-alkylen-$R_{14}$, —$C_0$-$C_4$-alkylene-Q-$C_1$-$C_6$-alkyl, —$C_0$-$C_4$-alkylene-Q-$C_3$-$C_8$-cycloalkyl, —$C_0$-$C_4$-alkylene-Q-$C_3$-$C_8$-heterocyclyl, —$C_0$-$C_4$-alkylene-Q-$C_5$-$C_{10}$-aryl, —$C_0$-$C_4$-alkylene-Q-$C_5$-$C_{10}$-heteroaryl, —$C_0$-$C_4$-alkylene-O-Q-N($R_{15}$,$R_{15'}$), and —$C_0$-$C_4$-alkylene-N($R_{16}$)-Q-O—($R_{17}$)

wherein Q is selected from among —C(O)— and —$SO_2$— wherein $R_{12}$, $R_{16}$, are independently selected from among —H, —$C_1$-$C_6$-alkyl, and —$C_3$-$C_6$-cycloalkyl, wherein $R_9$, $R_{9'}$, $R_{10}$, $R_{11}$, $R_{11'}$, $R_{13}$, $R_{13'}$, $R_{15}$, $R_{15'}$ are independently selected from among —H and —$C_1$-$C_6$-alkyl, and —$C_3$-$C_6$-cycloalkyl, or wherein $R_9$ and $R_{9'}$, $R_{11}$ and $R_{11'}$, $R_{13}$ and $R_{13'}$, $R_{15}$ and $R_{15'}$, together form a —$C_2$-$C_6$-alkylene group, preferably a —$C_5$-$C_6$-alkylene group, wherein $R_{14}$ and $R_{17}$ are independently selected from among —H, —$C_1$-$C_6$-alkyl, —$C_5$-$C_{10}$-aryl, —$C_5$-$C_{10}$-heteroaryl, —$C_3$-$C_8$-cycloalkyl, and —$C_3$-$C_8$-heterocyclyl, wherein said —$C_3$-$C_8$-heterocyclyl optionally comprises nitrogen and/or —$SO_2$— in the ring, and wherein $R_{14}$ and $R_{17}$ are optionally substituted with one or more groups selected from among —OH, —$OCH_3$, —$CF_3$, —$OCF_3$, —CN, -halogen, —$C_1$-$C_4$-alkyl, =O, and —$SO_2$—$C_1$-$C_4$-alkyl, or wherein $R_4$ and/or $R_5$ are independently a group of the structure -$L_2$-$R_{18}$, wherein $L_2$ is selected from among —NH—, and —N($C_1$-$C_4$-alkyl)-, wherein $R_{18}$ is selected from among —$C_5$-$C_{10}$-aryl, —$C_5$-$C_{10}$-heteroaryl, —$C_3$-$C_8$-cycloalkyl, and —$C_3$-$C_8$-heterocyclyl, wherein $R_{18}$ is optionally substituted by one or more groups selected from among halogen, —$CF_3$, —$OCF_3$, —CN, —OH, —O—$C_1$-$C_4$-alkyl, —$C_1$-$C_6$-alkyl, —NH—C(O)—$C_1$-$C_6$-alkyl, —N($C_1$-$C_4$-alkyl)-C(O)—$C_1$-$C_6$-alkyl, —C(O)—$C_1$-$C_6$-alkyl, —S(O)$_2$—$C_1$-$C_6$-alkyl, —NH—S(O)$_2$—$C_1$-$C_6$-alkyl, —N($C_1$-$C_4$-alkyl)-S(O)$_2$—$C_1$-$C_6$-alkyl, and —C(O)—O—$C_1$-$C_6$-alkyl, and wherein $R_4$, $R_5$ and $R_{18}$ are optionally further substituted by spiro-$C_3$-$C_8$-cycloalkyl or spiro-$C_3$-$C_8$-heterocyclyl such that together with $R_4$, $R_5$ and/or $R_{18}$ a spirocycle is formed, wherein said spiro-$C_3$-$C_8$-heterocyclyl optionally comprises one or more groups selected from among nitrogen, —C(O)—, —$SO_2$—, and —N($SO_2$—$C_1$-$C_4$-alkyl)- in the ring, or wherein $R_4$, $R_5$ and $R_{18}$ are optionally further bi-valently substituted by one or more spirocyclic or annellated ring forming groups selected from among —$C_1$-$C_6$-alkylene, —$C_2$-$C_6$-alkenylene, and —$C_4$-$C_6$-alkynylene, in which one ore two carbon centers may optionally be replaced by one or two hetero atoms selected from among N, O and S and which may optionally be substituted by one or more groups on one ring atom or on two neighbouring ring atoms selected from among —OH, —$NH_2$, —$C_1$-$C_3$-alkyl, 0-$C_1$-$C_6$-alkyl, —CN, —$CF_3$, —$OCF_3$, and halogen;

$R_6$ is selected from among —H, —$C_1$-$C_4$-alkyl, —OH, —O—$C_1$-$C_4$-alkyl, -halogen, —CN, —$CF_3$, and —$OCF_3$;

A is selected from among a single bond, =CH—, —$CH_2$—, —O—, —S—, and —NH—;

n is 1, 2 or 3;

Z is C or N, as well as in form of their acid addition salts with pharmacologically acceptable acids, as well as in form of their solvates and/or hydrates.

Preferred compounds of formula (I) according to the invention are compounds with $R_2$, $R_3$, $R_4$, $R_5$, $R_6$, $R_8$, $R_{8'}$, $R_9$, $R_{9'}$, $R_{10}$, $R_{11}$, $R_{11'}$, $R_{12}$, $R_{13}$, $R_{13'}$, $R_{14}$, $R_{15}$, $R_{15'}$, $R_{16}$, $R_{17}$, $R_{18}$, A, $L_2$, Z, Q, and n as herein before or below defined, wherein $R_1$ is -$L_1$-$R_7$, with $L_1$ being a linker selected from a bond or a group selected from among —$C_1$-$C_2$-alkylene, and —$C_1$-$C_2$-alkenylene optionally comprising one or more groups selected from among —O—, —C(O)—, and, —NH— in the chain and optionally being substituted by a group selected from among —OH, —$NH_2$, —$C_1$-$C_3$-alkyl, 0-$C_1$-$C_6$-alkyl, and —CN, wherein $R_7$ is a ring selected from among —$C_3$-$C_8$-cycloalkyl, —$C_5$-$C_{10}$-aryl, —$C_3$-$C_8$-heterocyclyl comprising 1 or 2 hetero atoms selected from among N, and O, and —$C_5$-$C_{10}$-heteroaryl comprising 1 or 2 hetero atoms selected from among N, and O, wherein the ring $R_7$ is optionally substituted with one or more groups selected from among —$CF_3$, —O—$CF_3$, —CN, and -halogen, or wherein the ring $R_7$ is optionally substituted with one or more groups selected from among —$C_1$-$C_6$-alkyl, —O—$C_1$-$C_6$-alkyl, —$C_5$-$C_{10}$-aryl, —$C_3$-$C_8$-cycloalkyl, —$C_3$-$C_8$-heterocyclyl, —$C_1$-$C_6$-alkenyl, and —$C_1$-$C_6$-alkynyl, optionally being substituted by one or more groups selected from —OH, —$NH_2$, —$C_1$-$C_3$-alkyl, —O—$C_1$-$C_6$-alkyl, —CN, —$CF_3$, —$OCF_3$, halogen, and =O, or wherein the ring $R_7$ is optionally further bi-valently substituted by one or more annellated ring forming groups selected from among —$C_1$-$C_6$-alkylene, —$C_2$-$C_6$-alkenylene and —$C_4$-$C_6$-alkynylene, in which one or two carbon centers may optionally by replaced by 1 or 2 hetero atoms selected from N, and O, wherein the bivalent group is optionally substituted by one or more groups selected from —OH, —$NH_2$, —$C_1$-$C_3$-alkyl, —O—$C_1$-$C_6$-alkyl, —CN, —$CF_3$, —$OCF_3$, halogen, and =O;

Preferred compounds of formula (I) according to the invention are compounds with $R_2$, $R_3$, $R_4$, $R_5$, $R_6$, $R_8$, $R_{8'}$, $R_9$, $R_{9'}$, $R_{10}$, $R_{11}$, $R_{11'}$ $R_{12}$, $R_{13}$, $R_{13'}$, $R_{14}$, $R_{15}$, $R_{15'}$, $R_{16}$, $R_{17}$, $R_{18}$, A, $L_2$, Z, Q, and n as herein before or below defined, wherein $R_1$ is -$L_1$-$R_7$, wherein $L_1$ is a linker selected from among a bond, methylene, ethylene, methenylene, and ethenylene, wherein $L_1$, if different from a bond, is optionally substituted with one or more groups selected from among methyl, and ethyl, wherein $R_7$ is a ring selected from among cyclopropyl, cyclobutyl, cyclopentyl, cyclohexyl, cycloheptyl, pyrrolidinyl, piperidinyl, azepanyl, tetrahydrofuranyl, tetrahydropyranyl, oxepanyl, phenyl, pyridyl, and furanyl, wherein the ring $R_7$ is optionally substituted with one or more groups selected from among —F, —Cl, -methyl, -ethyl, -propyl, -i-propyl, -cyclopropyl, -t-butyl, —$CF_3$, —O—$CF_3$, —CN, —O-methyl, -furanyl and -phenyl, wherein said furanyl and said phenyl are optionally independently substituted by one or more groups selected from among —$C_1$-$C_6$-alkyl, or halogen, —$OCH_3$, —$CF_3$, and —$OCF_3$.

or wherein $R_7$ is bi-valently substituted by one or more groups selected from among

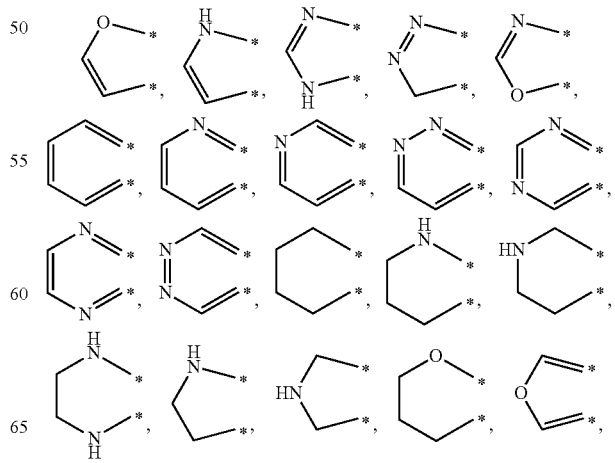

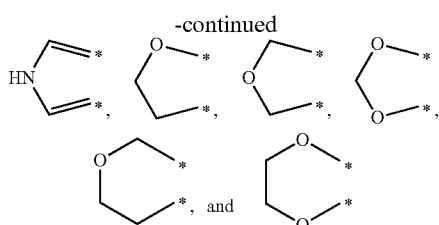

on two neighbouring ring atoms, such that an annellated ring is formed.

Preferred compounds of formula (I) according to the invention are compounds with $R_2$, $R_3$, $R_4$, $R_5$, $R_6$, $R_7$, $R_8$, $R_{8'}$, $R_9$, $R_{9'}$, $R_{10}$, $R_{11}$, $R_{11'}$, $R_{12}$, $R_{13}$, $R_{13'}$, $R_{14}$, $R_{15}$, $R_{15'}$, $R_{16}$, $R_{17}$, $R_{18}$, A, $L_2$, Z, Q, and n as herein before or below defined, wherein $R_1$ is -$L_1$-$R_7$, and wherein $L_1$ is a linker selected from among a bond, methylene, ethylene, methenylene, and ethenylene and wherein $L_1$ is optionally substituted with one or more of methyl or ethyl and wherein $L_1$ optionally comprises one or more —O— atoms.

Preferred compounds of formula (I) according to the invention are compounds with $R_2$, $R_3$, $R_4$, $R_5$, $R_6$, $R_7$, $R_8$, $R_{8'}$, $R_9$, $R_{9'}$, $R_{10}$, $R_{11}$, $R_{11'}$, $R_{12}$, $R_{13}$, $R_{13'}$, $R_{14}$, $R_{15}$, $R_{15'}$, $R_{16}$, $R_{17}$, $R_{18}$, A, $L_2$, Z, Q, and n as herein before or below defined, wherein $R_1$ is selected from among

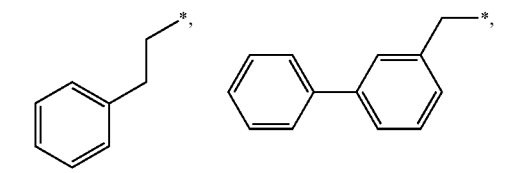
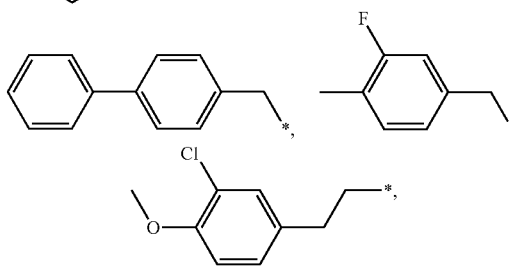
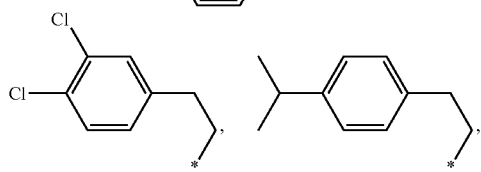
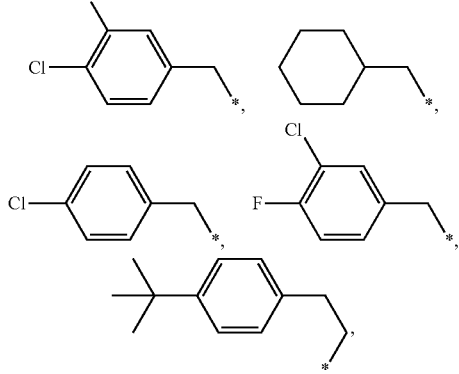
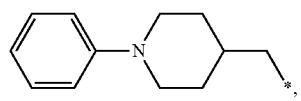
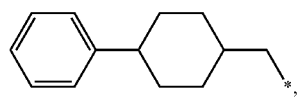
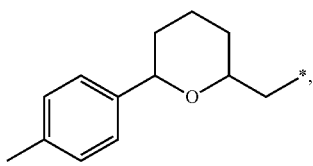
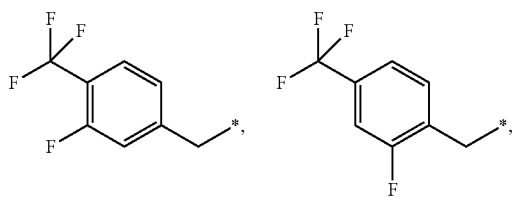
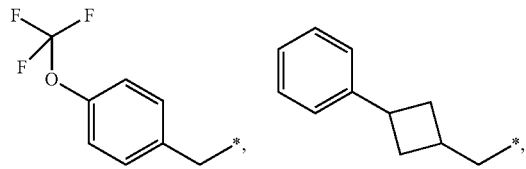
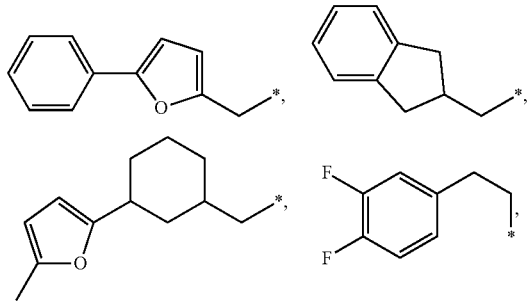
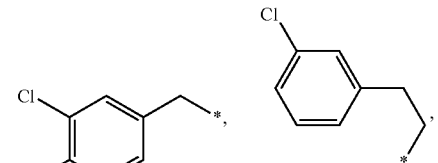
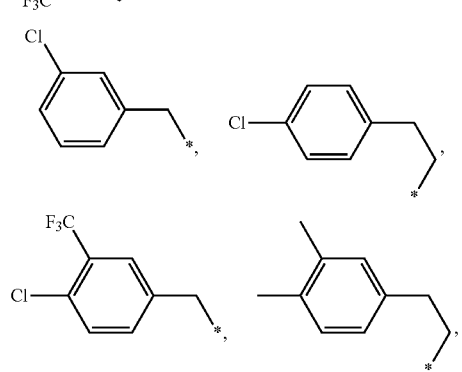

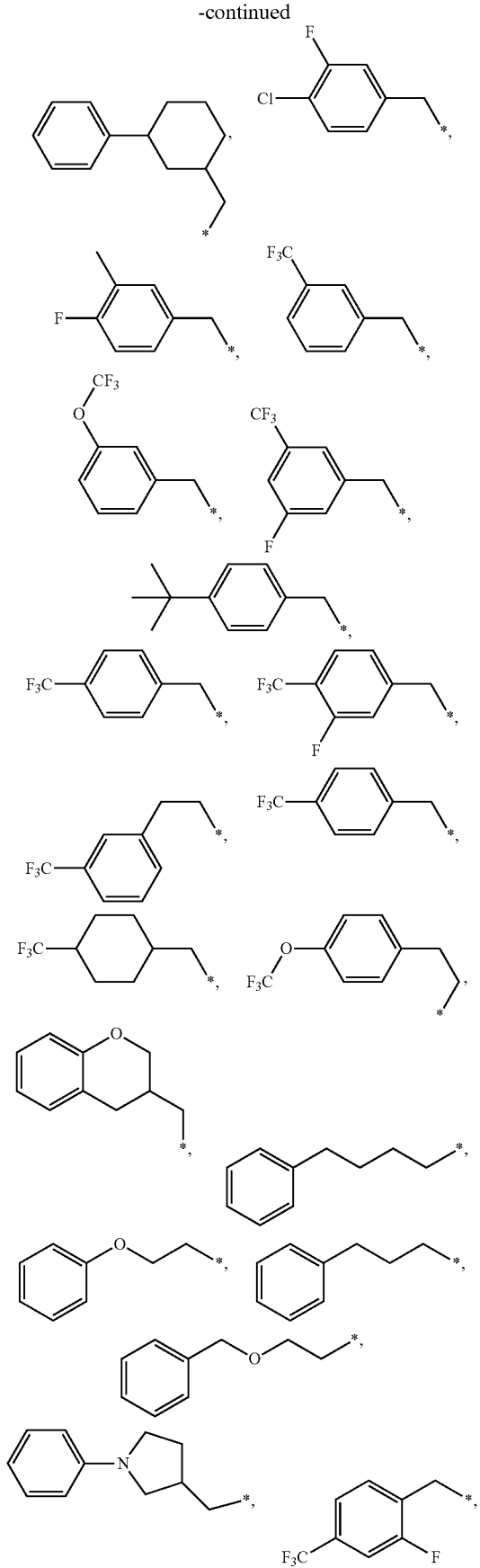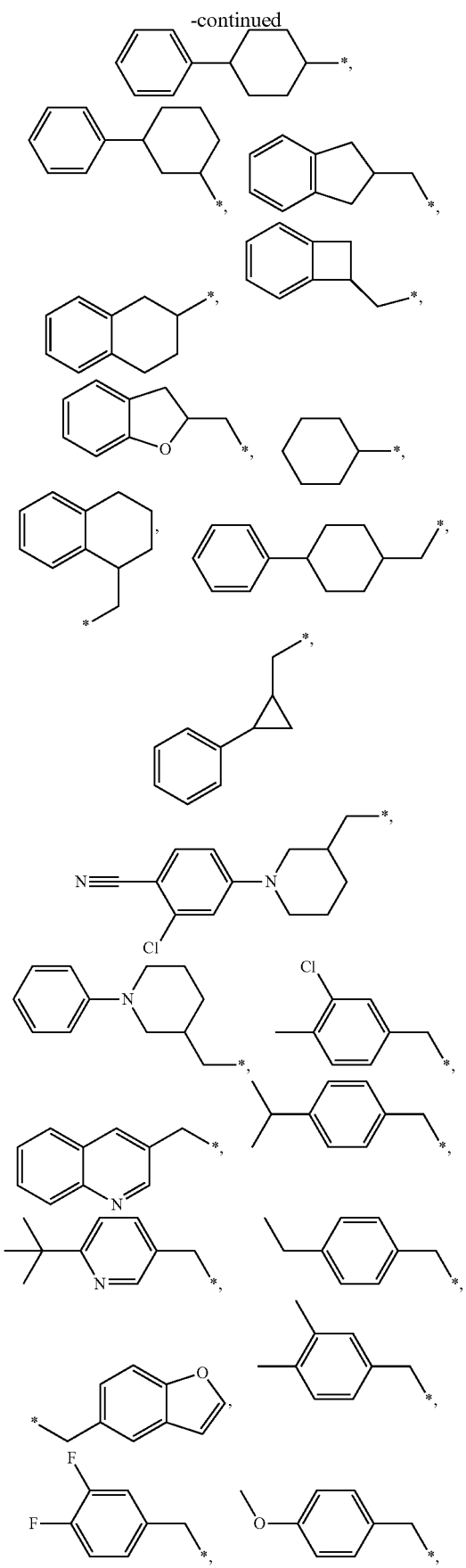

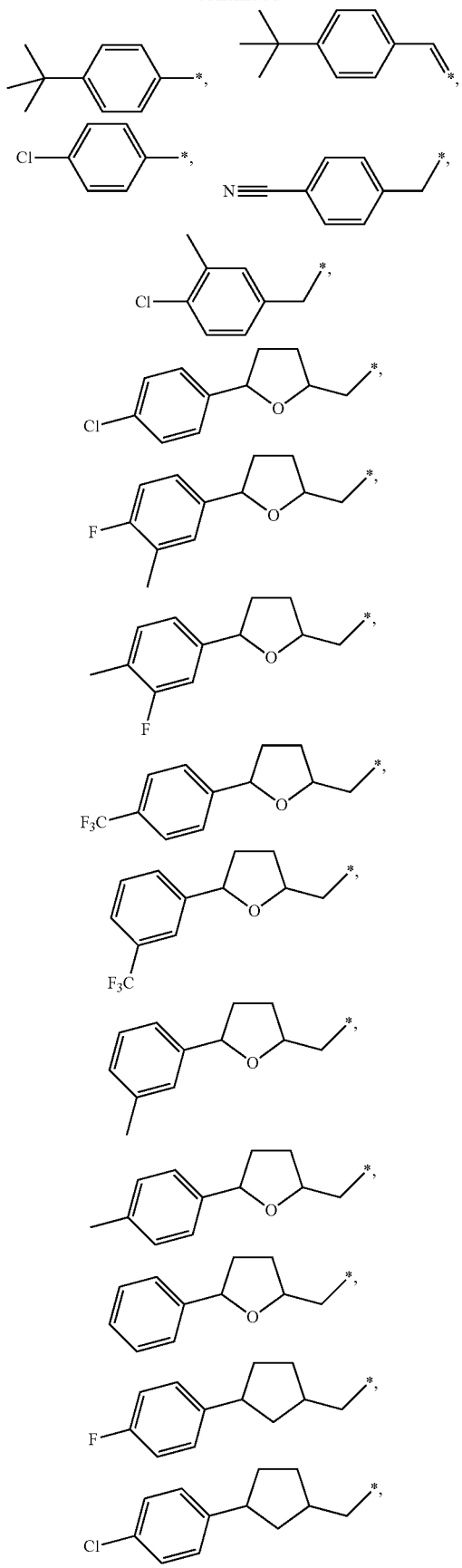
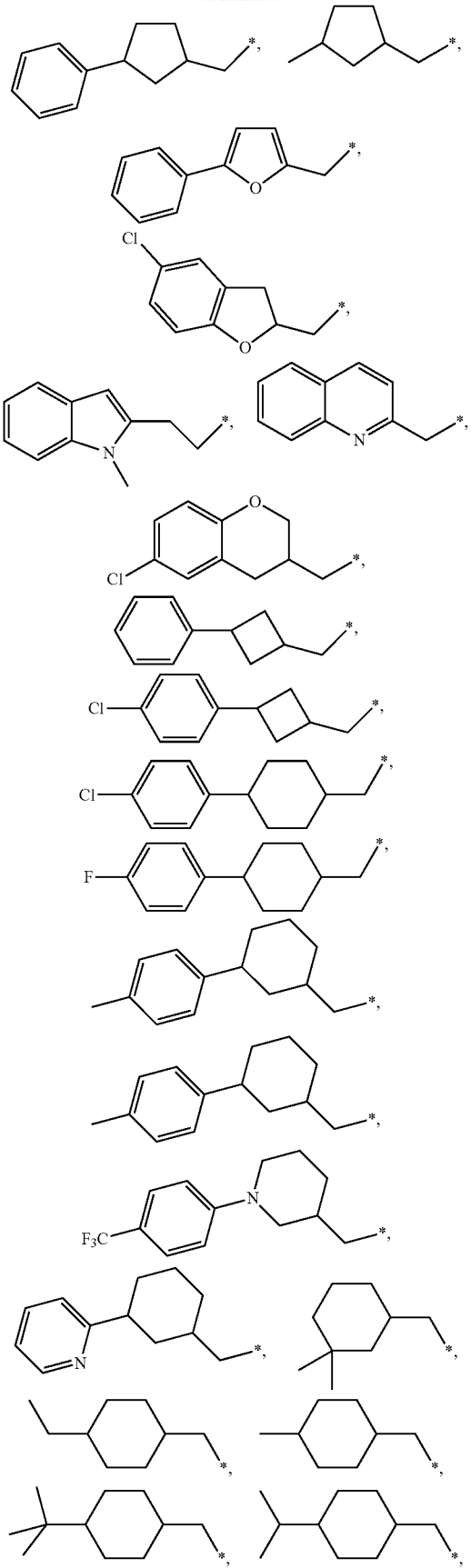

-continued

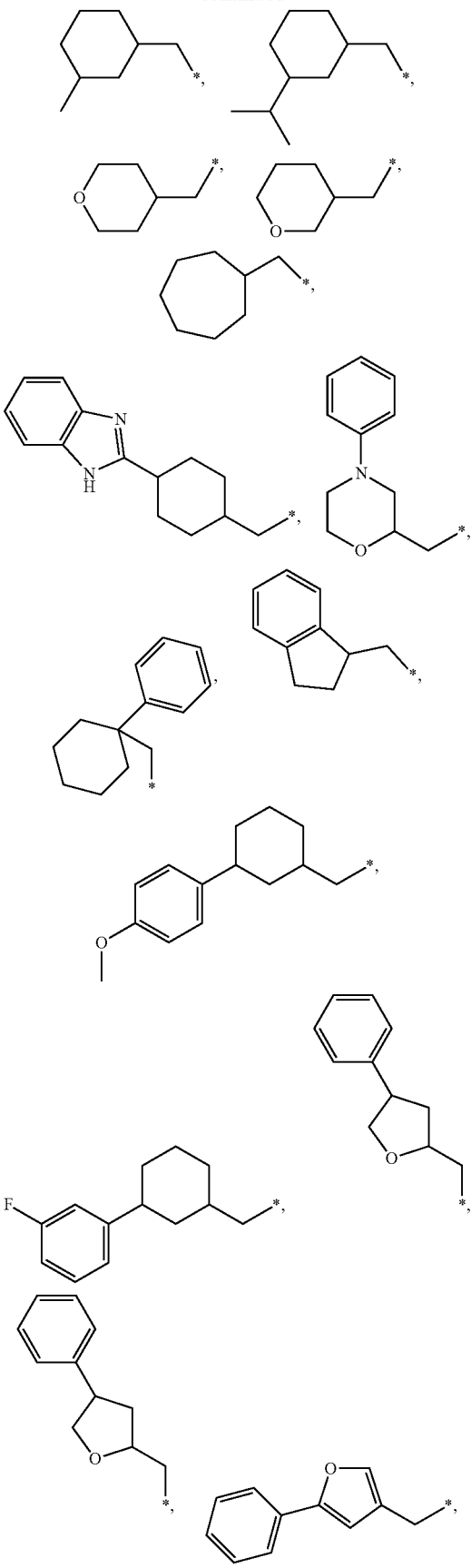

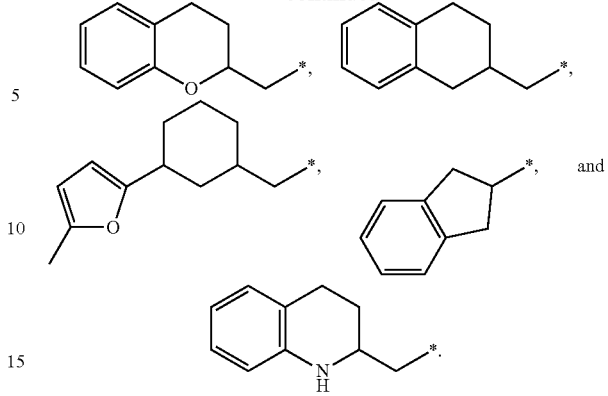

Preferred compounds of formula (I) according to the invention are compounds with $R_1$, $R_3$, $R_4$, $R_5$, $R_6$, $R_7$, $R_8$, $R_{8'}$, $R_9$, $R_{9'}$, $R_{10}$, $R_{11}$, $R_{11'}$, $R_{12}$, $R_{13}$, $R_{13'}$, $R_{14}$, $R_{15}$, $R_{15'}$, $R_{16}$, $R_{17}$, $R_{18}$, A, $L_1$, $L_2$, Z, Q, and n as herein before or below defined, wherein $R_2$ is selected from among —H, -methyl, -ethyl, -propyl, -i-propyl, -cyclopropyl, -butyl, -i-butyl, -t-butyl, —F, —Cl, —Br, —I, —CN, —CH=CH$_2$, —C≡CH, and —OCH$_3$, more preferred from among H, -methyl, -ethyl, -propyl, -i-propyl, -cyclopropyl, and —OCH$_3$.

Preferred compounds of formula (I) according to the invention are compounds with $R_1$, $R_3$, $R_4$, $R_5$, $R_6$, $R_7$, $R_8$, $R_{8'}$, $R_9$, $R_{9'}$, $R_{10}$, $R_{11}$, $R_{11'}$, $R_{12}$, $R_{13}$, $R_{13'}$, $R_{14}$, $R_{15}$, $R_{15'}$, $R_{16}$, $R_{17}$, $R_{18}$, A, $L_1$, $L_2$, Z, Q, and n as herein before or below defined, wherein $R_2$ is selected from among —H, -Methyl, -Ethyl, —Br, and —OCH$_3$.

Preferred compounds of formula (I) according to the invention are compounds with $R_1$, $R_2$, $R_4$, $R_5$, $R_6$, $R_7$, $R_8$, $R_{8'}$, $R_9$, $R_{9'}$, $R_{10}$, $R_{11}$, $R_{11'}$, $R_{12}$, $R_{13}$, $R_{13'}$, $R_{14}$, $R_{15}$, $R_{15'}$, $R_{16}$, $R_{17}$, $R_{18}$, A, $L_1$, $L_2$, Z, Q, and n as herein before or below defined, wherein $R_3$ is selected from among —H, and -methyl.

Preferred compounds of formula (I) according to the invention are compounds with $R_1$, $R_2$, $R_3$, $R_6$, $R_7$, $R_9$, $R_{9'}$, $R_{10}$, $R_{11}$, $R_{11'}$, $R_{12}$, $R_{13}$, $R_{13'}$, $R_{14}$, $R_{15}$, $R_{15'}$, $R_{16}$, $R_{17}$, $R_{18}$, A, $L_1$, $L_2$, Z, Q, and n as herein before or below defined, wherein $R_4$ and $R_5$ are independently selected from among an electron pair, —H, -i-propyl, -amino, -pyrrolidinyl, -piperidinyl, -morpholinyl, -azepanyl, -oxazepanyl, -piperazinyl, -azetidinyl, -tetrahydropyranyl, -cyclopentyl, -cyclohexyl, and —C(O)—N($R_8$, $R_{8'}$), with $R_8$ and $R_{8'}$ independently being selected from among —H and —C$_1$-C$_6$-alkyl, wherein $R_4$ and $R_5$ are optionally independently substituted with one or more groups selected from among -fluoro, -methyl, -ethyl, propyl, -i-propyl, -butyl, -i-butyl, -t-butyl, -hydroxy, —CF$_3$, —OCF$_3$, —CN, —O—CH$_3$, —O—C$_2$H$_5$, —O—C$_3$H$_7$, —CH$_2$—CN, —CH$_2$—O—CH$_3$, —(CH$_2$)$_2$—O—CH$_3$, —C(O)—CH$_3$, —C(O)—C$_2$H$_5$, —C(O)—C$_3$H$_7$, —COOH, —C(O)—NH$_2$, —C(O)—NH—CH$_3$, —C(O)—N(CH$_3$)$_2$, —NH—C(O)—CH$_3$, —N(CH$_3$)C(O)—CH$_3$, —NH—C(O)—C$_2$H$_5$, —N(CH$_3$)—C(O)—C$_2$H$_5$, —NH—C(O)—C$_3$H$_7$, —N(CH$_3$)—C(O)—C$_3$H$_7$, —NH—SO$_2$—CH$_3$, —N(CH$_3$)—SO$_2$—CH$_3$, —N(C$_2$H$_5$)—SO$_2$—CH$_3$, —N(C$_3$H$_7$)—SO$_2$—CH$_3$, —NH—SO$_2$—C$_2$H$_5$, —N(CH$_3$)—SO$_2$—C$_2$H$_5$, —N(C$_2$H$_5$)—SO$_2$—C$_2$H$_5$, —N(C$_3$H$_7$)—SO$_2$—C$_2$H$_5$, —NH—SO$_2$—C$_3$H$_7$, —N(CH$_3$)—SO$_2$—C$_3$H$_7$, —N(C$_2$H$_5$)—SO$_2$—C$_3$H$_7$, —N(C$_3$H$_7$)—SO$_2$—C$_3$H$_7$, —NH—SO$_2$—C$_3$H$_5$, —N(CH$_3$)—SO$_2$—C$_3$H$_5$, —N(C$_2$H$_5$)—SO$_2$—C$_3$H$_5$, —N(C$_3$H$_7$)—SO$_2$—C$_2$H$_5$, —CH$_2$—NH—SO$_2$—CH$_3$, —CH$_2$—N(CH$_3$)—SO$_2$—CH$_3$, —CH$_2$—NH—SO$_2$—

C$_2$H$_5$, —CH$_2$—N(CH$_3$)—SO$_2$—C$_2$H$_5$, —CH$_2$—NH—SO$_2$—C$_3$H$_7$, —CH$_2$—N(CH$_3$)—SO$_2$—C$_3$H$_7$, —CH$_2$—NH—SO$_2$—C$_3$H$_5$, —CH$_2$—N(CH$_3$)—SO$_2$—C$_3$H$_5$, —NH—C(O)—NH$_2$, —N(CH$_3$)—C(O)—NH$_2$, —NH—C(O)—NH—CH$_3$, —N(CH$_3$)—C(O)—NH—CH$_3$, —NH—C(O)—N(CH$_3$)$_2$, —N(CH$_3$)—C(O)—N(CH$_3$)$_2$, —SO$_2$—NH$_2$, —SO$_2$—NH(CH$_3$), —SO$_2$—N(CH$_3$)$_2$, —C(O)—NH—C$_2$H$_5$, —C(O)—N(CH$_3$)—C$_2$H$_5$, —C(O)—N(CH$_3$)—C$_3$H$_7$, —C(O)—N(CH$_3$)—C$_4$H$_9$, —C(O)—NH—CH(CH$_3$)—C$_2$H$_5$, —C(O)—N(CH$_3$)—CH(CH$_3$)—C$_2$H$_5$, —CH$_2$—C(O)—NH$_2$, —CH$_2$—C(O)—NH—CH$_3$, —CH$_2$—C(O)—N(CH$_3$)$_2$, —N(CH$_3$)—SO$_2$—N(CH$_3$)$_2$, -phenyl, -pyridin-4-yl, —CH$_2$-3-methyl-oxetan-3-yl, —O-1,2-difluoro-phen-5-yl, —O-pyridin-2-yl, -pyrrolidine-2-one-1-yl, -3,5-dimethyl-[1,2,4]triazol-4-yl, -3-methyl-[1,2,4]oxadiazol-5-yl,

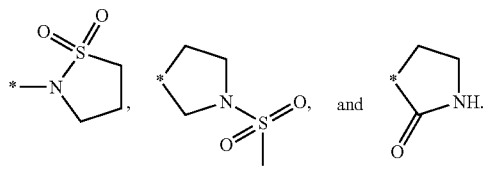

Preferred compounds of formula (I) according to the invention are compounds with R$_1$, R$_2$, R$_3$, R$_6$, R$_7$, R$_8$, R$_8'$, R$_9$, R$_9'$, R$_{10}$, R$_{11}$, R$_{11'}$, R$_{12}$, R$_{13}$, R$_{13'}$, R$_{14}$, R$_{15}$, R$_{15'}$, R$_{16}$, R$_{17}$, R$_{18}$, A, L$_1$, L$_2$, Z, Q, and n as herein before or below defined, wherein R$_4$ and R$_5$ are independently selected from among an electron pair, —H, -amino, -piperidinyl, -tetrahydropyranyl, and -pyrrolidinyl, wherein R$_4$ and R$_5$ are optionally independently substituted with one or more groups selected from among -fluoro, —CF$_3$, -hydroxy, —O—CH$_3$, —OCF$_3$, —CN, —NH—SO$_2$—CH$_3$, —N(CH$_3$)—SO$_2$—CH$_3$, —N(C$_2$H$_5$)—SO$_2$—CH$_3$, —N(C$_3$H$_7$)—SO$_2$—CH$_3$, —NH—SO$_2$—C$_2$H$_5$, —N(CH$_3$)—SO$_2$—C$_2$H$_5$, —N(C$_2$H$_5$)—SO$_2$—C$_2$H$_5$, —N(C$_3$H$_7$)—SO$_2$—C$_2$H$_5$, —NH—SO$_2$—C$_3$H$_7$, —N(CH$_3$)—SO$_2$—C$_3$H$_7$, —N(C$_2$H$_5$)—SO$_2$—C$_3$H$_7$, —N(C$_3$H$_7$)—SO$_2$—C$_3$H$_7$, —NH—SO$_2$—C$_3$H$_5$, —N(CH$_3$)—SO$_2$—C$_3$H$_5$, —N(C$_2$H$_5$)—SO$_2$—C$_3$H$_5$, —N(C$_3$H$_7$)—SO$_2$—C$_2$H$_5$, —CH$_2$—NH—SO$_2$—CH$_3$, —CH$_2$—N(CH$_3$)—SO$_2$—CH$_3$, —CH$_2$—NH—SO$_2$—C$_2$H$_5$, —CH$_2$—N(CH$_3$)—SO$_2$—C$_2$H$_5$, —CH$_2$—NH—SO$_2$—C$_3$H$_7$, —CH$_2$—N(CH$_3$)—SO$_2$—C$_3$H$_7$, —CH$_2$—NH—SO$_2$—C$_3$H$_5$, —CH$_2$—N(CH$_3$)—SO$_2$—C$_3$H$_5$, —NH—C(O)—NH$_2$, —N(CH$_3$)—C(O)—NH$_2$, —NH—C(O)—NH—CH$_3$, —N(CH$_3$)—C(O)—NH—CH$_3$, —NH—C(O)—N(CH$_3$)$_2$, —N(CH$_3$)—C(O)—N(CH$_3$)$_2$, —SO$_2$—NH$_2$, —SO$_2$—NH(CH$_3$), —SO$_2$—N(CH$_3$)$_2$, —C(O)—NH—C$_2$H$_5$, —C(O)—N(CH$_3$)—C$_2$H$_5$, —C(O)—N(CH$_3$)—C$_3$H$_7$, —C(O)—N(CH$_3$)—C$_4$H$_9$, —C(O)—NH—CH(CH$_3$)—C$_2$H$_5$, —C(O)—N(CH$_3$)—CH(CH$_3$)—C$_2$H$_5$, —CH$_2$—C(O)—NH$_2$, —CH$_2$—C(O)—NH—CH$_3$, —CH$_2$—C(O)—N(CH$_3$)$_2$, —N(CH$_3$)—SO$_2$—N(CH$_3$)$_2$, -pyridin-4-yl, —CH$_2$-3-methyl-oxetan-3-yl, —O-1,2-difluoro-phen-5-yl, —O-pyridin-2-yl, -pyrrolidine-2-one-1-yl, -3,5-dimethyl-[1,2,4]triazol-4-yl, -3-methyl-[1,2,4]oxadiazol-5-yl,

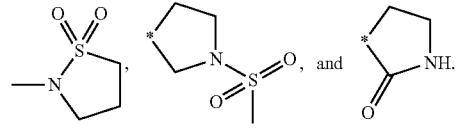

Preferred compounds of formula (I) according to the invention are compounds with R$_1$, R$_2$, R$_3$, R$_6$, R$_7$, R$_8$, R$_8'$, R$_9$, R$_9'$, R$_{10}$, R$_{11}$, R$_{11'}$, R$_{12}$, R$_{13}$, R$_{13'}$, R$_{14}$, R$_{15}$, R$_{15'}$, R$_{16}$, R$_{17}$, A, L$_1$, Z, Q, and n as herein before or below defined, wherein R$_4$ and R$_5$ are independently a group of the structure -L$_2$-R$_{18}$, wherein L$_2$ is selected from among —NH—, —N(CH$_3$)— and —N(C$_2$H$_5$)—, wherein R$_{18}$ is selected from among -tetrahydropyranyl, -cyclopropyl, -cyclobutyl, -cyclopentyl, -cyclohexyl, -cycloheptyl, -cyclooctyl, -pyrrolidinyl, -piperidinyl, -piperazinyl, -morpholinyl, -chromanyl, -octahydropyrano-pyrrolyl, -octahydro-pyrano-pyridinyl, -octahydropyrano-oxazinyl, -oxaspirodecanyl, and -tetrahydronaphthyridinyl, wherein R$_{18}$ is optionally substituted by one or more groups selected from among —F, —CF$_3$, —OCF$_3$, —CN, —OH, —O—CH$_3$, —CH$_3$, —NH—C(O)—CH$_3$, —N(CH$_3$)—C(O)—CH$_3$, —C(O)—CH$_3$, —S(O)$_2$—CH$_3$, —NH—S(O)$_2$—CH$_3$, —N(CH$_3$)—S(O)$_2$—CH$_3$, and —C(O)—O—C$_2$H$_5$.

Preferred compounds of formula (I) according to the invention are compounds with R$_1$, R$_2$, R$_3$, R$_4$, R$_5$, R$_6$, R$_7$, R$_8$, R$_8'$, R$_9$, R$_9'$, R$_{10}$, R$_{11}$, R$_{11'}$, R$_{12}$, R$_{13}$, R$_{13'}$, R$_{14}$, R$_{15}$, R$_{15'}$, R$_{16}$, R$_{17}$, R$_{18}$, A, L$_1$, L$_2$, Z, Q, and n as herein before or below defined, wherein R$_4$, R$_5$ and R$_{18}$ are optionally further bi-valently substituted by one or more groups selected from among

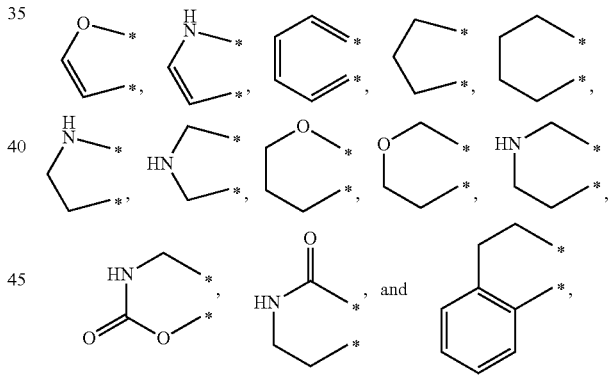

on one ring atom or on two neighboring ring atoms, such that spirocyclic or annellated rings are formed.

Preferred compounds of formula (I) according to the invention are compounds with R$_1$, R$_2$, R$_3$, R$_5$, R$_6$, R$_7$, R$_8$, R$_8'$, R$_9$, R$_9'$, R$_{10}$, R$_{11}$, R$_{11'}$, R$_{12}$, R$_{13}$, R$_{13'}$, R$_{14}$, R$_{15}$, R$_{15'}$, R$_{16}$, R$_{17}$, R$_{18}$, A, L$_1$, L$_2$, Z, Q, and n as herein before or below defined, wherein R$_4$ is selected from among

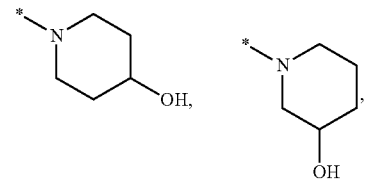

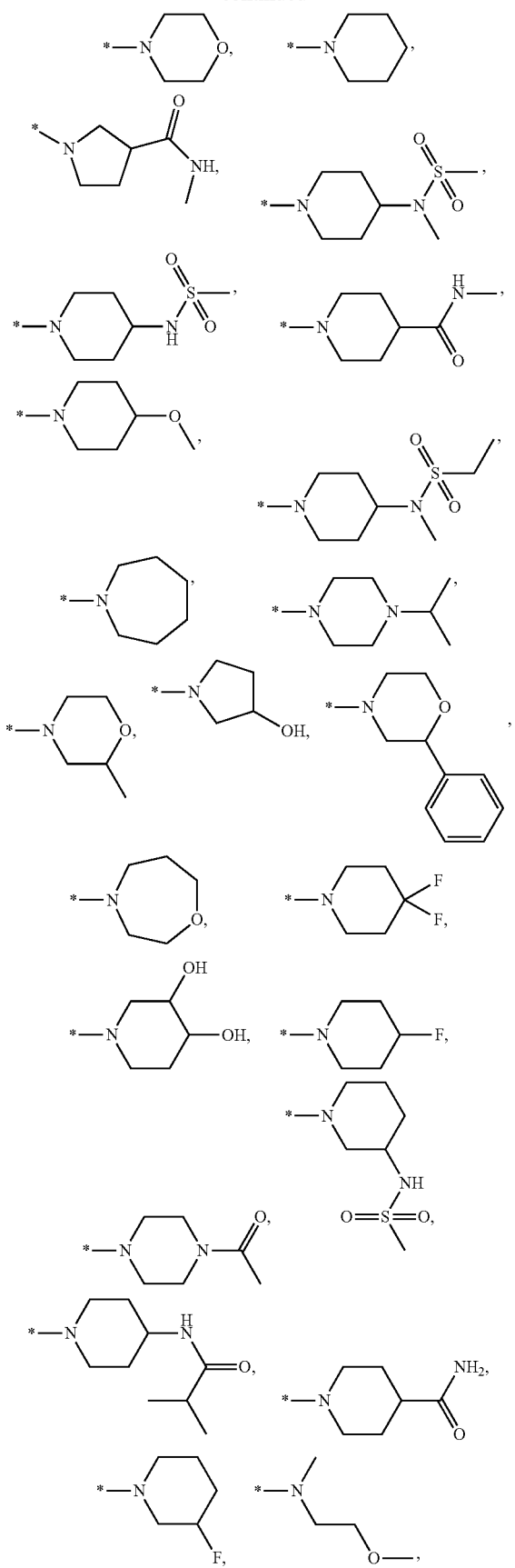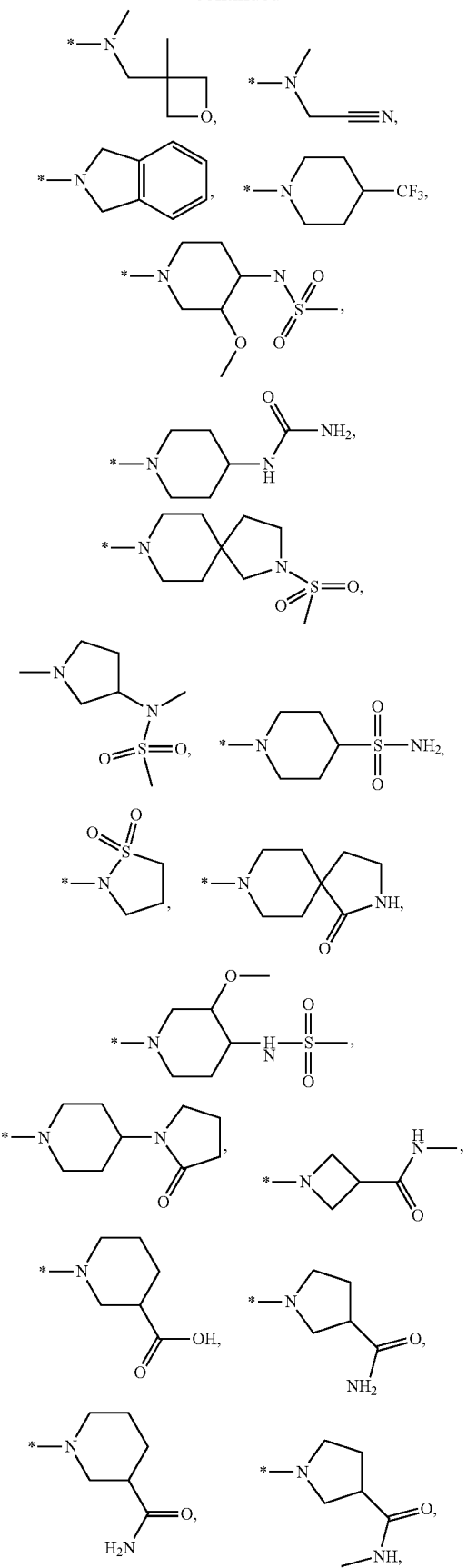

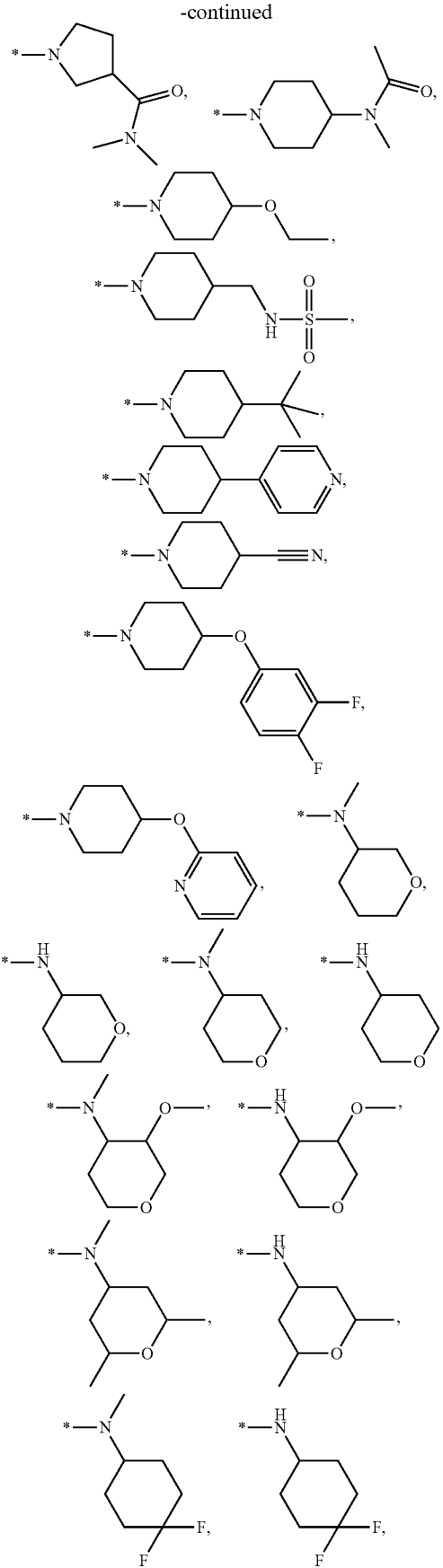
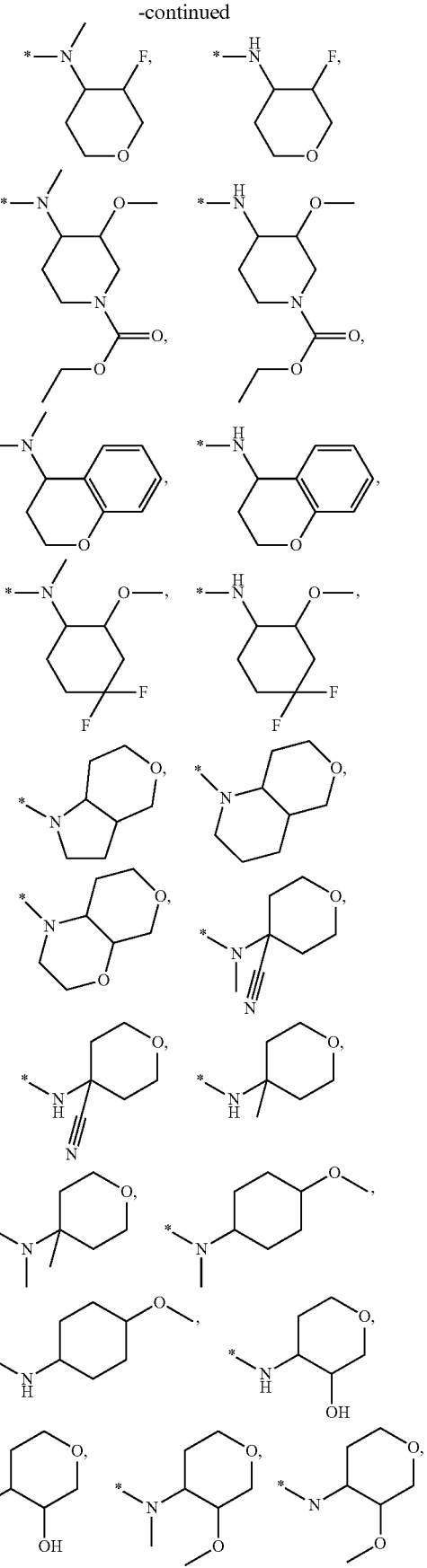

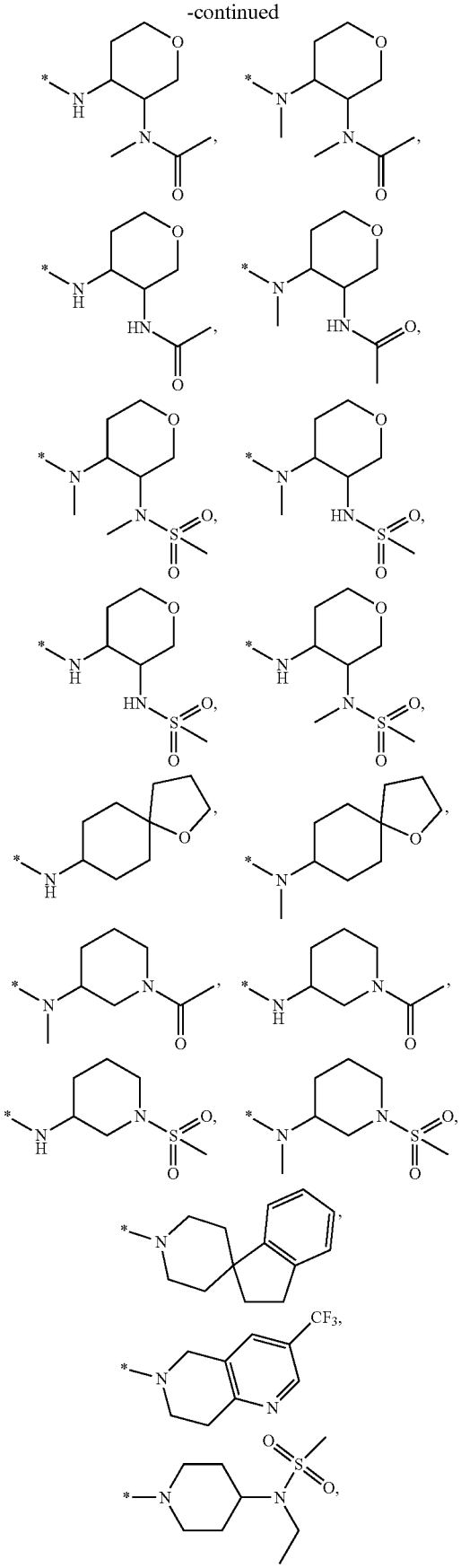
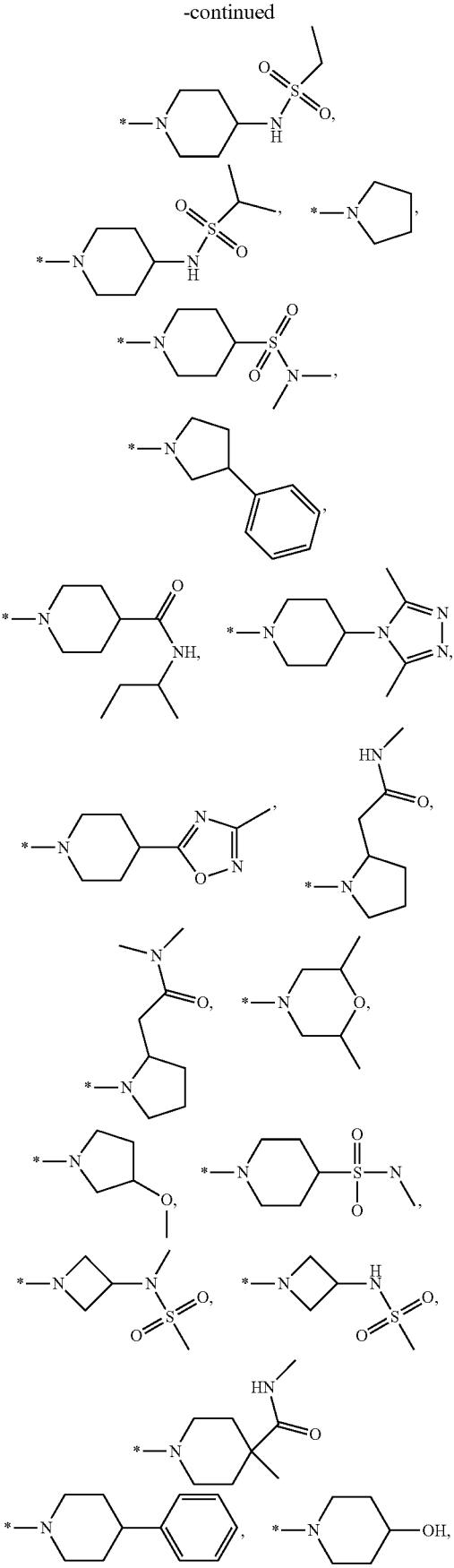

-continued

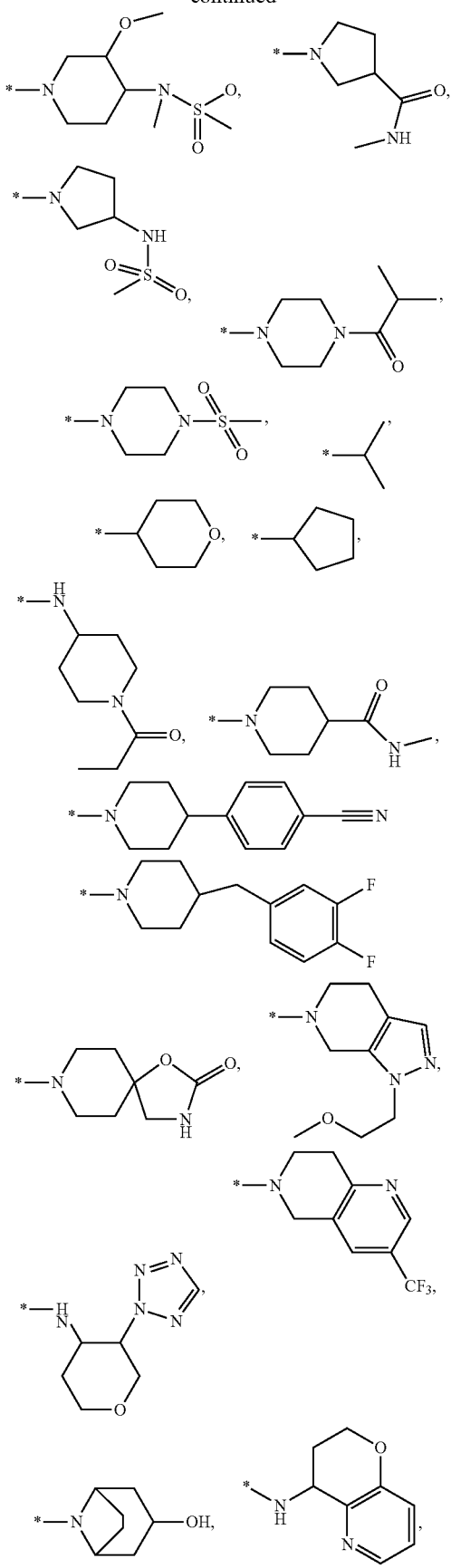

-continued

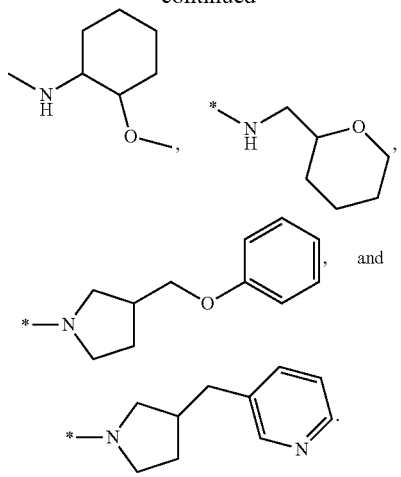

Preferred compounds of formula (I) according to the invention are compounds with $R_1$, $R_2$, $R_3$, $R_4$, $R_6$, $R_7$, $R_8$, $R_{8'}$, $R_9$, $R_{9'}$, $R_{10}$, $R_{11}$, $R_{11'}$, $R_{12}$, $R_{13}$, $R_{13'}$, $R_{14}$, $R_{15}$, $R_{15'}$, $R_{16}$, $R_{17}$, $R_{18}$, A, $L_1$, $L_2$, Z, Q, and n as herein before or below defined, wherein $R_5$ is selected from among an electron pair, —H, and —C(O)—$NH_2$.

Preferred compounds of formula (I) according to the invention are compounds with $R_1$, $R_2$, $R_3$, $R_4$, $R_5$, $R_7$, $R_8$, $R_{8'}$, $R_9$, $R_{9'}$, $R_{10}$, $R_{11}$, $R_{11'}$, $R_{12}$, $R_{13}$, $R_{13'}$, $R_{14}$, $R_{15}$, $R_{15'}$, $R_{16}$, $R_{17}$, $R_{18}$, A, $L_1$, $L_2$, Z, Q, and n as herein before or below defined, wherein $R_6$ is selected from among —H, —$CH_3$, —$C_2H_5$, —O—$CH_3$, —O—$C_2H_5$, —F, —$CF_3$, and —$OCF_3$, and more preferred wherein $R_6$ is selected from among H, and —O—$CH_3$, and most preferred wherein $R_6$ is —H.

Preferred compounds of formula (I) according to the invention are compounds with $R_1$, $R_2$, $R_3$, $R_4$, $R_5$, $R_6$, $R_7$, $R_8$, $R_{8'}$, $R_9$, $R_{9'}$, $R_{10}$, $R_{11}$, $R_{11'}$, $R_{12}$, $R_{13}$, $R_{13'}$, $R_{14}$, $R_{15}$, $R_{15'}$, $R_{16}$, $R_{17}$, $R_{18}$, $L_1$, $L_2$, Z, Q, and n as herein before or below defined, wherein A is selected from among a single bond, =CH—, —$CH_2$, —O—, and —NH—, and more preferred wherein A is selected from among —O— and —NH—, and most preferred wherein A is —NH—.

Preferred compounds of formula (I) according to the invention are compounds with $R_1$, $R_2$, $R_3$, $R_4$, $R_5$, $R_6$, $R_7$, $R_8$, $R_{8'}$, $R_9$, $R_{9'}$, $R_{10}$, $R_{11}$, $R_{11'}$, $R_{12}$, $R_{13}$, $R_{13'}$, $R_{14}$, $R_{15}$, $R_{15'}$, $R_{16}$, $R_{17}$, $R_{18}$, A, $L_1$, $L_2$, Q, and n as herein before or below defined, wherein Z is selected from among C, and N, and more preferred wherein Z is C.

All of the above embodiments under formula (I) have to be understood to optionally be present in form of their individual optical isomers, mixtures of their individual optical isomers, or racemates, as well as in form of their acid addition salts with pharmacologically acceptable acids, as well as in form of their solvates and/or hydrates.

DEFINITIONS

Unless otherwise stated, all the substituents are independent of one another. If for example there might be a plurality of $C_1$-$C_6$-alkyl groups as substituents in one group, in the case of three substituents $C_1$-$C_6$-alkyl, one may represent methyl, one n-propyl and one tert-butyl.

Within the scope of this application, in the definition of possible substituents, these may also be represented in the form of a structural formula. An asterisk (*) in the structural formula of the substituent is to be understood as being the linking point to the rest of the molecule. Moreover, the atom of the substituent which follows the linking point is referred to as the atom in position number 1. Thus, for example, the groups N-piperidinyl (Piperidin-A), 4-piperidinyl (Piperidin-B), 2-tolyl (Tolyl-C), 3-tolyl (Tolyl-D), and 4-tolyl (Tolyl-E) are shown as follows:

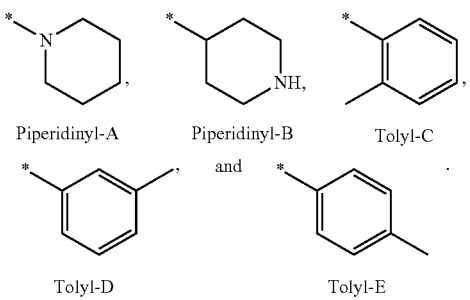

Piperidinyl-A    Piperidinyl-B    Tolyl-C

Tolyl-D    Tolyl-E

If there is no asterisk (*) in the structural formula of the substituent, each hydrogen atom may be removed from the substituent and the valency thus freed may act as a binding site to the rest of a molecule. Thus, for example, (Tolyl-F) may represent 2-tolyl, 3-tolyl, 4-tolyl, and benzyl

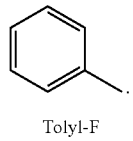

Tolyl-F

By the term "branched or unbranched, saturated or unsaturated $C_1$-$C_6$-carbon chain" it is meant a chain of carbon atoms, which is constituted by six carbon atoms arranged in a row and which can optionally further comprise branches or one or more hetero atoms selected from N, O or S. Said carbon chain can be saturated or unsaturated by comprising double or triple bonds.

By the term "$C_1$-$C_6$-alkyl" (including those which are part of other groups) are meant branched and unbranched alkyl groups with 1 to 6 carbon atoms and by the term "$C_1$-$C_4$-alkyl" are meant branched and unbranched alkyl groups with 1 to 4 carbon atoms. Alkyl groups with 1 to 4 carbon atoms are preferred. Examples for alkyl groups with 1-6 carbon atoms include: methyl, ethyl, n-propyl, iso-propyl, n-butyl, iso-butyl, sec-butyl, tert-butyl, n-pentyl, iso-pentyl, neo-pentyl or hexyl. Optionally the abbreviations Me, Et, n-Pr, i-Pr, n-Bu, i-Bu, t-Bu, etc. may also be used for the above-mentioned groups. Unless stated otherwise, the definitions propyl, butyl, pentyl and hexyl include all the possible isomeric forms of the groups in question. Thus, for example, propyl includes n-propyl and iso-propyl, butyl includes iso-butyl, sec-butyl and tert-butyl etc.

By the term "$C_1$-$C_8$-alkylene" (including those which are part of other groups) are meant branched and unbranched alkylene groups with 1 to 8 carbon atoms. By the term "$C_2$-$C_8$-alkylene" are meant branched and unbranched alkylene groups with 2 to 8 carbon atoms. By the term "$C_2$-$C_6$-alkylene" are meant branched and unbranched alkylene groups with 2 to 6 carbon atoms. By the term "$C_1$-$C_4$-alkylene" are meant branched and unbranched alkylene groups with 1 to 4 carbon atoms. By the term "$C_1$-$C_2$-alkylene" are meant branched and unbranched alkylene groups with 1 to 2 carbon atoms. By the term "$C_0$-$C_4$-alkylene" are meant branched and unbranched alkylene groups with 0 to 4 carbon atoms, thus also a single bond is encompassed. By the term "$C_1$-$C_3$-alkylene" are meant branched and unbranched alkylene groups with 1 to 3 carbon atoms. Examples for $C_1$-$C_8$-alkylene include: methylene, ethylene, propylene, 1-methylethylene, butylene, 1-methylpropylene, 1,1-dimethylethylene, 1,2-dimethylethylene, pentylene, 1,1-dimethylpropylene, 2,2-dimethylpropylene, 1,2-dimethylpropylene, 1,3-dimethylpropylene, hexylene, heptylene or octylene. Unless stated otherwise, the definitions propylene, butylene, pentylene, hexylene, heptylene and octylene include all the possible isomeric forms of the groups in question with the same number of carbons. Thus, for example, propyl also includes 1-methylethylene and butylene includes 1-methylpropylene, 1,1-dimethylethylene, 1,2-dimethylethylene.

If the carbon chain is to be substituted by a group which together with one or two carbon atoms of the alkylene chain forms a carbocyclic ring with 3, 5 or 6 carbon atoms, this includes the following examples of the rings:

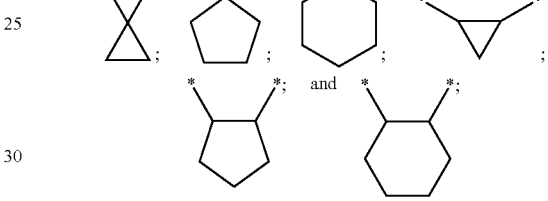

By the term "$C_2$-$C_6$-alkenyl" (including those which are part of other groups) are meant branched and unbranched alkenyl groups with 2 to 6 carbon atoms and by the term "$C_2$-$C_4$-alkenyl" are meant branched and unbranched alkenyl groups with 2 to 4 carbon atoms, provided that they have at least one double bond. Alkenyl groups with 2 to 4 carbon atoms are preferred. Examples for $C_2$-$C_6$-alkenyls include: ethenyl or vinyl, propenyl, butenyl, pentenyl, or hexenyl. Unless stated otherwise, the definitions propenyl, butenyl, pentenyl and hexenyl include all the possible isomeric forms of the groups in question. Thus, for example, propenyl includes 1-propenyl and 2-propenyl, butenyl includes 1-, 2- and 3-butenyl, 1-methyl-1-propenyl, 1-methyl-2-propenyl etc.

By the term "methenylene" is meant a group with 1 carbon atom, provided that it is linked by a single bond as well as on the other side by a double bond:

By the term "$C_2$-$C_8$-alkenylene" (including those which are part of other groups) are meant branched and unbranched alkenylene groups with 2 to 8 carbon atoms and by the term "$C_2$-$C_6$-alkenylene" are meant branched and unbranched alkenylene groups with 2 to 6 carbon atoms. By the term "$C_1$-$C_2$-alkenylene" are meant alkenylene groups with 1 to 2 carbon atoms, provided that they have at least one double bond, whereas by the term "$C_1$-alkenylene" is meant "methenylene". Examples for $C_2$-$C_8$-alkenylenes include: ethenylene, propenylene, 1-methylethenylene, butenylene, 1-methylpropenylene, 1,1-dimethylethenylene, 1,2-dimethylethenylene, pentenylene, 1,1-dimethylpropenylene, 2,2-dimethylpropenylene, 1,2-dimethylpropenylene, 1,3-dimethylpropenylene, hexenylene, heptenylene or octenylene. Unless stated otherwise, the definitions propenylene, butenylene, pentenylene and hexenylene include all the possible isomeric forms of the groups in question with the same number of carbons. Thus, for example, propenyl also includes 1-methylethenylene and butenylene includes 1-methylpropenylene, 1,1-dimethylethenylene, 1,2-dimethylethenylene.

By the term "$C_2$-$C_6$-alkynyl" (including those which are part of other groups) are meant branched and unbranched alkynyl groups with 2 to 6 carbon atoms and by the term "$C_2$-$C_4$-alkynyl" are meant branched and unbranched alkynyl groups with 2 to 4 carbon atoms, provided that they have at least one triple bond. Examples for $C_2$-$C_6$-alkynyls include: ethynyl, propynyl, butynyl, pentynyl or hexynyl. Unless stated otherwise, the definitions propynyl, butynyl, pentynyl and hexynyl include all the possible isomeric forms of the groups in question. Thus for example propynyl includes 1-propynyl and 2-propynyl, butynyl includes 1-, 2-, and 3-butynyl, 1-methyl-1-propynyl, 1-methyl-2-propynyl etc.

By the term "$C_2$-$C_8$-alkynylene" (including those which are part of other groups) are meant branched and unbranched alkynylene groups with 2 to 8 carbon atoms and by the term "$C_2$-$C_6$-alkynylene" are meant branched and unbranched alkylene groups with 2 to 6 carbon atoms. Examples of $C_2$-$C_8$-alkynylenes include: ethynylene, propynylene, 1-methylethynylene, butynylene, 1-methylpropynylene, 1,1-dimethylethynylene, 1,2-dimethylethynylene, pentynylene, 1,1-dimethylpropynylene, 2,2-dimethylpropynylene, 1,2-dimethylpropynylene, 1,3-dimethylpropynylene, hexynylene, heptynylene or octynylene. Unless stated otherwise, the definitions propynylene, butynylene, pentynylene and hexynylene include all the possible isomeric forms of the groups in question with the same number of carbons. Thus for example propynyl also includes 1-methylethynylene and butynylene includes 1-methylpropynylene, 1,1-dimethylethynylene, 1,2-dimethylethynylene.

By the term "ring" are meant carbocycles, which can be saturated, unsaturated or aromatic and which optionally can comprise one or more hetero atoms selected from N, O or S.

By the term "—$C_3$-$C_8$-heterocyclyl" are meant three-, four-, five-, six-, or seven-membered, saturated or unsaturated heterocyclic rings which may contain one, two, or three heteroatoms, selected from among oxygen, sulfur, and nitrogen, while the ring may be linked to the molecule through a carbon atom or through a nitrogen atom, if there is one. By the term "—$C_5$-$C_8$-heterocyclyl" are meant five-, six-, or seven-membered, saturated or unsaturated heterocyclic rings which may contain one, two, or three heteroatoms, selected from among oxygen, sulfur, and nitrogen, while the ring may be linked to the molecule through a carbon atom or through a nitrogen atom, if there is one. Examples include:

Unless otherwise mentioned, a heterocyclic ring (or "heterocycle") may be provided with a keto group. Examples include:

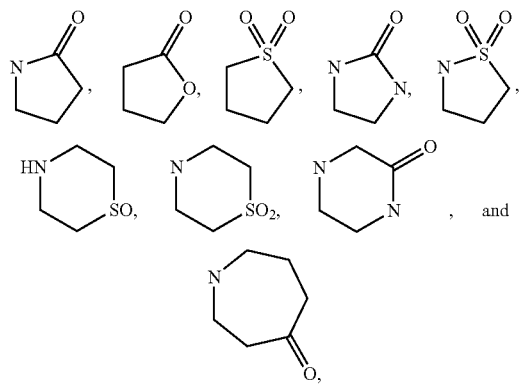

By the term "$C_3$-$C_8$-cycloalkyl" (including those which are part of other groups) are meant cyclic alkyl groups with 3 to 8 carbon atoms. Likewise, by the term "$C_3$-$C_6$-cycloalkyl" are meant cyclic alkyl groups with 3 to 6 carbon atoms. Examples of $C_3$-$C_8$-cycloalkyls include: cyclopropyl, cyclobutyl, cyclopentyl, cyclohexyl, cycloheptyl or cyclooctyl. Unless otherwise stated, the cyclic alkyl groups may be substituted by one or more groups selected from among methyl, ethyl, isopropyl, tert-butyl, hydroxy, fluorine, chlorine, bromine, and iodine.

By the term "aryl" (including those which are part of other groups) are meant aromatic ring systems. By the term "$C_5$-$C_{10}$-aryl" (including those which are part of other groups) are meant aromatic ring systems with 5 to 10 carbon atoms. Preferred are "$C_6$-$C_{10}$-aryl" groups whereas aromatic rings are meant with 6 to 10 carbon atoms. Examples include: phenyl or naphthyl. Also preferred are "$C_5$-$C_6$-aryl" groups whereas aromatic rings are meant with 5 to 6 carbon atoms. Unless otherwise stated, the aromatic ring systems may be substituted by one or more groups selected from among methyl, ethyl, iso-propyl, tert-butyl, hydroxy, fluorine, chlorine, bromine and iodine.

By the term "$C_5$-$C_{10}$-heteroaryl" (including those which are part of other groups) are meant five- or six-membered heterocyclic aromatic groups or 5-10-membered, bicyclic heteroaryl rings which may contain one, two, or three heteroatoms selected from among oxygen, sulfur, and nitrogen, and contain so many conjugated double bonds that an aromatic system is formed. The following are examples of five- or six- or nine-membered heterocyclic aromatic groups:

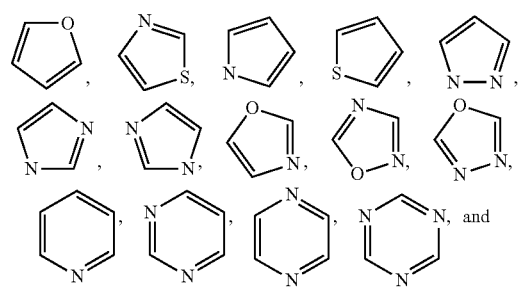

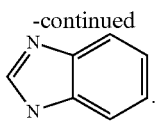

Preferred are "$C_5$-$C_6$-heteroaryl" groups whereas aromatic rings are meant five- or six-membered heterocyclic aromatic groups. Unless otherwise stated, these heteroaryls may be substituted by one or more groups selected from among methyl, ethyl, isopropyl, tert-butyl, hydroxy, fluorine, chlorine, bromine, and iodine.

When a generic combined groups are used, for example —X—$C_1$-$C_4$-alkyl- with X being a functional group such as —CO—, —NH—, —C(OH)— and the like, the functional group X can be located at either of the ends of the —$C_1$-$C_4$-alkyl chain.

By the term "spiro-$C_3$-$C_8$-cycloalkyl" (spiro) are meant 3-8 membered, spirocyclic rings while the ring is linked to the molecule through a carbon atom. By the term "spiro-$C_3$-$C_8$-heterocyclyl" (spiro) are meant 3-8 membered, spirocyclic rings which may contain one, two, or three heteroatoms selected from among oxygen, sulfur, and nitrogen, while the ring may be linked to the molecule through a carbon atom or through a nitrogen atom, if there is one.

Unless otherwise mentioned, a spirocyclic ring may be provided with an oxo, methyl, or ethyl group. Examples include:

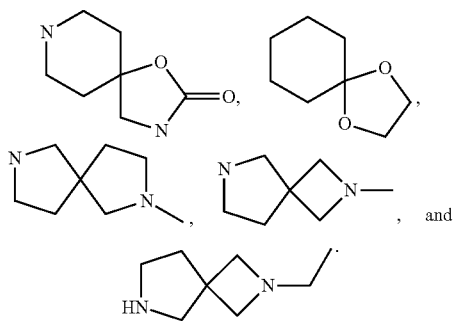

"Halogen" within the scope of the present invention denotes fluorine, chlorine, bromine or iodine. Unless stated to the contrary, fluorine, chlorine and bromine are regarded as preferred halogens.

"Linker" within the scope of the present invention denominates a bivalent group or a bond.

The above listed groups and residues can be combined to form more complex structures composed from carbon chains and rings or the like.

Compounds of general formula (I) may have acid groups, chiefly carboxyl groups, and/or basic groups such as e.g. amino functions. Compounds of general formula (I) may therefore occur as internal salts, as salts with pharmaceutically useable inorganic acids such as hydrochloric acid, sulphuric acid, phosphoric acid, sulphonic acid or organic acids (such as for example maleic acid, fumaric acid, citric acid, tartaric acid or acetic acid) or as salts with pharmaceutically useable bases such as alkali or alkaline earth metal hydroxides or carbonates, zinc or ammonium hydroxides or organic amines such as e.g. diethylamine, triethylamine, triethanolamine inter alia.

As mentioned hereinbefore, the compounds of formula (I) may be converted into the salts thereof, particularly for pharmaceutical use, into the physiologically and pharmacologically acceptable salts thereof. These salts may on the one hand be in the form of the physiologically and pharmacologically acceptable acid addition salts of the compounds of formula (I) with inorganic or organic acids. On the other hand, if R is hydrogen, the compound of formula (I) may also be converted by reaction with inorganic bases into physiologically and pharmacologically acceptable salts with alkali or alkaline earth metal cations as counter ion. The acid addition salts may be prepared for example using hydrochloric acid, hydrobromic acid, sulphuric acid, phosphoric acid, methanesulphonic acid, acetic acid, fumaric acid, succinic acid, lactic acid, citric acid, tartaric acid or maleic acid. It is also possible to use mixtures of the above-mentioned acids. The alkali and alkaline earth metal salts of the compound of formula (I) are preferably prepared using the alkali and alkaline earth metal hydroxides and hydrides thereof, of which the hydroxides and hydrides of the alkaline earth metals, particularly of sodium and potassium, are preferred and sodium and potassium hydroxide are particularly preferred.

If desired, the compounds of general formula (I) may be converted into the salts thereof, particularly, for pharmaceutical use, into the pharmacologically acceptable acid addition salts with an inorganic or organic acid. Suitable acids include for example succinic acid, hydrobromic acid, acetic acid, fumaric acid, maleic acid, methanesulphonic acid, lactic acid, phosphoric acid, hydrochloric acid, sulphuric acid, tartaric acid or citric acid. It is also possible to use mixtures of the above-mentioned acids.

The invention relates to the compounds in question, optionally in the form of the individual optical isomers, mixtures of the individual enantiomers or racemates, in the form of the tautomers as well as in the form of the free bases or the corresponding acid addition salts with pharmacologically acceptable acids—such as for example acid addition salts with hydrohalic acids—for example hydrochloric or hydrobromic acid or organic acids—such as for example oxalic, fumaric, diglycolic or methanesulphonic acid.

The compounds according to the invention may optionally occur as racemates, but they may also be obtained as pure enantiomers/diastereomers.

The invention relates to the compounds in question, optionally in the form of the individual optical isomers, mixtures of the individual enantiomers or racemates, in the form of the tautomers as well as in the form of the free bases or the corresponding acid addition salts with pharmacologically acceptable acids—such as for example acid addition salts with hydrohalic acids—for example hydrochloric or hydrobromic acid or organic acids—such as for example oxalic, fumaric, diglycolic or methanesulphonic acid.

The compounds according to formula (I) according to the invention have the meanings hereinbefore whereas in particular the preferred embodiments defined by $R_1$, $R_2$, $R_3$, $R_4$, $R_5$, $R_6$, $R_7$, $R_8$, $R_9$, $R_{9'}$, $R_{10}$, $R_{11}$, $R_{11'}$, $R_{12}$, $R_{13}$, $R_{13'}$, $R_{14}$, $R_{15}$, $R_{15'}$, $R_{16}$, $R_{17}$, $R_{18}$, A, $L_1$, $L_2$, Z, Q, and n in each case are independently selected of one another.

Therapeutic Applications

The above exemplary substances have been tested for binding to CCR2 using a binding assay as outlined herein below:

Cell Culture:

THP-1 cells (human acute monocytic leukaemia cells) were cultured under standardized conditions at 37° C. and 5% $CO_2$ in a humidified incubator. THP-1 cells were cultivated in RPMI 1640 medium (Gibco 21875) containing 1% MEM-NEAA (Gibso 11140) 2 mM L-glutamine, 1.5 g/L sodium bicarbonate, 4.5 g/L glucose, 10 mM HEPES and 1.0 mM sodium pyruvate, 90%; 10% fetal calf serum (FCS Gibco 10500-064).

Membranes were prepared from THP-1 cells. THP-1 cells were centrifuged at 300×g at 4° C. for 10 min. The cell pellet was resuspended in Phosphate Buffer Saline (PBS, including 10 μM Pefabloc and a protease inhibitor mix 'complete', Boehringer Mannheim (1 tablet/50 ml)), to a concentration of 80 cells/ml. The membrane preparation was performed by disrupting the cells by nitrogen decomposition (at 50 bar, for 1 h) in a "Nitrogen Bombe" (Parr Instrument). Cell debris was removed by centrifugation (800×g at 4° C., 1 min) The supernatant was centrifuged at 80000×g, 4° C. for 30 min to sediment the cell membranes. Usually 50 mg of protein (Bradford assay) were yielded from 1×10E9 cells. The membranes were resuspended in 25 mM HEPES, 25 mM MgCl2, 1 mM CaCl2, 10% Glycerine for storage in aliquots at −80° C. in 25 mM HEPES, 25 mM MgCl2, 1 mM CaCl2, 10% Glycerine and stored at −80° C.

Receptor Membrane Binding Assay:

Perkin Elmer NEX 332 Jod 125 MCP-1, Stock: 2200 Ci/mmol solved in 2000 μl assay buffer, stored at −20° C. THP-1 membrane were adjusted with 25 mM HEPES, pH 7.2; 5 mM MgCl2; 0.5 mM CaCl2; 0.2% BSA assay buffer to a concentration of 2.5 μg/15 μl. Amersham Biosciences PVT-WGA Beads (RPNQ0001) were adjusted with assay buffer to a concentration of 0.24 mg/30 μl. For preparation of the membrane-bead-suspension membranes and beads were incubated for 30 min at RT under rotation (60 rpm) with a ratio of 1:2. Test compounds dissolved in 100% DMSO to a concentration of 10 mM and are further diluted with 100% DMSO to 1 mM. All additional compound dilutions were obtained with assay buffer, final 1% DMSO. Compounds, membrane-bead-suspension and [125I]MCP-1 (ca. 25000 cpm/10 μl) were incubated. Bound radioactivity was determined by scintillation counter after 8 h. Determination of affinity of test compounds (dissociation constant hKi) is calculated by iterative fitting of experimental data using the "easy sys" program, which is based on law of mass action (Schittkowski K. (1994), Numerische Mathematik, Vol. 68, 129-142).

All of the above-referenced examples have been found to have an activity in this assay of 10 μM or less.

| Example | hKi | CCR2 % ctrl @ 10 μM | Example | hKi | CCR2 % ctrl @ 10 μM |
|---|---|---|---|---|---|
| 1 | 32 | 1 | 15 | 200 | 14 |
| 2 | 222 | 13 | 16 | 1904 | 40 |
| 3 | 204 | 14 | 17 | 302 | 18 |
| 4 | 1593 | 43 | 18 | 3505 | 52 |
| 5 | 616 | 26 | 19 | 269 | 40 |
| 6 | 1928 | 41 | 20 | 303 | 24 |
| 7 | 306 | 16 | 21 | 2660 | 51 |
| 8 | 1023 | 36 | 22 | 466 | 24 |
| 9 | 974 | 32 | 23 | 169 | 7 |
| 10 | 650 | 27 | 24 | 4029 | 58 |
| 11 | 1710 | 38 | 25 | 2406 | 47 |
| 12 | 664 | 29 | 26 | 914 | 30 |
| 13 | 1332 | 42 | 27 | 620 | 25 |
| 14 | 387 | 22 | 28 | 4176 | 58 |
| 29 | 2097 | 40 | 59 | 55 | 5 |
| 30 | 446 | 18 | 60 | 44 | 5 |
| 31 | 790 | 28 | 61 | 46 | 2 |
| 32 | 37 | 2 | 62 | 38 | 3 |
| 33 | 22 | 0 | 63 | 54 | 7 |
| 34 | 62 | 4 | 64 | 65 | 8 |
| 35 | 24 | 5 | 65 | 176 | 8 |
| 36 | 10 | 1 | 66 | 138 | 8 |
| 37 | 11 | 4 | 67 | 1423 | 27 |
| 38 | 69 | 13 | 68 | 98 | 7 |
| 39 | 36 | 2 | 69 | 63 | 7 |
| 40 | 174 | 9 | 70 | 80 | 6 |
| 41 | 11 | 6 | 71 | 117 | 12 |
| 42 | 433 | 16 | 72 | 81 | 7 |
| 43 | 566 | 17 | 73 | 38 | 2 |
| 44 | 1639 | 27 | 74 | 71 | 2 |
| 45 | 501 | 17 | 75 | 67 | 7 |
| 46 | 225 | 12 | 76 | 132 | 12 |
| 47 | 222 | 14 | 77 | 650 | 27 |
| 48 | 1778 | 26 | 78 | 740 | 28 |
| 49 | 97 | 7 | 79 | 89 | 10 |
| 50 | 928 | 22 | 80 | 53 | 7 |
| 51 | 290 | 13 | 81 | 52 | 8 |
| 52 | 175 | 12 | 82 | 43 | 4 |
| 53 | 18 | 4 | 83 | 43 | 3 |
| 54 | 356 | 13 | 84 | 69 | 4 |
| 55 | 200 | 17 | 85 | 55 | 13 |
| 56 | 127 | 8 | 86 | 39 | 3 |
| 57 | 93 | 10 | 87 | 78 | 9 |
| 58 | 336 | 12 | 88 | 58 | 6 |
| 89 | 770 | 29 | 119 | 1033 | 37 |
| 90 | 127 | 10 | 120 | 499 | 30 |
| 91 | 236 | 23 | 121 | 147 | 15 |
| 92 | 175 | 14 | 122 | 415 | 23 |
| 93 | 123 | 6 | 123 | 542 | 26 |
| 94 | 211 | 8 | 124 | 361 | 20 |
| 95 | 170 | 2 | 125 | 446 | 25 |
| 96 | 939 | 21 | 126 | 399 | 23 |
| 97 | 665 | 17 | 127 | 665 | 35 |
| 98 | 214 | 2 | 128 | 445 | 26 |
| 99 | 1826 | 32 | 129 | 336 | 21 |
| 100 | 395 | 18 | 130 | 4266 | 50 |
| 101 | 986 | 35 | 131 | 55 | 6 |
| 102 | 224 | 15 | 132 | 672 | 31 |
| 103 | 1605 | 30 | 133 | 205 | 15 |
| 104 | 617 | 31 | 134 | 399 | 23 |
| 105 | 687 | 31 | 135 | 888 | 19 |
| 106 | 405 | 13 | 136 | 773 | 14 |
| 107 | 232 | 12 | 137 | 634 | 14 |
| 108 | 627 | 20 | 138 | 145 | 6 |
| 109 | 213 | 11 | 139 | 443 | 9 |
| 110 | 527 | 28 | 140 | 692 | 16 |
| 111 | 464 | 27 | 141 | 422 | 7 |
| 112 | 378 | 21 | 142 | 529 | 8 |
| 113 | 3306 | 46 | 143 | 422 | 8 |
| 114 | 62 | 8 | 144 | 91 | 7 |
| 115 | 847 | 33 | 145 | 181 | 17 |
| 116 | 198 | 16 | 146 | 3 | 7 |
| 117 | 285 | 19 | 147 | 40 | 8 |
| 118 | 2162 | 41 | 148 | 119 | 4 |
| 149 | 41 | 10 | 179 | 1637 | 42 |
| 150 | 12 | 3 | 189 | 4812 | 60 |
| 151 | 14 | 7 | 181 | 3607 | 58 |
| 152 | 44 | 7 | 182 | 2991 | 53 |
| 153 | 27 | 1 | 183 | 426 | 45 |
| 154 | 123 | 15 | 184 | 908 | 30 |
| 155 | 76 | 8 | 185 | 4209 | 53 |
| 156 | 18 | 8 | 186 | 78 | 8 |
| 157 | 1147 | 23 | 187 | 256 | 15 |
| 158 | 6 | 0 | 188 | 3934 | 53 |
| 159 | 25 | 4 | 189 | 170 | 13 |
| 160 | 43 | 3 | 190 | 783 | 27 |
| 161 | 1996 | 30 | 191 | 519 | 20 |
| 162 | 3798 | 43 | 192 | 1446 | 37 |
| 163 | 1560 | 32 | 193 | 1536 | 35 |
| 164 | 353 | 15 | 194 | 491 | 25 |
| 165 | 222 | 15 | 195 | 141 | 14 |
| 166 | 227 | 16 | 196 | 666 | 19 |
| 167 | 246 | 16 | 197 | 33 | 4 |
| 168 | 51 | 9 | 198 | 58 | 1 |
| 169 | 2287 | 54 | 199 | 534 | 9 |
| 170 | 705 | 31 | 200 | 108 | 5 |
| 171 | 356 | 16 | 201 | 101 | 6 |
| 172 | 736 | 28 | 202 | 292 | 7 |
| 173 | 89 | 6 | 203 | 641 | 11 |
| 174 | 2718 | 53 | 204 | 123 | 6 |
| 175 | 434 | 14 | 205 | 135 | 11 |
| 176 | 648 | 31 | 206 | 44 | 3 |

| Example | hKi | Example | hKi |
|---|---|---|---|
| 177 | 1252 | 43 | 207 | 1180 | 35 |
| 178 | 27 | 0 | 208 | 99 | 7 |
| 209 | 177 | 7 | 239 | 2319 | 33 |
| 210 | 83 | 0 | 240 | 104 | 7 |
| 211 | 140 | 5 | 241 | 522 | 21 |
| 212 | 731 | 24 | 242 | 516 | 21 |
| 213 | 430 | 14 | 243 | 1615 | 40 |
| 214 | 711 | 20 | 244 | 366 | 24 |
| 215 | 2146 | 42 | 245 | 555 | 15 |
| 216 | 4283 | 59 | 246 | 306 | 2 |
| 217 | 4326 | 54 | 247 | 149 | 6 |
| 218 | 281 | 8 | 248 | 576 | 17 |
| 219 | 476 | 22 | 249 | 3249 | 36 |
| 220 | 979 | 27 | 250 | 1263 | 32 |
| 221 | 172 | 12 | 251 | 439 | 75 |
| 222 | 1306 | 31 | 252 | 38 | 6 |
| 223 | 244 | 14 | 253 | 350 | 17 |
| 224 | 1230 | 35 | 254 | 101 | 11 |
| 225 | 21 | 0 | 255 | 33 | 5 |
| 226 | 1170 | 36 | 256 | 438 | 25 |
| 227 | 333 | 22 | 257 | 186 | 14 |
| 228 | 331 | 16 | 258 | 64 | 4 |
| 229 | 1133 | 39 | 259 | 277 | 16 |
| 230 | 1845 | 45 | 260 | 493 | 20 |
| 231 | 215 | 15 | 261 | 120 | 8 |
| 232 | 924 | 34 | 262 | 224 | 13 |
| 233 | 194 | 8 | 263 | 1968 | 27 |
| 234 | 401 | 19 | 264 | 41 | 3 |
| 235 | 460 | 26 | 265 | 462 | 23 |
| 236 | 175 | 14 | 266 | 149 | |
| 237 | 133 | 9 | 267 | 487 | 20 |
| 238 | 239 | 14 | 268 | 119 | 5 |
| 228a | 1564 | 9 | 228e | 3720 | 40 |
| 228b | 2 | 4 | 228f | 15 | 1 |
| 228c | 29 | 0 | 228g | 169 | 6 |
| 228d | 91 | 1 | 228h | 5 | 0 |
| 269 | 2340 | 36 | 285 | 1306 | 35 |
| 270 | 179 | 9 | 286 | 965 | 19 |
| 271 | 1608 | 15 | 287 | 2547 | 33 |
| 272 | 155 | 8 | 288 | 738 | 13 |
| 273 | 1435 | 27 | 289 | 1667 | 34 |
| 274 | 4421 | 48 | 290 | 1601 | 28 |
| 275 | 593 | 19 | 291 | 3123 | 32 |
| 276 | 1842 | 23 | 292 | 136 | 15 |
| 277 | 1376 | 34 | 293 | 717 | 27 |
| 278 | 1078 | 32 | 294 | 230 | 16 |
| 279 | 192 | 9 | 295 | 140 | 0 |
| 280 | 1435 | 32 | 296 | 69 | 3 |
| 281 | 1012 | 24 | 297 | 164 | 10 |
| 282 | 1527 | 39 | 298 | 599 | 17 |
| 283 | 4421 | 48 | 299 | 70 | 6 |
| 284 | 1514 | 42 | 300 | 136 | 8 |
| 275a | 29 | 0 | 275c | 2932 | 38 |
| 275b | 26 | 3 | 275d | 318 | 10 |

| Example | hKi | Example | hKi |
|---|---|---|---|
| 228go | 54 | 159e | 28 |
| 228gp | 1354 | 159f | 14 |
| 228ga | 23 | 159g | 15 |
| 228gb | 3828 | 159h | 39 |
| 228gc | 561 | 159i | 24 |
| 228gd | 1094 | 159k | 22 |
| 228ge | 37 | 159l | 22 |
| 228gf | 145 | 159m | 9 |
| 228gg | 1026 | 159n | 233 |
| 228gh | 4066 | 159o | 12 |
| 228gi | 1101 | 159p | 7 |
| 228gj | 55 | 159q | 10 |
| 228gk | 44 | 159r | 2578 |
| 228gl | 537 | 159s | 1314 |
| 228gm | 28 | 159t | 1202 |
| 228gn | 333 | 159u | 29 |
| 275da | 4 | 159w | 9 |
| 275db | 33 | 159y | 169 |
| 275dc | 11 | 159x | 147 |
| 275dd | 40 | 159z | 11 |
| 275de | 16 | 159aa | 18 |
| 275df | 15 | 159ba | 11 |
| 275dg | 12 | 159ca | 3 |
| 275dh | 3 | 159da | 5 |
| 275di | 1 | 159ea | 7 |
| 275dj | 4 | 159fa | 35 |
| 159a | 10 | 159ga | 28 |
| 159b | 7 | 159ha | 27 |
| 159c | 13 | 159ia | 17 |
| 159d | 15 | 159ja | 18 |
| 159ka | 19 | 159pb | 10 |
| 159la | 19 | 159qb | 69 |
| 159ma | 20 | 159rb | 54 |
| 159na | 21 | 159sb | 21 |
| 159oa | 29 | 159tb | 13 |
| 159pa | 32 | 159ub | 18 |
| 159qa | 19 | 159wb | 16 |
| 159ra | 22 | 159yb | 15 |
| 159sa | 22 | 159xb | 6 |
| 159ta | 27 | 159zb | 15 |
| 159ua | 23 | 159ac | 5936 |
| 159wa | 33 | 159bc | 3492 |
| 159ya | 18 | 159cc | 10 |
| 159xa | 21 | 159dc | 38 |
| 159za | 6 | 159ec | 961 |
| 159ab | 27 | 159fc | 13 |
| 159bb | 48 | 159gc | 26 |
| 159cb | 39 | 228ha | 32 |
| 159db | 16 | 301 | 22 |
| 159eb | 72 | 302 | 32 |
| 159fb | 199 | 275dk | 17 |
| 159gb | 39 | 275dl | 372 |
| 159hb | 20 | | |
| 159ib | 15 | | |
| 159jb | 39 | | |
| 159kb | 24 | | |
| 159lb | 12 | | |
| 159mb | 14 | | |
| 159nb | 88 | | |
| 159ob | 118 | | |

Based on the ability of the substances described by formula (I) to effectively bind to CCR2 a range of therapeutic applications can be envisaged. The present invention provides a method for modulating or treating at least one MCP-1 related disease, in a cell, tissue, organ, animal, or patient, as known in the art or as described herein, using at least one CCR2 antagonist of the present invention. The present invention also provides a method for modulating or treating at least one MCP-1 related disease, in a cell, tissue, organ, animal, or patient including, but not limited to, at least one of malignant disease, metabolic disease, an immune or inflammatory related disease, a cardiovascular disease, an infectious disease, or a neurologic disease. Such conditions are selected from, but not limited to, diseases or conditions mediated by cell adhesion and/or angiogenesis. Such diseases or conditions include an immune disorder or disease, a cardiovascular disorder or disease, an infectious, malignant, and/or neurologic disorder or disease, or other known or specified MCP-1 related conditions. In particular, the CCR2 antagonists are useful for the treatment of diseases that involve inflammation such as COPD, angiogenesis such as disease of the eye and neoplastic disease, tissue remodeling such as restenosis, and proliferation of certain cells types particularly epithelial and squamous cell carcinomas. Particular indications include use in the treatment of atherosclerosis, restenosis, cancer metastasis, rheumatoid arthritis, diabetic retinopathy and macular degeneration. The antagonists may also be useful in the treatment of various fibrotic diseases such as idiopathic pulmonary fibrosis, diabetic nephropathy, hepatitis, and cirrhosis. Thus, the present invention provides a method for modulating or treating at least one CCR2 related disease, in a cell, tissue, organ, animal, or patient, as known in the art or as described herein, using at least one CCR2 antagonist of the present invention. Particular indications are discussed below:

Pulmonary Diseases

The present invention also provides a method for modulating or treating at least one malignant disease in a cell, tissue, organ, animal or patient, including, but not limited to, at least one of: pneumonia; lung abscess; occupational lung diseases caused be agents in the form or dusts, gases, or mists; asthma, bronchiolitis fibrosa obliterans, respiratory failure, hypersensitivity diseases of the lungs including hypersensitivity pneumonitis (extrinsic allergic alveolitis), allergic bronchopulmonary aspergillosis, and drug reactions; adult respiratory distress syndrome (ARDS), Goodpasture's Syndrome, chronic obstructive airway disorders (COPD), idiopathic interstitial lung diseases such as idiopathic pulmonary fibrosis and sarcoidosis, desquamative interstitial pneumonia, acute interstitial pneumonia, respiratory bronchiolitis-associated interstitial lung disease, idiopathic bronchiolitis obliterans with organizing pneumonia, lymphocytic interstitial pneumonitis, Langerhans' cell granulomatosis, idiopathic pulmonary hemosiderosis; acute bronchitis, pulmonary alveolar, proteinosis, bronchiectasis, pleural disorders, atelectasis, cystic fibrosis, and tumors of the lung, and pulmonary embolism.

Malignant Diseases

The present invention also provides a method for modulating or treating at least one malignant disease in a cell, tissue, organ, animal or patient, including, but not limited to, at least one of: leukemia, acute leukemia, acute lymphoblastic leukemia (ALL), B-cell, T-cell or FAB ALL, acute myeloid leukemia (AML), chromic myelocytic leukemia (CML), chronic lymphocytic leukemia (CLL), hairy cell leukemia, myelodyplastic syndrome (MDS), a lymphoma, Hodgkin's disease, a malignant lymphoma, non-hodgkin's lymphoma, Burkitt's lymphoma, multiple myeloma, Kaposi's sarcoma, colorectal carcinoma, pancreatic carcinoma, renal cell carcinoma, breast cancer, nasopharyngeal carcinoma, malignant histiocytosis, paraneoplastic syndrome/hypercalcemia of malignancy, solid tumors, adenocarcinomas, squamous cell carcinomas, sarcomas, malignant melanoma, particularly metastatic melanoma, hemangioma, metastatic disease, cancer related bone resorption, cancer related bone pain, and the like.

Immune Related Diseases

The present invention also provides a method for modulating or treating at least one immune related disease, in a cell, tissue, organ, animal, or patient including, but not limited to, at least one of rheumatoid arthritis, juvenile rheumatoid arthritis, systemic onset juvenile rheumatoid arthritis, psoriatic arthritis, ankylosing spondilitis, gastric ulcer, seronegative arthropathies, osteoarthritis, inflammatory bowel disease, ulcerative colitis, systemic lupus erythematosis, antiphospholipid syndrome, iridocyclitisluveitisloptic neuritis, idiopathic pulmonary fibrosis, systemic vasculitis/wegener's granulomatosis, sarcoidosis, orchitislvasectomy reversal procedures, allergiclatopic diseases, asthma, allergic rhinitis, eczema, allergic contact dermatitis, allergic conjunctivitis, hypersensitivity pneumonitis, transplants, organ transplant rejection, graft-versus-host disease, systemic inflammatory response syndrome, sepsis syndrome, gram positive sepsis, gram negative sepsis, culture negative sepsis, fungal sepsis, neutropenic fever, urosepsis, meningococcemia, traumalhemo—hage, burns, ionizing radiation exposure, acute pancreatitis, adult respiratory distress syndrome, rheumatoid arthritis, alcohol-induced hepatitis, chronic inflammatory pathologies, sarcoidosis, Crohn's pathology, sickle cell anemia, diabetes, nephrosis, atopic diseases, hypersensitity reactions, allergic rhinitis, hay fever, perennial rhinitis, conjunctivitis, endometriosis, asthma, urticaria, systemic anaphalaxis, dermatitis, pernicious anemia, hemolytic diseases, thrombocytopenia, graft rejection of any organ or tissue, kidney transplant rejection, heart transplant rejection, liver transplant rejection, pancreas transplant rejection, lung transplant rejection, bone marrow transplant (BMT) rejection, skin allograft rejection, cartilage transplant rejection, bone graft rejection, small bowel transplant rejection, fetal thymus implant rejection, parathyroid transplant rejection, xenograft rejection of any organ or tissue, allograft rejection, anti-receptor hypersensitivity reactions, Graves disease, Raynoud's disease, type B insulin-resistant diabetes, asthma, myasthenia gravis, antibody-meditated cytotoxicity, type IU hypersensitivity reactions, systemic lupus erythematosus, POEMS syndrome (polyneuropathy, organomegaly, endocrinopathy, monoclonal gammopathy, and skin changes syndrome), polyneuropathy, organomegaly, endocrinopathy, monoclonal gammopathy, skin changes syndrome, antiphospholipid syndrome, pemphigus, scleroderma, mixed connective tissue disease, idiopathic Addison's disease, diabetes mellitus, chronic active hepatitis, primary billiary cirrhosis, vitiligo, vasculitis, post-MI cardiotomy syndrome, type IV hypersensitivity, contact dermatitis, hypersensitivity pneumonitis, allograft rejection, granulomas due to intracellular organisms, drug sensitivity, metabolic/idiopathic, Wilson's disease, hemachromatosis, alpha-1-antitrypsin deficiency, diabetic retinopathy, hashimoto's thyroiditis, osteoporosis, hypothalamic-pituitary-adrenal axis evaluation, primary biliary cirrhosis, thyroiditis, encephalomyelitis, cachexia, cystic fibrosis, neonatal chronic lung disease, chronic obstructive pulmonary disease (COPD), familial hematophagocytic lymphohistiocytosis, dermatologic conditions, psoriasis, alopecia, nephrotic syndrome, nephritis, glomerular nephritis, acute renal failure, hemodialysis, uremia, toxicity, preeclampsia, OKT3 therapy, anti-CD3 therapy, cytokine therapy, chemotherapy, radiation therapy (e.g., including but not limited toasthenia, anemia, cachexia, and the like), chronic salicylate intoxication, and the like.

Cardiovascular Diseases

The present invention also provides a method for modulating or treating at least one cardiovascular disease in a cell, tissue, organ, animal, or patient, including, but not limited to, at least one of cardiac 25 stun syndrome, myocardial infarction, congestive heart failure, stroke, ischemic stroke, hemorrhage, arteriosclerosis, atherosclerosis, restenosis, diabetic arteriosclerotic disease, hypertension, arterial hypertension, renovascular hypertension, syncope, shock, syphilis of the cardiovascular system, heart failure, cor pulmonale, primary pulmonary hypertension, cardiac arrhythmias, atrial ectopic beats, atrial flutter, atrial fibrillation (sustained or paroxysmal), post perfusion syndrome, cardiopulmonary bypass inflammation response, chaotic or multifocal atrial tachycardia, regular narrow QRS tachycardia, specific arrythmias, ventricular fibrillation, His bundle arrythmias, atrioventricular block, bundle branch block, myocardial ischemic disorders, coronary artery disease, angina pectoris, myocardial infarction, cardiomyopathy, dilated congestive cardiomyopathy, restrictive cardiomyopathy, valvular heart diseases, endocarditis, pericardial disease, cardiac tumors, aordic and peripheral aneuryisms, aortic dissection, inflammation of the aorta, occlusion of the abdominal aorta and its branches, peripheral vascular disorders, occlusive arterial disorders, peripheral atherosclerotic disease, thromboangiitis obliterans, functional peripheral arterial disorders, Raynaud's phenomenon and disease, acrocyanosis, erythromelalgia, venous diseases, venous thrombosis, varicose veins, arteriovenous fistula, lymphederma, lipedema, unstable angina, reperfusion injury, post pump syndrome, ischemia-reperfusion injury, and the like. Such a method can optionally comprise administering an effective amount of a composition or pharmaceutical composition comprising at least one CCR2 antagonist to a cell, tissue, organ, animal or patient in need of such modulation, treatment or therapy.

Neurologic Diseases

The present invention also provides a method for modulating or treating at least one neurologic disease in a cell, tissue, organ, animal or patient, including, but not limited to, at least one of: Neuropathic pain such as low back pain, hip pain, leg pain, non-herpetic neuralgia, post herpetic neuralgia, diabetic neuropathy, nerve injury-induced pain, acquired immune deficiency syndrome (AIDS) related neuropathic pain, head trauma, toxin and chemotherapy caused nerve injuries, phantom limb pain, multiple sclerosis, root avulsions, painful traumatic mononeuropathy, painful polyneuropathy, thalamic pain syndrome, post-stroke pain, central nervous system injury, post surgical pain, carpal tunnel syndrome, trigeminal neuralgia, post mastectomy syndrome, postthoracotomy syndrome, stump pain, repetitive motion pain, neuropathic pain associated hyperalgesia and allodynia, alcoholism and other drug-induced pain; neurodegenerative diseases, multiple sclerosis, migraine headache, AIDS dementia complex, demyelinating diseases, such as multiple sclerosis and acute transverse myelitis; extrapyramidal and cerebellar disorders' such as lesions of the corticospinal system; disorders of the basal ganglia or cerebellar disorders; hyperkinetic movement disorders such as Huntington's Chorea and senile chorea; drug-induced movement disorders, such as those induced by drugs which block CNS dopamine receptors; hypokinetic movement disorders, such as Parkinson's disease; Progressive supra-nucleo Palsy; structural lesions of the cerebellum; spinocerebellar degenerations, such as spinal ataxia, Friedreich's ataxia, cerebellar cortical degenerations, multiple systems degenerations (Mencel, Dejerine-Thomas, Shi-Drager, and Machado-Joseph); systemic disorders (Refsum's disease, abetalipoprotemia, ataxia, telangiectasia, and mitochondrial multi.system disorder); demyelinating core disorders, such as multiple sclerosis, acute transverse myelitis; and disorders of the motor unit' such as neurogenic muscular atrophies (anterior horn cell degeneration, such as amyotrophic lateral sclerosis, infantile spinal muscular atrophy and juvenile spinal muscular atrophy); Alzheimer's disease; Down's Syndrome in middle age; Diffuse Lewy body disease; Senile Dementia of Lewy body type; Wernicke-Korsakoff syndrome; chronic alcoholism; Creutzfeldt-Jakob disease; Subacute sclerosing panencephalitis, Hallerrorden-Spatz disease; and Dementia pugilistica, and the like.

Fibrotic Conditions

In addition to the above described conditions and diseases, the present invention also provides a method for modulating or treating fibrotic conditions of various etiologies such as liver fibrosis (including but not limited to alcohol-induced cirrhosis, viral-induced cirrhosis, autoimmune-induced hepatitis); lung fibrosis (including but not limited to scleroderma, idiopathic pulmonary fibrosis); kidney fibrosis (including but not limited to scleroderma, diabetic nephritis, glomerular pehpritis, lupus nephritis); dermal fibrosis (including but not limited to scleroderma, hypertrophic and keloid scarring, burns); myelofibrosis; Neurofibromatosis; fibroma; intestinal fibrosis; and fibrotic adhesions resulting from surgical procedures.

The present invention also provides a method for modulating or treating at least one wound, trauma or tissue injury or chronic condition resulting from or related thereto, in a cell, tissue, organ, animal or patient, including, but not limited to, at least one of: bodily injury or a trauma associated with surgery including thoracic, abdominal, cranial, or oral surgery; or wherein the wound is selected from the group consisting of aseptic wounds, contused wounds, incised wounds, lacerated wounds, non-penetrating wounds, open wounds, penetrating wounds, perforating wounds, puncture wounds, septic wounds, infarctions and subcutaneous wounds; or wherein the wound is selected from the group consisting of ischemic ulcers, pressure sores, fistulae, severe bites, thermal burns and donor site wounds; or wherein the wound is an aphthous wound, a traumatic wound or a herpes associated wound. Donor site wounds are wounds which e.g. occur in connection with removal of hard tissue from one part of the body to another part of the body e.g. in connection with transplantation. The wounds resulting from such operations are very painful and an improved healing is therefore most valuable. Wound fibrosis is also amenable to CCR2 antagonist therapy as the first cells to invade the wound area are neutrophils followed by monocytes which are activated by macrophages. Macrophages are believed to be essential for efficient wound healing in that they also are responsible for phagocytosis of pathogenic organisms and a clearing up of tissue debris. Furthermore, they release numerous factors involved in subsequent events of the healing process. The macrophages attract fibroblasts which start the production of collagen. Almost all tissue repair processes include the early connective tissue formation, a stimulation of this and the subsequent processes improve tissue healing, however, overproduction of connective tissue and collagen can lead to a fibrotic tissue characterized as inelastic and hypoxic. The CCR2 antagonist of the invention can be used in methods for modulating, treating or preventing such sequalae of wound healing.

Other Therapeutic Uses of CCR2 Antagonists

The present invention also provides a method for modulating or treating at least one infectious disease in a cell, tissue, organ, animal or patient, including, but not limited to, at least one of:

acute or chronic bacterial infection, acute and chronic parasitic or infectious processes, including bacterial, viral and fungal infections, HIV infection, HIV neuropathy, meningitis, hepatitis (A, B or C, or the like), septic arthritis, peritonitis, pneumonia, epiglottitis, *e. coli* 0157:h7, hemolytic uremic syndrome/thrombolytic thrombocytopenic purpura, malaria, dengue hemorrhagic fever, leishmaniasis, leprosy, toxic shock syndrome, streptococcal myositis, gas gangrene, *mycobacterium tuberculosis, mycobacterium avium intracellulare, pneumocystis carinii* pneumonia, pelvic inflammatory disease, orchitislepidydimitis, legionella, lyme disease, influenza a, epstein-barr virus, vital-associated hemaphagocytic syndrome, vital encephalitisiaseptic meningitis, and the like.

Any method of the present invention can comprise administering an effective amount of a composition or pharmaceutical composition comprising at least one CCR2 antagonist to a cell, tissue, organ, animal or patient in need of such modulation, treatment or therapy.

Besides being useful for human treatment, these compounds are also useful for veterinary treatment of companion animals, exotic animals and farm animals, including mammals, rodents, and the like.

Combinations The compounds of formula I may be used on their own or in conjunction with other active substances of formula I according to the invention. If desired the compounds of formula I may also be used in combination with other pharmacologically active substances. It is preferable to use for this purpose active substances selected for example from among betamimetics, anticholinergics, corticosteroids, other PDE4-inhibitors, LTD4-antagonists, EGFR-inhibitors, MRP4-inhibitors, dopamine agonists, H1-antihistamines, PAF-antagonists and PI3-kinase inhibitors or double or triple combinations thereof, such as for example combinations of compounds of formula I with one or two compounds selected from among
- betamimetics, corticosteroids, PDE4-inhibitors, EGFR-inhibitors and LTD4-antagonists,
- anticholinergics, betamimetics, corticosteroids, PDE4-inhibitors, EGFR-inhibitors and LTD4-antagonists,
- PDE4-inhibitors, corticosteroids, EGFR-inhibitors and LTD4-antagonists
- EGFR-inhibitors, PDE4-inhibitors and LTD4-antagonists
- EGFR-inhibitors and LTD4-antagonists
- CCR3-inhibitors, iNOS-inhibitors (inducible nitric oxide synthase-inhibitors), (6R)-L-erythro-5,6,7,8-tetrahydrobiopterin (hereinafter referred to as "BH4") and the derivatives thereof as mentioned in WO 2006/120176 and SYK-inhibitors (spleen tyrosine kinase-inhibitors)
- anticholinergics, betamimetics, corticosteroids, PDE4-inhibitors and MRP4-inhibitors.

The invention also encompasses combinations of three active substances, each selected from one of the above-mentioned categories of compounds.

The betamimetics used are preferably compounds selected from among albuterol, bambuterol, bitolterol, broxaterol, carbuterol, clenbuterol, fenoterol, formoterol, arformoterol, zinterol, hexoprenaline, ibuterol, isoetharine, isoprenaline, levosalbutamol, mabuterol, meluadrine, metaproterenol, orciprenaline, pirbuterol, procaterol, reproterol, rimiterol, ritodrine, salmeterol, salmefamol, soterenol, sulphonterol, tiaramide, terbutaline, tolubuterol, CHF-1035, HOKU-81, KUL-1248, 3-(4-{6-[2-hydroxy-2-(4-hydroxy-3-hydroxymethyl-phenyl)-ethylamino]-hexyloxy}-butyl)-benzyl-sulphonamide, 5-[2-(5,6-diethyl-indan-2-ylamino)-1-hydroxy-ethyl]-8-hydroxy-1H-quinolin-2-one, 4-hydroxy-7-[2-{[2-{[3-(2-phenylethoxy)propyl]sulphonyl}ethyl]-amino}ethyl]-2(3H)-benzothiazolone, 1-(2-fluoro-4-hydroxyphenyl)-2-[4-(1-benzimidazolyl)-2-methyl-2-butylamino]ethanol, 1-[3-(4-methoxybenzyl-amino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, 5-hydroxy-8-(1-hydroxy-2-isopropylaminobutyl)-2H-1,4-benzoxazin-3-(4H)-one, 1-(4-amino-3-chloro-5-trifluoromethylphenyl)-2-tert.-butylamino)ethanol, 6-hydroxy-8-{1-hydroxy-2-[2-(4-methoxy-phenyl)-1,1-dimethyl-ethylamino]-ethyl}-4H-benzo[1,4]oxazin-3-one, 6-hydroxy-8-{1-hydroxy-2-[2-(4-phenoxy-acetate ethyl)-1,1-dimethyl-ethylamino]-ethyl}-4H-benzo[1,4]oxazin-3-one, 6-hydroxy-8-{1-hydroxy-2-[2-(4-phenoxy-acetic acid)-1,1-dimethyl-ethylamino]-ethyl}-4H-benzo[1,4]oxazin-3-one, 8-{2-[1,1-dimethyl-2-(2,4,6-trimethylphenyl)-ethylamino]-1-hydroxy-ethyl}-6-hydroxy-4H-benzo[1,4]oxazin-3-one, 6-hydroxy-8-{1-hydroxy-2-[2-(4-hydroxy-phenyl)-1,1-dimethyl-ethylamino]-ethyl}-4H-benzo[1,4]oxazin-3-one, 6-hydroxy-8-{1-hydroxy-2-[2-(4-isopropyl-phenyl)-1,1-dimethyl-ethylamino]-ethyl}-4H-benzo[1,4]oxazin-3-one, 8-{2-[2-(4-ethyl-phenyl)-1,1-dimethyl-ethylamino]-1-hydroxy-ethyl}-6-hydroxy-4H-benzo[1,4]oxazin-3-one, 8-{2-[2-(4-ethoxy-phenyl)-1,1-dimethyl-ethylamino]-1-hydroxy-ethyl}-6-hydroxy-4H-benzo[1,4]oxazin-3-one, 4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid, 8-{2-[2-(3,4-difluoro-phenyl)-1,1-dimethyl-ethylamino]-1-hydroxy-ethyl}-6-hydroxy-4H-benzo[1,4]oxazin-3-one and 1-(4-ethoxy-carbonylamino-3-cyano-5-fluorophenyl)-2-(tert.-butylamino)ethanol, optionally in the form of the racemates, enantiomers, diastereomers thereof and optionally in the form of the pharmacologically acceptable acid addition salts, solvates or hydrates thereof.

Preferably the beta mimetics are selected from among bambuterol, bitolterol, carbuterol, clenbuterol, fenoterol, formoterol, hexoprenaline, ibuterol, pirbuterol, procaterol, reproterol, salmeterol, sulphonterol, terbutaline, tolubuterol, 3-(4-{6-[2-hydroxy-2-(4-hydroxy-3-hydroxymethyl-phenyl)-ethylamino]-hexyloxy}-butyl)-benzenesulphonamide, 5-[2-(5,6-diethyl-indan-2-ylamino)-1-hydroxy-ethyl]-8-hydroxy-1H-quinolin-2-one, 4-hydroxy-7-[2-{[2-{[3-(2-phenylethoxy)propyl]sulphonyl}ethyl]-amino}ethyl]-2(3H)-benzothiazolone, 1-(2-fluoro-4-hydroxyphenyl)-2-[4-(1-benzimidazolyl)-2-methyl-2-butylamino]ethanol, 1-[3-(4-methoxybenzyl-amino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, 5-hydroxy-8-(1-hydroxy-2-isopropylaminobutyl)-2H-1,4-benzoxazin-3-(4H)-one, 1-(4-amino-3-chloro-5-trifluoromethylphenyl)-2-tert.-butylamino)ethanol, 6-hydroxy-8-{1-hydroxy-2-[2-(4-methoxy-phenyl)-1,1-dimethyl-ethylamino]-ethyl}-4H-benzo[1,4]oxazin-3-one, 6-hydroxy-8-{1-hydroxy-2-[2-(4-phenoxy-acetate ethyl)-1,1-dimethyl-ethylamino]-ethyl}-4H-benzo[1,4]oxazin-3-one, 6-hydroxy-8-{1-hydroxy-2-[2-(4-phenoxy-acetic acid)-1,1-dimethyl-ethylamino]-ethyl}-4H-benzo[1,4]oxazin-3-one, 8-{2-[1,1-dimethyl-2-(2,4,6-trimethylphenyl)-ethylamino]-1-hydroxy-ethyl}-6-hydroxy-4H-benzo[1,4]oxazin-3-one, 6-hydroxy-8-{1-hydroxy-2-[2-(4-hydroxy-phenyl)-1,1-dimethyl-ethylamino]-ethyl}-4H-benzo[1,4]oxazin-3-one, 6-hydroxy-8-{1-hydroxy-2-[2-(4-isopropyl-phenyl)-1,1dimethyl-ethylamino]-ethyl}-4H-benzo[1,4]oxazin-3-one, 8-{2-[2-(4-ethyl-phenyl)-1,1-dimethyl-ethyl amino]-1-hydroxy-ethyl}-6-hydroxy-4H-benzo[1,4]oxazin-3-one, 8-{2-[2-(4-ethoxy-phenyl)-1,1-dimethyl-ethylamino]-1-hydroxy-ethyl}-6-hydroxy-4H-benzo[1,4]oxazin-3-one, 4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid, 8-{2-[2-(3,4-difluoro-phenyl)-1,1-dimethyl-ethylamino]-1-hydroxy-ethyl}-6-hydroxy-4H-benzo[1,4]oxazin-3-one and 1-(4-ethoxycarbonylamino-3-cyano-5-fluorophenyl)-2-(tert.-butylamino)ethanol, optionally in the form of the racemates, enantiomers, diastereomers thereof and optionally in the form of the pharmacologically acceptable acid addition salts, solvates or hydrates thereof.

Particularly preferred betamimetics are selected from among fenoterol, formoterol, salmeterol, 3-(4-{6-[2-hydroxy-2-(4-hydroxy-3-hydroxymethyl-phenyl)-ethylamino]-hexyloxy}-butyl)-benzenesulphonamide, 5-[2-(5,6-diethyl-indan-2-ylamino)-1-hydroxy-ethyl]-8-hydroxy-1H- quinolin-2-one, 1-[3-(4-methoxybenzyl-amino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 6-hydroxy-8-{1-hydroxy-2-[2-(4-methoxy-phenyl)-1,1-dimethyl-ethylamino]-ethyl}-4H-benzo[1,4]oxazin-3-one, 6-hydroxy-8-{1-hydroxy-2-[2-(4-phenoxy-acetate ethyl)-1,1-dimethyl-ethylamino]-ethyl}-4H-benzo[1,4]oxazin-3-one, 6-hydroxy-8-{1-hydroxy-2-[2-(4-phenoxy-acetic acid)-1,1-dimethyl-ethylamino]-ethyl}-4H-benzo[1,4]oxazin-3-one, 8-{2-[1,1-dimethyl-2-(2,4,6-trimethylphenyl)-ethylamino]-1-hydroxy-ethyl}-6-hydroxy-4H-benzo[1,4]oxazin-3-one, 6-hydroxy-8-{1-hydroxy-2-[2-(4-hydroxy-phenyl)-1,1-dimethyl-ethylamino]-ethyl}-4H-benzo[1,4]oxazin-3-one, 6-hydroxy-8-{1-hydroxy-2-[2-(4-isopropyl-phenyl)-1,1dimethyl-ethylamino]-ethyl}-4H-benzo[1,4]oxazin-3-one, 8-{2-[2-(4-ethyl-phenyl)-1,1-dimethyl-ethylamino]-1-hydroxy-ethyl}-6-hydroxy-4H-benzo[1,4]oxazin-3-one, 8-{2-[2-(4-ethoxy-phenyl)-1,1-dimethyl-ethylamino]-1-hydroxy-ethyl}-6-hydroxy-4H-benzo[1,4]oxazin-3-one, 4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid, 8-{2-[2-(3,4-difluoro-phenyl)-1,1-dimethyl-ethylamino]-1-hydroxy-ethyl}-6-hydroxy-4H-benzo[1,4]oxazin-3-one and 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, optionally in the form of the racemates, enantiomers, diastereomers thereof and optionally in the form of the pharmacologically acceptable acid addition salts, solvates or hydrates thereof.

Of these betamimetics those which are particularly preferred according to the invention are formoterol, salmeterol, 3-(4-{6-[2-hydroxy-2-(4-hydroxy-3-hydroxymethyl-phenyl)-ethylamino]-hexyloxy}-butyl)-benzenesulphonamide, 6-hydroxy-8-{1-hydroxy-2-[2-(4-methoxy-phenyl)-1,1-dimethyl-ethylamino]-ethyl}-4H-benzo[1,4]oxazin-3-one, 6-hydroxy-8-{1-hydroxy-2-[2-(ethyl 4-phenoxy-acetate)-1,1-dimethyl-ethylamino]-ethyl}-4H-benzo[1,4]oxazin-3-one, 6-hydroxy-8-{1-hydroxy-2-[2-(4-phenoxy-acetic acid)-1,1-dimethyl-ethylamino]-ethyl}-4H-benzo[1,4]oxazin-3-one, 8-{2-[1,1-dimethyl-2-(2,4,6-trimethylphenyl)-ethylamino]-1-hydroxy-ethyl}-6-hydroxy-4H-benzo[1,4]oxazin-3-one, 6-hydroxy-8-{1-hydroxy-2-[2-(4-hydroxy-phenyl)-1,1-dimethyl-ethylamino]-ethyl}-4H-benzo[1,4]oxazin-3-one, 6-hydroxy-8-{1-hydroxy-2-[2-(4-isopropyl-phenyl)-1,1dimethyl-ethylamino]-ethyl}-4H-benzo[1,4]oxazin-3-one, 8-{2-[2-(4-ethyl-phenyl)-1,1-dimethyl-ethylamino]-1-hydroxy-ethyl}-6-hydroxy-4H-benzo[1,4]oxazin-3-one, 8-{2-[2-(4-ethoxy-phenyl)-1,1-dimethyl-ethylamino]-1-hydroxy-ethyl}-6-hydroxy-4H-benzo[1,4]oxazin-3-one, 4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid, 8-{2-[2-(3,4-difluoro-phenyl)-1,1-dimethyl-ethylamino]-1-hydroxy-ethyl}-6-hydroxy-4H-benzo[1,4]oxazin-3-one and 5-[2-(5,6-diethyl-indan-2-ylamino)-1-hydroxy-ethyl]-8-hydroxy-1H-quinolin-2-one, optionally in the form of the racemates, enantiomers, diastereomers thereof and optionally in the form of the pharmacologically acceptable acid addition salts, solvates or hydrates thereof.

According to the invention the acid addition salts of the betamimetics are preferably selected from among hydrochloride, hydrobromide, hydriodide, hydrosulphate, hydrophosphate, hydromethanesulphonate, hydronitrate, hydromaleate, hydroacetate, hydrobenzoate, hydrocitrate, hydrofumarate, hydrotartrate, hydroxalate, hydrosuccinate, hydrobenzoate and hydro-p-toluenesulphonat, preferably hydrochloride, hydrobromide, hydrosulphate, hydrophosphate, hydrofumarate and hydromethanesulphonate. Of the above-mentioned acid addition salts the salts of hydrochloric acid, methanesulphonic acid, benzoic acid and acetic acid are particularly preferred according to the invention.

The anticholinergics used are preferably compounds selected from among the tiotropium salts, oxitropium salts, flutropium salts, ipratropium salts, glycopyrronium salts, trospium salts, tropenol 2,2-diphenylpropionate methobromide, scopine 2,2-diphenylpropionate methobromide, scopine 2-fluoro-2,2-diphenylacetate methobromide, tropenol 2-fluoro-2,2-diphenylacetate methobromide, tropenol 3,3',4,4'-tetrafluorobenzilate methobromide, scopine 3,3',4,4'-tetrafluorobenzilate methobromide, tropenol 4,4'-difluorobenzilate methobromide, scopine 4,4'-difluorobenzilate methobromide, tropenol 3,3'-difluorobenzilate methobromide, -scopine 3,3'-difluorobenzilate methobromide, tropenol 9-hydroxy-fluorene-9-carboxylate-methobromide, tropenol 9-fluoro-fluorene-9-carboxylate-methobromide, scopine 9-hydroxy-fluoren-9-carboxylate methobromide, scopine 9-fluoro-fluorene-9-carboxylate methobromide, tropenol 9-methyl-fluorene-9-carboxylate methobromide, scopine 9-methyl-fluorene-9-carboxylate methobromide, cyclopropyltropine benzilate methobromide, cyclopropyltropine 2,2-diphenylpropionate methobromide, cyclopropyltropine 9-hydroxy-xanthene-9-carboxylate methobromide, cyclopropyltropine 9-methyl-fluorene-9-carboxylate methobromide, cyclopropyltropine 9-methyl-xanthene-9-carboxylate methobromide, cyclopropyltropine 9-hydroxy-fluorene-9-carboxylate methobromide, methyl-cyclopropyltropine 4,4'-difluorobenzilate methobromide, tropenol 9-hydroxy-xanthene-9-carboxylate-methobromide, scopine 9-hydroxy-xanthene-9-carboxylate methobromide, tropenol 9-methyl-xanthene-9-carboxylate methobromide, scopine 9-methyl-xanthene-9-carboxylate methobromide, tropenol 9-ethyl-xanthene-9-carboxylate methobromide, tropenol 9-difluoromethyl-xanthene-9-carboxylate methobromide, scopine 9-hydroxymethyl-xanthene-9-carboxylate methobromide, optionally in the form of the solvates or hydrates thereof.

In the above-mentioned salts the cations tiotropium, oxitropium, flutropium, ipratropium, glycopyrronium and trospium are the pharmacologically active ingredients. As anions, the above-mentioned salts may preferably contain chloride, bromide, iodide, sulphate, phosphate, methanesulphonate, nitrate, maleate, acetate, citrate, fumarate, tartrate, oxalate, succinate, benzoate or p-toluenesulphonate, while chloride, bromide, iodide, sulphate, methanesulphonate or p-toluenesulphonate are preferred as counter-ions. Of all the salts, the chlorides, bromides, iodides and methanesulphonate are particularly preferred.

Of particular importance is tiotropium bromide. In the case of tiotropium bromide the pharmaceutical combinations according to the invention preferably contain it in the form of the crystalline tiotropium bromide monohydrate, which is known from WO 02/30928. If the tiotropium bromide is used in anhydrous form in the pharmaceutical combinations according to the invention, it is preferable to use anhydrous crystalline tiotropium bromide, which is known from WO 03/000265.

Corticosteroids used here are preferably compounds selected from among prednisolone, prednisone, butixocortpropionate, flunisolide, beclomethasone, triamcinolone, budesonide, fluticasone, mometasone, ciclesonide, rofleponide, dexamethasone, betamethasone, deflazacort, RPR-106541, NS-126, (S)-fluoromethyl 6,9-difluoro-17-[(2-furanylcarbonyl)oxy]-11-hydroxy-16-methyl-3-oxo-androsta-1,4-diene-17-carbothionate and (S)-(2-oxo-tetrahydro-furan-3S-yl) 6,9-difluoro-11-hydroxy-16-methyl-3-oxo-17-propionyloxy-androsta-1,4-diene-17-carbothionate, optionally in the form of the racemates, enantiomers or diastereomers thereof and optionally in the form of the salts and derivatives, solvates and/or hydrates thereof.

Particularly preferred is the steroid selected from among flunisolide, beclomethasone, triamcinolone, budesonide, fluticasone, mometasone, ciclesonide, rofleponide, dexamethasone, NS-126, (S)-fluoromethyl 6,9-difluoro-17-[(2-furanylcarbonyl)oxy]-11-hydroxy-16-methyl-3-oxo-androsta-1,4-diene-17-carbothionate and (S)-(2-oxo-tetrahydro-furan-3S-yl) 6,9-difluoro-11-hydroxy-16-methyl-3-oxo-17-propionyloxy-androsta-1,4-diene-17-carbothionate, optionally in the form of the racemates, enantiomers or diastereomers thereof and optionally in the form of the salts and derivatives, solvates and/or hydrates thereof.

Particularly preferred is the steroid selected from among budesonide, fluticasone, mometasone, ciclesonide and (S)-fluoromethyl 6,9-difluoro-17-[(2-furanylcarbonyl)oxy]-11-hydroxy-16-methyl-3-oxo-androsta-1,4-diene-17-carbothionate, optionally in the form of the racemates, enantiomers or diastereomers thereof and optionally in the form of the salts and derivatives, solvates and/or hydrates thereof.

Any reference to steroids includes a reference to any salts or derivatives, hydrates or solvates thereof which may exist. Examples of possible salts and derivatives of the steroids may be: alkali metal salts, such as for example sodium or potassium salts, sulphobenzoates, phosphates, isonicotinates, acetates, propionates, dihydrogen phosphates, palmitates, pivalates or furoates thereof.

Other PDE4 inhibitors which may be used are preferably compounds selected from among enprofyllin, theophyllin, roflumilast, ariflo (cilomilast), tofimilast, pumafentrin, lirimilast, arofyllin, atizoram, D-4396 (Sch-351591), AWD-12-281 (GW-842470), NCS-613, CDP-840, D-4418, PD-168787, T-440, T-2585, V-11294A, C1-1018, CDC-801, CDC-3052, D-22888, YM-58997, Z-15370, N-(3,5-dichloro-1-oxo-pyridin-4-yl)-4-difluoromethoxy-3-cyclopropyl-methoxybenzamide, (−)p-[(4aR*,10bS*)-9-ethoxy-1,2,3,4,4a,10b-hexahydro-8-methoxy-2-methylbenzo[s][1,6]naphthyridin-6-yl]-N,N-diisopropylbenzamide, (R)-(+)-1-(4-bromobenzyl)-4-[(3-cyclopentyloxy)-4-methoxyphenyl]-2-pyrrolidone, 3-(cyclopentyloxy-4-methoxyphenyl)-1-(4-N'-[N-2-cyano-S-methyl-isothioureido]benzyl)-2-pyrrolidone, cis[4-cyano-4-(3-cyclopentyloxy-4-methoxyphenyl)cyclohexane-1-carboxylic acid], 2-carbomethoxy-4-cyano-4-(3-cyclopropylmethoxy-4-difluoromethoxyphenyl)cyclohexane-1-one, cis[4-cyano-4-(3-cyclopropylmethoxy-4-difluoromethoxyphenyl)cyclohexan-1-ol], (R)-(+)-ethyl[4-(3-cyclopentyloxy-4-methoxyphenyl)pyrrolidin-2-ylidene]acetate, (S)-(−)-ethyl [4-(3-cyclopentyloxy-4-methoxyphenyl)pyrrolidin-2-ylidene]acetate, 9-cyclopentyl-5,6-dihydro-7-ethyl-3-(2-thienyl)-9H-pyrazolo[3,4-c]-1,2,4-triazolo[4,3-a]pyridine and 9-cyclopentyl-5,6-dihydro-7-ethyl-3-(tert-butyl)-9H-pyrazolo[3,4-c]-1,2,4-triazolo[4,3-a]pyridine, optionally in the form of the racemates, enantiomers or diastereomers and optionally in the form of the pharmacologically acceptable acid addition salts, solvates and/or hydrates thereof.

Particularly preferably the PDE4-inhibitor is selected from among enprofyllin, roflumilast, ariflo (cilomilast), arofyllin, atizoram, AWD-12-281 (GW-842470), T-440, T-2585, PD-168787, V-11294A, C1-1018, CDC-801, D-22888, YM-58997, Z-15370, N-(3,5-dichloro-1-oxo-pyridin-4-yl)-4-difluoromethoxy-3-cyclopropylmethoxybenzamide, cis[4-cyano-4-(3-cyclopentyloxy-4-methoxyphenyl)cyclohexane-1-carboxylic acid], 2-carbomethoxy-4-cyano-4-(3-cyclopropylmethoxy-4-difluoromethoxyphenyl) cyclohexan-1-one, cis[4-cyano-4-(3-cyclopropylmethoxy-4-difluoromethoxyphenyl)cyclohexan-1-ol], 9-cyclopentyl-5,6-dihydro-7-ethyl-3-(2-thienyl)-9H-pyrazolo[3,4-c]-1,2,4-triazolo[4,3-a]pyridine and 9-cyclopentyl-5,6-dihydro-7-ethyl-3-(tert-butyl)-9H-pyrazolo[3,4-c]-1,2,4-triazolo[4,3-a]pyridine, optionally in the form of the racemates, enantiomers or diastereomers and optionally in the form of the pharmacologically acceptable acid addition salts, solvates and/or hydrates thereof.

By acid addition salts with pharmacologically acceptable acids which the above-mentioned PDE4-inhibitors might be in a position to form are meant, for example, salts selected from among the hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably hydrochloride, hydrobromide, hydrosulphate, hydrophosphate, hydrofumarate and hydromethanesulphonate.

LTD4-antagonists which may be used are preferably compounds selected from among montelukast, pranlukast, zafirlukast, MCC-847 (ZD-3523), MN-001, MEN-91507 (LM-1507), VUF-5078, VUF-K-8707, L-733321, 1-(((R)-(3-(2-(6,7-difluoro-2-quinolinyl)ethenyl)phenyl)-3-(2-(2-hydroxy-2-propyl)phenyl)thio)methylcyclopropane-acetic acid, 1-(((1(R)-3(3-(2-(2,3-dichlorothieno[3,2-b]pyridin-5-yl)-(E)-ethenyl)phenyl)-3-(2-(1-hydroxy-1-methylethyl)phenyl)propyl)thio)methyl)cyclopropane-acetic acid and [2-[[2-(4-tert-butyl-2-thiazolyl)-5-benzofuranyl]oxymethyl]phenyl]acetic acid, optionally in the form of the racemates, enantiomers or diastereomers, optionally in the form of the pharmacologically acceptable acid addition salts and optionally in the form of the salts and derivatives, solvates and/or hydrates thereof.

Preferably the LTD4-antagonist is selected from among montelukast, pranlukast, zafirlukast, MCC-847 (ZD-3523), MN-001, MEN-91507 (LM-1507), VUF-5078, VUF-K-8707 and L-733321, optionally in the form of the racemates, enantiomers or diastereomers, optionally in the form of the pharmacologically acceptable acid addition salts and optionally in the form of the salts and derivatives, solvates and/or hydrates thereof.

Particularly preferably the LTD4-antagonist is selected from among montelukast, pranlukast, zafirlukast, MCC-847 (ZD-3523), MN-001 and MEN-91507 (LM-1507), optionally in the form of the racemates, enantiomers or diastereomers, optionally in the form of the pharmacologically acceptable acid addition salts and optionally in the form of the salts and derivatives, solvates and/or hydrates thereof.

By acid addition salts with pharmacologically acceptable acids which the LTD4-antagonists may be capable of forming are meant, for example, salts selected from among the hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably hydrochloride, hydrobromide, hydrosulphate, hydrophosphate, hydrofumarate and hydromethanesulphonate. By salts or derivatives which the LTD4-antagonists may be capable of forming are meant, for example: alkali metal salts, such as, for example, sodium or potassium salts, alkaline earth metal salts, sulphobenzoates, phosphates, isonicotinates, acetates, propionates, dihydrogen phosphates, palmitates, pivalates or furoates.

The EGFR-inhibitors used are preferably compounds selected from among 4-[(3-chloro-4-fluorophenyl)amino]-6-{[4-(morpholin-4-yl)-1-oxo-2-buten-1-yl]amino}-7-cyclopropylmethoxy-quinazoline, 4-[(3-chloro-4-fluorophenyl)amino]-6-{[4-(N,N-diethylamino)-1-oxo-2-buten-1-yl]amino}-7-cyclopropylmethoxy-quinazoline, 4-[(3-chloro-4-fluorophenyl)amino]-6-{[4-(N,N-dimethylamino)-1-oxo-2-buten-1-yl]amino}-7-cyclopropylmethoxy-quinazoline, 4-[(R)-(1-phenyl-ethyl)amino]-6-{[4-(morpholin-4-yl)-1-oxo-2-buten-1-yl]amino}-7-cyclopentyloxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline, 4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline, 4-[(3-chloro-4-fluoro-phenyl)amino]-6-[2-((S)-6-methyl-2-oxo-morpholin-4-yl)-ethoxy]-7-methoxy-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline, 4-[(3-chloro-4-fluorophenyl)amino]-6-{[4-(N,N-dimethylamino)-1-oxo-2-buten-1-yl]amino}-7-cyclopentyloxy-quinazoline, 4-[(R)-(1-phenyl-ethyl)amino]-6-{[4-(N,N-bis-(2-methoxy-ethyl)-amino)-1-oxo-2-buten-1-yl]amino}-cyclopropylmethoxy-quinazoline, 4-[(R)-(1-phenyl-ethyl)amino]-6-({4-[N-(2-methoxy-ethyl)-N-ethyl-amino]-1-oxo-2-buten-1-yl}amino)-7-cyclopropylmethoxy-quinazoline, 4-[(R)-(1-phenyl-ethyl)amino]-6-({4-[N-(2-methoxy-ethyl)-N-methyl-amino]-1-oxo-2-buten-1-yl}amino)-7-cyclopropylmethoxy-quinazoline, 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline, 4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline, 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline, 4-[(3-chloro-4-fluorophenyl)amino]-6-{[4-(N-cyclopropyl-N-methyl-amino)-1-oxo-2-buten-1-yl]amino}-7-cyclopentyloxy-quinazoline, 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline, 4-[(3-chloro-4-fluorophenyl)amino]-6-{[4-(N, N-dimethylamino)-1-oxo-2-buten-1-yl]amino}-7-[(S)-(tetrahydrofuran-2-yl)methoxy]-quinazoline, 4-[(3-ethynyl-phenyl)amino]-6,7-bis-(2-methoxy-ethoxy)-quinazoline, 4-[(3-chloro-4-fluorophenyl)amino]-7-[3-(morpholin-4-yl)-propyloxy]-6-[(vinylcarbonyl)amino]-quinazoline, 4-[(R)-(1-phenyl-ethyl)amino]-6-(4-hydroxy-phenyl)-7H-pyrrolo[2,3-d]pyrimidin, 3-cyano-4-[(3-chloro-4-fluorophenyl)amino]-6-{[4-(N, N-dimethylamino)-1-oxo-2-buten-1-yl]amino}-7-ethoxy-quinoline, 4-{[3-chloro-4-(3-fluoro-benzyloxy)-phenyl]amino}-6-(5-{[(2-methanesulphonyl-ethyl)amino]methyl}-furan-2-yl) quinazoline, 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline, 4-[(3-chloro-4-fluorophenyl) amino]-6-{[4-(morpholin-4-yl)-1-oxo-2-buten-1-yl]amino}-7-[(tetrahydrofuran-2-yl)methoxy]-quinazoline, 4-[(3-chloro-4-fluorophenyl)amino]-6-({4-[N,N-bis-(2-methoxy-ethyl)-amino]-1-oxo-2-buten-1-yl}amino)-7-[(tetrahydrofuran-2-yl)methoxy]-quinazoline, 4-[(3-ethynyl-phenyl)amino]-6-{[4-(5,5-dimethyl-2-oxo-morpholin-4-yl)-1-oxo-2-buten-1-yl]amino}-quinazoline, 4-[(3-chloro-4-fluoro-phenyl)amino]-6-[2-(2,2-dimethyl-6-oxo-morpholin-4-yl)-ethoxy]-7-methoxy-quinazoline, 4-[(3-chloro-4-fluoro-phenyl)amino]-6-[2-(2,2-dimethyl-6-oxo-morpholin-4-yl)-ethoxy]-7-[(R)-(tetrahydrofuran-2-yl)methoxy]-quinazoline, 4-[(3-chloro-4-fluoro-phenyl)amino]-7-[2-(2, 2-dimethyl-6-oxo-morpholin-4-yl)-ethoxy]-6-[(S)-(tetrahydrofuran-2-yl)methoxy]-quinazoline, 4-[(3-chloro-4-fluoro-phenyl)amino]-6-{2-[4-(2-oxo-morpholin-4-yl)-piperidin-1-yl]-ethoxy}-7-methoxy-quinazoline, 4-[(3-chloro-4-fluoro-phenyl)amino]-6-[1-(tert.-butyloxycarbonyl)-piperidin-4-yloxy]-7-methoxy-quinazoline, 4-[(3-chloro-4-fluoro-phenyl)amino]-6-(trans-4-amino-cyclohexan-1-yloxy)-7-methoxy-quinazoline, 4-[(3-chloro-4-fluoro-phenyl)amino]-6-(trans-4-methanesulphonylamino-cyclohexan-1-yloxy)-7-methoxy-quinazoline, 4-[(3-chloro-4-fluoro-phenyl)amino]-6-(tetrahydropyran-3-yloxy)-7-methoxy-quinazoline, 4-[(3-chloro-4-fluoro-phenyl)amino]-6-(1-methyl-piperidin-4-yloxy)-7-methoxy-quinazoline, 4-[(3-chloro-4-fluoro-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(methoxymethyl)carbonyl]-piperidin-4-yloxy}-7-methoxy-quinazoline, 4-[(3-chloro-4-fluoro-phenyl)amino]-6-(piperidin-3-yloxy)-7-methoxy-quinazoline, 4-[(3-chloro-4-fluoro-phenyl)amino]-6-[1-(2-acetylamino-ethyl)-piperidin-4-yloxy]-7-methoxy-quinazoline, 4-[(3-chloro-4-fluoro-phenyl)amino]-6-(tetrahydropyran-4-yloxy)-7-ethoxy-quinazoline, 4-[(3-chloro-4-fluoro-phenyl)amino]-6-((S)-tetrahydrofuran-3-yloxy)-7-hydroxy-quinazoline, 4-[(3-chloro-4-fluoro-phenyl)amino]-6-(tetrahydropyran-4-yloxy)-7-(2-methoxy-ethoxy)-quinazoline, 4-[(3-chloro-4-fluoro-phenyl)amino]-6-{trans-4-[(dimethylamino) sulphonylamino]-cyclohexan-1-yloxy}-7-methoxy-quinazoline, 4-[(3-chloro-4-fluoro-phenyl)amino]-6-{trans-4-[(morpholin-4-yl)carbonylamino]-cyclohexan-1-yloxy}-7-methoxy-quinazoline, 4-[(3-chloro-4-fluoro-phenyl) amino]-6-{trans-4-[(morpholin-4-yl)sulphonylamino]-cyclohexan-1-yloxy}-7-methoxy-quinazoline, 4-[(3-chloro-4-fluoro-phenyl)amino]-6-(tetrahydropyran-4-yloxy)-7-(2-acetylamino-ethoxy)-quinazoline, 4-[(3-chloro-4-fluoro-phenyl)amino]-6-(tetrahydropyran-4-yloxy)-7-(2-methanesulphonylamino-ethoxy)-quinazoline, 4-[(3-chloro-4-fluoro-phenyl)amino]-6-{1-[(piperidin-1-yl)carbonyl]-piperidin-4-yloxy}-7-methoxy-quinazoline, 4-[(3-chloro-4-fluoro-phenyl)amino]-6-(1-aminocarbonylmethyl-piperidin-4-yloxy)-7-methoxy-quinazoline, 4-[(3-chloro-4-fluoro-phenyl)amino]-6-(cis-4-{N-[(tetrahydropyran-4-yl) carbonyl]-N-methyl-amino}-cyclohexan-1-yloxy)-7-methoxy-quinazoline, 4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-(cis-4-{N-[(morpholin-4-yl)sulphonyl]-N-methyl-amino}-cyclohexan-1-yloxy)-7-methoxy-quinazoline, 4-[(3-chloro-4-fluoro-phenyl)amino]-6-(trans-4-ethanesulphonylamino-cyclohexan-1-yloxy)-7-methoxy-quinazoline, 4-[(3-chloro-4-fluoro-phenyl)amino]-6-(1-methanesulphonyl-piperidin-4-yloxy)-7-ethoxyquinazoline, 4-[(3-chloro-4-fluoro-phenyl)amino]-6-(1-methanesulphonyl-piperidin-4-yloxy)-7-(2-methoxy-ethoxy)-quinazoline, 4-[(3-chloro-4-fluoro-phenyl)amino]-6-[1-(2-methoxy-acetyl)-piperidin-4-yloxy]-7-(2-methoxy-ethoxy)-quinazoline, 4-[(3-chloro-4-fluoro-phenyl)amino]-6-(cis-4-acetylamino-cyclohexan-1-yloxy)-7-methoxy-quinazoline, 4-[(3-ethynyl-phenyl)amino]-6-[1-(tert.-butyloxycarbonyl)-piperidin-4-yloxy]-7-methoxy-quinazoline, 4-[(3-ethynyl-phenyl)amino]-6-(tetrahydropyran-4-yloxy)-7-methoxy-quinazoline, 4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline, 4-[(3-chloro-4-fluoro-phenyl)amino]-6-(cis-4-{N-[(4-methyl-piperazin-1-yl)carbonyl]-N-methyl-amino}-cyclohexan-1-yloxy)-7-methoxy-quinazoline, 4-[(3-chloro-4-fluoro-phenyl)amino]-6-{cis-4-[(morpholin-4-yl)carbonylamino]-cyclohexan-1-yloxy}-7-methoxy-quinazoline, 4-[(3-chloro-4-fluoro-phenyl)amino]-6-{1-[2-(2-oxopyrrolidin-1-yl)ethyl]-piperidin-4-yloxy}-7-methoxy-quinazoline, 4-[(3-chloro-4-fluoro-phenyl)amino]-6-{1-[(morpholin-4-yl)carbonyl]-piperidin-4-yloxy}-7-(2-methoxy-ethoxy)-quinazoline, 4-[(3-ethynyl-phenyl)amino]-6-(1-acetyl-piperidin-4-yloxy)-7-methoxy-quinazoline, 4-[(3-ethynyl-phenyl)amino]-6-(1-methyl-piperidin-4-yloxy)-7-methoxy-quinazoline, 4-[(3-ethynyl-phenyl)amino]-6-(1-methanesulphonyl-piperidin-4-yloxy)-7-methoxy-quinazoline, 4-[(3-chloro-4-fluoro-phenyl)amino]-6-(1-methyl-piperidin-4-yloxy)-7(2-methoxy-ethoxy)-quinazoline, 4-[(3-chloro-4-fluoro-phenyl)amino]-6-(1-isopropyloxycarbonyl-piperidin-4-yloxy)-7-methoxy-quinazoline, 4-[(3-chloro-4-fluoro-phenyl)amino]-6-(cis-4-methylamino-cyclohexan-1-yloxy)-7-methoxy-quinazoline, 4-[(3-chloro-4-fluoro-phenyl)amino]-6-{cis-4-[N-(2-methoxy-acetyl)-N-methyl-amino]-cyclohexan-1-yloxy}-7-methoxy-quinazoline, 4-[(3-ethynyl-phenyl)amino]-6-(piperidin-4-yloxy)-7-methoxy-quinazoline, 4-[(3-ethynyl-phenyl)amino]-6-[1-(2-methoxy-acetyl)-piperidin-4-yloxy]-7-methoxy-quinazoline, 4-[(3-ethynyl-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(cis-2,6-dimethyl-morpholin-4-yl)carbonyl]-piperidin-4-yloxy}-7-methoxy-quinazoline, 4-[(3-chloro-4-fluoro-phenyl)amino]-6-{1-[(2-methyl-morpholin-4-yl)carbonyl]-piperidin-4-yloxy}-7-methoxy-quinazoline, 4-[(3-chloro-4-fluoro-phenyl)amino]-6-{1-[(S,S)-(2-oxa-5-aza-bicyclo[2,2,1]hept-5-yl)carbonyl]-piperidin-4-yloxy}-7-methoxy-quinazoline, 4-[(3-chloro-4-fluoro-phenyl)amino]-6-{1-[(N-methyl-N-2-methoxyethyl-amino)carbonyl]-piperidin-4-yloxy}-7-methoxy-quinazoline, 4-[(3-chloro-4-fluoro-phenyl)amino]-6-(1-ethyl-piperidin-4-yloxy)-7-methoxy-quinazoline, 4-[(3-chloro-4-fluoro-phenyl)amino]-6-{1-[(2-methoxyethyl)carbonyl]-piperidin-4-yloxy}-7-methoxy-quinazoline, 4-[(3-chloro-4-fluoro-phenyl)amino]-6-{1-[(3-methoxypropyl-amino)-carbonyl]-piperidin-4-yloxy}-7-methoxy-quinazoline, 4-[(3-chloro-4-fluoro-phenyl)amino]-6-[cis-4-(N-methanesulphonyl-N-methyl-amino)-cyclohexan-1-yloxy]-7-methoxy-quinazoline, 4-[(3-chloro-4-fluoro-phenyl)amino]-6-[cis-4-(N-acetyl-N-methyl-amino)-cyclohexan-1-yloxy]-7-methoxy-quinazoline, 4-[(3-chloro-4-fluoro-phenyl)amino]-6-(trans-4-methylamino-cyclohexan-1-yloxy)-7-methoxy-quinazoline, 4-[(3-chloro-4-fluoro-phenyl)amino]-6-[trans-4-(N-methanesulphonyl-N-methyl-amino)-cyclohexan-1-yloxy]-7-methoxy-quinazoline, 4-[(3-chloro-4-fluoro-phenyl)amino]-6-(trans-4-dimethylamino-cyclohexan-1-yloxy)-7-methoxy-quinazoline, 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline, 4-[(3-chloro-4-fluoro-phenyl)amino]-6-(1-methanesulphonyl-piperidin-4-yloxy)-7-methoxy-quinazoline, 4-[(3-chloro-4-fluoro-phenyl)amino]-6-(1-cyano-piperidin-4-yloxy)-7-methoxy-quinazoline, Cetuximab, Trastuzumab, ABX-EGF and Mab ICR-62, optionally in the form of the racemates, enantiomers or diastereomers thereof, optionally in the form of the pharmacologically acceptable acid addition salts, the solvates and/or hydrates thereof.

Preferred EGFR inhibitors are selected from among 4-[(3-chloro-4-fluorophenyl)amino]-6-{[4-(morpholin-4-yl)-1-oxo-2-buten-1-yl]amino}-7-cyclopropylmethoxy-quinazoline, 4-[(3-chloro-4-fluorophenyl)amino]-6-{[4-(N,N-diethylamino)-1-oxo-2-buten-1-yl]amino}-7-cyclopropylmethoxy-quinazoline, 4-[(3-chloro-4-fluorophenyl)amino]-6-{[4-(N,N-dimethylamino)-1-oxo-2-buten-1-yl]amino}-7-cyclopropylmethoxy-quinazoline, 4-[(R)-(1-phenyl-ethyl)amino]-6-{[4-(morpholin-4-yl)-1-oxo-2-buten-1-yl]amino}-7-cyclopentyloxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline, 4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline, 4-[(3-chloro-4-fluoro-phenyl)amino]-6-[2-((S)-6-methyl-2-oxo-morpholin-4-yl)-ethoxy]-7-methoxy-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline, 4-[(3-chloro-4-fluorophenyl)amino]-6-{[4-(N,N-dimethylamino)-1-oxo-2-buten-1-yl]amino}-7-cyclopentyloxy-quinazoline, 4-[(R)-(1-phenyl-ethyl)amino]-6-{[4-(N,N-bis-(2-methoxy-ethyl)-amino)-1-oxo-2-buten-1-yl]amino}-7-cyclopropylmethoxy-quinazoline, 4-[(R)-(1-phenyl-ethyl)amino]-6-({4-[N-(2-methoxy-ethyl)-N-ethyl-amino]-1-oxo-2-buten-1-yl}amino)-7-cyclopropylmethoxy-quinazoline, 4-[(R)-(1-phenyl-ethyl)amino]-6-({4-[N-(2-methoxy-ethyl)-N-methyl-amino]-1-oxo-2-buten-1-yl}amino)-7-cyclopropylmethoxy-quinazoline, 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline, 4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline, 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline, 4-[(3-chloro-4-fluorophenyl)amino]-6-{[4-(N-cyclopropyl-N-methyl-amino)-1-oxo-2-buten-1-yl]amino}-7-cyclopentyloxy-quinazoline, 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline, 4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]-quinazoline, 4-[(3-ethynyl-phenyl)amino]-6,7-bis-(2-methoxy-ethoxy)-quinazoline, 4-[(3-chloro-4-fluorophenyl)amino]-7-[3-(morpholin-4-yl)-propyloxy]-6-[(vinylcarbonyl)amino]-quinazoline, 4-[(R)-(1-phenyl-ethyl)amino]-6-(4-hydroxy-phenyl)-7H-pyrrolo[2,3-d]

pyrimidine, 3-cyano-4-[(3-chloro-4-fluorophenyl)amino]-6-{[4-(N,N-dimethylamino)-1-oxo-2-buten-1-yl]amino}-7-ethoxy-quinoline, 4-{[3-chloro-4-(3-fluoro-benzyloxy)-phenyl]amino}-6-(5-{[(2-methanesulphonyl-ethyl)amino]methyl}-furan-2-yl)quinazoline, 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline, 4-[(3-chloro-4-fluorophenyl)amino]-6-{[4-(morpholin-4-yl)-1-oxo-2-buten-1-yl]amino}-7-[(tetrahydrofuran-2-yl)methoxy]-quinazoline, 4-[(3-chloro-4-fluorophenyl)amino]-6-({4-[N,N-bis-(2-methoxy-ethyl)-amino]-1-oxo-2-buten-1-yl}amino)-7-[(tetrahydrofuran-2-yl)methoxy]-quinazoline, 4-[(3-ethynyl-phenyl)amino]-6-{[4-(5,5-dimethyl-2-oxo-morpholin-4-yl)-1-oxo-2-buten-1-yl]amino}-quinazoline, 4-[(3-chloro-4-fluoro-phenyl)amino]-6-[2-(2,2-dimethyl-6-oxo-morpholin-4-yl)-ethoxy]-7-methoxy-quinazoline, 4-[(3-chloro-4-fluoro-phenyl)amino]-6-[2-(2,2-dimethyl-6-oxo-morpholin-4-yl)-ethoxy]-7-[(R)-(tetrahydrofuran-2-yl)methoxy]-quinazoline, 4-[(3-chloro-4-fluoro-phenyl)amino]-7-[2-(2,2-dimethyl-6-oxo-morpholin-4-yl)-ethoxy]-6-[(S)-(tetrahydrofuran-2-yl)methoxy]-quinazoline, 4-[(3-chloro-4-fluoro-phenyl)amino]-6-{2-[4-(2-oxo-morpholin-4-yl)-piperidin-1-yl]-ethoxy}-7-methoxy-quinazoline, 4-[(3-chloro-4-fluoro-phenyl)amino]-6-[1-(tert.-butyloxycarbonyl)-piperidin-4-yloxy]-7-methoxy-quinazoline, 4-[(3-chloro-4-fluoro-phenyl)amino]-6-(trans-4-amino-cyclohexan-1-yloxy)-7-methoxy-quinazoline, 4-[(3-chloro-4-fluoro-phenyl)amino]-6-(trans-4-methanesulphonylamino-cyclohexan-1-yloxy)-7-methoxy-quinazoline, 4-[(3-chloro-4-fluoro-phenyl)amino]-6-(tetrahydropyran-3-yloxy)-7-methoxy-quinazoline, 4-[(3-chloro-4-fluoro-phenyl)amino]-6-(1-methyl-piperidin-4-yloxy)-7-methoxy-quinazoline, 4-[(3-chloro-4-fluoro-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(methoxymethyl)carbonyl]-piperidin-4-yloxy}-7-methoxy-quinazoline, 4-[(3-chloro-4-fluoro-phenyl)amino]-6-(piperidin-3-yloxy)-7-methoxy-quinazoline, 4-[(3-chloro-4-fluoro-phenyl)amino]-6-[1-(2-acetylamino-ethyl)-piperidin-4-yloxy]-7-methoxy-quinazoline, 4-[(3-chloro-4-fluoro-phenyl)amino]-6-(tetrahydropyran-4-yloxy)-7-ethoxy-quinazoline, 4-[(3-chloro-4-fluoro-phenyl)amino]-6-((S)-tetrahydrofuran-3-yloxy)-7-hydroxy-quinazoline, 4-[(3-chloro-4-fluoro-phenyl)amino]-6-(tetrahydropyran-4-yloxy)-7-(2-methoxy-ethoxy)-quinazoline, 4-[(3-chloro-4-fluoro-phenyl)amino]-6-{trans-4-[(dimethylamino)sulphonylamino]-cyclohexan-1-yloxy}-7-methoxy-quinazoline, 4-[(3-chloro-4-fluoro-phenyl)amino]-6-{trans-4-[(morpholin-4-yl)carbonylamino]-cyclohexan-1-yloxy}-7-methoxy-quinazoline, 4-[(3-chloro-4-fluoro-phenyl)amino]-6-{trans-4-[(morpholin-4-yl)sulphonylamino]-cyclohexan-1-yloxy}-7-methoxy-quinazoline, 4-[(3-chloro-4-fluoro-phenyl)amino]-6-(tetrahydropyran-4-yloxy)-7-(2-acetylamino-ethoxy)-quinazoline, 4-[(3-chloro-4-fluoro-phenyl)amino]-6-(tetrahydropyran-4-yloxy)-7-(2-methanesulphonylamino-ethoxy)-quinazoline, 4-[(3-chloro-4-fluoro-phenyl)amino]-6-{1-[(piperidin-1-yl)carbonyl]-piperidin-4-yloxy}-7-methoxy-quinazoline, 4-[(3-chloro-4-fluoro-phenyl)amino]-6-(1-aminocarbonylmethyl-piperidin-4-yloxy)-7-methoxy-quinazoline, 4-[(3-chloro-4-fluoro-phenyl)amino]-6-(cis-4-{N-[(tetrahydropyran-4-yl)carbonyl]-N-methyl-amino}-cyclohexan-1-yloxy)-7-methoxy-quinazoline, 4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-(cis-4-{N-[(morpholin-4-yl)sulphonyl]-N-methyl-amino}-cyclohexan-1-yloxy)-7-methoxy-quinazoline, 4-[(3-chloro-4-fluoro-phenyl)amino]-6-(trans-4-ethanesulphonylamino-cyclohexan-1-yloxy)-7-methoxy-quinazoline, 4-[(3-chloro-4-fluoro-phenyl)amino]-6-(1-methanesulphonyl-piperidin-4-yloxy)-7-ethoxy-quinazoline, 4-[(3-chloro-4-fluoro-phenyl)amino]-6-(1-methanesulphonyl-piperidin-4-yloxy)-7-(2-methoxy-ethoxy)-quinazoline, 4-[(3-chloro-4-fluoro-phenyl)amino]-6-[1-(2-methoxy-acetyl)-piperidin-4-yloxy]-7-(2-methoxy-ethoxy)-quinazoline, 4-[(3-chloro-4-fluoro-phenyl)amino]-6-(cis-4-acetylamino-cyclohexan-1-yloxy)-7-methoxy-quinazoline, 4-[(3-ethynyl-phenyl)amino]-6-[1-(tert.-butyloxycarbonyl)-piperidin-4-yloxy]-7-methoxy-quinazoline, 4-[(3-ethynyl-phenyl)amino]-6-(tetrahydropyran-4-yloxy)-7-methoxy-quinazoline, 4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline, 4-[(3-chloro-4-fluoro-phenyl)amino]-6-(cis-4-{N-[(4-methyl-piperazin-1-yl)carbonyl]-N-methyl-amino}-cyclohexan-1-yloxy)-7-methoxy-quinazoline, 4-[(3-chloro-4-fluoro-phenyl)amino]-6-{cis-4-[(morpholin-4-yl)carbonylamino-cyclohexan-1-yloxy}-7-methoxy-quinazoline, 4-[(3-chloro-4-fluoro-phenyl)amino]-6-{1-[2-(2-oxopyrrolidin-1-yl)ethyl]-piperidin-4-yloxy}-7-methoxy-quinazoline, 4-[(3-chloro-4-fluoro-phenyl)amino]-6-{1-[(morpholin-4-yl)carbonyl]-piperidin-4-yloxy}-7-(2-methoxy-ethoxy)-quinazoline, 4-[(3-ethynyl-phenyl)amino]-6-(1-acetyl-piperidin-4-yloxy)-7-methoxy-quinazoline, 4-[(3-ethynyl-phenyl)amino]-6-(1-methyl-piperidin-4-yloxy)-7-methoxy-quinazoline, 4-[(3-ethynyl-phenyl)amino]-6-(1-methanesulphonyl-piperidin-4-yloxy)-7-methoxy-quinazoline, 4-[(3-chloro-4-fluoro-phenyl)amino]-6-(1-methyl-piperidin-4-yloxy)-7-(2-methoxy-ethoxy)-quinazoline, 4-[(3-chloro-4-fluoro-phenyl)amino]-6-(1-isopropyloxycarbonyl-piperidin-4-yloxy)-7-methoxy-quinazoline, 4-[(3-chloro-4-fluoro-phenyl)amino]-6-(cis-4-methylamino-cyclohexan-1-yloxy)-7-methoxy-quinazoline, 4-[(3-chloro-4-fluoro-phenyl)amino]-6-{cis-4-[N-(2-methoxy-acetyl)-N-methyl-amino]-cyclohexan-1-yloxy}-7-methoxy-quinazoline, 4-[(3-ethynyl-phenyl)amino]-6-(piperidin-4-yloxy)-7-methoxy-quinazoline, 4-[(3-ethynyl-phenyl)amino]-6-[1-(2-methoxy-acetyl)-piperidin-4-yloxy]-7-methoxy-quinazoline, 4-[(3-ethynyl-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(cis-2,6-dimethyl-morpholin-4-yl)carbonyl]-piperidin-4-yloxy}-7-methoxy-quinazoline, 4-[(3-chloro-4-fluoro-phenyl)amino]-6-{1-[(2-methyl-morpholin-4-yl)carbonyl]-piperidin-4-yloxy}-7-methoxy-quinazoline, 4-[(3-chloro-4-fluoro-phenyl)amino]-6-{1-[(S,S)-(2-oxa-5-aza-bicyclo[2,2,1]hept-5-yl)carbonyl]-piperidin-4-yloxy}-7-methoxy-quinazoline, 4-[(3-chloro-4-fluoro-phenyl)amino]-6-{1-[(N-methyl-N-2-methoxyethyl-amino)carbonyl]-piperidin-4-yloxy}-7-methoxy-quinazoline, 4-[(3-chloro-4-fluoro-phenyl)amino]-6-(1-ethyl-piperidin-4-yloxy)-7-methoxy-quinazoline, 4-[(3-chloro-4-fluoro-phenyl)amino]-6-{1-[(2-methoxyethyl)carbonyl]-piperidin-4-yloxy}-7-methoxy-quinazoline, 4-[(3-chloro-4-fluoro-phenyl)amino]-6-{1-[(3-methoxypropyl-amino)-carbonyl]-piperidin-4-yloxy}-7-methoxy-quinazoline, 4-[(3-chloro-4-fluoro-phenyl)amino]-6-[cis-4-(N-methanesulphonyl-N-methyl-amino)-cyclohexan-1-yloxy]-7-methoxy-quinazoline, 4-[(3-chloro-4-fluoro-phenyl)amino]-6-[cis-4-(N-acetyl-N-methyl-amino)-cyclohexan-1-yloxy]-7-methoxy-quinazoline, 4-[(3-chloro-4-fluoro-phenyl)amino]-6-(trans-4-methylamino-cyclohexan-1-yloxy)-7-methoxy-quinazoline, 4-[(3-chloro-4-fluoro-phenyl)amino]-6-[trans-4-(N-methanesulphonyl-N-methyl-amino)-cyclohexan-1-yloxy]-7-methoxyquinazoline, 4-[(3-chloro-4-fluoro-phenyl)amino]-6-(trans-4-dimethylamino-cyclohexan-1-yloxy)-7-methoxy-quinazoline, 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline, 4-[(3-chloro-4-fluoro-phenyl)amino]-6-(1-methanesulphonyl-piperidin-4-yloxy)-7-methoxy-quinazoline, 4-[(3-chloro-4-fluoro-phenyl)amino]-6-(1-cyano-piperidin-4-yloxy)-7-methoxy-quinazoline, and Cetuximab, optionally in the form of the racemates, enantiomers or diastereomers thereof, optionally in the form of the pharmacologically acceptable acid addition salts, the solvates and/or hydrates thereof.

It is particularly preferable within the scope of the present invention to use those EGFR-inhibitors which are selected from among 4-[(3-chloro-4-fluorophenyl)amino]-6-{[4-(morpholin-4-yl)-1-oxo-2-buten-1-yl]amino}-7-cyclopropylmethoxy-quinazoline, 4-[(R)-(1-phenyl-ethyl)amino]-6-{[4-(morpholin-4-yl)-1-oxo-2-buten-1-yl]amino}-7-cyclopentyloxy-quinazoline, 4-[(3-chloro-4-fluoro-phenyl)amino]-6-{[4((R)-6-methyl-2-oxo-morpholin-4-yl)-1-oxo-2-buten-1-yl]amino}-7-[(S)-(tetrahydrofuran-3-yl)oxy]-quinazoline, 4-[(3-chloro-4-fluoro-phenyl)amino]-6-[2-((S)-6-methyl-2-oxo-morpholin-4-yl)-ethoxy]-7-methoxy-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline, 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline, 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline, 4-[(3-ethynyl-phenyl)amino]-6,7-bis-(2-methoxy-ethoxy)-quinazoline, 4-[(R)-(1-phenyl-ethyl)amino]-6-(4-hydroxy-phenyl)-7H-pyrrolo[2,3-d]pyrimidine, 3-cyano-4-[(3-chloro-4-fluorophenyl)amino]-6-{[4-(N,N-dimethylamino)-1-oxo-2-buten-1-yl]amino}-7-ethoxy-quinoline, 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline, 4-[(3-chloro-4-fluorophenyl)amino]-6-{[4-(morpholin-4-yl)-1-oxo-2-buten-1-yl]amino}-7-[(tetrahydrofuran-2-yl)methoxy]-quinazoline, 4-[(3-ethynyl-phenyl)amino]-6-{[4-(5,5-dimethyl-2-oxo-morpholin-4-yl)-1-oxo-2-buten-1-yl]amino}-quinazoline, 4-[(3-chloro-4-fluoro-phenyl)amino]-6-{2-[4-(2-oxo-morpholin-4-yl)-piperidin-1-yl]-ethoxy}-7-methoxy-quinazoline, 4-[(3-chloro-4-fluoro-phenyl)amino]-6-(trans-4-amino-cyclohexan-1-yloxy)-7-methoxy-quinazoline, 4-[(3-chloro-4-fluoro-phenyl)amino]-6-(trans-4-methanesulphonylamino-cyclohexan-1-yloxy)-7-methoxy-quinazoline, 4-[(3-chloro-4-fluoro-phenyl)amino]-6-(tetrahydropyran-3-yloxy)-7-methoxy-quinazoline, 4-[(3-chloro-4-fluoro-phenyl)amino]-6-{1-[(morpholin-4-yl)carbonyl]-piperidin-4-yloxy}-7-methoxy-quinazoline, 4-[(3-chloro-4-fluoro-phenyl)amino]-6-(piperidin-3-yloxy)-7-methoxy-quinazoline, 4-[(3-chloro-4-fluoro-phenyl)amino]-6-[1-(2-acetylamino-ethyl)-piperidin-4-yloxy]-7-methoxy-quinazoline, 4-[(3-chloro-4-fluoro-phenyl)amino]-6-(tetrahydropyran-4-yloxy)-7-ethoxy-quinazoline, 4-[(3-chloro-4-fluoro-phenyl)amino]-6-{trans-4-[(morpholin-4-yl)carbonylamino]-cyclohexan-1-yloxy}-7-methoxy-quinazoline, 4-[(3-chloro-4-fluoro-phenyl)amino]-6-{1-[(piperidin-1-yl)carbonyl]-piperidin-4-yloxy}-7-methoxy-quinazoline, 4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-(trans-4-ethanesulphonylamino-cyclohexan-1-yloxy)-7-methoxy-quinazoline, 4-[(3-chloro-4-fluoro-phenyl)amino]-6-(1-methanesulphonyl-piperidin-4-yloxy)-7-(2-methoxy-ethoxy)-quinazoline, 4-[(3-chloro-4-fluoro-phenyl)amino]-6-[1-(2-methoxy-acetyl)-piperidin-4-yloxy]-7-(2-methoxy-ethoxy)-quinazoline, 4-[(3-ethynyl-phenyl)amino]-6-(tetrahydropyran-4-yloxy]-7-methoxy-quinazoline, 4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline, 4-[(3-chloro-4-fluoro-phenyl)amino]-6-{cis-4-[(morpholin-4-yl)carbonylamino]-cyclohexan-1-yloxy}-7-methoxy-quinazoline, 4-[(3-chloro-4-fluoro-phenyl)amino]-6-{1-[2-(2-oxopyrrolidin-1-yl)ethyl]-piperidin-4-yloxy}-7-methoxy-quinazoline, 4-[(3-ethynyl-phenyl)amino]-6-(1-acetyl-piperidin-4-yloxy)-7-methoxy-quinazoline, 4-[(3-ethynyl-phenyl)amino]-6-(1-methyl-piperidin-4-yloxy)-7-methoxy-quinazoline, 4-[(3-ethynyl-phenyl)amino]-6-(1-methanesulphonyl-piperidin-4-yloxy)-7-methoxy-quinazoline, 4-[(3-chloro-4-fluoro-phenyl)amino]-6-(1-methyl-piperidin-4-yloxy)-7-(2-methoxy-ethoxy)-quinazoline, 4-[(3-ethynyl-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(N-methyl-N-2-methoxyethyl-amino)carbonyl]-piperidin-4-yloxy}-7-methoxy-quinazoline, 4-[(3-chloro-4-fluoro-phenyl)amino]-6-(1-ethyl-piperidin-4-yloxy)-7-methoxy-quinazoline, 4-[(3-chloro-4-fluoro-phenyl)amino]-6-[cis-4-(N-methanesulphonyl-N-methyl-amino)-cyclohexan-1-yloxy]-7-methoxy-quinazoline, 4-[(3-chloro-4-fluoro-phenyl)amino]-6-[cis-4-(N-acetyl-N-methyl-amino)-cyclohexan-1-yloxy]-7-methoxy-quinazoline, 4-[(3-chloro-4-fluoro-phenyl)amino]-6-(trans-4-methylamino-cyclohexan-1-yloxy)-7-methoxy-quinazoline, 4-[(3-chloro-4-fluoro-phenyl)amino]-6-[trans-4-(N-methanesulphonyl-N-methyl-amino)-cyclohexan-1-yloxy]-7-methoxy-quinazoline, 4-[(3-chloro-4-fluoro-phenyl)amino]-6-(trans-4-dimethylamino-cyclohexan-1-yloxy)-7-methoxy-quinazoline, 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline, 4-[(3-chloro-4-fluoro-phenyl)amino]-6-(1-methanesulphonyl-piperidin-4-yloxy)-7-methoxy-quinazoline, 4-[(3-chloro-4-fluoro-phenyl)amino]-6-(1-cyano-piperidin-4-yloxy)-7-methoxy-quinazoline, and 4-[(3-chloro-4-fluoro-phenyl)amino]-6-{1-[(2-methoxyethyl)carbonyl]-piperidin-4-yloxy}-7-methoxy-quinazoline, optionally in the form of the racemates, enantiomers or diastereomers thereof, optionally in the form of the pharmacologically acceptable acid addition salts, the solvates and/or hydrates thereof.

Particularly preferred EGFR-inhibitors according to the invention are the compounds selected from among 4-[(3-chloro-4-fluorophenyl)amino]-6-{[4-(morpholin-4-yl)-1-oxo-2-buten-1-yl]amino}-7-cyclopropylmethoxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline, 4-[(3-chloro-4-fluoro-phenyl)amino]-6-[2-((S)-6-methyl-2-oxo-morpholin-4-yl)-ethoxy]-7-methoxy-quinazoline, 4-[(3-chloro-4-fluorophenyl)amino]-6-({4-[N-(2-methoxy-ethyl)-

N-methyl-amino]-1-oxo-2-buten-1-yl}amino)-7-cyclopropylmethoxy-quinazoline, 4-[(3-ethynyl-phenyl)amino]-6,7-bis-(2-methoxy-ethoxy)-quinazoline, 4-[(3-chloro-4-fluorophenyl)amino]-6-{[4-(morpholin-4-yl)-1-oxo-2-buten-1-yl]amino}-7-[(tetrahydrofuran-2-yl)methoxy]-quinazoline, 4-[(3-ethynyl-phenyl)amino]-6-{[4-(5,5-dimethyl-2-oxo-morpholin-4-yl)-1-oxo-2-buten-1-yl]amino}-quinazoline, 4-[(3-chloro-4-fluoro-phenyl)amino]-6-(trans-4-methanesulphonylamino-cyclohexan-1-yloxy)-7-methoxy-quinazoline, 4-[(3-chloro-4-fluoro-phenyl)amino]-6-(tetrahydropyran-3-yloxy)-7-methoxy-quinazoline, 4-[(3-chloro-4-fluoro-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[2-(2-oxopyrrolidin-1-yl)ethyl]-piperidin-4-yloxy}-7-methoxy-quinazoline, 4-[(3-ethynyl-phenyl)amino]-6-(1-acetyl-piperidin-4-yloxy)-7-methoxy-quinazoline, 4-[(3-ethynyl-phenyl)amino]-6-(1-methyl-piperidin-4-yloxy)-7-methoxy-quinazoline, 4-[(3-ethynyl-phenyl)amino]-6-(1-methanesulphonyl-piperidin-4-yloxy)-7-methoxy-quinazoline, 4-[(3-ethynyl-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(2-methoxyethyl)carbonyl]-piperidin-4-yloxy}-7-methoxy-quinazoline, 4-[(3-chloro-4-fluoro-phenyl)amino]-6-[cis-4-(N-methanesulphonyl-N-methyl-amino)-cyclohexan-1-yloxy]-7-methoxy-quinazoline, 4-[(3-chloro-4-fluoro-phenyl)amino]-6-[cis-4-(N-acetyl-N-methyl-amino)-cyclohexan-1-yloxy]-7-methoxy-quinazoline, 4-[(3-chloro-4-fluoro-phenyl)amino]-6-(trans-4-methylamino-cyclohexan-1-yloxy)-7-methoxy-quinazoline, 4-[(3-chloro-4-fluoro-phenyl)amino]-6-[trans-4-(N-methanesulphonyl-N-methyl-amino)-cyclohexan-1-yloxy]-7-methoxy-quinazoline, 4-[(3-chloro-4-fluoro-phenyl)amino]-6-(trans-4-dimethylamino-cyclohexan-1-yloxy)-7-methoxy-quinazoline, 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline, 4-[(3-chloro-4-fluoro-phenyl)amino]-6-(1-methanesulphonyl-piperidin-4-yloxy)-7-methoxy-quinazoline and 4-[(3-chloro-4-fluoro-phenyl)amino]-6-(1-cyano-piperidin-4-yloxy)-7-methoxy-quinazoline optionally in the form of the racemates, enantiomers or diastereomers thereof, optionally in the form of the pharmacologically acceptable acid addition salts, the solvates and/or hydrates thereof.

By acid addition salts with pharmacologically acceptable acids which the EGFR-inhibitors may be capable of forming are meant, for example, salts selected from among the hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably hydrochloride, hydrobromide, hydrosulphate, hydrophosphate, hydrofumarate and hydromethanesulphonate.

Examples of dopamine agonists which may be used preferably include compounds selected from among bromocriptine, cabergoline, alpha-dihydroergocryptine, lisuride, pergolide, pramipexol, roxindol, ropinirol, talipexol, terguride and viozan. Any reference to the above-mentioned dopamine agonists within the scope of the present invention includes a reference to any pharmacologically acceptable acid addition salts and optionally hydrates thereof which may exist. By the physiologically acceptable acid addition salts which may be formed by the above-mentioned dopamine agonists are meant, for example, pharmaceutically acceptable salts which are selected from the salts of hydrochloric acid, hydrobromic acid, sulphuric acid, phosphoric acid, methanesulphonic acid, acetic acid, fumaric acid, succinic acid, lactic acid, citric acid, tartaric acid and maleic acid.

Examples of H1-antihistamines preferably include compounds selected from among epinastine, cetirizine, azelastine, fexofenadine, levocabastine, loratadine, mizolastine, ketotifen, emedastine, dimetinden, clemastine, bamipin, cexchlorpheniramine, pheniramine, doxylamine, chlorophenoxamine, dimenhydrinate, diphenhydramine, promethazine, ebastine, desloratidine and meclozine. Any reference to the above-mentioned H1-antihistamines within the scope of the present invention includes a reference to any pharmacologically acceptable acid addition salts which may exist.

Examples of PAF-antagonists preferably include compounds selected from among 4-(2-chlorophenyl)-9-methyl-2-[3(4-morpholinyl)-3-propanon-1-yl]-6H-thieno-[3,24]-[1,2,4]triazolo[4,3-a][1,4]diazepines, 6-(2-chlorophenyl)-8,9-dihydro-1-methyl-8-[(4-morpholinyl)carbonyl]-4H,7H-cyclo-penta-[4,5]thieno-[3,2-f][1,2,4]triazolo[4,3-a][1,4]diazepines.

MRP4-inhibitors used are preferably compounds selected from among N-acetyl-dinitrophenyl-cysteine, cGMP, cholate, diclofenac, dehydroepiandrosterone 3-glucuronide, dehydroepiandrosterone 3-sulphate, dilazep, dinitrophenyl-s-glutathione, estradiol 17-β-glucuronide, estradiol 3,17-disulphate, estradiol 3-glucuronide, estradiol 3-sulphate, estrone 3-sulphate, flurbiprofen, folate, N5-formyl-tetrahydrofolate, glycocholate, glycolithocholic acid sulphate, ibuprofen, indomethacin, indoprofen, ketoprofen, lithocholic acid sulphate, methotrexate, MK571 ((E)-3-[[[3-[2-(7-chloro-2-quinolinyl)ethenyl]phenyl]-[[3-dimethylamino)-3-oxopropyl]thio]methyl]thio]-propanoic acid), α-naphthyl-β-D-glucuronide, nitrobenzyl mercaptopurine riboside, probenecid, PSC833, sildenafil, sulfinpyrazone, taurochenodeoxycholate, taurocholate, taurodeoxycholate, taurolithocholate, taurolithocholic acid sulphate, topotecan, trequinsin and zaprinast, dipyridamole, optionally in the form of the racemates, enantiomers, diastereomers and the pharmacologically acceptable acid addition salts and hydrates thereof.

Preferably the invention relates to the use of MRP4-inhibitors for preparing a pharmaceutical composition for the treatment of respiratory complaints, containing the PDE4B-inhibitors and MRP4-inhibitors, the MRP4-inhibitors preferably being selected from among N-acetyl-dinitrophenyl-cysteine, dehydroepiandrosterone 3-sulphate, dilazep, dinitrophenyl-S-glutathione, estradiol 3,17-disulphate, flurbiprofen, glycocholate, glycolithocholic acid sulphate, ibuprofen, indomethacin, indoprofen, lithocholic acid sulphate, MK571, PSC833, sildenafil, taurochenodeoxycholate, taurocholate, taurolithocholate, taurolithocholic acid sulphate, trequinsin and zaprinast, dipyridamole, optionally in the form of the racemates, enantiomers, diastereomers and the pharmacologically acceptable acid addition salts and hydrates thereof.

The invention relates more preferably to the use of MRP4-inhibitors for preparing a pharmaceutical composition for treating respiratory complaints, containing the PDE4B-inhibitors and MRP4-inhibitors according to the invention, the MRP4-inhibitors preferably being selected from among dehydroepiandrosterone 3-sulphate, estradiol 3,17-disulphate, flurbiprofen, indomethacin, indoprofen, MK571, taurocholate, optionally in the form of the racemates, enantiomers, diastereomers and the pharmacologically acceptable acid addition salts and hydrates thereof. The separation of enantiomers from the racemates can be carried out using methods known from the art (e.g. chromatography on chiral phases, etc.).

By acid addition salts with pharmacologically acceptable acids are meant, for example, salts selected from among the hydrochlorides, hydrobromides, hydroiodides, hydrosulphates, hydrophosphates, hydromethanesulphonates, hydronitrates, hydromaleates, hydroacetates, hydrobenzoates, hydrocitrates, hydrofumarates, hydrotartrates, hydrooxalates, hydrosuccinates, hydrobenzoates and hydro-p-toluenesulphonates, preferably the hydrochlorides, hydrobromides, hydrosulphates, hydrophosphates, hydrofumarates and hydromethanesulphonates.

The invention further relates to pharmaceutical preparations which contain a triple combination of the PDE4B-inhibitors, MRP4-inhibitors and another active substance according to the invention, such as, for example, an anticholinergic, a steroid, an LTD4-antagonist or a betamimetic, and the preparation thereof and the use thereof for treating respiratory complaints.

The iNOS-inhibitors used are preferably compounds selected from among: S-(2-aminoethyl)isothiourea, aminoguanidine, 2-aminomethylpyridine, AMT, L-canavanine, 2-iminopiperidine, S-isopropylisothiourea, S-methylisothiourea, S-ethylisothiourea, S-methyltiocitrulline, S-ethylthiocitrulline, L-NA ($N^\omega$-nitro-L-arginine), L-NAME ($N^\omega$-nitro-L-arginine methylester), L-NMMA ($N^G$-monomethyl-L-arginine), L-NIO ($N^\omega$-iminoethyl-L-ornithine), L-NIL ($N^\omega$-iminoethyl-lysine), (S)-6-acetimidoylamino-2-aminohexanoic acid (1H-tetrazol-5-yl)-amide (SC-51) (*J. Med. Chem.* 2002, 45, 1686-1689), 1400W, (S)-4-(2-acetimidoylamino-ethylsulphanyl)-2-amino-butyric acid (GW274150) (*Bioorg. Med. Chem. Lett.* 2000, 10, 597-600), 2-[2-(4-methoxy-pyridin-2-yl)-ethyl]-3H-imidazo[4,5-b]pyridine (BYK191023) (*Mol. Pharmacol.* 2006, 69, 328-337), 2-((R)-3-amino-1-phenyl-propoxy)-4-chloro-5-fluorobenzonitrile (WO 01/62704), 2-((1R.3S)-3-amino-4-hydroxy-1-thiazol-5-yl-butylsulphanyl)-6-trifluoromethyl-nicotinonitrile (WO 2004/041794), 2-((1R.3S)-3-amino-4-hydroxy-1-thiazol-5-yl-butylsulphanyl)-4-chloro-benzonitrile (WO 2004/041794), 2-((1R.3S)-3-amino-4-hydroxy-1-thiazol-5-yl-butylsulphanyl)-5-chloro-benzonitrile (WO 2004/041794), (2S,4R)-2-amino-4-(2-chloro-5-trifluoromethyl-phenylsulphanyl)-4-thiazol-5-yl-butan-1-ol (WO 2004/041794), 2-((1R.3S)-3-amino-4-hydroxy-1-thiazol-5-yl-butylsulphanyl)-5-chloro-nicotinonitrile (WO 2004/041794), 4-((S)-3-amino-4-hydroxy-1-phenyl-butylsulphanyl)-6-methoxy-nicotinonitrile (WO 02/090332), substituted 3-phenyl-3,4-dihydro-1-isoquinolinamines such as e.g. AR-C102222 (*J. Med. Chem.* 2003, 46, 913-916), (1S.5S.6R)-7-chloro-5-methyl-2-aza-bicyclo[4.1.0]hept-2-en-3-ylamine (ONO-1714) (*Biochem. Biophys. Res. Commun.* 2000, 270, 663-667), (4R.5R)-5-ethyl-4-methyl-thiazolidin-2-ylideneamine (*Bioorg. Med. Chem.* 2004, 12, 4101), (4R.5R)-5-ethyl-4-methyl-selenazolidin-2-ylideneamine (*Bioorg. Med. Chem. Lett.* 2005, 15, 1361), 4-aminotetrahydrobiopterine (*Curr. Drug Metabol.* 2002, 3, 119-121), (E)-3-(4-chloro-phenyl)-N-(1-{2-oxo-2-[4-(6-trifluoromethyl-pyrimidin-4-yloxy)-piperidin-1-yl]-ethylcarbamoyl}-2-pyridin-2-yl-ethyl)-acrylamide (FR260330) (*Eur. J. Pharmacol.* 2005, 509, 71-76), 3-(2,4-difluoro-phenyl)-6-[2-(4-imidazol-1-ylmethyl-phenoxy)-ethoxy]-2-phenyl-pyridine (PPA250) (*J. Pharmacol. Exp. Ther.* 2002, 303, 52-57), methyl 3-{[(benzo[1.3]dioxol-5-ylmethyl)-carbamoyl]-methyl}-4-(2-imidazol-1-yl-pyrimidin-4-yl)-piperazin-1-carboxylate (BBS-1) (*Drugs Future* 2004, 29, 45-52), (R)-1-(2-imidazol-1-yl-6-methyl-pyrimidin-4-yl)-pyrrolidine-2-carboxylic acid (2-benzo[1.3]dioxol-5-yl-ethyl)-amide (BBS-2) (*Drugs Future* 2004, 29, 45-52) and the pharmaceutical salts, prodrugs or solvates thereof.

Other iNOS-inhibitors which may be used within the scope of the present invention are antisense oligonucleotides, particularly antisense oligonucleotides that bind iNOS-coding nucleic acids. For example, WO 01/52902 describes antisense oligonucleotides, particularly antisense-oligonucleotides, which bind iNOS-coding nucleic acids, for modulating the expression of iNOS. Those iNOS-antisense-oligonucleotides as described particularly in WO 01/52902 may therefore also be combined with the PDE4-inhibitors of the present invention on the basis of their similar activity to the iNOS inhibitors.

Compounds which may be used as SYK-inhibitors are preferably compounds selected from among: R343 or R788.

Pharmaceutical Formulations

Suitable forms for administration are for example tablets, capsules, solutions, syrups, emulsions or inhalable powders or aerosols. The content of the pharmaceutically effective compound(s) in each case should be in the range from 0.1 to 90 wt. %, preferably 0.5 to 50 wt. % of the total composition, i.e. in amounts which are sufficient to achieve the dosage range specified hereinafter.

The preparations may be administered orally in the form of a tablet, as a powder, as a powder in a capsule (e.g. a hard gelatine capsule), as a solution or suspension. When administered by inhalation the active substance combination may be given as a powder, as an aqueous or aqueous-ethanolic solution or using a propellant gas formulation.

Preferably, therefore, pharmaceutical formulations are characterised in that they contain one or more compounds of formula I according to the preferred embodiments above.

It is particularly preferable if the compounds of formula I are administered orally, and it is also particularly preferable if they are administered once or twice a day. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral administration the tablets may, of course, contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

It is also preferred if the compounds of formula I are administered by inhalation, particularly preferably if they are administered once or twice a day. For this purpose, the compounds of formula I have to be made available in forms suitable for inhalation. Inhalable preparations include inhalable powders, propellant-containing metered-dose aerosols or propellant-free inhalable solutions, which are optionally present in admixture with conventional physiologically acceptable excipients.

Within the scope of the present invention, the term propellant-free inhalable solutions also includes concentrates or sterile ready-to-use inhalable solutions. The preparations which may be used according to the invention are described in more detail in the next part of the specification.

Inhalable Powders

If the active substances of formula I are present in admixture with physiologically acceptable excipients, the following physiologically acceptable excipients may be used to prepare the inhalable powders according to the invention: monosaccharides (e.g. glucose or arabinose), disaccharides (e.g. lactose, saccharose, maltose), oligo- and polysaccharides (e.g. dextran), polyalcohols (e.g. sorbitol, mannitol, xylitol), salts (e.g. sodium chloride, calcium carbonate) or mixtures of these excipients with one another. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred. Methods of preparing the inhalable powders according to the invention by grinding and micronising and by finally mixing the components together are known from the prior art.

Propellant-Containing Inhalable Aerosols

The propellant-containing inhalable aerosols which may be used according to the invention may contain 1 dissolved in the propellant gas or in dispersed form. The propellant gases which may be used to prepare the inhalation aerosols according to the invention are known from the prior art. Suitable propellant gases are selected from among hydrocarbons such as n-propane, n-butane or isobutane and halohydrocarbons such as preferably fluorinated derivatives of methane, ethane, propane, butane, cyclopropane or cyclobutane. The propellant gases mentioned above may be used on their own or in mixtures thereof. Particularly preferred propellant gases are fluorinated alkane derivatives selected from TG134a (1,1,1,2-tetrafluoroethane), TG227 (1,1,1,2,3,3,3-heptafluoropropane) and mixtures thereof. The propellant-driven inhalation aerosols used within the scope of the use according to the invention may also contain other ingredients such as co-solvents, stabilisers, surfactants, antioxidants, lubricants and pH adjusters. All these ingredients are known in the art.

Propellant-Free Inhalable Solutions

The compounds of formula I according to the invention are preferably used to prepare propellant-free inhalable solutions and inhalable suspensions. Solvents used for this purpose include aqueous or alcoholic, preferably ethanolic solutions. The solvent may be water on its own or a mixture of water and ethanol. The solutions or suspensions are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulphuric acids. It is also possible to use the acids which have already formed an acid addition salt with one of the active substances. Of the organic acids, ascorbic acid, fumaric acid and citric acid are preferred. If desired, mixtures of the above acids may also be used, particularly in the case of acids which have other properties in addition to their acidifying qualities, e.g. as flavourings, antioxidants or complexing agents, such as citric acid or ascorbic acid, for example. According to the invention, it is particularly preferred to use hydrochloric acid to adjust the pH.

Co-solvents and/or other excipients may be added to the propellant-free inhalable solutions used for the purpose according to the invention. Preferred co-solvents are those which contain hydroxyl groups or other polar groups, e.g. alcohols—particularly isopropyl alcohol, glycols—particularly propyleneglycol, polyethyleneglycol, polypropyleneglycol, glycolether, glycerol, polyoxyethylene alcohols and polyoxyethylene fatty acid esters. The terms excipients and additives in this context denote any pharmacologically acceptable substance which is not an active substance but which can be formulated with the active substance or substances in the pharmacologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilisers, complexing agents, antioxidants and/or preservatives which guarantee or prolong the shelf life of the finished pharmaceutical formulation, flavourings, vitamins and/or other additives known in the art. The additives also include pharmacologically acceptable salts such as sodium chloride as isotonic agents. The preferred excipients include antioxidants such as ascorbic acid, for example, provided that it has not already been used to adjust the pH, vitamin A, vitamin E, tocopherols and similar vitamins or provitamins occurring in the human body. Preservatives may be used to protect the formulation from contamination with pathogens. Suitable preservatives are those which are known in the art, particularly cetyl pyridinium chloride, benzalkonium chloride or benzoic acid or benzoates such as sodium benzoate in the concentration known from the prior art. For the treatment forms described above, ready-to-use packs of a medicament for the treatment of respiratory complaints are provided, containing an enclosed description including for example the words respiratory disease, COPD or asthma, a pteridine and one or more combination partners selected from those described above.

EXPERIMENTAL PROCEDURES AND SYNTHETIC EXAMPLES

List of Abbreviations

ACN acetonitrile
APCI atmospheric pressure chemical ionization (in MS)
Ctrl control
DAD diode array detector
DMA N,N-dimethylacetamide'
DMF N,N-dimethylformamide
DMSO dimethyl sulfoxide
EI electron impact (in MS)
ESI electrospray ionization (in MS)
ex example
GC/MS gas chromatography with mass spectrometric detection
h hour(s)
HATU O-(7-azabenzotriazol-1-yl)-N,N,N',N'-tetramethyluronium hexafluoro-phosphate
HPLC high performance liquid chromatography
HPLC/MS coupled high performance liquid chromatography-mass spectrometry
min minutes
MS mass spectrometry
NMR nuclear magnetic resonance
$R_t$ retention time (in HPLC)
sec secondary
TBTU O-(1H-benzo-1,2,3-triazol-1-yl)-N,N,N',N'-tetramethyluronium tetrafluoroborate
tert tertiary
TFA trifluoroacetic acid
TLC thin-layer chromatography
UV ultraviolet absorption
Analytical Methods
HPLC Methods
Methods:
    1A
    Column: Sunfire MS-C8, 5 μm, 4.6×100 mm
        Mobile phase: A=(10 nM aqueous solution of $NH_4COOH$)+10% ACN;
        B=ACN+10% (10 nM aqueous solution of $NH_4COOH$).
    Flow rate: 1500 μL/min
    Gradient: A/B (95/5%) for 1 min then to A/B (5/95%) in 10 min for 2 min
    1E
    Column: Symmetry C8, 5 μm, 3×150 mm
        Mobile phase: A=(10 nM aqueous solution of $NH_4COOH$)+10% ACN;
        B=ACN+10% (10 nM aqueous solution of $NH_4COOH$).
    Flow rate: 1200 μL/min
    Gradient: A (100%) for 1.5 min then to B (100%) in 10 min for 3 min
    1E (Fusion)
    Column: Synergy Fusion RP80A, 4 μm, 4.6×100 mm
        Mobile phase: A=(10 nM aqueous solution of $NH_4COOH$)+10% ACN;
        B=ACN+10% (10 nM aqueous solution of $NH_4COOH$).
    Flow rate: 1200 μL/min
    Gradient: A (100%) for 1.5 min then to B (100%) in 10 min for 3 min
    1E (Hydro)
    Column: Synergy Hydro RP80A, 4 μm, 4.6×100 mm
        Mobile phase: A=(10 nM aqueous solution of $NH_4COOH$)+10% ACN;
        B=ACN+10% (10 nM aqueous solution of $NH_4COOH$).
    Flow rate: 1200 μL/min
    Gradient: A (100%) for 1.5 min then to B (100%) in 10 min for 3 min
    Equipment:
    Instrument: HPLC/MS ThermoFinnigan HPLC Surveyor DAD,
    Detection: UV @ 254 nm
    Detection: Finnigan MSQ, quadrupole
    Ion source: APCI
Method:
    1F
    Column: Xterra MS-C8, 3.5 μm, 4.6×50 mm
    Mobile phase: A=($H_2O$+0.1% TFA)+10% ACN; B=ACN
    Flow rate: 1300 μL/min
    Gradient: A (100%) then to A/B (10/90%) in 3.25 min for 0.75 min
    1Fa
    Column: Xterra MS-C18, 5 μm, 4.6×50 mm
    Mobile phase: A=($H_2O$+0.1% NH4COOH)+10% ACN; B=ACN
    Flow rate: 1300 μL/min
    Gradient: A (100%) then to A/B (10/90%) in 3.25 min for 0.75 min
    Equipment:
    Instrument: HPLC/MS Waters. Hplc Alliance 2695 DAD, ZQ Quadrupole
    Detection: UV @ 254 nm
    Detection: Waters ZQ, Quadrupole;
    Ion source: ESI
Methods:
    2A
    Column: X-Terra MS C18 4.6×50 mm, 3.5 μm;
        Column Temperature: 40.0° C.
    Mobile phase: A=$H_2O$+0.1% TFA; B=ACN+0.1% TFA
    Flow rate: 1500 μL/min

| | Gradient: | |
|---|---|---|
| Time | A % | B % |
| 0.00 | 95.00 | 5.00 |
| 2.00 | 0.00 | 100.00 |
| 2.49 | 0.00 | 100.00 |
| 2.50 | 95.00 | 5.00 |

2B
    Column: X-Terra MS C18 4.6×50 mm, 3.5 μm;
        Column Temperature: 40.0° C.
    Mobile phase: A=$H_2O$+0.1% TFA; B=ACN+0.1% TFA
    Flow rate: 1000 μL/min

| Gradient: | | |
|---|---|---|
| Time | A % | B % |
| 0.00 | 95.00 | 5.00 |
| 0.40 | 95.00 | 5.00 |
| 4.00 | 2.00 | 98.00 |
| 4.35 | 2.00 | 98.00 |
| 4.50 | 95.00 | 5.00 |

2C
Column: Sunfire C18 4.6×50 mm, 3.5 μm;
  Column Temperature: 40.0° C.
Mobile phase: A=$H_2O$+0.1% TFA; B=ACN+0.1% TFA
Flow rate: 1500 μL/min

| Gradient: | | |
|---|---|---|
| Time: | A % | B % |
| 0.00 | 95.00 | 5.00 |
| 2.00 | 0.00 | 100.00 |
| 2.49 | 0.00 | 100.00 |
| 2.50 | 95.00 | 5.00 |

Equipment
Instrument: Waters ZQ2000 mass spectrometer
Detection: HP1100 HPLC+DAD (Wavelength range: 210 to 500 nM)+Gilson 215 Autosampler
Ion source: ESI+
Method:
2Ca
Column: MERCK; Chromolith Flash; RP18e; 25×4.6 mm
Mobile phase: A=water+0.1% HCOOH; B=ACN+0.1% HCOOH
Flow rate: 1.6 ml/min

| Gradient: | | |
|---|---|---|
| A % | B % | Time [min] |
| 90 | 10 | 0.00 |
| 10 | 90 | 2.70 |
| 10 | 90 | 3.00 |
| 90 | 10 | 3.30 |

2Cb
Column: MERCK; Chromolith Flash; RP18e; 25×4.6 mm
Mobile: A=water+0.1% HCOOH; B=MeOH
Flow rate: 1.6 ml/min

| Gradient: | | |
|---|---|---|
| A % | B % | Time [min] |
| 90 | 10 | 0.00 |
| 0 | 100 | 2.50 |
| 0 | 100 | 3.50 |

Equipment
Instrument: Agilent Technology; HP 1200 Series, DAD SL
Detection: UV 240-254 nm
Detection: Waters ZQ Single Quad
Ion source: ESI+
Method:
2F
Column: Symmetry Shield RP8, 5 μm, 4.6×150 mm
Mobile phase: A=($H_2O$+HCOOH 0.1%)+10% ACN
  B=ACN+10% ($H_2O$+0.1% HCOOH)
Flow rate: 1000 μL/min
Gradient: A/B (95/5%) for 1.5 min then to A/B (5/95%) in 10 min for 1.5 min
2M
Column: Symmetry Shield RP8, 5 μm, 4.6×150 mm
Mobile phase: A=($H_2O$+HCOOH 0.1%)+10% ACN
  B=ACN+10% ($H_2O$+0.1% HCOOH)
Flow rate: 1200 μL/min
Gradient: A/B (90/10%) for 1.5 min then to A/B (5/95%) in 10 min for 2 min
Equipment:
Instrument: HPLC/MS ThermoFinnigan HPLC Surveyor DAD, LCQDuo Ion Trap
Detection: UV λ54 nm
Detection: Finnigan LCQDuo Ion Trap
Ion source: ESI
Method:
2G
Eluent: A=H2O+0.05% TFA; B=ACN
Column: Waters SunFire C18 30×100 mm 5 μm

| Gradient: | slope 5%/min | | |
|---|---|---|---|
| Initial: | Flow = 40 mL/min | % A = 80 | % B = 20 |
| 8 min | Flow = 40 mL/min | % A = 40 | % B = 60 |
| 9 min | Flow = 40 mL/min | % A = 40 | % B = 60 |
| 10 min | Flow = 40 mL/min | % A = 5 | % B = 95 |
| 11 min | Flow = 40 mL/min | % A = 5 | % B = 95 |
| 11.5 min | Flow = 40 mL/min | % A = 80 | % B = 20 |

Stop run after 12 min Pre-run method: Initial condition for 3 min

Equipment:

| Detector MS Waters ZQ: | | Detector DAD Waters 996: | |
|---|---|---|---|
| File: | APrep_ESI.ipr | Start Wavelength: | 210 nm |
| Polarity: | ESI+ | End Wavelength: | 600 nm |
| Mass range: | 130 to 900 amu | Resolution: | 1.2 nm |
| | | Sampling rate: | 1 spectra/sec |
| Sample Manager mod Waters 2767: | | Make up pump mod Waters 515: | |
| Injection type: | partial loop | Flow = | 1000 μL/min |
| Injection Volume: | set to Open Access Login mask | Solvent = | ACN/Water/Formic acid (90/10/0.1) |
| Syringe size: | 5000 uL | Splitter: | 1:1000 |
| Trigger: | mixed Total scan UV plus MS A | | |
| Loop Volume: | 5000 uL | | |

Method:
  2Ga
    Column: BEH C18, 1.8 um, 2.1×100 mm
    Mobile phase: A=(H₂O+NH4COOH 0.1%)
      B=ACN+10% H₂O
    Flow rate: 450 μL/min
    Gradient: 100% A for 1.5 min then to 100% B in 2.2 min
  2Gb
    Column: BEH C18, 1.7 um, 2.1×50 mm
    Mobile phase: A=H₂O 90%+0.1% TFA+10% ACN
      B=ACN+10% H₂O
    Flow rate: 480 μL/min
    Gradient: A/B (90:10), then to A/B (10:90) in 1.2 minutes for 0.46 minute
  Equipment:
  Instrument: UPLC/MS AcquityWaters
  Detection: UV λ254 nm
  Detection: Waters SQD, Quadrupole
  Ion source: ESI
Method:
  2H (Isocratic)
    Column: DAICEL (IC) 5 μm, 4.6×250 mm
    Mobile phase: A=(hexane+0.2% diethylamine); B=(MeOH/EtOH 50/50%).
      A/B=50/50%
    Flow rate: 1 ml/min
  2I (Isocratic)
    Column: DAICEL AS-H 5 μm, 4.6×250 mm
    Mobile phase: A=Hexane; B=EtOH (con AS-H), IPA (con AD-H)
      A/B=98/2%
    Flow rate: 1 ml/min
  Equipment
  Instrument: LC Agilent Technologies. HPLC 1100 Serie, DAD Version A.
  Detection: UV 220-300 nm
GC-MS Methods:
Method:
  3A
    Column: Agilent DB-5MS, 25 m×0.25 mm×0.25 μm
    Carrier gas: Helium, 1 ml/min costant flow
    Oven Program: 50° C. (hold 1 min), to 100° C. in 10° C./min, to 200° C. in 20° C./min, to 300° C. in 30° C./min
  Equipment
  Instrument: GC/MS Finnigan TRACE GC, TRACE MS quadrupole
  Detection: TRACE MS quadrupole
  Ion source: EI
Microwave Heating:
  Discover® CEM instruments, equipped with 10 and 35 mL vessels.

SYNTHESIS OF INTERMEDIATES

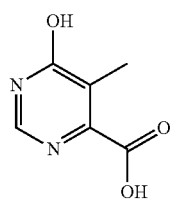

Intermediate 1a

Potassium hydroxide (37.9 g, 0.67 mol) was suspended in 200 ml of dry ethanol, formamidine acetate (28.1 g, 0.27 mol) and diethyl oxalpropionate (50 ml, 0.27 mol) were added and the reaction mixture was stirred under reflux overnight. The reaction mixture was cooled to room temperature and the precipitate formed was filtered, washed with ethanol and diethyl ether, dissolved in 200 ml of water and the solution obtained acidified by a 37% aqueous solution of hydrochloric acid until pH=2. The acidic aqueous solution was concentrated under vacuum and the residue obtained was suspended and stirred in 100 ml of methanol. The insoluble inorganic salts were filtered off. The solution was concentrated. 15 g (97.4 mmol) of the desired compound were obtained.

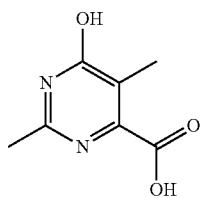

Intermediate 1b was synthesized in analogy to Intermediate 1a, starting from acetamidine hydrochloride.

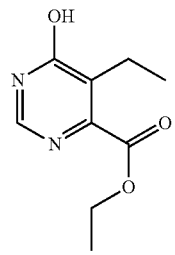

Intermediate 1c

Potassium-tert-butylate (185.4 g, 1.65 mol) was dissolved in 650 ml of dry ethanol and added slowly at −10° C. to a suspension of 2-ethyl-3-oxo-succinic-acid diethyl ester (274.3 g, 1.27 mol) and formamidine acetate (171.4 g, 1.65 mol). The reaction mixture was stirred at room temperature overnight, concentrated in vacuum and ice water was added. The mixture was acidified by a 37% aqueous solution of hydrochloric acid until pH=5 and extracted with chloroform. After drying the organic layer, evaporation of the solvent in vacuum and crystallization from ethyl acetate/hexane (2:3) gave 38 g (0.19 mol) of the desired compound.

Intermediate 1d

A suspension of sodium tert-butoxide (3.9 g, 40.5 mmol) in 25 ml dry ethanol was added to a solution of diethyl oxalpropionate (3.0 ml, 16.2 mmol) and O-methylisourea hydrochloride (2.15 g, 19.5 mmol) in 25 ml dry ethanol and the reaction mixture was refluxed for 18 h. The reaction mixture was allowed to cool to room temperature and the precipitate removed by filtration. The filtrate was concentrated in vacuum, and the residue was purified by reversed phase HPLC to give the desired product (752 mg, 3.5 mmol).

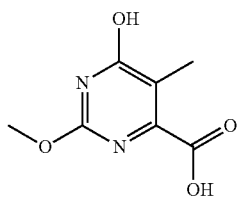

Intermediate 1e

Intermediate 1d (550 mg, 2.6 mmol) was dissolved in a 4 M aqueous solution of sodium hydroxide (3.0 ml, 12.0 mmol) and stirred for 3 h at room temperature. The reaction mixture was acidified with concentrated hydrochloric acid to yield the desired product as precipitate (443 mg, 2.4 mmol).

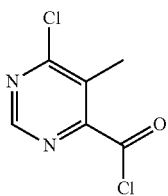

Intermediate 2a

Intermediate 1a (7.0 g, 45.4 mmol) was suspended in 35 ml of thionyl chloride (0.45 mol), 0.10 ml of DMF was added and the reaction mixture was refluxed for 1 h. The reaction mixture was concentrated in vacuum. 8.6 g (45 mmol) of the desired product were obtained and used in the next steps without further purification.

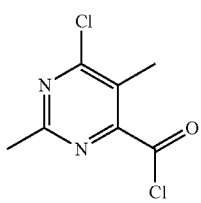

Intermediate 2b was synthesized in analogy to Intermediate 2a, starting from Intermediate 1b.

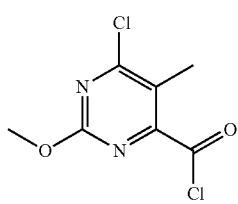

Intermediate 2c was synthesized in analogy to Intermediate 2a, starting from Intermediate 1e.

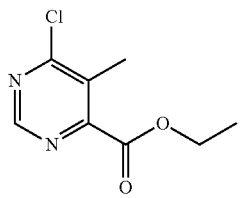

Intermediate 3a

Potassium carbonate (43.34 g, 0.31 mol) was suspended in 350 ml of dry ethanol. A solution of Intermediate 2a (20 g, 0.10 mol) in 10 ml of dichloromethane was added slowly at 0° C. The reaction mixture was allowed to reach room temperature and stirred for 1 h. Potassium carbonate was filtered off and the solvent was removed under vacuum. The crude product was purified by flash chromatography (BIOTAGE SP1; silica gel cartridge: 65i; eluent: dichloromethane/ethyl acetate=95/5%). 5.3 g (26 mmol) of the desired compound were obtained.

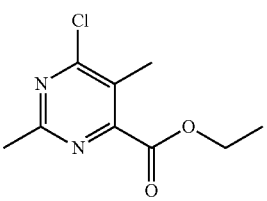

Intermediate 3b was synthesized in analogy to Intermediate 3a, starting from Intermediate 2b.

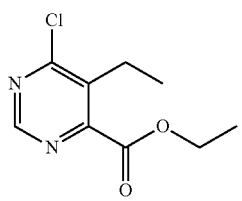

Intermediate 3c

Intermediate 1c (38 g, 0.19 mol) was added to a mixture of phosphorpentachloride (40.3 g, 0.19 mol) in 240 ml of phosphoroxychloride. The reaction mixture was refluxed until a clear solution was observed. The reaction mixture was concentrated in vacuum. The crude product obtained was purified by distillation in vacuum. 12 g (94.5 mmol) of the desired compound were obtained and used in the next steps without further purification.

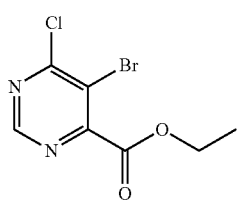

Intermediate 3d

5-Bromo-6-hydroxy-pyrimidine-4-carboxylic acid ethyl ester (63 g, 0.26 mol) was suspended in 140 ml of phosphoroxychloride. Phosphorpentachloride (54 g, 0.26 mmol) was added and the reaction mixture was refluxed 72 h. The reaction mixture was concentrated in vacuum and the crude product was suspended and stirred in warmed-up hexane (50° C.); a precipitate was formed and filtered off. The filtrate was concentrated under vacuum to obtain 64 g (243 mmol) of the desired product which was used in the next steps without further purification.

Intermediate 4a

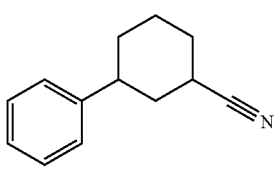

3-Phenylcyclohexanone (500 mg, 2.87 mmol) and 1-isocyanomethanesulfonyl-4-methyl-benzene (750 mg, 3.84 mmol) in 10 ml of 1,2-dimethoxyethane were stirred at 0° C. A solution of potassium tert-butoxide (650 mg, 5.79 mmol) in 10 ml of 1,2-dimethoxyethane and 20 ml of tert-butanol was added dropwise and the reaction mixture was allowed to reach room temperature and stirred overnight. The reaction mixture was diluted with diethyl ether and washed with ice water. The organic phase was separated, washed with brine, dried over sodium sulfate and concentrated under vacuum. 439 mg (2.3 mmol) of the desired product were obtained.

Intermediate 4b

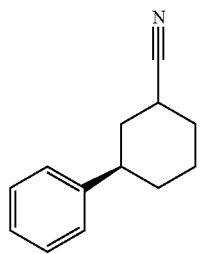

was synthesized in analogy to Intermediate 4a, starting from (R)-3-Phenylcyclohexanone.
GC/MS (method 3A) $R_t$=11.52 min and 11.68 min (diastereoisomeric mixture)
$[M]^+$=185

Intermediate 4c

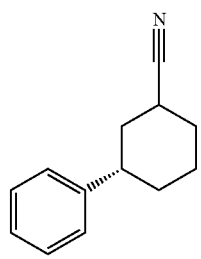

was synthesized in analogy to Intermediate 4a, starting from (S)-3-Phenylcyclohexanone.
GC/MS (method 3A) $R_t$=11.50 min and 11.65 min (diastereoisomeric mixture)
$[M]^+$=185

The following intermediates were synthesized in analogy to Intermediates 4a.

| Starting ketone | Intermediate | STRUCTURE |
|---|---|---|
| 3-(4-Chloro-phenyl)-cyclohexanone | 4d | 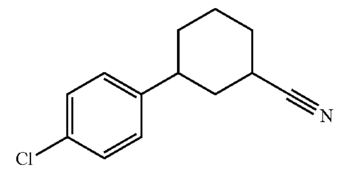 [SMILES: N#CC1CCCC(c2ccc(Cl)cc2)C1] |
| 3-(4-Fluoro-phenyl)-cyclohexanone | 4e | 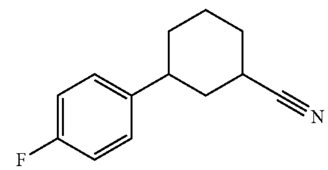 [SMILES: N#CC1CCCC(c2ccc(F)cc2)C1] |
| 3-(4-Methoxy-phenyl)-cyclohexanone | 4f | 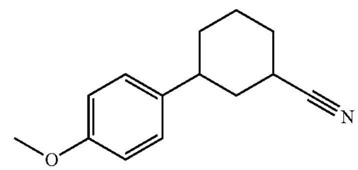 [SMILES: COc1ccc(C2CCCC(C#N)C2)cc1] |
| 3-(4-Methyl-phenyl)-cyclohexanone | 4g | 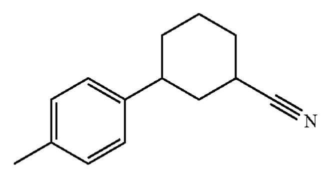 |
| 3-(3-Fluoro-phenyl)-cyclohexanone | 4h | 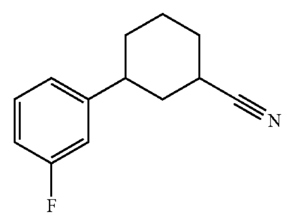 [SMILES: N#CC1CCCC(c2cccc(F)c2)C1] |
| 3-isopropyl-cyclohexanone | 4i | 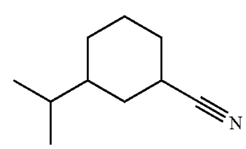 |
| 3-(5-Methyl-furan-2-yl)-cyclohexanone | 4j | 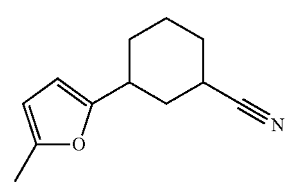 |
| 3-Phenylcyclo-pentanone | 4k | |

| Starting ketone | Intermediate | STRUCTURE |
|---|---|---|
| 3-(4-Chloro-phenyl)-cyclopentanone | 4l | 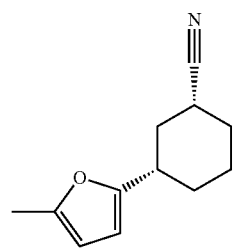 |
| 3-(4-Fluoro-phenyl)-cyclopentanone | 4m | 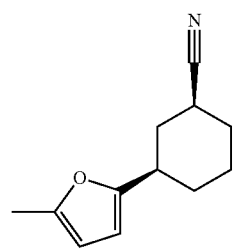 |

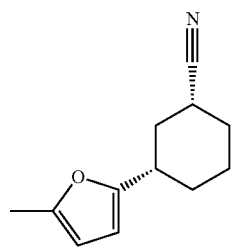

Intermediate 4n

Intermediate 4j (400 mg, 2.11 mmol) was purified by flash chromatography (Biotage SP1 cartridge 25 g; eluent: cyclohexane/ethyl acetate=99/1%). 60 mg (0.22 mmol) of diastereoisomerically pure cis-intermediate was eluted as second fraction (relative stereochemistry assigned by NMR).

GC/MS (method 3A) $R_t$=9.62 min $[M]^+$=189

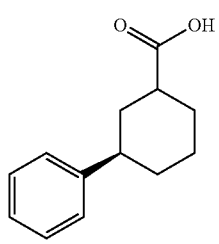

Intermediate 4o

Intermediate 4n (120 mg, 4.22 mmol) was separated by chiral semipreparative HPLC. 20 mg of enantiomerically pure intermediate 4o were obtained (absolute stereochemistry unknown). Chiral HPLC (method 2I (isocratic)) $R_t$=6.94 min Intermediate 4p Further elution of the column gave 20 mg of enantiomerically pure intermediate 4p (absolute stereochemistry unknown).

Chiral HPLC (method 2I (isocratic)) $R_t$=7.27

Intermediate 5

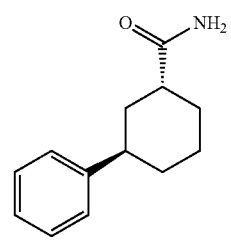

Intermediate 4b (2.1 g, 11.28 mmol) was stirred under reflux in 20 ml of 96% sulfuric acid and 20 ml of water overnight. The reaction mixture was cooled, treated with a 30% aqueous solution of sodium hydroxide and ice and washed with dichloromethane. The basic water phase was treated with 37% aqueous solution of hydrochloric acid. The acidic aqueous solution was extracted with dichloromethane. The organic phase was washed with brine, dried over sodium sulfate and concentrated under vacuum. 1.85 g (9.1 mmol) of the desired compound were obtained as a diastereoisomeric mixture and used in the next steps without further purification.

Intermediate 6a

Intermediate 5 (1.85 g, 9.06 mmol, mixture of 2 diastereomers) and triethylamine (2.02 ml, 14 mmol) were stirred at 0° C. in 10 ml of tetrahydrofuran. A solution of ethylchloroformate (1.29 ml, 13.58 mmol) in 5 ml of tetrahydrofuran was added dropwise and the reaction mixture was stirred at 0° C. for 1 h. Then, 10 ml of a 30% aqueous solution of ammonium hydroxide were added dropwise and the reaction mixture was allowed to reach room temperature and stirred overnight. The reaction mixture was concentrated under vacuum, dissolved with dichloromethane, washed with a 1M aqueous solution of sodium hydroxide, washed with brine, dried over sodium sulfate and concentrated under vacuum. The crude product was purified by flash chromatography (Isolute silica cartridge 70 g; eluent: dichloromethane/methanol=99/1%). 145 mg (0.71 mmol) of diastereoisomerically pure (1R,3R)-3-phenyl-cyclohexanecarboxylic acid amide (relative stereochemistry assigned by NMR) were obtained.

GC/MS (method 3A) R$_t$=12.88 min
[M]$^+$=203

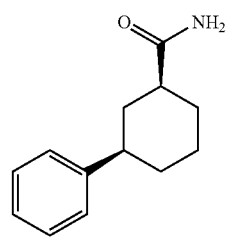

Intermediate 6b

Further elution of the column gave 230 mg (1.13 mmol) of the diastereoisomerically pure (1S,3R)-3-phenyl-cyclohexanecarboxylic acid amide (relative stereochemistry assigned by NMR).

GC/MS (method 3A) R$_t$=13.03 min
[M]$^+$=203

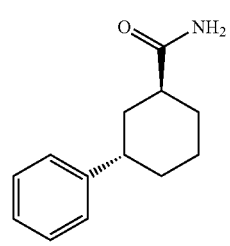

Intermediate 6c

Intermediate 4c (300 mg, 1.61 mmol) was stirred under reflux in 2 ml of 96% sulfuric acid and 2 ml of water for 3 h. The reaction mixture was cooled, treated with a 30% aqueous solution of sodium hydroxide and ice and washed with ethyl acetate. The organic phase was washed with brine, dried over sodium sulfate and concentrated under vacuum. The crude product was purified by flash chromatography (Isolute silica cartridge 20 g; eluent: dichloromethane/methanol=99/1%). 37 mg (0.18 mmol) of the diastereomerically pure (1S,3S)-3-phenyl-cyclohexanecarboxylic acid amide were obtained (relative stereochemistry assigned by NMR).

GC/MS (method 3A) R$_t$=12.88 min
[M]$^+$=203

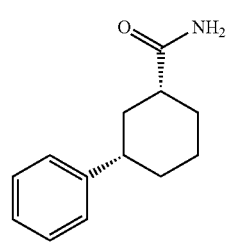

Intermediate 6d

Further elution of the column gave 40 mg of the diastereomerically pure (1R,3S)-3-phenyl-cyclohexanecarboxylic acid amide (0.2 mmol) (relative stereochemistry assigned by NMR).

GC/MS (method 3A) R$_t$=13.03 min
[M]$^+$=203

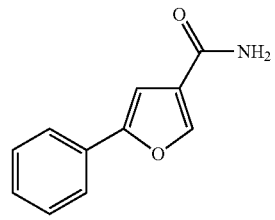

Intermediate 6e

5-Bromo-3-furan carboxylic acid (1.0 g, 5.23 mmol), phenylboronic acid (0.77 g, 6.28 mmol), tetrakis(triphenylphosphine)palladium(0) (1.21 g, 1.04 mmol) and a 2M solution of sodium carbonate (6.28 ml, 12.57 mmol) were dissolved in 12 ml of 1,2-dimethoxy-ethane and the reaction mixture was stirred under nitrogen atmosphere at 80° C. for 18 h. The reaction mixture was cooled to room temperature, diluted with dichloromethane and treated with a 1M aqueous solution of hydrochloric acid until pH 1. The organic phase was separated, dried over sodium sulphate and concentrated under vacuum. The carboxylic acid was obtained and used without further purification for the synthesis of intermediate 6e in analogy to intermediate 6a.

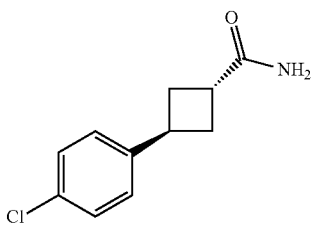

Intermediate 6f

Intermediate 6f was synthesized in analogy to intermediate 6a, starting from trans 3-(4-chlorophenyl)-cyclobutan carboxylic acid (prepared as described in literature for the preparation of trans 3-phenyl-cyclobutan-carboxylic acid: Wiberg, K. B.; Dailey, W. P.; Walker, F. H.; Waddell, S. T.; Crocker, L. S.; Newton, M. Journal of the American Chemical Society; 1985, 107, 7247-7257).

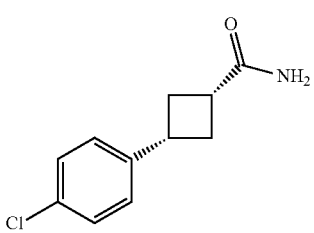

Intermediate 6g

Intermediate 6g was synthesized in analogy to Intermediate 6a, starting from cis 3-(4-chlorophenyl)-cyclobutan carboxylic acid (prepared as described in literature for the preparation of cis 3-phenyl-cyclobutan-carboxylic acid: Wiberg, K. B.; Dailey, W. P.; Walker, F. H.; Waddell, S. T.; Crocker, L. S.; Newton, M. Journal of the American Chemical Society; 1985, 107, 7247-7257).

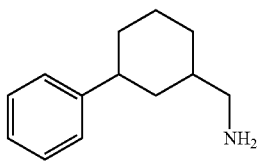

Intermediate 7a

Intermediate 4a (390 mg, 2.10 mmol) and Raney-Nickel (10 mg) in 10 ml of 1M solution of ammonia in ethanol was stirred under a hydrogen atmosphere (4 bar) overnight. The reaction mixture was filtered on a celite pad and concentrated under vacuum. The crude product was purified by flash chromatography (dichloromethane/methanol/NH$_3$ (30% aqueous solution)=95/5/0.1%) to obtain 217 mg (1.15 mmol) of the desired product.

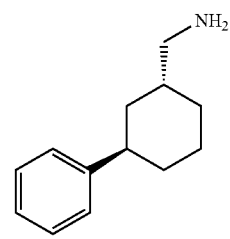

Intermediate 7b 2.85 ml of a 1M solution of lithium aluminium hydride (2.85 mmol) in tetrahydrofuran was dissolved in 10 ml of tetrahydrofuran and stirred at 0° C. under nitrogen atmosphere.

Intermediate 6a (145 mg, 0.71 mmol) in 10 ml of tetrahydrofuran was added dropwise. The reaction mixture was stirred at 0° C. for 2 h and then quenched with water and ice. The reaction mixture was extracted with dichloromethane. The organic phase was washed with a 1M aqueous solution of sodium hydroxide, brine, dried over sodium sulfate and concentrated under vacuum. 100 mg (0.55 mmol) of the desired product were obtained.

GC/MS (method 3A) R$_t$=11.53 min

[M]$^+$=189

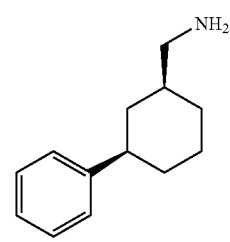

Intermediate 7c was synthesized in analogy to Intermediate 7b, starting from Intermediate 6b.

GC/MS (method 3A) R$_t$=11.47 min

[M]$^+$=189

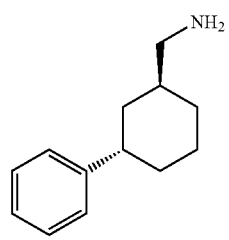

Intermediate 7d was synthesized in analogy to Intermediate 7b, starting from Intermediate 6c.

GC/MS (method 3A) R$_t$=11.53 min

[M]$^+$=189

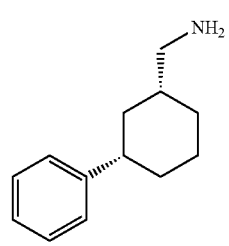

Intermediate 7e was synthesized in analogy to Intermediate 7b, starting from Intermediate 6d.

GC/MS (method 3A) R$_t$=13.03 min

[M]$^+$=189

The following intermediates were synthesised in atalogy to Intermediate 7a.

| Starting Intermediate | Intermediate | STRUCTURE |
|---|---|---|
| 4d | 7f | 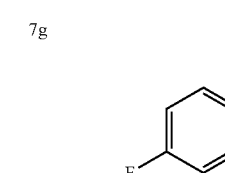 |
| 4e | 7g | 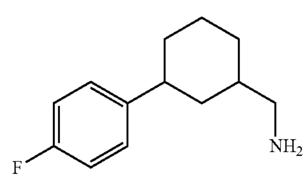 [SMILES: NCC1CCCC(c2ccc(F)cc2)C1] |
| 4f | 7h | 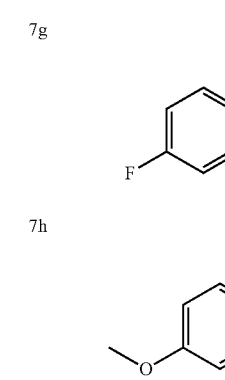 |

73
-continued

| Starting Intermediate | Intermediate | STRUCTURE |
|---|---|---|
| 4g | 7i | 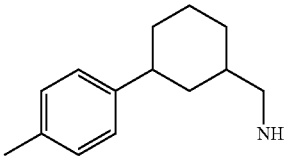 |
| 4h | 7j | 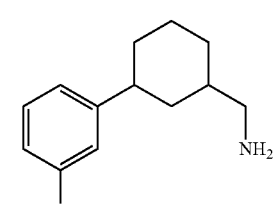 |
| 4i | 7k | 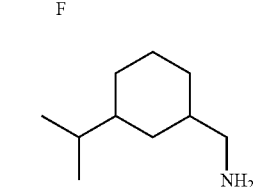 |
| 4k | 7l | 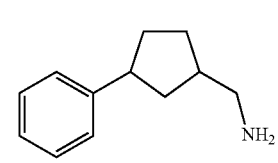 [SMILES: NCC1CCC(c2ccccc2)C1] |
| 4l | 7m | 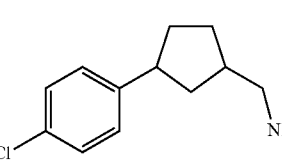 |
| 4m | 7n | 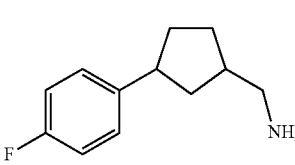 |
| 4n | 7o | 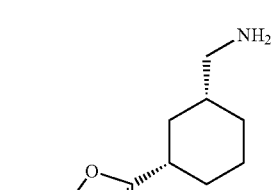 |
| 4o | 7p | 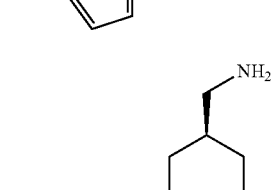 |

74
-continued

| Starting Intermediate | Intermediate | STRUCTURE |
|---|---|---|
| 4p | 7q | 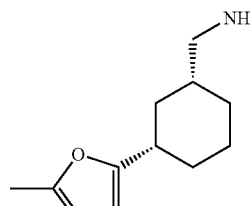 |

Intermediate 7r

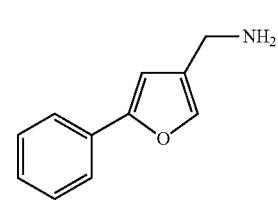

was synthesized in analogy to intermediate 7b, starting from intermediate 6e.

Intermediate 7s

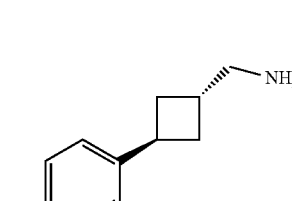

was synthesized in analogy to intermediate 7b, starting from intermediate 6f.

Intermediate 7t

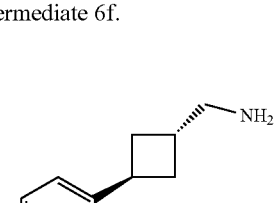

was obtained and isolated as side product in the preparation of Intermediate 7s

Intermediate 7u

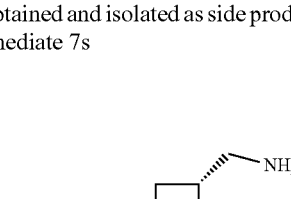

was synthesized in analogy to Intermediate 7b, starting from Intermediate 6g.

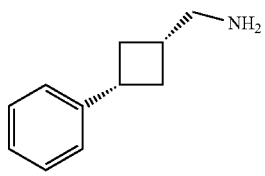

Intermediate 7v was obtained and isolated as side product in the preparation of Intermediate 7u.

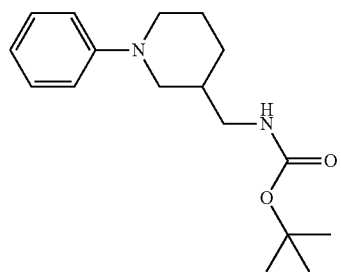

Intermediate 8a

Tris(dibenzylideneacetone)dipalladium (1.71 g, 1.87 mmol) and 2,2'-bis(diphenylphosphino)-1,1'-binapthyl (2.32 g, 3.72 mmol) were stirred in 30 ml of toluene for 10 min under argon atmosphere.

Piperidine-3-yl-methyl-carbamic acid tert-butyl ester (2 g, 9.33 mmol), bromobenzene (1.27 ml, 0.01 mol) and sodium tert-butoxide (1.43 g, 14.93 mmol) were added and the reaction mixture was stirred under reflux overnight. The reaction mixture was concentrated under vacuum, the crude product was dissolved in dichloromethane and the organic phase was filtered on a celite pad. The organic phase was washed with an aqueous saturated sodium carbonate solution, with brine, dried over sodium sulfate, concentrated under vacuum. The crude product obtained was dissolved in methanol and loaded onto a SCX cartridge (25 g). After washing with methanol the product was eluted with a 2M solution of ammonia in methanol. 1.17 g (4.03 mmol) of the desired product were obtained and used in next steps without any other purification.

Intermediate 9a

To a solution of Intermediate 8a (1.1 g, 3.79 mmol) in 10 ml of 1,4-dioxane, a 4M solution of hydrochloric acid in 1,4-dioxane (15 ml, 60 mmol) was added dropwise; the reaction mixture was stirred at room temperature overnight before being concentrated under vacuum. The crude product was purified by flash chromatography (Isolute silica gel cartridge: 50 g; eluent: dichloromethane/methanol=95/5%). 250 mg (1.31 mmol) of the desired compound were obtained.

The following intermediates were synthesized in analogy to Intermediates 8a and 9a.

| Starting amine | Starting bromide | Intermediate | STRUCTURE | Intermediate | STRUCTURE |
|---|---|---|---|---|---|
| (S)-1-Pyrrolidin-3-ylmethyl-carbamic acid tert-butyl ester | bromobenzene | 8b | 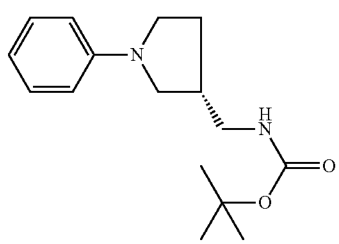 [SMILES: CC(C)(C)OC(=O)NC[C@H]1CCN(c2ccccc2)C1] | 9b | 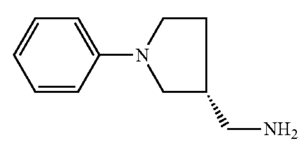 |
| (R)-1-Pyrrolidin-3-ylmethyl-carbamic acid tert-butyl ester | bromobenzene | 8c | 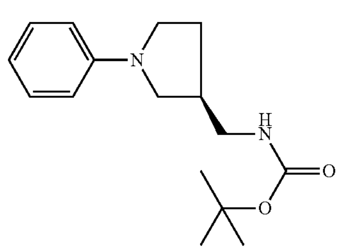 [SMILES: CC(C)(C)OC(=O)NC[C@@H]1CCN(c2ccccc2)C1] | 9c | 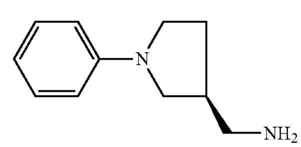 |

-continued

| Starting amine | Starting bromide | Intermediate | STRUCTURE | Intermediate | STRUCTURE |
|---|---|---|---|---|---|
| Piperidine-3-yl-methyl-carbamic acid tert-butyl ester | 1-bromo-4-trifluoromethyl-benzene | 8d | 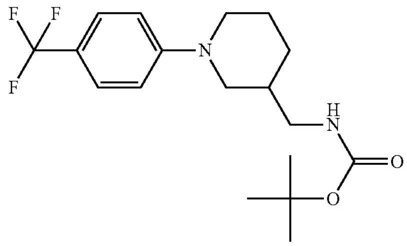 [SMILES: CC(C)(C)OC(=O)NCC1CCCN(c2ccc(C(F)(F)F)cc2)C1] | 9d | 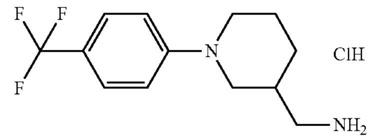 |

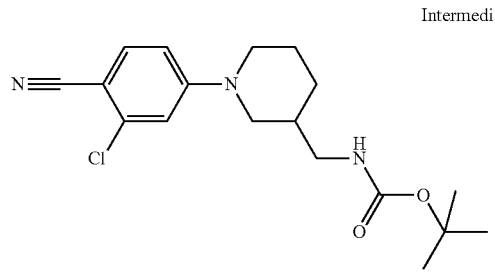

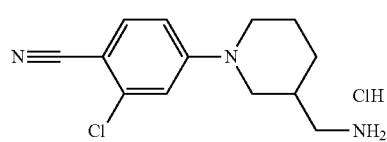

Intermediate 10

Piperidine-3-yl-methyl-carbamic acid tert-butyl ester (100 mg, 0.47 mmol), 2-chloro-4-fluoro-benzonitrile (72.5 mg, 0.47 mmol) and N,N-diisopropylethylamine (0.160 ml, 1.23 mmol) were dissolved in 10 ml of DMF and the reaction mixture was stirred at 125° C. overnight. The reaction mixture was concentrated under vacuum and the crude product was purified by flash chromatography (Isolute silica gel cartridge: 5 g; eluent: ethyl acetate). 125 mg (0.36 mmol) of the desired compound were obtained.

Intermediate 11

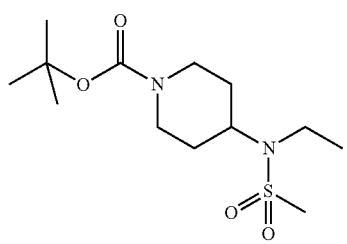

To a solution of Intermediate 10 (125 mg, 0.36 mmol) in 5 ml of 1,4-dioxane, a 4M solution of hydrochloric acid in 1,4-dioxane (0.12 ml, 480 mmol) was added dropwise; the reaction mixture was stirred at room temperature overnight before being concentrated under vacuum. 102 mg (0.36 mmol) of the desired compound were obtained.

Intermediate 12

A solution of 4-methanesulfonylamino-piperidine-1-carboxylic acid tert-butyl ester (500 mg; 1.79 mmol) in 5 ml of acetonitrile was cooled to −5° C., iodoethane (308 mg, 1.79 mmol) and sodium hydride (96 mg, 3.59 mmol) were added; the reaction mixture was allowed to warm to room temperature and stirred for 72 h.

The reaction mixture was concentrated under vacuum; the residue was dissolved in ethyl acetate and washed with an aqueous saturated sodium bicarbonate solution and then with water.

The organic phase was dried over sodium sulfate, filtered and concentrated under vacuum. The crude product was purified by flash chromatography (Isolute silica gel cartridge: 10 g, eluent: dichloromethane) to obtain 332 mg (1.1 mmol) of the desired compound.

Intermediate 13

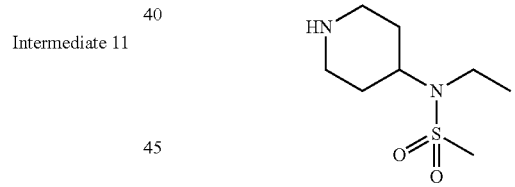

To a solution of intermediate 12 (330 mg, 1.1 mmol) in 20 ml of 1,4-dioxane, a 4M solution of hydrochloric acid in 1,4-dioxane (4.06 ml, 16 mmol) was added dropwise; the reaction mixture was stirred at room temperature overnight. The reaction mixture was concentrated under vacuum to obtain 262 mg (1.1 mmol) of the desired compound.

Intermediate 14

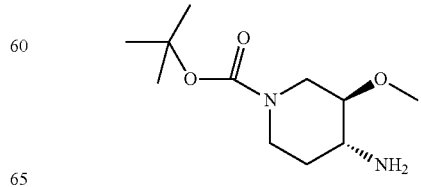

trans-4-Azido-3-methoxy-piperidine-1-carboxylic acid tert-butyl ester (1.6 g, 6.24 mmol), Pd/C 10% (200 mg) and acetic acid (1.6 ml) were dissolved in 25 ml of methanol and the reaction mixture was stirred under hydrogen atmosphere (4 bar) for 3 h. The reaction mixture was filtered on a celite pad and concentrated under vacuum. The crude product was purified by flash chromatography (Biotage SP1 cartridge 65i, eluent: dichloromethane/methanol=95/5%). 900 mg (3.91 mol) of the desired compound were obtained.

Intermediate 15a

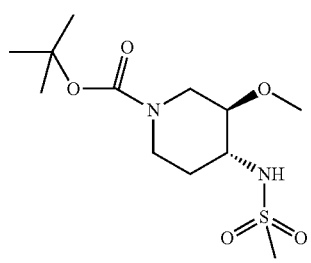

Intermediate 14 (900 mg, 3.91 mmol) and N,N-diisopropylethylamine (0.86 ml, 5 mmol were dissolved in 25 ml of dichloromethane. The reaction mixture was cooled to 0° C. and methanesulfonylchloride (0.33 ml, 4.30 mmol) was added. The reaction mixture was stirred at 0° C. for 20 min, then, water was added. The organic phase was separated, washed with an aqueous saturated sodium bicarbonate solution, dried over sodium sulfate and concentrated under vacuum. The crude product was purified by flash chromatography (Isolute silica cartridge: 10 g, eluent: hexane/ethyl acetate=50/50%). 170 mg (0.55 mol) of the desired compound were obtained.

Intermediate 15b

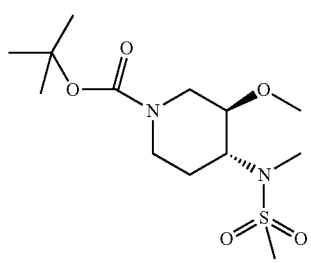

Intermediate 15a (350 mg, 1.13 mmol) and potassium carbonate (157 mg, 1.13 mmol) were dissolved and stirred in 15 ml of acetonitrile. A solution of iodomethane (0.071 ml, 1.13 mmol) in 5 ml of acetonitrile was added dropwise and the reaction mixture was warmed to 60° C. overnight. The reaction mixture was concentrated under vacuum and the crude product was dissolved in ethyl acetate. The organic phase was washed with an aqueous saturated sodium bicarbonate solution, separated, dried over sodium sulfate and concentrated under vacuum. 300 mg (0.93 mmol) of the desired compound were obtained and used in the next steps without further purification.

Intermediate 16a

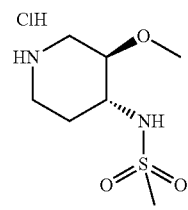

Intermediate 15a (170 mg, 0.55 mmol) in 2 ml of 1,4-dioxane was stirred at 10° C. A 4M solution of hydrochloric acid in 1,4-dioxane (8 ml, 32 mmol) was added dropwise and the reaction mixture was stirred at room temperature for 5 h. The reaction mixture was concentrated under vacuum to obtain 115 mg (0.55 mmol) of the desired compound.

Intermediate 16b

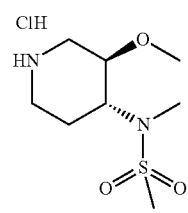

was synthesized in analogy to Intermediate 16a, starting from Intermediate 15b.

Intermediate 17

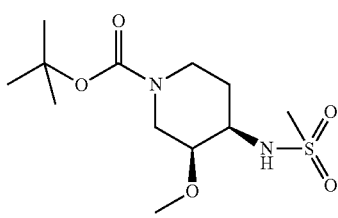

was synthesized in analogy to Intermediate 15a, starting from (3S,4R)-4-amino-3-methoxy-piperidine-1-carboxylic acid tert-butyl ester.

Intermediate 18

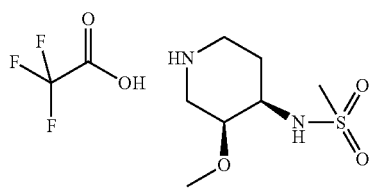

Intermediate 17 (660 mg, 2.14 mmol) in 10 ml of 1,4-dioxane was stirred at 10° C. Trifluoroacetic acid (2 ml, 26 mmol) was added dropwise and the reaction mixture was stirred at room temperature 18 h. The reaction mixture was concentrated under vacuum to obtain 600 mg (1.86 mmol) of the desired compound, used in the next step without further purification.

Intermediate 19a

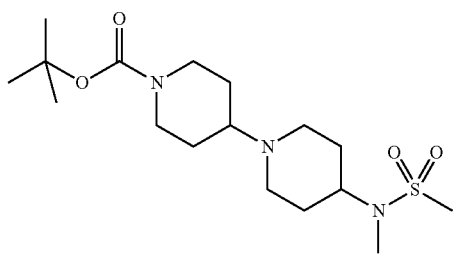

N-methyl-N-piperidin-4-yl-methanesulfonamide hydrochloride (11 g, 47.91 mmol) was suspended in 200 ml of 1,2-dichloroethane, N,N-diisopropylethylamine (17.12 ml, 96.17 mmol) and 1-(tert-butoxycarbonyl)-piperidin-4-one (9.58 g, 48.08 mmol) were added and the reaction mixture was stirred at room temperature for 30 min Sodium triacetoxyborohydride (12.23 g, 57.50 mmol) was added and the reaction mixture was stirred at room temperature for 72 h. The reaction mixture was diluted with dichloromethane and washed with an aqueous saturated sodium bicarbonate solution. The organic phase was dried over sodium sulfate and concentrated under vacuum. The crude product was purified by flash chromatography (Biotage SP1; silica gel cartridge: 65i; eluent: ethyl acetate/methanol=50/50%) to obtain 7.2 g (19.2 mmol) of the desired compound.

Intermediate 20a

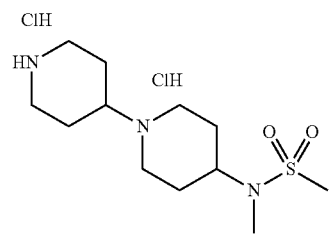

Intermediate 19a (7.2 g, 19.2 mmol) was suspended in 20 ml of 1,4-dioxane, a 4M solution of hydrochloric acid (48 ml, 192 mmol) in 1,4-dioxane was added dropwise. The reaction mixture was stirred at room temperature overnight. The reaction mixture was concentrated under vacuum. 6.3 g (18 mmol) of the desired compound were obtained.

The following intermediates were synthesized in analogy to Intermediates 19a and 20a.

| Starting ketone | Starting amine | Carbamate Intermediate | STRUCTURE | Diamino Intermediate | STRUCTURE |
|---|---|---|---|---|---|
| 1-(tert-butoxycarbonyl)-4-oxo-piperidine | Ethanesulfonic acid methyl-piperidin-4-yl-amide | 19b | | 20b | |
| 1-(tert-butoxycarbonyl)-4-oxo-piperidine | (R)-N-Pyrrolidin-3-yl-methanesulfonamide | 19c | | 20c | |
| 1-(tert-butoxycarbonyl)-4-oxo-piperidine | (S)-N-Pyrrolidin-3-yl-methanesulfonamide | 19d | | 20d | |

| Starting ketone | Starting amine | Carbamate Intermediate | STRUCTURE | Diamino Intermediate | STRUCTURE |
|---|---|---|---|---|---|
| 1-(tert-butoxy-carbonyl)-4-oxo-piperidine | Ethane-sulfonic acid piperidin-4-yl-amide | 19e | | 20e | |
| 1-(tert-butoxy-carbonyl)-4-oxo-piperidine | Piperidine-4-carboxylic acid methyl amide | 19f | | 20f | |
| 1-(tert-butoxy-carbonyl)-4-oxo-piperidine | Piperidine-4-sulfonic acid methyl amide | 19g | | 20g | |
| 1-(tert-butoxy-carbonyl)-4-oxo-piperidine | (R)-Pyrrolidine-3-carboxylic acid methylamide | 19h | | 20h | |
| 1-(tert-butoxy-carbonyl)-4-oxo-piperidine | (S)-Pyrrolidine-3-carboxilic acid methylamide | 19i | | 20i | |
| 1-(tert-butoxy-carbonyl)-4-oxo-piperidine | (S)-Pyrrolidine-3-carboxilic acid amide | 19j | | 20j | |

-continued

| Starting ketone | Starting amine | Carbamate Intermediate | STRUCTURE | Diamino Intermediate | STRUCTURE |
|---|---|---|---|---|---|
| 1-(tert-butoxy-carbonyl)-4-oxo-piperidine | 16a | 19k | | 20k | |
| 1-(tert-butoxy-carbonyl)-4-oxo-piperidine | (R)-Pyrrolidine-3-carboxilic acid amide | 19l | | 20l | |
| 1-(tert-butoxy-carbonyl)-4-oxo-piperidine | 47b | 19lf | | 20lf | |
| 1-(tert-butoxy-carbonyl)-4-oxo-piperidine | 47c | 19lg | | 20lg | |

Intermediate 191a

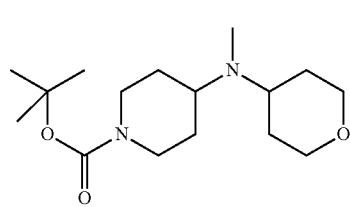

4-Methylamino-piperidine-1-carboxylic acid tert-butyl ester (500 mg, 1.87 mmol) was suspended in 10 ml of 1,2-dichloroethane. Tetrahydro-pyran-4-one (0.17 ml, 1.87 mmol) was added and the reaction mixture was stirred at room temperature for 30 min Sodium triacetoxyborohydride (593 mg, 2.80 mol) was added and the reaction mixture was stirred for 18 h. The reaction mixture was diluted with dichloromethane and washed with an aqueous saturated sodium bicarbonate solution.

The organic phase was dried over sodium sulfate and concentrated under vacuum. The crude product was purified by flash chromatography (Isolute silica gel cartridge 10 g; eluent: dichloromethane/methanol=94/6%). 240 mg (0.80 mmol) of the desired compound were obtained.

Intermediate 201a

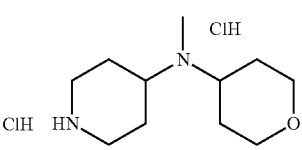

Intermediate 191a (240 mg, 0.80 mmol) was suspended in 10 ml of 1,4-dioxane, a 4M solution of hydrochloric acid (2.0 ml, 8.0 mmol) in 1,4-dioxane was added dropwise. The reaction mixture was stirred at room temperature for 18 h. The reaction mixture was concentrated under vacuum. 200 mg (0.74 mmol) of the desired compound were obtained.

The following intermediates were synthesized in analogy to Intermediates 191a and 201a

| Starting amine | Starting ketone | Carbamate Intermediate | STRUCTURE | Amino Intermediate | STRUCTURE |
|---|---|---|---|---|---|
| 4-Methyl-amino-piperidine-1-carboxylic acid tert-butyl ester | 3-Methoxy-tetra-hydro-pyran-4-one | 19lb | | 20lb | |
| 4-Methyl-amino-piperidine-1-carboxylic acid tert-butyl ester | 2,6-dimethyl-tetra-hydro-pyran-4-one | 19lc | | 20lc | |
| 4-Methyl-amino-piperidine-1-carboxylic acid tert-butyl ester | 4,4-difluoro-cyclo-hexanone | 19ld | | 20ld | |
| 4-amino-piperidine-1-carboxylic acid tert-butyl ester | 3-Methoxy-tetra-hydro-pyran-4-one | 19le | | 20le | |

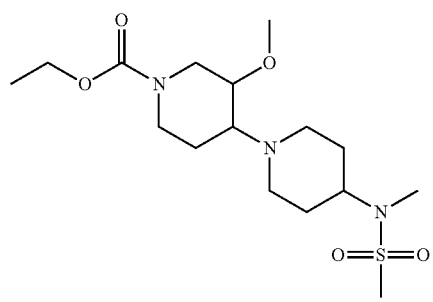

Intermediate 19m

N-methyl-N-piperidin-4-yl-methanesulfonamide hydrochloride (1.13 g, 4.95 mmol) was suspended in 10 ml of 1,2-dichloroethane, N,N-diisopropylethylamine (2.6 ml, 14.9 mmol) and N-carbethoxy-3-methoxy-piperidin-4-one (1 g, 4.95 mmol) were added and the reaction mixture was stirred at room temperature for 30 min Sodium triacetoxyborohydride (3.16 g, 14.85 mol) was added and the reaction mixture was stirred at room temperature for 72 h. The reaction mixture was diluted with dichloromethane and washed with an aqueous saturated sodium bicarbonate solution.

The organic phase was dried over sodium sulfate and concentrated under vacuum. 1.5 g (3.97 mmol) of the desired compound were obtained and used without further purification.

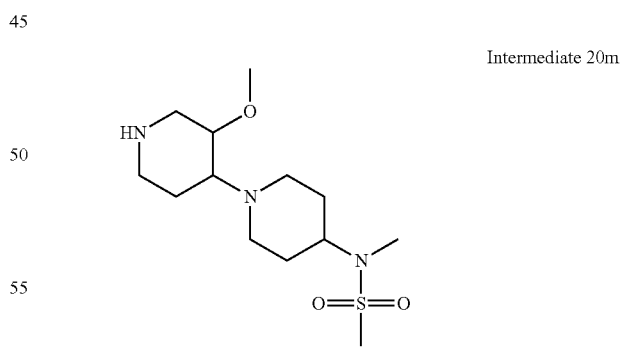

Intermediate 20m

Intermediate 19m (1.5 g, 3.97 mmol) and potassion hydroxide (4.46 g, 7.94 mmol) were suspended in 25 ml of ethanol and the reaction mixture was stirred under reflux overnight.

The reaction mixture was concentrated under vacuum and the crude product was loaded on a SCX cartridge (25 g) and eluted with a 2M solution of ammonia in methanol. 1.2 g (3.97 mmol) of the desired compound were obtained.

Intermediate 21

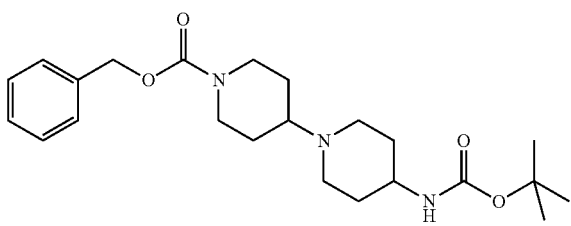

Piperidin-4-yl-carbamic acid tert-butyl ester (6 g, 30 mmol) and 1-(benzyloxycarbonyl)-4-oxopiperidine (9.6 g, 48 mmol) were dissolved in 50 ml of dichloromethane and the reaction mixture was stirred at room temperature for 30 min; sodium triacetoxyborohydride (12.23 g, 57.5 mmol) was added and the reaction mixture was stirred at room temperature overnight.

The reaction mixture was diluted with dichloromethane and washed with an aqueous saturated sodium bicarbonate solution. The organic phase was dried over sodium sulfate and concentrated under vacuum. The crude product was treated with acetone/isopropyl ether and the precipitate obtained was filtered off. 8.4 g (20 mmol) of the desired product were obtained.

Intermediate 22

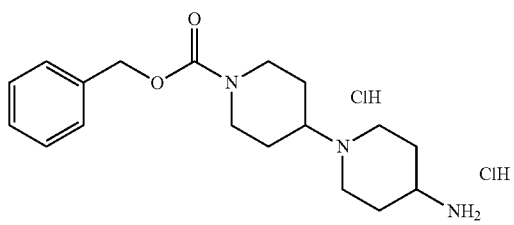

To a solution of intermediate 21 (8.4 g, 20 mmol) in 150 ml of 1,4-dioxane previously cooled to 0° C., 12.6 ml (50 mmol) of a 4M solution of hydrochloric acid in 1,4-dioxane were added dropwise; the reaction mixture was allowed to warm to room temperature and was stirred at that temperature overnight. The solid precipitated from the reaction mixture was filtered off and dried at 50° C. under vacuum to obtain 6 g (15 mmol) of the desired compound.

Intermediate 23

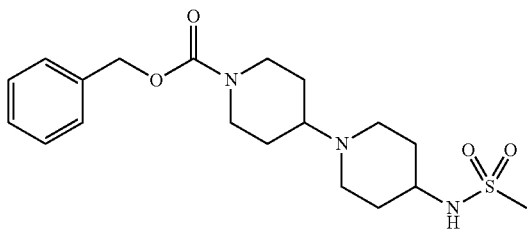

Intermediate 22 (6.0 g, 15 mmol) was suspended in 55 ml of dichloromethane; triethylamine (6.43 ml, 46 mmol) was added and the reaction mixture was cooled to 0° C. and stirred at that temperature for 30 min Methanesulfonyl chloride (1.43 ml, 18 mmol) in 5 ml of dichloromethane was added dropwise. The reaction mixture was stirred at 0° C. for 1 h; then water was added and the reaction mixture was extracted with dichloromethane. The organic phase was washed with an aqueous saturated sodium bicarbonate solution, with brine, dried over sodium sulfate and concentrated under vacuum. The crude product was treated with diisopropyl ether, the precipitate was filtered off and dried. 5 g (13 mmol) of the desired product were obtained.

Intermediate 24

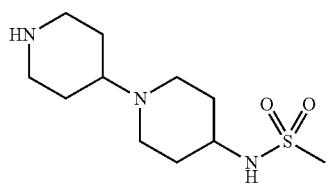

Intermediate 23 (5 g, 13 mmol) was dissolved in 50 ml of methanol; acetic acid (1.5 ml, 25.3 mmol) and Pd/C 10% (500 mg) were added in sequence and the reaction mixture was stirred under a hydrogen atmosphere (3 bar) at room temperature for 5 days. The reaction mixture was filtered on a celite pad and the organic phase was loaded on a SCX cartridge (10 g). After washing with methanol, the desired compound was eluted with a 2M solution of ammonia in methanol. 3.7 g (4.6 mmol) of the title compound were obtained.

Intermediate 25a

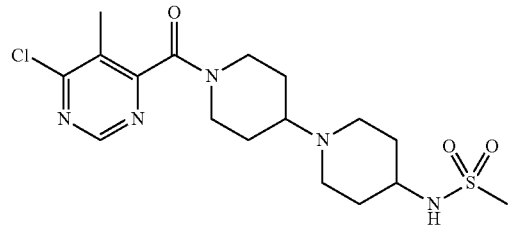 [SMILES: Cc1nc(Cl)c(C)c(C(=O)N2CCC(N3CCC(NS(C)(=O)=O)CC3)CC2)n1]

Intermediate 24 (1.1 g, 4.21 mmol) was suspended in 20 ml of dry dichloromethane, N,N-diisopropylethylamine (1.47 ml, 8.42 mmol) and DMF (137 µl, 1.67 mmol) were added and the reaction mixture was stirred under nitrogen atmosphere and cooled to 0° C. Intermediate 2a (812 mg, 4.21 mmol) in 5 ml of dichloromethane was added dropwise and the reaction mixture was allowed to warm up to room temperature and stirred for 1.5 h; the reaction mixture was diluted with dichloromethane and washed with an aqueous saturated sodium bicarbonate solution. The organic phase was separated, dried over sodium sulfate and concentrated under vacuum. The crude product was purified by flash chromatography (isolute silica gel cartridge: 10 g; eluent: dichloromethane/methanol=95/5%). 1.0 g (2.41 mmol) of the title compound were obtained.

The following intermediates were synthesized in analogy to Intermediate 25a.

| Core Intermediate | Piperidine Intermediate | Chloropyrimidine Intermediate | STRUCTURE |
|---|---|---|---|
| 2a | 20a | 25b | |
| 2a | 20b | 25c | |
| 2a | 20f | 25d | |
| 2a | 20h | 25e | |
| 2a | [1,4']-Bipiperidinyl-4-ol | 25f | |
| 2a | 4-Methoxy-[1,4']bipiperidinyl | 25g | |

-continued

| Core Intermediate | Piperidine Intermediate | Chloropyrimidine Intermediate | STRUCTURE |
|---|---|---|---|
| 2a | 4-Piperidin-4-yl-morpholine | 25h | |
| 2a | [1,4']Bi-piperidinyl | 25i | |
| 2a | [1,4']-Bi-piperidinyl-3-ol | 25j | |
| 2b | 24 | 25k | |
| 2b | 20a | 25l | |
| 2b | [1,4']-Bi-piperidinyl-4-ol | 25m | |

-continued

| Core Intermediate | Piperidine Intermediate | Chloro-pyrimidine Intermediate | STRUCTURE |
|---|---|---|---|
| 2c | 20a | 25n | 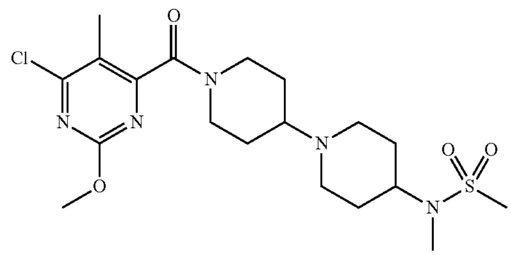 [SMILES: COc1nc(Cl)c(C)c(C(=O)N2CCC(N3CCC(N(C)S(C)(=O)=O)CC3)CC2)n1] |
| 2a | 20le | 25o | 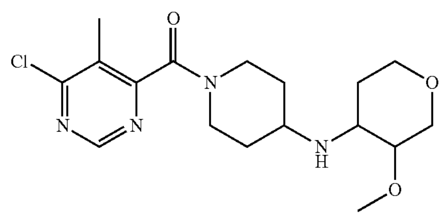 [SMILES: COC1COCCC1NC1CCN(C(=O)c2ncnc(Cl)c2C)CC1] |

Intermediate 26a

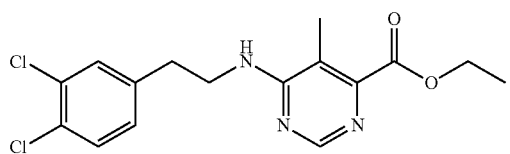

Intermediate 27a

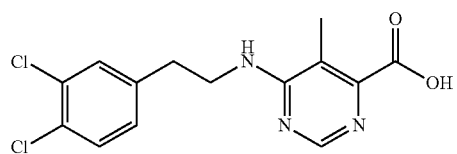

Intermediate 3a (10 g, 49.35 mmol) and N,N-diisopropylethylamine (17 ml, 99 mmol) were dissolved in 20 ml of dry DMF; 2-(3,4-dichloro-phenyl)-ethylamine (9.57 g, 49.35 mmol) in 10 ml of dry DMF was added and the reaction mixture was stirred at 90° C. for 2 h. The reaction mixture was cooled to room temperature, water was added and the reaction mixture was extracted with dichloromethane; the organic phase was concentrated under vacuum, the crude product was suspended and stirred in diethyl ether and the precipitate was filtered off and dried. 10.2 g (28.8 mmol) of the desired compound were obtained.

Intermediate 26a (10.0 g, 28.25 mmol) was dissolved in 70 ml of ethanol and a solution of LiOH (3.52 g, 83.88 mmol) in 70 ml of water was added. The reaction mixture was stirred at 70° C. for 1 hour, concentrated under vacuum and the remaining aqueous solution was acidified by 20 ml of 4M solution of hydrochloric acid in 1,4-dioxane; the precipitate formed was filtered off and dried. 8.6 g (26.37 mmol) of the desired product were obtained.

The following intermediates were synthesized in analogy to Intermediates 26a and 27a.

| Core Intermediate | Amine | Ester Intermediate | STRUCTURE | Acid Intermediate | STRUCTURE |
|---|---|---|---|---|---|
| 3a | 3,4-Dichloro-benzyl-amine | 26b | 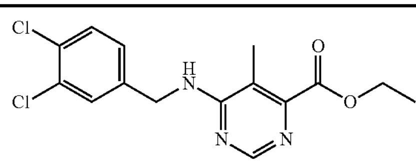 | 27b | 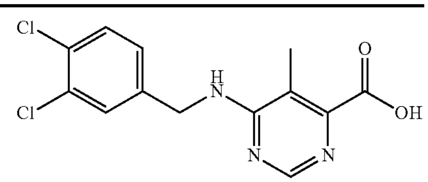 |
| 3b | 4-tert-butyl-benzyl-amine | 26c | 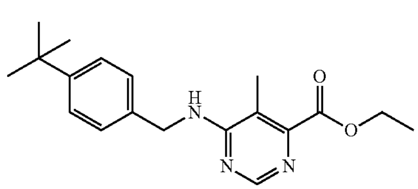 [SMILES: CCOC(=O)c1ncnc(NCc2ccc(C(C)(C)C)cc2)c1C] | 27c | 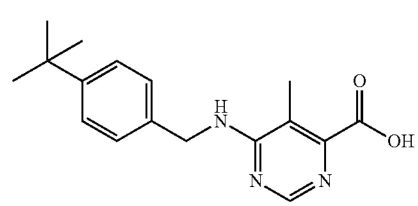 [SMILES: Cc1c(NCc2ccc(C(C)(C)C)cc2)ncnc1C(=O)O] |

| Core Intermediate | Amine | Ester Intermediate | STRUCTURE | Acid Intermediate | STRUCTURE |
|---|---|---|---|---|---|
| 3a | biphenyl-3-ylmethanamine | 26d | 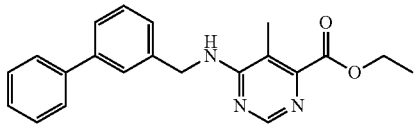 [SMILES: CCOC(=O)c1ncnc(NCc2cccc(-c3ccccc3)c2)c1C] | 27d | 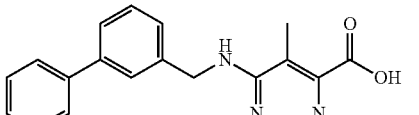 |
| 3b | 4-tert-butyl-benzyl-amine | 26e | 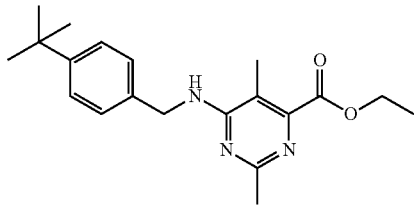 [SMILES: CCOC(=O)c1nc(C)nc(NCc2ccc(C(C)(C)C)cc2)c1C] | 27e | 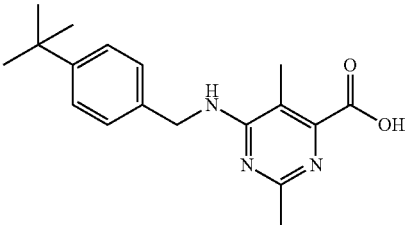 [SMILES: Cc1nc(NCc2ccc(C(C)(C)C)cc2)c(C)c(C(=O)O)n1] |
| 3c | 2-(3,4-dichloro-phenyl)-ethyl-amine | 26f | 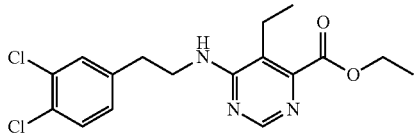 [SMILES: CCOC(=O)c1ncnc(NCCc2ccc(Cl)c(Cl)c2)c1CC] | 27f | 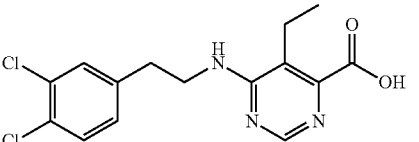 |
| 3c | biphenyl-3-yl-methan-amine | 26g | 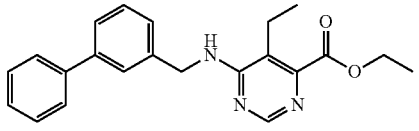 [SMILES: CCOC(=O)c1ncnc(NCc2cccc(-c3ccccc3)c2)c1CC] | 27g | 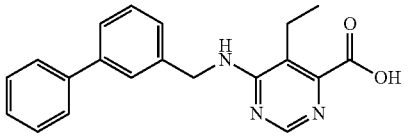 [SMILES: CCc1c(NCc2cccc(-c3ccccc3)c2)ncnc1C(=O)O] |
| 3d | biphenyl-3-yl-methan-amine | 26h | 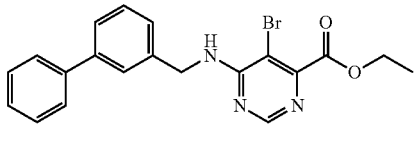 [SMILES: CCOC(=O)c1ncnc(NCc2cccc(-c3ccccc3)c2)c1Br] | 27h | 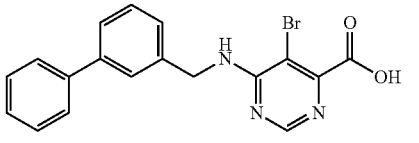 [SMILES: O=C(O)c1ncnc(NCc2cccc(-c3ccccc3)c2)c1Br] |
| 3a | Intermediate 7c | 26ha | 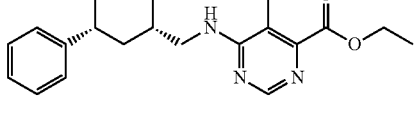 | 27ha | 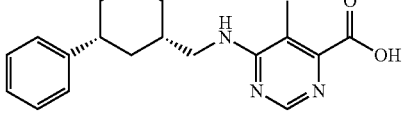 |
| 3d | Intermediate 7c | 26hb | 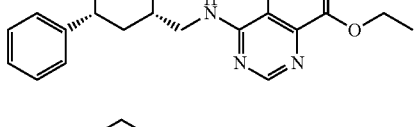 | 27hb | 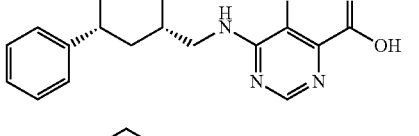 |
| 3a | Intermediate 7p | 26hc | 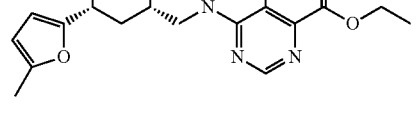 | 27hc | 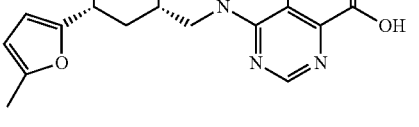 |
| 3a | Intermediate 7q | 26hd | 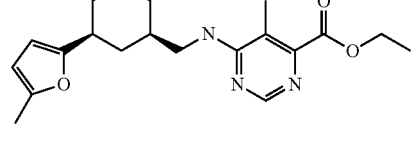 | 27hd | 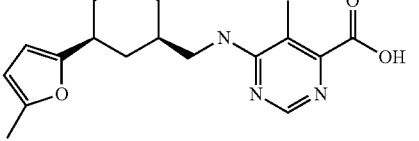 |

| Core Intermediate | Amine | Ester Intermediate | STRUCTURE | Acid Intermediate | STRUCTURE |
|---|---|---|---|---|---|
| 3a | Intermediate 7t | 26he | | 27he | |
| 3a | Intermediate 7v | 26hf | | 27hf | |
| 3b | Intermediate 7t | 26hr | | 27hr | |
| 3b | Intermediate 7v | 26hs | | 27hs | |

Intermediate 26i

Intermediate 3d (2 g, 7.53 mmol) and N,N-diisopropylethylamine (1.97 ml, 11.3 mmol) were dissolved in 15 ml of dry DMF; 4-tertbutyl-benzylamine (1.6 ml, 9.04 mmol) was added and the reaction mixture was stirred at 60° C. for 18 h. The reaction mixture was cooled to room temperature, water was added and the reaction mixture was extracted with dichloromethane; the organic phase was concentrated under vacuum and the crude product was purified by flash chromatography (BIOTAGE SP1; silica gel cartridge: 65i; eluent: hexane/ethyl acetate=70/30%). 1.5 g (3.82 mmol) of the desired compound were obtained.

Intermediate 26ib

Intermediate 26hb (75 mg, 179 μmol), tributyl(vinyl)tin (200 μl, 685 μmol) and bis(triphenylphosphine)palladium chloride (13 mg, 18 μmol) were added to 3 ml 1,2-dichloroethane. The reaction mixture was heated in the microwave for 4 h at 120° C. Then, the solvent was removed in vacuum and the residue was purified by reversed phase HPLC to give the desired product (56 mg, 117 mmol).

Intermediate 26ic

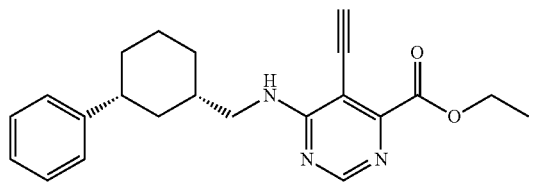

was synthesized in analogy to intermediate 26ib, starting from intermediate 26hb and tributyl(ethynyl)tin.

Intermediate 27i

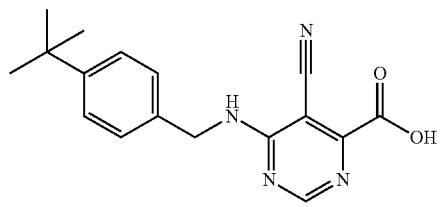

Intermediate 26i (500 mg, 1.27 mmol) and CuCN (114 mg, 1.27 mmol) were dissolved in 5 ml of DMA and the reaction mixture was stirred at 100° C. overnight. The reaction mixture was cooled, diluted with dichloromethane and the organic phase was washed with water, dried over sodium sulfate and concentrated under vacuum. 30 mg (0.1 mmol) of the crude product were obtained and used in the next step without purification.

Intermediate 27ib

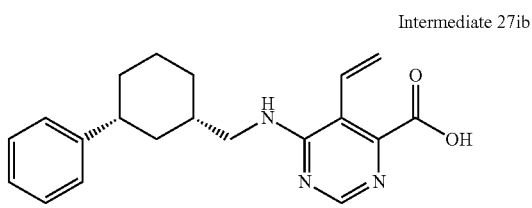 [SMILES: C=Cc1c(NC[C@H]2CCC[C@@H](c3ccccc3)C2)ncnc1C(=O)O]

was synthesized in analogy to 27a starting from intermediate 26ib.

Intermediate 27ic

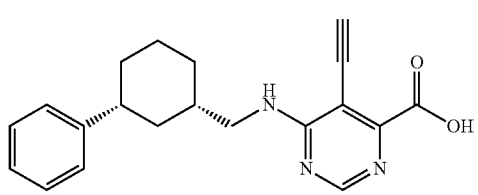

was synthesized in analogy to 27a starting from intermediate 26ic.

Intermediate 28a

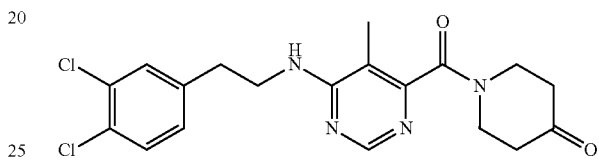

Intermediate 27a (4 g, 12.14 mmol), TBTU (3.9 g, 12.14 mmol) and N,N-diisopropylethylamine (5.34 ml, 30.35 mmol) were dissolved in 25 ml of DMF. The reaction mixture was stirred under nitrogen atmosphere at room temperature for 30 min; then piperidin-4-one hydrochloride (1.66 g, 12.14 mmol) was added and the reaction mixture was stirred at room temperature overnight. The reaction mixture was concentrated under vacuum and the crude product was dissolved in dichloromethane. The organic phase was washed with a saturated aqueous solution of sodium bicarbonate, with a 1M aqueous solution of sodium hydroxide, with brine, then dried over sodium sulfate, filtered and concentrated under vacuum. The crude product was purified by flash chromatography (BIOTAGE SP1; silica gel cartridge: 65i; eluent: dichloromethane/methanol=95/5%). 2.2 g (5.4 mmol) of the desired compound were obtained.

The following intermediates were synthesized in analogy to intermediate 28a.

| Acid Intermediate | Amine | Intermediate | STRUCTURE |
|---|---|---|---|
| 27b | Piperidin-4-one | 28b | 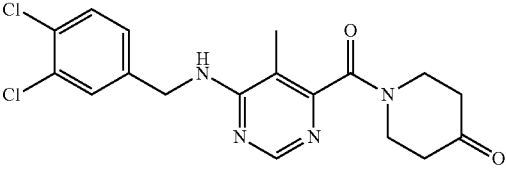 [SMILES: Cc1c(NCc2ccc(Cl)c(Cl)c2)ncnc1C(=O)N1CCC(=O)CC1] |
| 27c | Piperidin-4-one | 28c | 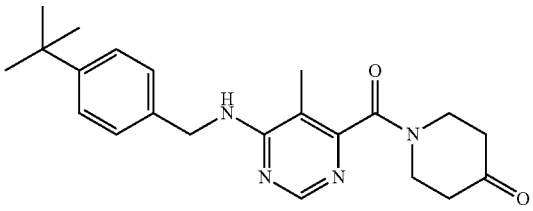 [SMILES: Cc1c(NCc2ccc(C(C)(C)C)cc2)ncnc1C(=O)N1CCC(=O)CC1] |

-continued

| Acid Intermediate | Amine | Intermediate | STRUCTURE |
|---|---|---|---|
| 27d | Piperidin-4-one | 28d | 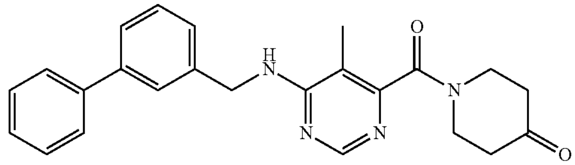 [SMILES: Cc1c(NCc2cccc(-c3ccccc3)c2)ncnc1C(=O)N1CCC(=O)CC1] |
| 27g | Piperidin-4-one | 28e | 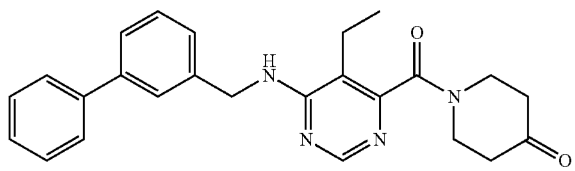 [SMILES: CCc1c(NCc2cccc(-c3ccccc3)c2)ncnc1C(=O)N1CCC(=O)CC1] |
| 27c | Azepan-4-one | 28f | 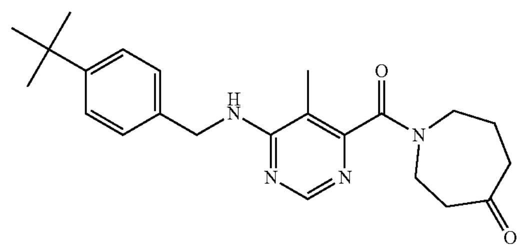 [SMILES: Cc1c(NCc2ccc(C(C)(C)C)cc2)ncnc1C(=O)N1CCCC(=O)CC1] |
| 27e | Piperidin-4-one | 28g | 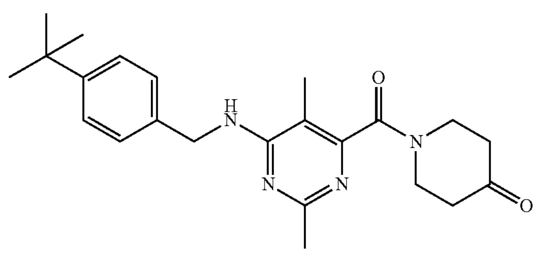 [SMILES: Cc1nc(NCc2ccc(C(C)(C)C)cc2)c(C)c(C(=O)N2CCC(=O)CC2)n1] |

Intermediate 28a (500 mg, 1.22 mmol), piperazine-1-carboxylic acid tert-butyl ester (228 mg, 1.23 mmol) and 2-picoline borane complex (131.3 mg, 1.22 mmol) in 15 ml of methanol were stirred at room temperature for 72 h; the reaction mixture was concentrated under vacuum and the crude product was dissolved in dichloromethane. The organic phase was washed with water, dried over sodium sulfate, filtered and concentrated under vacuum. The crude product was purified by flash chromatography (Isolute silica gel cartridge: 20 g; eluent: dichloromethane/methanol=98/2%). 280 mg (0.48 mmol) of the desired compound were obtained.

Intermediate 29

Intermediate 30

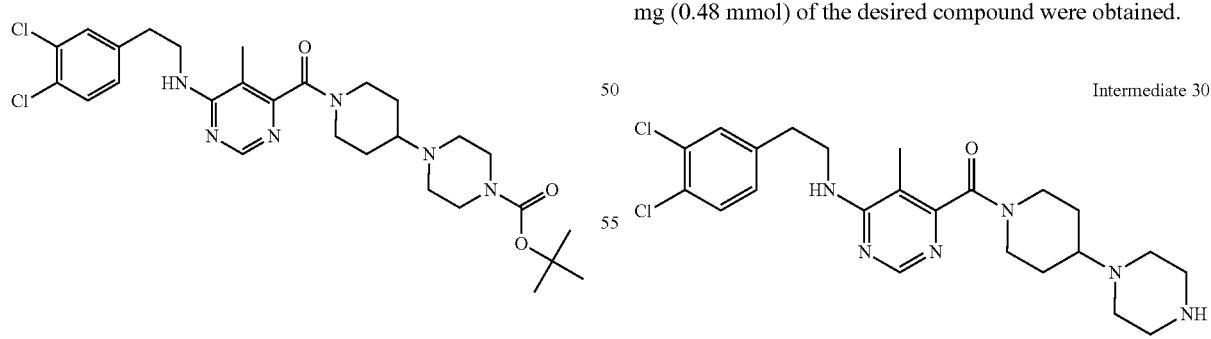

Intermediate 29 (280 mg, 0.48 mmol) was dissolved in 6 ml of 1,4-dioxane; 4 ml (16 mmol of a 4M solution of hydrochloric acid in 1,4-dioxane were added dropwise and the reaction mixture was stirred at room temperature overnight. The solvent was concentrated under vacuum. 240 mg (0.46 mmol) of the desired compound were obtained.

Intermediate 31

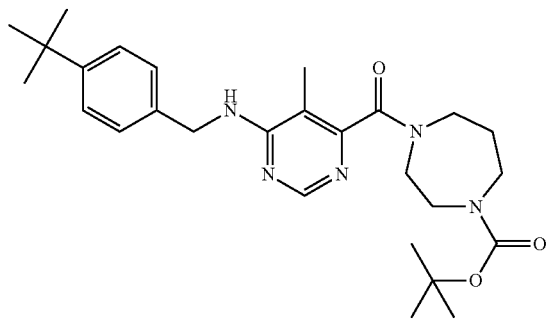

Intermediate 27c (500 mg, 1.67 mmol), TBTU (643 mg, 2 mmol) and N,N-diisopropylethylamine (0.29 ml, 1.67 mmol) were dissolved in 5 ml of DMF. The reaction mixture was stirred under nitrogen atmosphere at room temperature for 10 min; then [1,4]diazepan-1-carboxylic acid tert-butyl ester (334 mg, 1.67 mmol) was added and the reaction mixture was stirred at room temperature overnight. The reaction mixture was diluted with dichloromethane and washed with an aqueous saturated solution of sodium bicarbonate. The organic phase was separated, dried over sodium sulfate and concentrated under vacuum. The crude product was suspended in diisopropyl ether and stirred, the solid obtained was filtered and dried. 700 mg (1.45 mmol) of the desired compound were obtained.

Intermediate 32

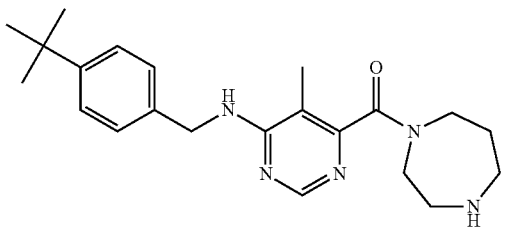

Intermediate 31 (600 mg; 1.24 mmol) was suspended in 5 ml of diethyl ether, 5 ml of a 1M solution of hydrochloric acid in diethyl ether was added dropwise and the reaction mixture was stirred at room temperature overnight. The solvent was concentrated under vacuum and the crude product was loaded on a SCX cartridge (10 g) and eluted with a 2M solution of ammonia in methanol. 470 mg (1.23 mmol) of the title compound were obtained.

Intermediate 33

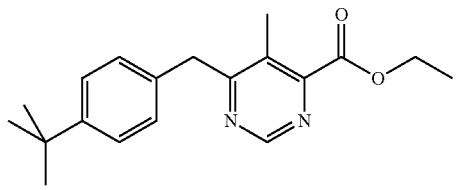

Intermediate 3a (1.5 g, 7.47 mmol) and tetrakis(triphenylphosphine)palladium (143.9 mg, 0.12 mmol) were suspended in 40 ml of toluene under nitrogen atmosphere; 4-tert-butyl-benzylzinc bromide (29.9 ml, 15 mmol) was added dropwise and then the reaction mixture was stirred at 20° C. for 8 h. 5 ml of methanol, 40 ml of water and 100 ml of dichloromethane were added. The organic phase was separated, dried over sodium sulfate and concentrated under vacuum. The crude product obtained was purified by flash chromatography (Biotage column 40M+; eluent: dichloromethane/ethyl acetate=95/5%). 230 mg (0.74 mmol) of the desired compound were obtained.

Intermediate 34

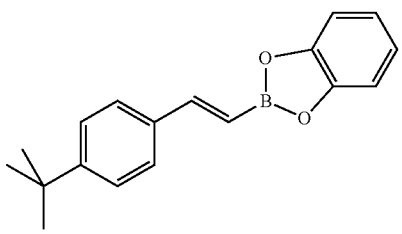

To a solution of 4-tert-butylphenylacetylene (5 ml, 28 mmol) in 20 ml of dry tetrahydrofuran under nitrogen atmosphere, a solution of catecholborane (3.41 ml, 31 mmol) in 20 ml of dry tetrahydrofuran was added dropwise. The reaction mixture was refluxed for 2 h and then concentrated under vacuum; the crude product obtained was dissolved in ethyl acetate and the organic phase was washed with a 2 M aqueous solution of hydrochloric acid. The organic phase was separated, washed with brine, dried over sodium sulfate and concentrated under vacuum. The crude product obtained was purified by flash chromatography (Biotage column 40M+; eluent: dichloromethane/ethyl acetate=95/5%). 230 mg (0.82 mmol) of the desired compound were obtained.

Intermediate 35

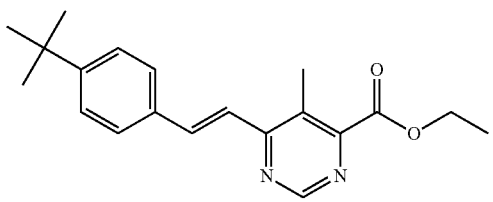

Intermediate 3a (600 mg, 3 mmol), intermediate 34 and tetrakis(triphenylphosphine)palladium (347 mg, 0.3 mmol) were dissolved in 3.6 ml of a 2 M aqueous solution of sodium carbonate and 40 ml of 1,2 dimethoxyethane. The reaction mixture was stirred at 80° C. overnight. Water was added and the reaction mixture was extracted with dichloromethane. The organic phase was separated, dried over sodium sulfate and concentrated under vacuum. The crude product obtained was purified by flash chromatography (Biotage column 40M+; eluent: dichloromethane/ethyl acetate=95/5%). 550 mg (1.60 mmol) of the desired compound were obtained.

Intermediate 36

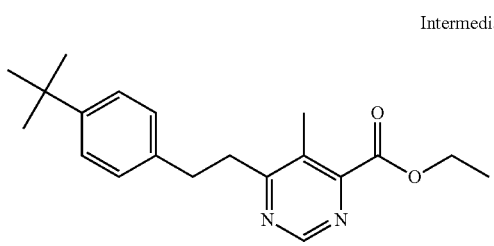

Intermediate 35 (250 mg, 0.77 mmol) was dissolved in 5 ml of ethanol and 5 ml of tetrahydrofuran. Pd/C (35 mg) was added and the reaction mixture was stirred under hydrogen atmosphere (1 atm) at room temperature overnight. The reaction mixture was filtered on a celite pad and concentrated under vacuum. 170 mg (0.52 mmol) of the desired compound were obtained.

Intermediate 37

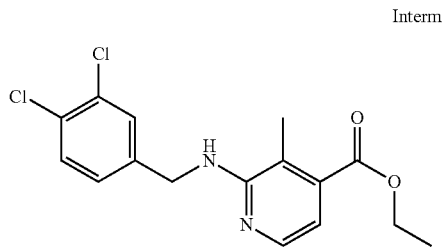

Palladium acetate (170 mg, 0.75 mmol) and 2,2'-bis(diphenylphosphino)-1,1'-binapthyl (936 mg, 1.5 mmol) were dissolved in 25 ml of 1,4-dioxane and stirred at 40° C. for 30 minutes. 2-chloro-3-methylpyridine-4-carboxylic acid ethyl ester (500 mg, 2.5 mmol), 3,4-dichlorobenzylamine (680 mg, 5 mmol) and cesium carbonate (715.5 mg, 3.76 mmol) were added and the reaction mixture was refluxed for 48 h. The solvent was concentrated under vacuum and the crude product was loaded on a SCX cartridge (10 g) and eluted with a 2M solution of ammonia in methanol. The solvent was concentrated under vacuum and the crude product obtained was purified by flash chromatography (Biotage column 25M+; eluent: ethyl acetate). 250 mg (0.73 mmol) of the desired compound were obtained.

Intermediate 38

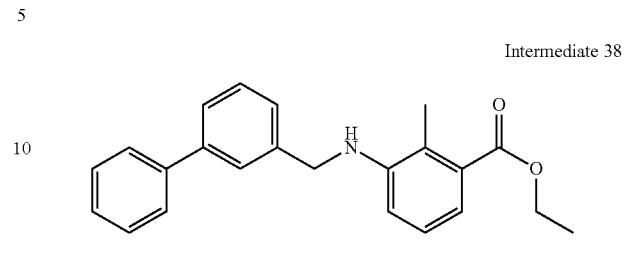

3-(Bromomethyl)biphenyl (150 mg, 0.58 mmol), sodium carbonate (188 mg, 1.75 mmol) and 3-amino-2-methyl-benzoic acid ethyl ester (0.1 ml, 0.58 mmol) were mixed in 2 ml of DMF and stirred at 100° C. for 2 hours. The solvent was then concentrated under vacuum and the crude product was purified by reverse phase preparative HPLC. 131 mg (0.37 mmol) of the desired compound were obtained.

Intermediate 39a

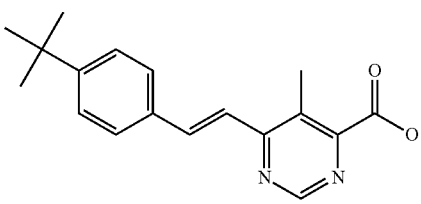

Intermediate 35 (300 mg, 0.92 mmol) was dissolved in 4 ml of ethanol and 4 ml of water. Lithium hydroxide (194 mg, 4.7 mmol) was added and the reaction mixture was stirred at 70° C. for 2 h, concentrated under vacuum and the remaining aqueous solution was acidified by 10 ml of a 4M solution of hydrochloric acid in 1,4-dioxane and extracted with dichloromethane; the organic phase was separated, washed with brine, dried over sodium sulfate and concentrated under vacuum. 250 mg (0.84 mmol) of the desired product were obtained.

The following intermediates were synthesized in analogy to intermediate 39a

| Ester Intermediate | Acid Intermediate | STRUCTURE |
|---|---|---|
| 33 | 39b | 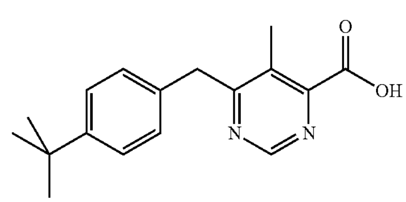 [SMILES: Cc1c(Cc2ccc(C(C)(C)C)cc2)ncnc1C(=O)O] |

| Ester Intermediate | Acid Intermediate | STRUCTURE |
|---|---|---|
| 36 | 39c | 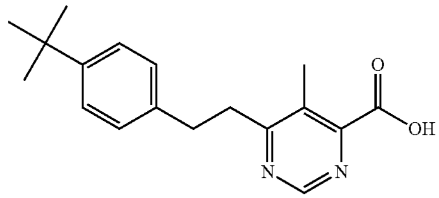 [SMILES: Cc1c(CCc2ccc(C(C)(C)C)cc2)ncnc1C(=O)O] |
| 37 | 39d | 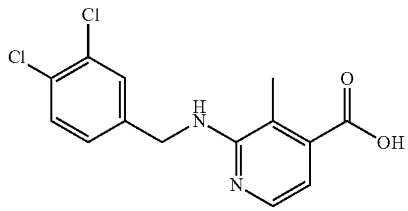 [SMILES: Cc1c(C(=O)O)ccnc1NCc1ccc(Cl)c(Cl)c1] |
| 38 | 39e | 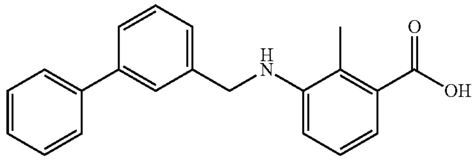 [SMILES: Cc1c(NCc2cccc(-c3ccccc3)c2)cccc1C(=O)O] |

Intermediate 40a

Intermediate 27c (660 mg, 2.20 mmol), TBTU (849 mg, 2.65 mmol) and N,N-diisopropylethylamine (0.57 ml, 3.31 mmol) were dissolved in 25 ml DMF. The reaction mixture was stirred under nitrogen atmosphere at room temperature for 10 min; then piperidin 4-yl carbamic acid tert-butyl ester (441 mg, 2.20 mmol) was added and the reaction mixture was stirred at room temperature for 18 h. The reaction mixture was diluted with dichloromethane and washed with an aqueous saturated solution of sodium bicarbonate. The organic phase was separated, dried over sodium sulfate and concentrated under vacuum. The crude product was purified by flash chromatography (Biotage SNAP column 50 g; eluent: dichloromethane/methanol=90/10%). 990 mg (2.05 mmol) of the desired compound were obtained.

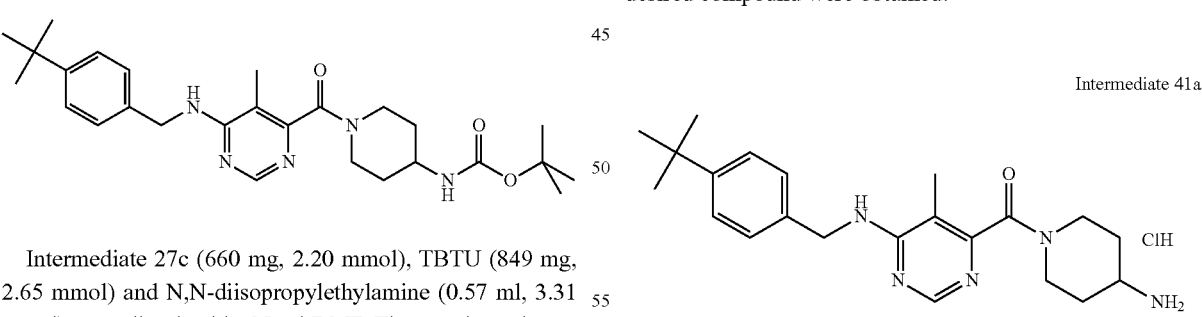

Intermediate 41a

Intermediate 40a (990 mg, 2.05 mmol) was suspended in 50 ml of 1,4-dioxane, a 4M solution of hydrochloric acid (8.5 ml, 34 mmol) in 1,4-dioxane was added dropwise. The reaction mixture was stirred at room temperature for 18 h. The reaction mixture was concentrated under vacuum. 780 mg (18 mmol) of the desired compound were obtained.

The following intermediates were synthesized in analogy to Intermediates 40a and 41a.

| Starting acid | Starting amine | Carbamate Intermediate | STRUCTURE | Amine intermediate | STRUCTURE |
|---|---|---|---|---|---|
| Intermediate 27ha | piperidin 4-yl carbamic acid tert-butyl ester | 40b | 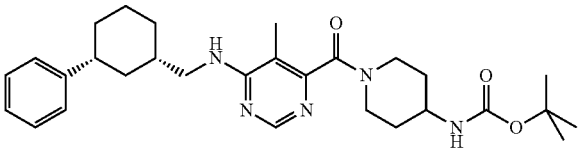 [SMILES: Cc1c(NC[C@H]2CCC[C@@H](c3ccccc3)C2)ncnc1C(=O)N1CCC(NC(=O)OC(C)(C)C)CC1] | 41b | 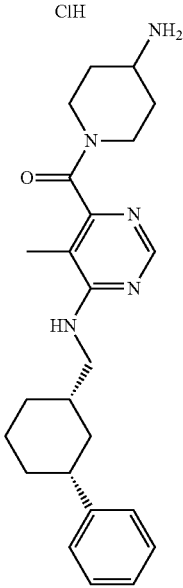 [SMILES: Cl ; Cc1c(NC[C@H]2CCC[C@@H](c3ccccc3)C2)ncnc1C(=O)N1CCC(N)CC1] |

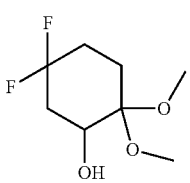

Intermediate 42

4,4-Difluorocyclohexanone (500 mg, 3.73 mmol) and potassium hydroxide (502 mg, 8.95 mmol) were dissolved in 10 ml of methanol. The reaction mixture was cooled to 0° C. and a solution of iodine (1.04 g, 4.10 mmol) in 20 ml of methanol was added dropwise within 1 h. The reaction mixture was stirred at room temperature for 18 h, and then concentrated under vacuum. The crude product was stirred in 10 ml of dichloromethane and the precipitate was filtered off. The filtrate was concentrated under vacuum and 480 mg of the desired product (2.45 mmol) were obtained as an oil.

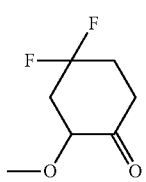

Intermediate 43

Sodium hydride (196 mg, 4.89 mmol) was suspended in 10 ml of tetrahydrofurane. The reaction mixture was cooled to 0° C. and a solution of Intermediate 42 (480 mg, 4.45 mmol) in 5 ml of tetrahydrofurane was added dropwise. The reaction mixture was stirred at 0° C. for 1 h, then iodomethane (0.305 ml, 4.89 mmol) was added. The reaction mixture was stirred at room temperature for 4 h. 0.1 ml of a 37% aqueous solution of hydrochloric acid and 0.1 ml of water were added, then additional 0.3 ml of a 37% aqueous solution of hydrochloric acid were added. The reaction mixture was stirred at room temperature for 18 h. The reaction mixture was concentrated under vacuum and 400 mg (2.44 mmol) of the desired product were obtained as an oil.

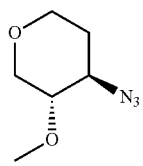

Intermediate 44

Iodomethane (3.48 ml, 55.88 mmol) was dissolved in 250 ml of tetrahydrofurane, the reaction mixture was stirred at 0° C. under nitrogen atmosphere and sodium hydride (60% on mineral oil, 2.23 mg, 5.88 mmol) was added. After 15 minutes, trans 4-azido-tetrahydropyran-3-ol (4.0 g, 27.94 mmol) was added and the reaction mixture was allowed to reach room temperature and stirred for 18 h. 50 ml of water were added, the organic phase was separated, dried over sodium sulphate and concentrated under vacuum. The crude oil obtained was purified by flash chromatography (Biotage SNAP column 100 g; eluent: dichloromethane/ethyl acetate=80/20%). 200 mg (1.27 mmol) of the desired regioisomer were obtained as trans racemate (relative configuration assigned by NMR).

Intermediate 45

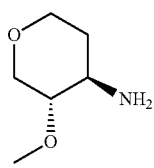

Intermediate 44 (200 mg, 1.27 mmol) was dissolved in 250 ml of methanol, Pd/C (50 mg was added and the reaction mixture was stirred under hydrogen atmosphere (4 bar) for 18 h. The reaction mixture was filtered on a celite pad and the organic phase was concentrated under vacuum. 110 mg (0.84 mmol) of the desired product were obtained as trans racemate.

Intermediate 46a

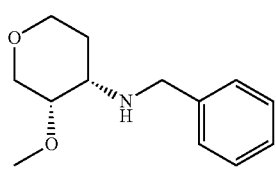

3-Methoxy-tetrahydro-pyran-4-one (500 mg, 3.84 mmol), benzylamine (0.42 ml, 3.84 mmol) and Raney-Nickel (100 mg) were suspended in 20 ml of dry ethanol and the reaction mixture was stirred under hydrogen atmosphere (4.5 bar) for 3 days. The reaction mixture was filtered on a celite pad and the organic phase was concentrated under vacuum. The crude product obtained was dissolved in 10 ml of methanol, loaded on a SCX cartridge (10 g) and eluted with a 2M solution of ammonia in methanol. The solvent was concentrated under vacuum and the crude product obtained was purified by flash chromatography (Isolute cartridge 10 g; eluent: dichloromethane/methanol=96/4%). 163 mg (0.73 mmol) of the desired product were obtained as cis racemate (relative configuration assigned by NMR).

Intermediate 46b

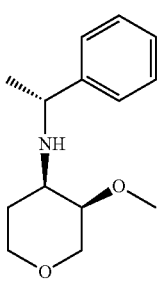

3-Methoxy-tetrahydro-pyran-4-one (1 g, 7.68 mmol), (R)-(+)-1-phenylethylamine (0.99 ml, 7.68 mmol) and Raney-Nickel (200 mg) in 10 ml dry ethanol were stirred under a hydrogen atmosphere (5 bar) for 15 days. The reaction mixture was diluted with 20 ml of methanol and 20 ml of tetrahydrofurane, stirred for 15 minutes, filtered on a celite pad and concentrated under vacuum. The crude product was loaded on a SCX cartridge (50 g). The cartridge was washed with methanol and the desired product was eluted with a 7 M solution of ammonia in methanol. The basic organic phase was concentrated under vacuum and the crude product obtained was purified by flash chromatography (dichloromethane/methanol=98/2%) to obtain 710 mg (3.02 mmol) of the desired product as single stereoisomer (diastereoisomeric purity confirmed and relative cis stereochemistry assigned by NMR).

Intermediate 46c

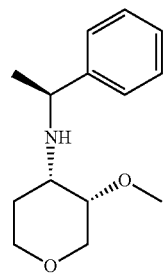

was synthesised in analogy to Intermediate 46b, starting from 3-Methoxy-tetrahydro-pyran-4-one and (S)-(−)-1-phenylethylamine (diastereoisomeric purity confirmed and relative cis stereochemistry assigned by NMR).

Intermediate 47a

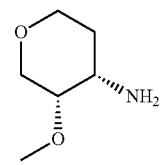

Intermediate 46a (163 mg, 0.73 mmol) was dissolved in 10 ml of methanol, Pd/C (50 mg) was added and the reaction mixture was stirred under hydrogen atmosphere (4.5 bar) for 18 h. The reaction mixture was filtered on a celite pad and the organic phase was concentrated under vacuum. 80 mg (0.61 mmol) of the desired product were obtained as cis racemate.

Intermediate 47b

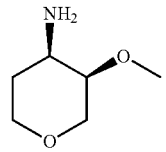

Intermediate 46b (1.18 g, 5.01 mmol), Pd/C 10% (200 mg) and acetic acid (0.3 ml, 5.01 mmol) in 20 ml of methanol were stirred under a hydrogen atmosphere (5 bar) for 18 h. The reaction mixture was diluted with 20 ml of methanol, stirred for 15 minutes, filtered on a celite pad and concentrated under vacuum. The crude product was loaded on a SCX cartridge (50 g). The cartridge was washed with methanol and the desired product was eluted with a 7 M solution of ammonia in methanol. The basic organic phase was concentrated under vacuum and 513 mg (3.91 mmol) of the desired product were obtained as single stereoisomer.

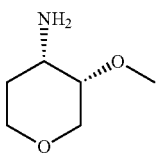
Intermediate 47c was synthesised in analogy to Intermediate 47b, starting from Intermediate 46c

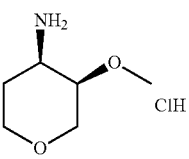
Intermediate 48b

Intermediate 47b was stirred in diethyl ether and a 2M solution of hydrochloric acid in diethyl ether was added dropwise until a white solid was formed. The reaction mixture was concentrated under vacuum, the crude product was suspended in methanol and the reaction mixture was concentrated under vacuum to give the desired hydrochloride.

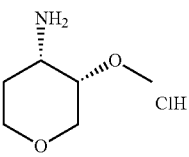
Intermediate 48c was synthesised in analogy to Intermediate 48b, starting from Intermediate 47c.

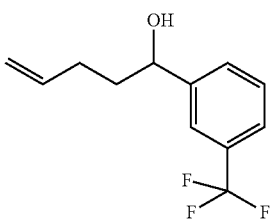
Intermediate 49a 3-(trifluoromethyl)benzaldehyde (6.46 ml, 48.24 mmol) was dissolved in 80 ml of dry tetrahydrofurane, the reaction mixture was cooled to −78° C. and a 0.5M solution of 3-butenylmagnesiumbromide in tetrahydrofurane (106.13 ml, 53.06 mmol) was added dropwise over 30 minutes. The reaction mixture was stirred at −78° C. for 30 minutes. Then, the reaction mixture was allowed to reach room temperature and stirred 18 h. Then, 100 ml of a saturated aqueous solution of ammonium chloride and 200 ml of ethyl acetate were added. the organic layer was separated, dried over sodium sulfate and concentrated under vacuum. 7.75 g (33.69 mmol) of the desired product were obtained.

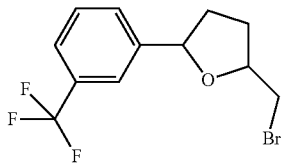
Intermediate 50a

Intermediate 49a was dissolved in 70 ml of dry dichloromethane, the reaction mixture was stirred under nitrogen atmosphere at 0° C. and N-bromosuccinimide was added. The reaction mixture was allowed to reach room temperature and stirred for 48 h. The reaction mixture was concentrated under vacuum. The crude product was purified by flash chromatography (Isolera cartridge eluent: hexane/ethyl acetate=90/10%) to obtain the desired product as diastereoisomeric mixture.

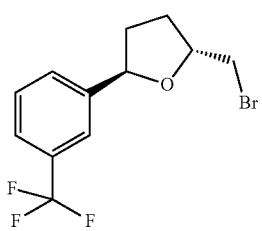
Intermediate 51a

Intermediate 50a was purified by flash chromatography (Isolera cartridge; eluent: hexane/ethyl acetate=98/2%). 2.3 g (7.44 mmol) of the trans diastereoisomer were obtained as racemic mixture (relative stereochemistry assigned by NMR).

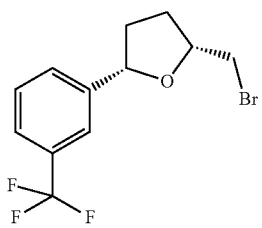
Intermediate 52a

Further elution of the column gave 1.05 g (3.39 mmol) of the cis diastereoisomer as racemic mixture (relative stereochemistry assigned by NMR).

The following intermediates were synthesized in analogy to Intermediates 49a, 50a, 51a and 52a

| Starting aldehyde | Intermediate | STRUCTURE |
|---|---|---|
| 3-Methyl-benzaldheyde | 49b | 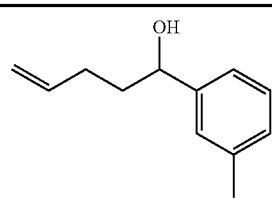 |

| Starting aldehyde | Intermediate | STRUCTURE |
|---|---|---|
| | 50b | 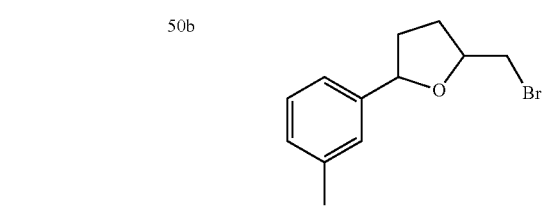 |
| | 51b | 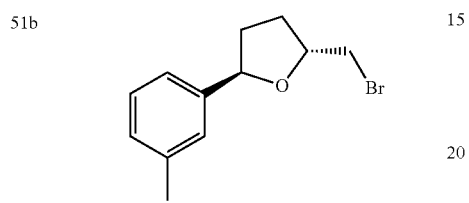 |
| | 52b | 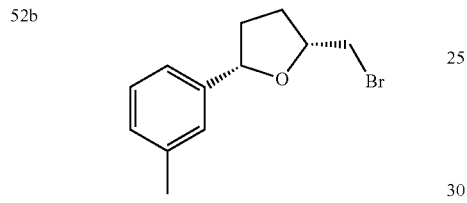 |
| 4-Methyl-benzaldheyde | 49c | 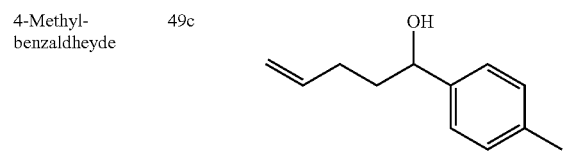 |
| | 50c | 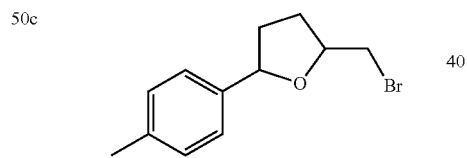 |
| | 51c | 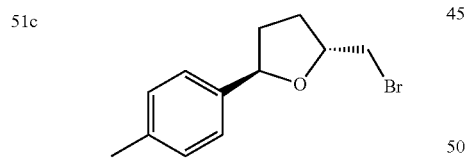 |
| | 52c | 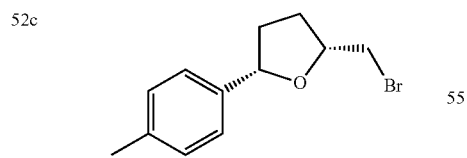 |
| 4-Fluoro-3-methyl-benzaldheyde | 49d | 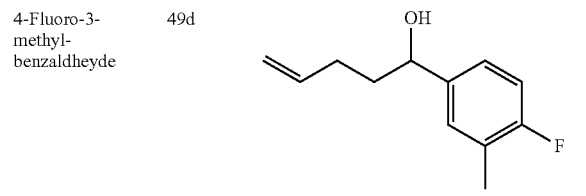 |
| Starting aldehyde | Intermediate | STRUCTURE |
|---|---|---|
| | 50d | 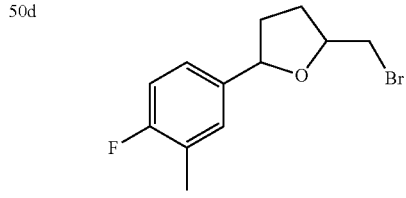 |
| | 51d | 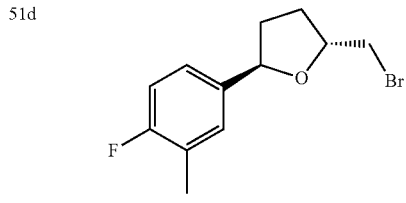 |
| | 52d | 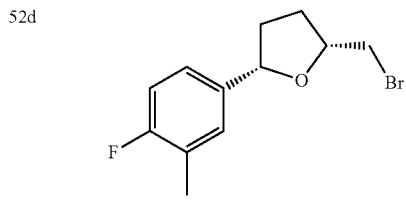 |
| 3-Fluoro-4-methyl-benzaldheyde | 49e | 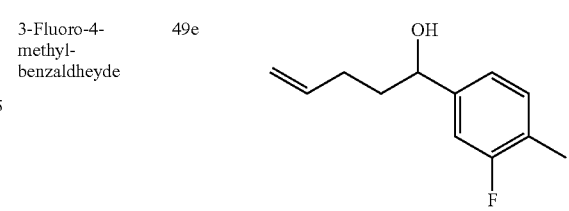 |
| | 50e | 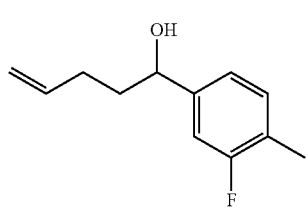 |
| | 51e | 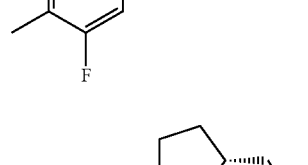 |
| | 52e | 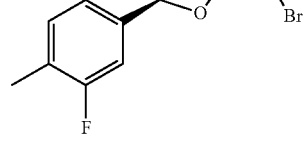 |

| Starting aldehyde | Intermediate | STRUCTURE |
|---|---|---|
| 4-Chloro-benzaldheyde | 49f | ![structure] |
| | 50f | |
| | 51f | |
| | 52f | |
| 4-Trifluoro-methyl-benzaldheyde | 49g | 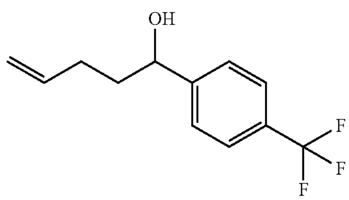 [SMILES: C=CCCC(O)c1ccc(C(F)(F)F)cc1] |
| | 50g | |
| | 51g | |
| | 52g | |

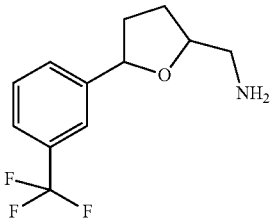

Intermediate 53a

Intermediate 50a (1.7 g, 5.49 mmol) was dissolved in 5 ml of DMSO and the reaction mixture was stirred under nitrogen atmosphere at room temperature. Phthalimide potassium salt (2.54 g, 13.75 mmol) and sodium iodide (240 mg, 1.60 mmol) were added and the reaction mixture was stirred at 70° C. for 18 h. The reaction mixture was cooled to room temperature and diluted with 40 ml of a saturated aqueous sodium bicarbonate solution and with 100 ml of ethyl acetate. The organic layer was separated, dried on sodium sulfate and concentrated under vacuum. The crude product was purified by flash chromatography (Isolera cartridge; eluent: hexane/ethyl acetate=85/15%) to yield 1.2 g (3.2 mmol) of the phthalimido intermediate. The phthalimido intermediate (1.2 g, 3.2 mmol) was dissolved in 15 ml of methanol. Hydrazine hydrate (1.24 ml, 25.60 mmol) was added and the reaction mixture was stirred at room temperature for 48 h. The reaction mixture was concentrated under vacuum. The crude product was dissolved in 10 ml of dichloromethane, the organic layer was washed with water, separated, dried on sodium sulfate and concentrate under vacuum. 474 mg (1.93 mmol) of the desired product were obtained.

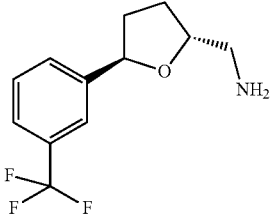

Intermediate 54a was synthesized in analogy to Intermediate 53a starting from intermediate 51a

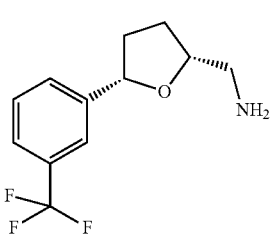

Intermediate 55a was synthesized in analogy to Intermediates 53a starting from intermediate 52a.

The following intermediates were synthesized in analogy to Intermediates 53a, 54a and 55a.

| Starting Intermediate | Intermediate | STRUCTURE | Starting intermediate | Intermediate | STRUCTURE |
|---|---|---|---|---|---|
| 50b | 53b | 5-(3-methylphenyl)tetrahydrofuran-2-ylmethanamine | 51b | 54b | (2R,5S)-5-(3-methylphenyl)tetrahydrofuran-2-ylmethanamine |
| 50c | 53c | 5-(4-methylphenyl)tetrahydrofuran-2-ylmethanamine | 51c | 54c | (2R,5S)-5-(4-methylphenyl)tetrahydrofuran-2-ylmethanamine |
| 50d | 53d | 5-(4-fluoro-3-methylphenyl)tetrahydrofuran-2-ylmethanamine | 51d | 54d | (2R,5S)-5-(4-fluoro-3-methylphenyl)tetrahydrofuran-2-ylmethanamine |
| 50e | 53e | 5-(3-fluoro-4-methylphenyl)tetrahydrofuran-2-ylmethanamine | 51e | 54e | (2R,5S)-5-(3-fluoro-4-methylphenyl)tetrahydrofuran-2-ylmethanamine |
| 50f | 53f | 5-(4-chlorophenyl)tetrahydrofuran-2-ylmethanamine | 51f | 54f | (2R,5S)-5-(4-chlorophenyl)tetrahydrofuran-2-ylmethanamine |
| 50g | 53g | 5-(4-trifluoromethylphenyl)tetrahydrofuran-2-ylmethanamine | 51g | 54g | (2R,5S)-5-(4-trifluoromethylphenyl)tetrahydrofuran-2-ylmethanamine |
| 2-bromomethyl-4-phenyl-tetrahydrofuran | 53h | 4-phenyltetrahydrofuran-2-ylmethanamine | 52e | 55e | (2S,5S)-5-(4-fluoro-3-methylphenyl)tetrahydrofuran-2-ylmethanamine |
| 52b | 55b | (2S,5S)-5-(3-methylphenyl)tetrahydrofuran-2-ylmethanamine | 52f | 55f | (2S,5S)-5-(4-chlorophenyl)tetrahydrofuran-2-ylmethanamine |

| Starting Intermediate | Intermediate | STRUCTURE | Starting intermediate | Intermediate | STRUCTURE |
|---|---|---|---|---|---|
| 52c | 55c | 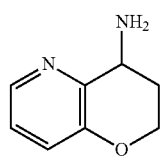 | 52g | 55g | 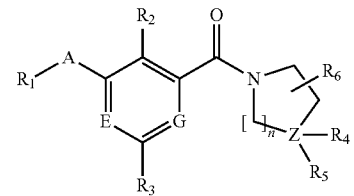 |
| 52d | 55d | 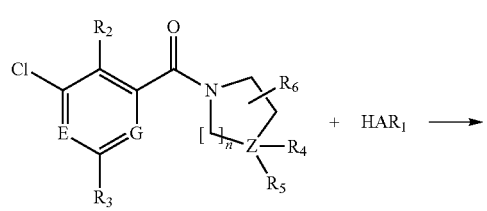 | | | |

Intermediate 56

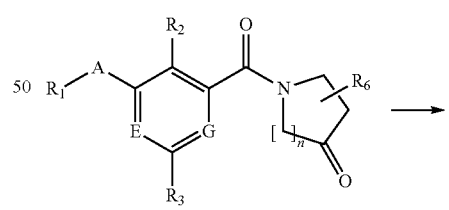

2,3-Dihydro-pyrano[3,2-b]pyridine-4one (250 mg, 1.7 mmol) and Raney-Nickel (25 mg) were added to a solution of ammonia in ethanol (10 ml) and the reaction mixture was stirred under hydrogen atmosphere (3 bar) for 18 h at room temperature. Then, the catalyst was removed by filtration on a celite pad and the mixture was concentrated under vacuum. The residue was purified by reversed phase HPLC to give the desired product (129 mg, 600 µmol).

SYNTHESIS OF EXAMPLES

E and G within the scope of this invention denotes C or N, preferred nitrogen.

The examples of this invention are synthesized according to the following general synthetic procedures:

Synthetic Procedure A

Examples: 1-159gc; 289-302

Synthetic Procedure B

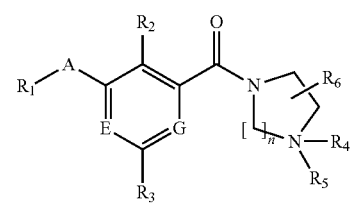

Examples: 160-247; 228a; 228ga-228gn; 229-247

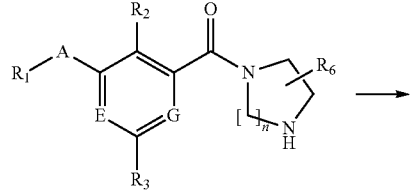

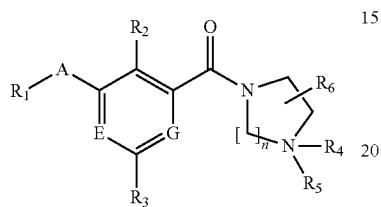

Examples: 286-288

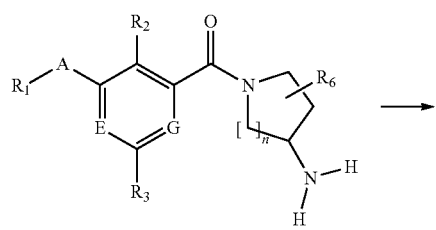

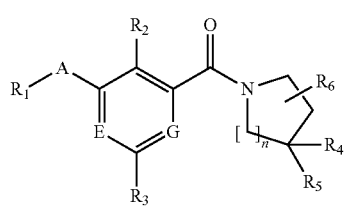

Examples: 228b-228g; 228go; 228gp

Synthetic Procedure C

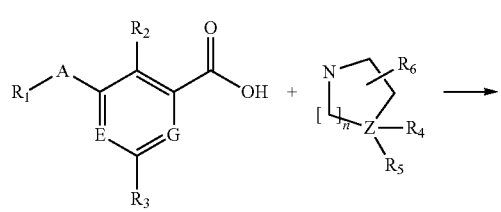

-continued

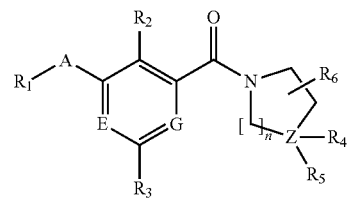

Examples: 248-283; 275a-275dj

Example 1

Intermediate 25b (70 mg, 0.16 mmol), 4-tert-butyl-benzylamine (32 mg, 0.19 mmol) and N,N-diisopropyl-ethylamine (0.042 ml, 0.24 mmol) in 2 ml of dry 1,4-dioxane were stirred at 70° C. overnight. The reaction mixture was concentrated under vacuum and the crude product was dissolved in dichloromethane. The organic phase was washed with a saturated aqueous sodium bicarbonate solution, dried over sodium sulfate and concentrated under vacuum. The crude product was purified by flash chromatography (Silica Isolute cartridge 5 g; eluent: ethyl acetate/methanol=90/10%). 16 mg (0.027 mmol) of the desired product were obtained.

HPLC (Method 2F): $R_t$. (min)=7.59

$[M+H]^+=557$

The following examples were synthesized in analogy to the preparation of Example 1.

| Ex # | STRUCTURE | Intermediate | Amine | [M + H]+ | HPLC R_t (min) | Method |
|---|---|---|---|---|---|---|
| 2 | 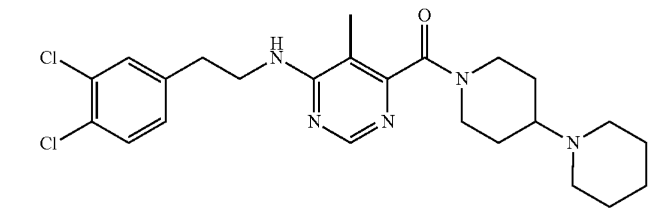 [SMILES: Cc1c(NCCc2ccc(Cl)c(Cl)c2)ncnc1C(=O)N1CCC(N2CCCCC2)CC1] | 25i | 2-(3,4-dichloro-phenyl)-ethyl-amine | 476 | 7.98 | 1E |
| 3 | 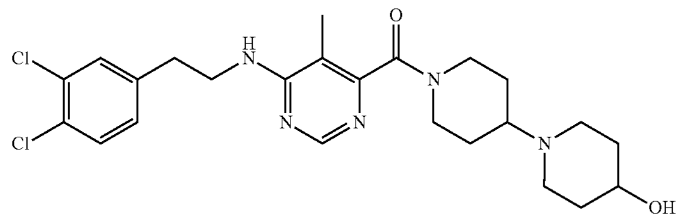 [SMILES: Cc1c(NCCc2ccc(Cl)c(Cl)c2)ncnc1C(=O)N1CCC(N2CCC(O)CC2)CC1] | 25f | 2-(3,4-dichloro-phenyl)-ethyl-amine | 492 | 2.91 | B |
| 4 | 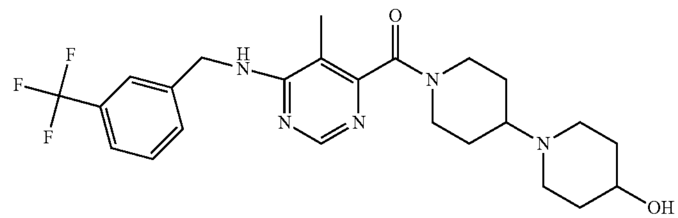 [SMILES: Cc1c(NCc2cccc(C(F)(F)F)c2)ncnc1C(=O)N1CCC(N2CCC(O)CC2)CC1] | 25f | 3-trifluoro methyl-benzyl-amine | 478 | 6.77 | 1E |
| 5 | 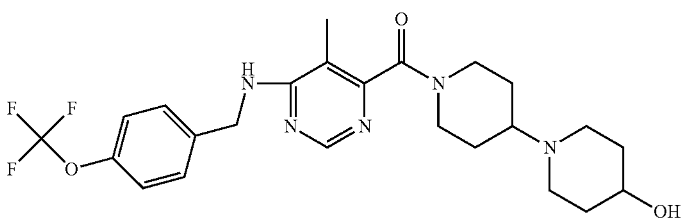 [SMILES: Cc1c(NCc2ccc(OC(F)(F)F)cc2)ncnc1C(=O)N1CCC(N2CCC(O)CC2)CC1] | 25f | 4-trifluoro-methoxy-benzyl-amine | 494 | 6.78 | 1E |
| 6 | 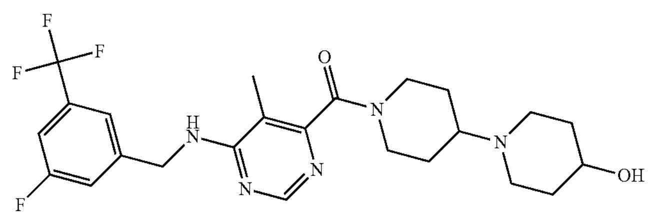 [SMILES: Cc1c(NCc2cc(F)cc(C(F)(F)F)c2)ncnc1C(=O)N1CCC(N2CCC(O)CC2)CC1] | 25f | 3-fluoro-5-trifluoro methyl-benzyl-amine | 496 | 6.73 | 1E |
| 7 | 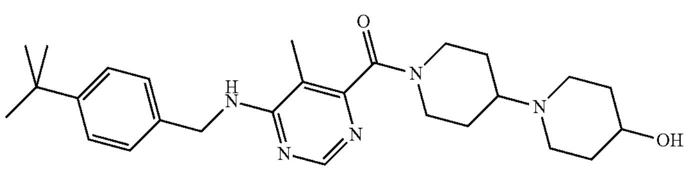 [SMILES: Cc1c(NCc2ccc(C(C)(C)C)cc2)ncnc1C(=O)N1CCC(N2CCC(O)CC2)CC1] | 25f | 4-tert-butyl-benzyl-amine | 466 | 7.45 | 1E |
| 8 | 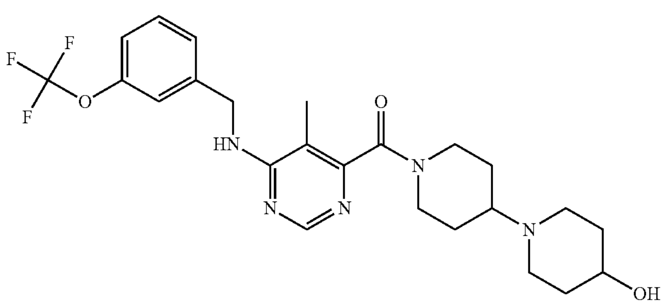 [SMILES: Cc1c(NCc2cccc(OC(F)(F)F)c2)ncnc1C(=O)N1CCC(N2CCC(O)CC2)CC1] | 25f | 3-trifluoro methoxy-benzyl-amine | 494 | 7.08 | 1E |

| Ex # | STRUCTURE | Intermediate | Amine | [M + H]+ | HPLC R_r(min) | Method |
|---|---|---|---|---|---|---|
| 9 | 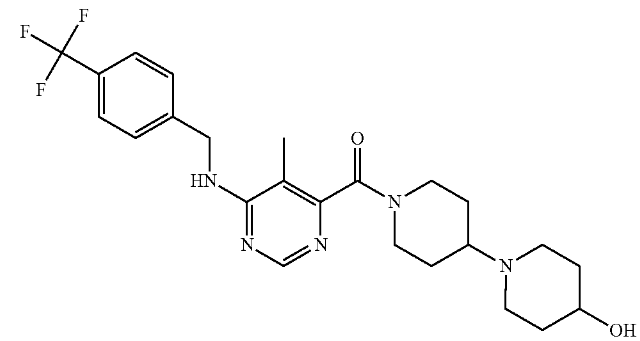 [SMILES: Cc1c(NCc2ccc(C(F)(F)F)cc2)ncnc1C(=O)N1CCC(N2CCC(O)CC2)CC1] | 25f | 4-trifluoromethyl-benzyl-amine | 478 | 6.63 | 1E |
| 10 | 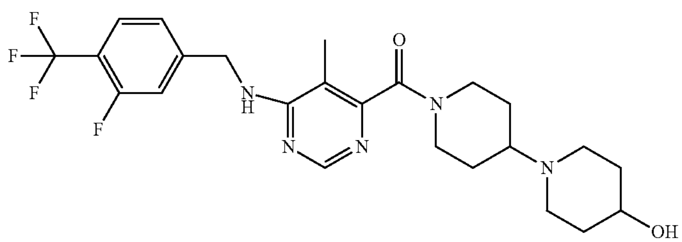 [SMILES: Cc1c(NCc2ccc(C(F)(F)F)c(F)c2)ncnc1C(=O)N1CCC(N2CCC(O)CC2)CC1] | 25f | 3-fluoro-4-trifluoromethyl-benzyl-amine | 496 | 6.85 | 1E |
| 11 | 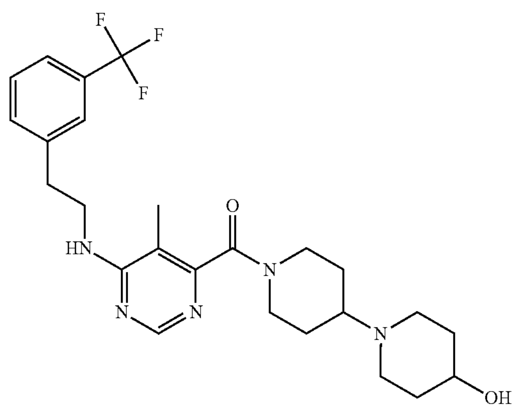 [SMILES: Cc1c(NCCc2cccc(C(F)(F)F)c2)ncnc1C(=O)N1CCC(N2CCC(O)CC2)CC1] | 25f | 2-(3-trifluoromethyl-phenyl)-ethyl-amine | 492 | 7.23 | 1E |
| 12 | 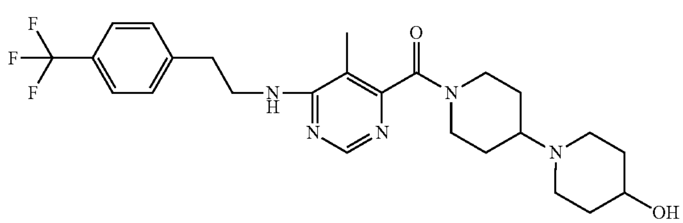 [SMILES: Cc1c(NCCc2ccc(C(F)(F)F)cc2)ncnc1C(=O)N1CCC(N2CCC(O)CC2)CC1] | 25f | 2-(4-trifluoromethyl-phenyl)-ethyl-amine | 492 | 7.37 | 1E |
| 13 | 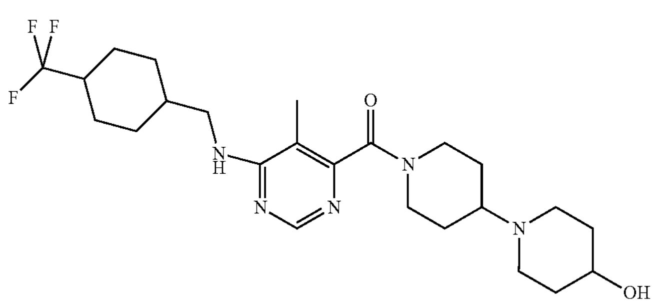 [SMILES: Cc1c(NCC2CCC(C(F)(F)F)CC2)ncnc1C(=O)N1CCC(N2CCC(O)CC2)CC1] | 25f | (4-(trifluoromethyl)-cyclohexyl)-methanamine | 484 | 6.82 | 1E |

| Ex # | STRUCTURE | Intermediate | Amine | [M + H]+ | HPLC R_t(min) | Method |
|---|---|---|---|---|---|---|
| 14 | 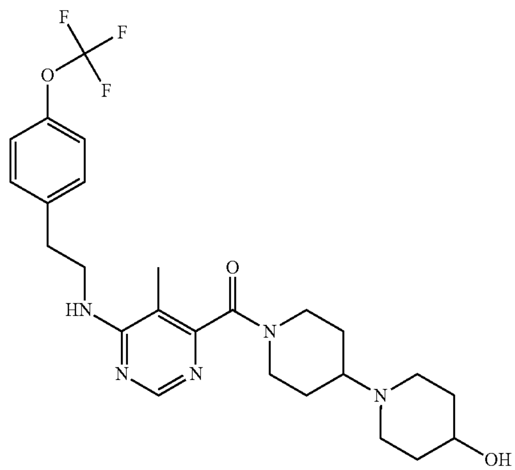 [SMILES: Cc1c(NCCc2ccc(OC(F)(F)F)cc2)ncnc1C(=O)N1CCC(N2CCC(O)CC2)CC1] | 25f | 2-(4-trifluoromethoxyphenyl)-ethylamine | 508 | 7.37 | 1E (Fusion) |
| 15 | 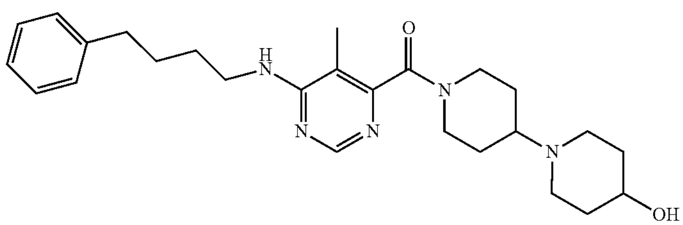 [SMILES: Cc1c(NCCCCc2ccccc2)ncnc1C(=O)N1CCC(N2CCC(O)CC2)CC1] | 25f | 4-phenylbutylamine | 452 | 7.15 | 1E |
| 16 | 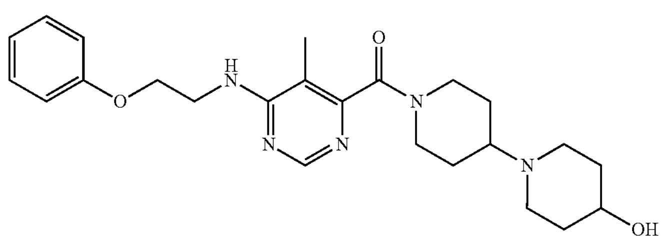 [SMILES: Cc1c(NCCOc2ccccc2)ncnc1C(=O)N1CCC(N2CCC(O)CC2)CC1] | 25f | 2-phenoxyethylamine | 440 | 7.10 | 1E (Fusion) |
| 17 | 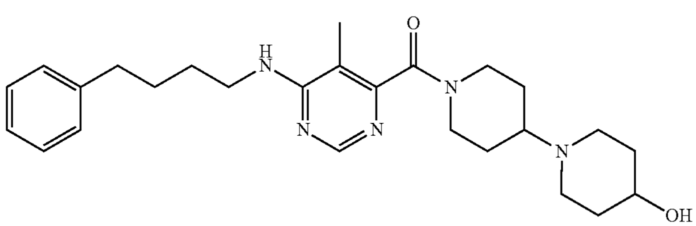 [SMILES: Cc1c(NCCCCc2ccccc2)ncnc1C(=O)N1CCC(N2CCC(O)CC2)CC1] | 25f | 3-phenylpropylamine | 438 | 7.83 | 1E (Fusion) |
| 18 | 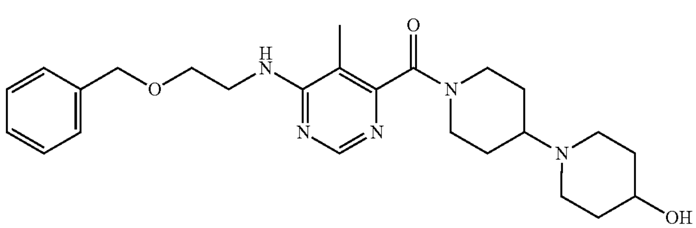 [SMILES: Cc1c(NCCOCc2ccccc2)ncnc1C(=O)N1CCC(N2CCC(O)CC2)CC1] | 25f | 2-benzyloxyethylamine | 454 | 5.83 | 1E (Hydro) |

-continued

| Ex # | STRUCTURE | Intermediate | Amine | [M + H]+ | HPLC Rt.(min) | Method |
|---|---|---|---|---|---|---|
| 19 | 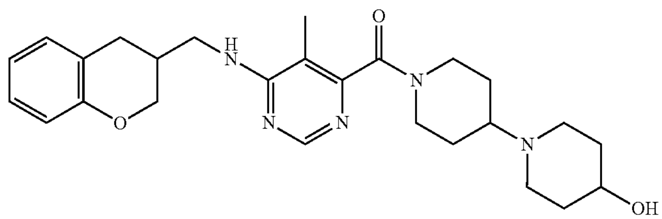 [SMILES: Cc1c(NCC2COc3ccccc3C2)ncnc1C(=O)N1CCC(N2CCC(O)CC2)CC1] | 25f | chroman-3-yl-methan-amine | 466 | 7.85 | 1E (Fusion) |
| 20 | 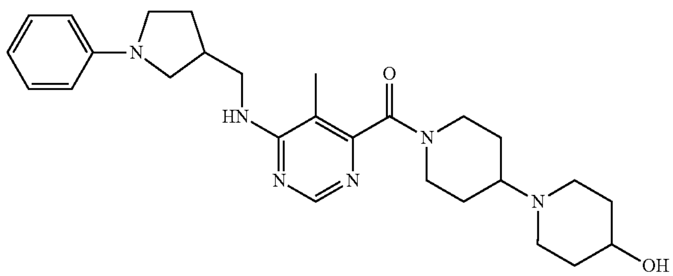 [SMILES: Cc1c(NCC2CCN(c3ccccc3)C2)ncnc1C(=O)N1CCC(N2CCC(O)CC2)CC1] | 25f | (1-phenyl-pyrrolidin-3-yl)-methan-amine | 479 | 7.05 | 1E (Hydro) |
| 21 | 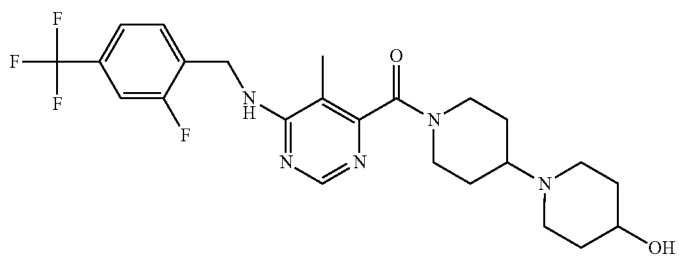 [SMILES: Cc1c(NCc2ccc(C(F)(F)F)cc2F)ncnc1C(=O)N1CCC(N2CCC(O)CC2)CC1] | 25f | 2-fluoro-4-trifluoro methyl-benzyl-amine | 496 | 8.38 | 1E (Fusion) |
| 22 | 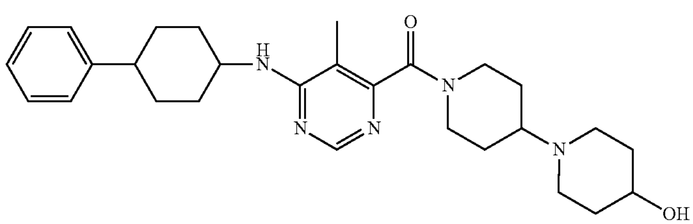 [SMILES: Cc1c(NC2CCC(c3ccccc3)CC2)ncnc1C(=O)N1CCC(N2CCC(O)CC2)CC1] | 25f | 4-phenyl-cyclo-hexyl-amine | 478 | 9.38 | 1E (Fusion) |
| 23 | 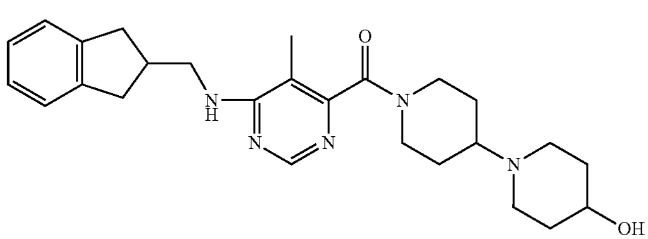 [SMILES: Cc1c(NCC2Cc3ccccc3C2)ncnc1C(=O)N1CCC(N2CCC(O)CC2)CC1] | 25f | indan-2-yl-methan-amine | 450 | 6.55 | 1E (Hydro) |
| 24 | 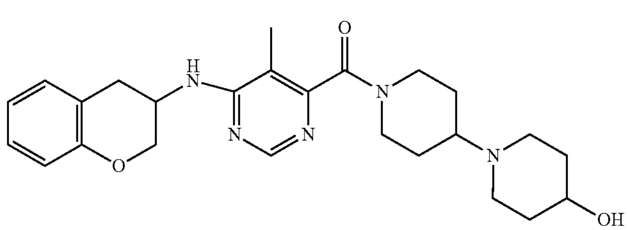 [SMILES: Cc1c(NC2COc3ccccc3C2)ncnc1C(=O)N1CCC(N2CCC(O)CC2)CC1] | 25f | chroman-3-ylamine | 452 | 6.18 | 1E (Hydro) |

-continued

| Ex # | STRUCTURE | Intermediate | Amine | [M + H]+ | HPLC R<sub>t</sub>(min) | Method |
|---|---|---|---|---|---|---|
| 25 | 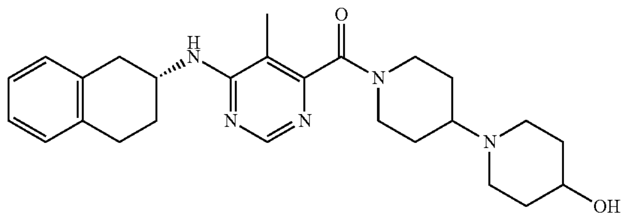 [SMILES: Cc1c(N[C@@H]2CCc3ccccc3C2)ncnc1C(=O)N1CCC(N2CCC(O)CC2)CC1] | 25f | (R)-(1,2,3,4-tetra-hydro-naphtalen-2-yl)amine | 450 | 7.08 | 1E (Hydro) |
| 26 | 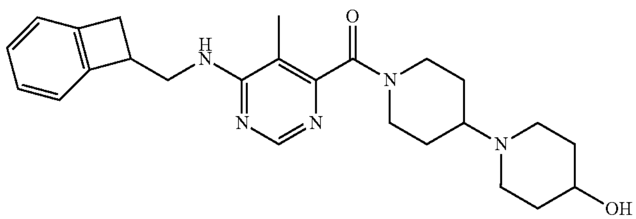 [SMILES: Cc1c(NCC2Cc3ccccc32)ncnc1C(=O)N1CCC(N2CCC(O)CC2)CC1] | 25f | (1,2-di-hydro-cyclo-buta-benzen-1-yl)-methan-amide | 436 | 6.93 | 1E (Hydro) |
| 27 | 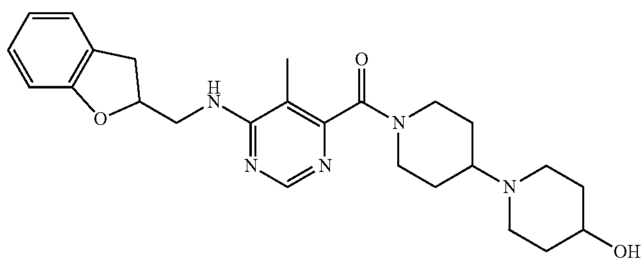 [SMILES: Cc1c(NCC2Cc3ccccc3O2)ncnc1C(=O)N1CCC(N2CCC(O)CC2)CC1] | 25f | (2,3-di-hydro-benzo-furan-2-yl)-methan-amine | 452 | 6.47 | 1E (Hydro) |
| 28 | 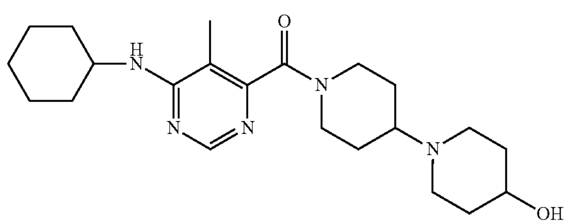 [SMILES: Cc1c(NC2CCCCC2)ncnc1C(=O)N1CCC(N2CCC(O)CC2)CC1] | 25f | Cyclo-hexyl-amine | 402 | 4.90 | 1E |
| 29 | 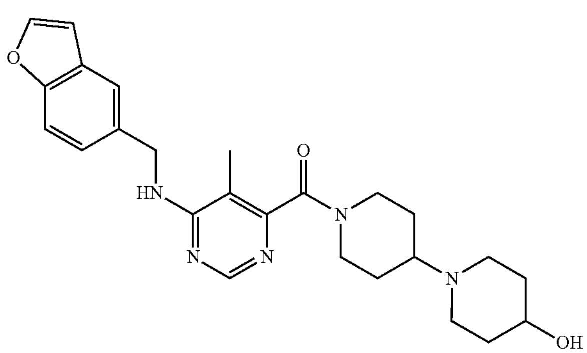 [SMILES: Cc1c(NCc2ccc3occc3c2)ncnc1C(=O)N1CCC(N2CCC(O)CC2)CC1] | 25f | benzo-furan-5-ylmethan-amine | 450 | 6.73 | 1E (Hydro) |
| 30 | 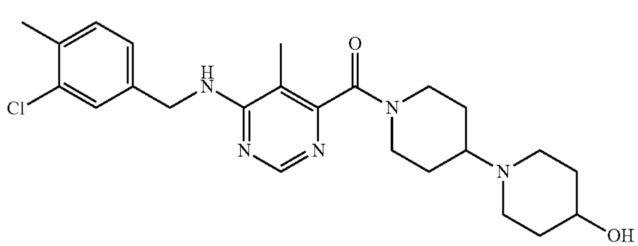 [SMILES: Cc1ccc(CNc2ncnc(C(=O)N3CCC(N4CCC(O)CC4)CC3)c2C)cc1Cl] | 25f | 3-chloro-4-methyl-benzyl-amine | 458 | 7.75 | 1E (Hydro) |

-continued

| Ex # | STRUCTURE | Intermediate | Amine | [M + H]+ | HPLC Rr.(min) | Method |
|---|---|---|---|---|---|---|
| 31 | 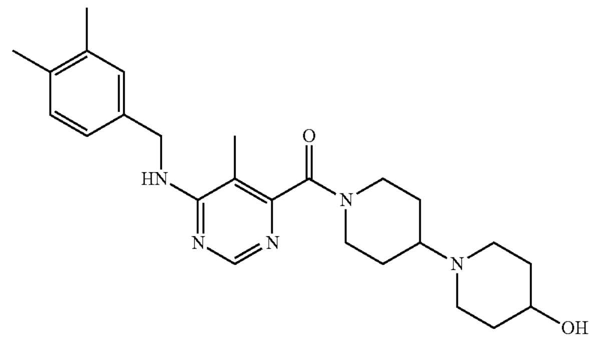 [SMILES: Cc1ccc(CNc2ncnc(C(=O)N3CCC(N4CCC(O)CC4)CC3)c2C)cc1C] | 25f | 3,4-dimethyl-benzyl-amine | 438 | 7.37 | 1E (Hydro) |
| 32 | 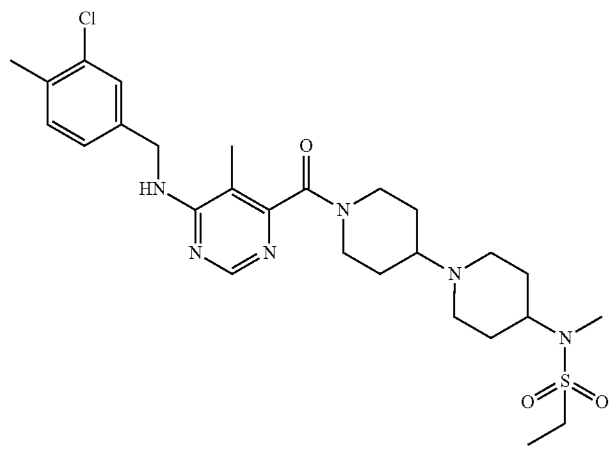 [SMILES: CCS(=O)(=O)N(C)C1CCN(C2CCN(C(=O)c3ncnc(NCc4ccc(C)c(Cl)c4)c3C)CC2)CC1] | 25c | 3-chloro-4-methyl-benzyl-amine | 563 | 6.98 | 2F |
| 33 | 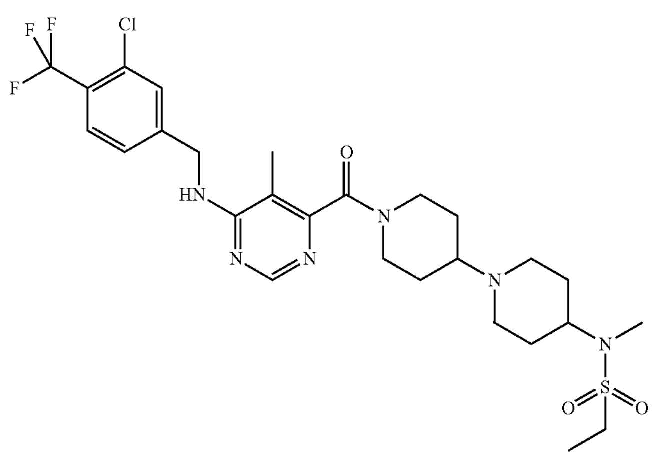 [SMILES: CCS(=O)(=O)N(C)C1CCN(C2CCN(C(=O)c3ncnc(NCc4ccc(C(F)(F)F)c(Cl)c4)c3C)CC2)CC1] | 25c | 3-chloro-4-trifluoromethyl-benzyl-amine | 617 | 9.47 | 1E (Hydro) |

-continued

| Ex # | STRUCTURE | Intermediate | Amine | [M + H]+ | HPLC R_t (min) | Method |
|---|---|---|---|---|---|---|
| 34 | 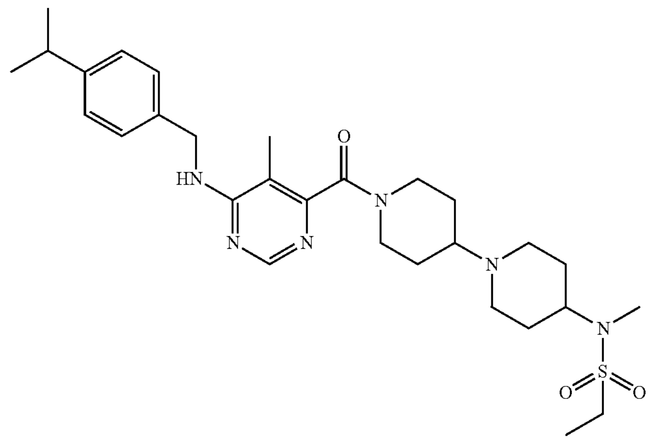 [SMILES: CCS(=O)(=O)N(C)C1CCN(C2CCN(C(=O)c3ncnc(NCc4ccc(C(C)C)cc4)c3C)CC2)CC1] | 25c | 4-isopropyl-benzyl-amine | 557 | 7.03 | 2F |
| 35 | 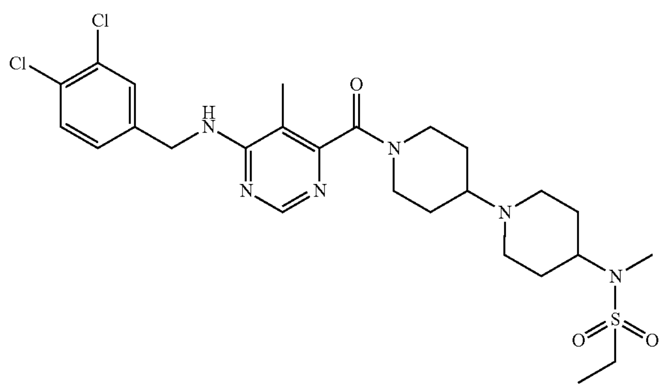 [SMILES: CCS(=O)(=O)N(C)C1CCN(C2CCN(C(=O)c3ncnc(NCc4ccc(Cl)c(Cl)c4)c3C)CC2)CC1] | 25c | 3,4-dichloro-benzyl-amine | 583 | 8.65 | 1E (Hydro) |
| 36 | 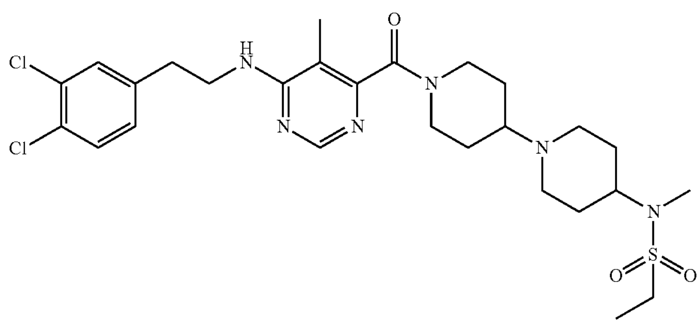 [SMILES: CCS(=O)(=O)N(C)C1CCN(C2CCN(C(=O)c3ncnc(NCCc4ccc(Cl)c(Cl)c4)c3C)CC2)CC1] | 25c | 2-(3,4-dichloro-phenyl)-ethyl-amine | 597 | 9.72 | 1E (Hydro) |
| 37 | 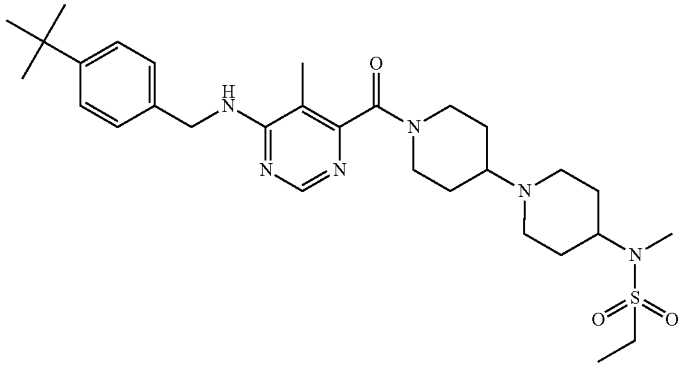 [SMILES: CCS(=O)(=O)N(C)C1CCN(C2CCN(C(=O)c3ncnc(NCc4ccc(C(C)(C)C)cc4)c3C)CC2)CC1] | 25c | 4-tert-butyl-benzyl-amine | 571 | 9.28 | 1E (Hydro) |

-continued

| Ex # | STRUCTURE | Intermediate | Amine | [M + H]⁺ | HPLC R_r.(min) | Method |
|---|---|---|---|---|---|---|
| 38 | 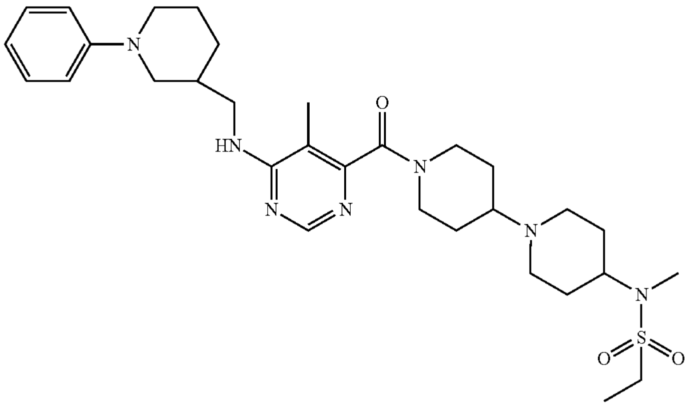 [SMILES: CCS(=O)(=O)N(C)C1CCN(C2CCN(C(=O)c3ncnc(NCC4CCCN(c5ccccc5)C4)c3C)CC2)CC1] | 25c | 9a | 598 | 1.45 | 2F |
| 39 | 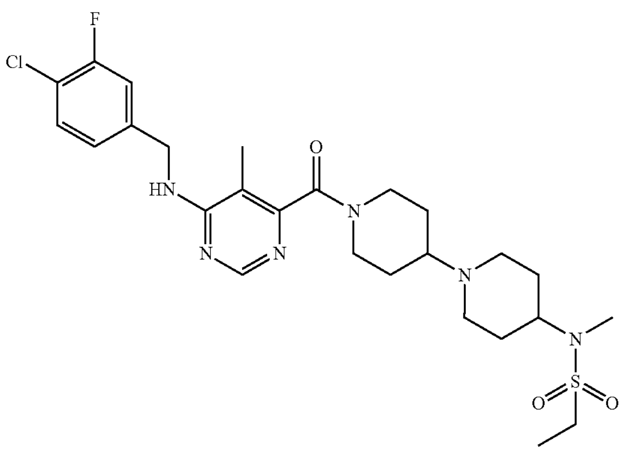 [SMILES: CCS(=O)(=O)N(C)C1CCN(C2CCN(C(=O)c3ncnc(NCc4ccc(Cl)c(F)c4)c3C)CC2)CC1] | 25c | 4-chloro-3-fluoro-benzyl-amine | 567 | 8.82 | 1E (Hydro) |
| 40 | 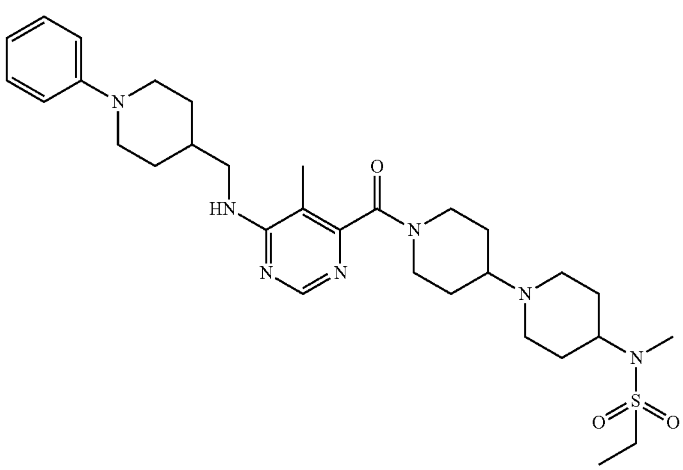 [SMILES: CCS(=O)(=O)N(C)C1CCN(C2CCN(C(=O)c3ncnc(NCC4CCN(c5ccccc5)CC4)c3C)CC2)CC1] | 25c | (1-phenyl-piperidin-4yl)-methan-amine | 598 | 8.98 | 1E (Hydro) |

-continued

| Ex # | STRUCTURE | Intermediate | Amine | [M + H]⁺ | HPLC R$_t$(min) | Method |
|---|---|---|---|---|---|---|
| 41 | 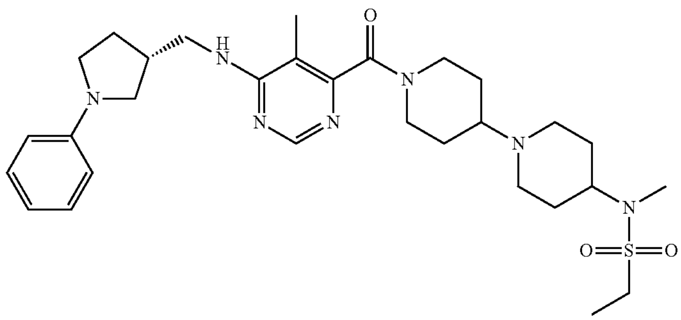 [SMILES: CCS(=O)(=O)N(C)C1CCN(C2CCN(C(=O)c3ncnc(NC[C@H]4CCN(c5ccccc5)C4)c3C)CC2)CC1] | 25c | 9b | 584 | 8.92 | 1E (Hydro) |
| 42 | 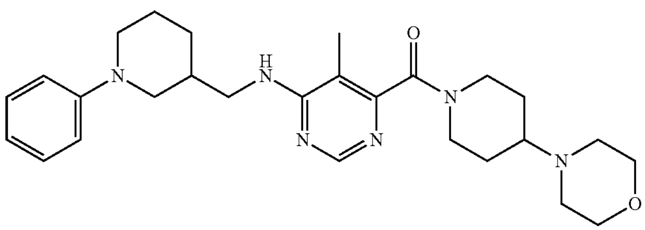 [SMILES: Cc1c(NCC2CCCN(c3ccccc3)C2)ncnc1C(=O)N1CCC(N2CCOCC2)CC1] | 25h | 9a | 479 | 8.67 | 1E (Hydro) |
| 43 | 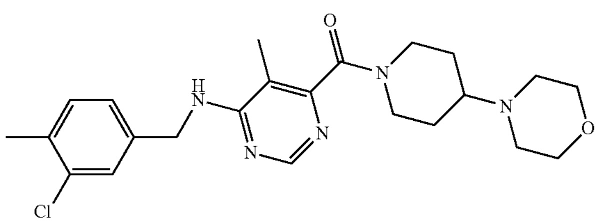 [SMILES: Cc1ccc(CNc2ncnc(C(=O)N3CCC(N4CCOCC4)CC3)c2C)cc1Cl] | 25h | 3-chloro-4-methyl-benzyl-amine | 444 | 8.63 | 1E (Hydro) |
| 44 | 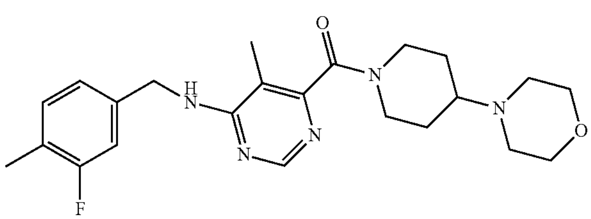 [SMILES: Cc1ccc(CNc2ncnc(C(=O)N3CCC(N4CCOCC4)CC3)c2C)cc1F] | 25h | 3-fluoro-4-methyl-benzyl-amine | 428 | 7.58 | 1E (Hydro) |
| 45 | 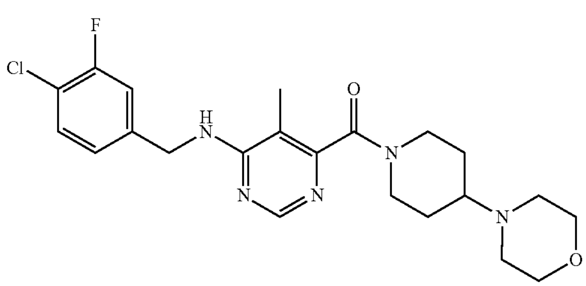 [SMILES: Cc1c(NCc2ccc(Cl)c(F)c2)ncnc1C(=O)N1CCC(N2CCOCC2)CC1] | 25h | 4-chloro-3-fluoro-bemzyl-amine | 448 | 7.88 | 1E (Hydro) |
| 46 | 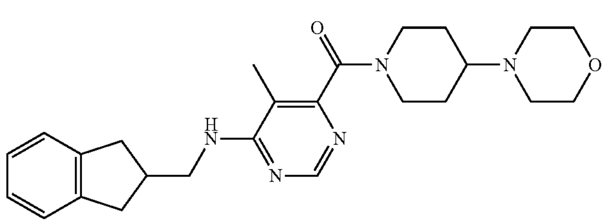 [SMILES: Cc1c(NCC2Cc3ccccc3C2)ncnc1C(=O)N1CCC(N2CCOCC2)CC1] | 25h | indan-2yl-methan-amine | 436 | 8.27 | 1E (Hydro) |

-continued

| Ex # | STRUCTURE | Intermediate | Amine | [M + H]+ | HPLC Rt(min) | Method |
|---|---|---|---|---|---|---|
| 47 | 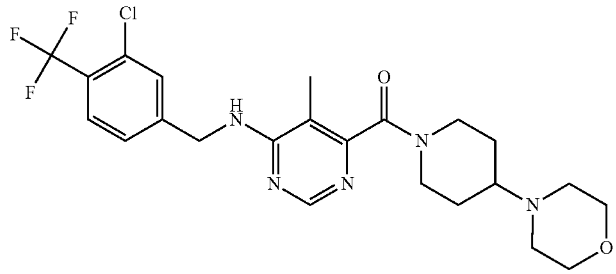 [SMILES: Cc1c(NCc2ccc(C(F)(F)F)c(Cl)c2)ncnc1C(=O)N1CCC(N2CCOCC2)CC1] | 25h | 3-chloro-4-trifluoromethyl-benzylamine | 498 | 7.30 | 2F |
| 48 | 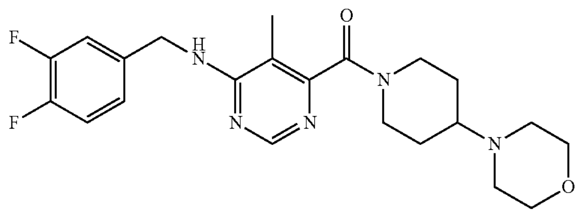 [SMILES: Cc1c(NCc2ccc(F)c(F)c2)ncnc1C(=O)N1CCC(N2CCOCC2)CC1] | 25h | 3,4-difluoro-benzylamine | 432 | 4.20 | 2G |
| 49 | 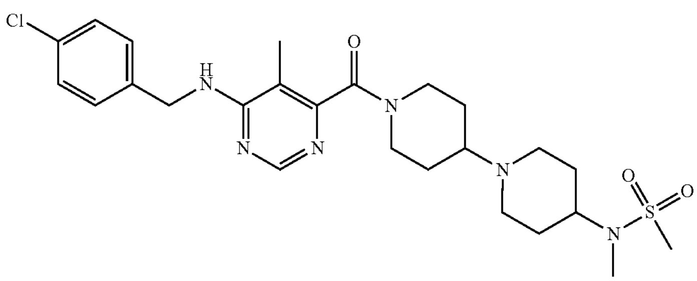 [SMILES: Cc1c(NCc2ccc(Cl)cc2)ncnc1C(=O)N1CCC(N2CCC(N(C)S(C)(=O)=O)CC2)CC1] | 25b | 4-chloro-benzylamine | 535 | 7.38 | 2F |
| 50 | 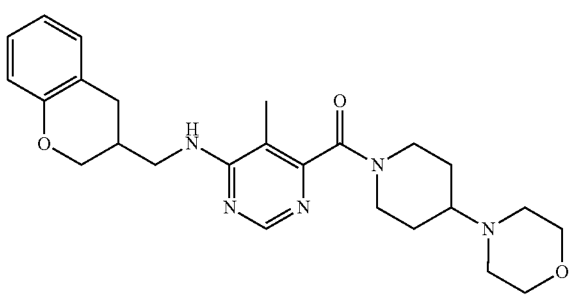 [SMILES: Cc1c(NCC2COc3ccccc3C2)ncnc1C(=O)N1CCC(N2CCOCC2)CC1] | 25h | chroman-3-yl-methanamine | 452 | 7.85 | 1E (Hydro) |
| 51 | 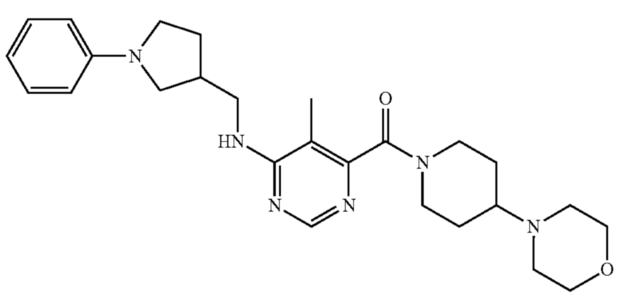 [SMILES: Cc1c(NCC2CCN(c3ccccc3)C2)ncnc1C(=O)N1CCC(N2CCOCC2)CC1] | 25h | (1-phenyl-pyrrolidin-3-yl)-methanamine | 465 | 8.93 | 1E (Hydro) |
| 52 | 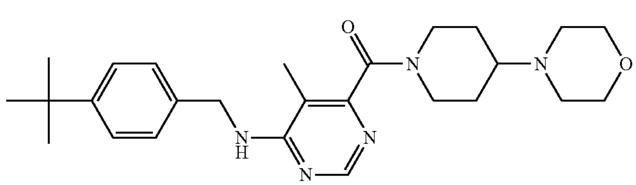 [SMILES: Cc1c(NCc2ccc(C(C)(C)C)cc2)ncnc1C(=O)N1CCC(N2CCOCC2)CC1] | 25h | 4-tert-butyl-benzylamine | 452 | 7.18 | 2F |

| Ex # | STRUCTURE | Intermediate | Amine | [M + H]+ | HPLC Rt.(min) | Method |
|---|---|---|---|---|---|---|
| 53 | 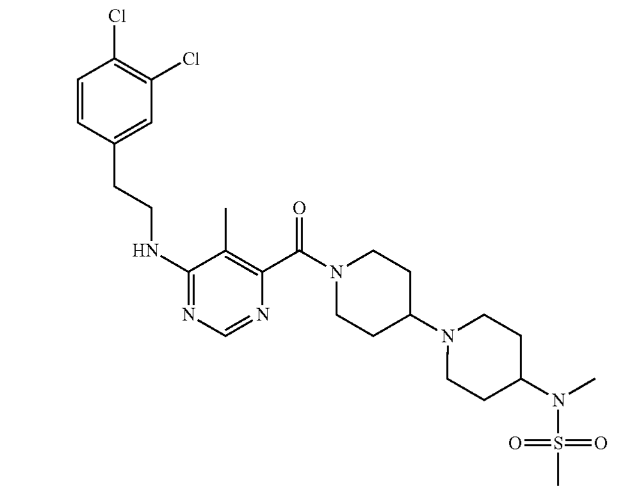 [SMILES: Cc1c(NCCc2ccc(Cl)c(Cl)c2)ncnc1C(=O)N1CCC(N2CCC(N(C)S(C)(=O)=O)CC2)CC1] | 25b | 2-(3,4-dichlorophenyl)-ethyl-amine | 583 | 7.97 | 1E (Hydro) |
| 54 | 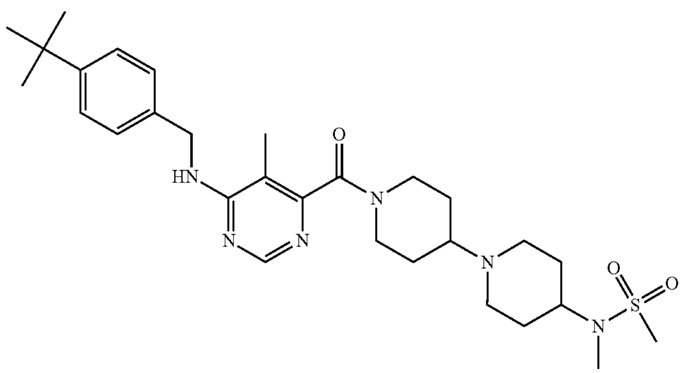 [SMILES: Cc1c(NCc2ccc(C(C)(C)C)cc2)ncnc1C(=O)N1CCC(N2CCC(N(C)S(C)(=O)=O)CC2)CC1] | 25b | (6-tert-butyl-pyridin-3-yl)-methan-amine | 558 | 7.73 | 1E (Hydro) |
| 55 | 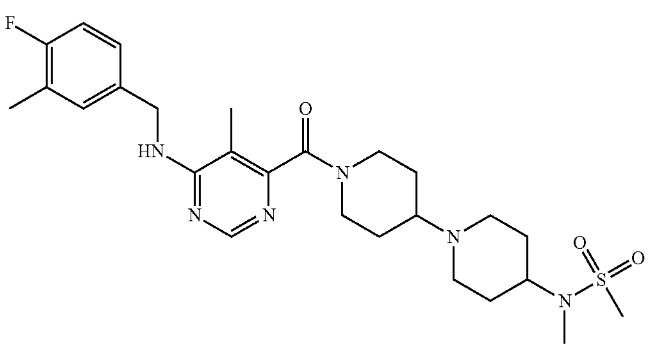 [SMILES: Cc1cc(CNc2ncnc(C(=O)N3CCC(N4CCC(N(C)S(C)(=O)=O)CC4)CC3)c2C)ccc1F] | 25b | 4-fluoro-3-methyl-benzyl-amine | 533 | 8.05 | 1E (Hydro) |
| 56 | 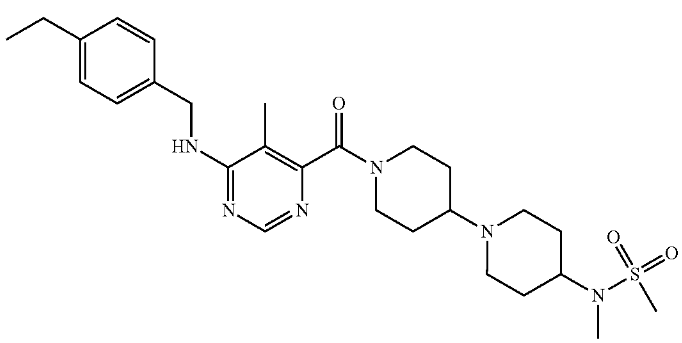 [SMILES: CCc1ccc(CNc2ncnc(C(=O)N3CCC(N4CCC(N(C)S(C)(=O)=O)CC4)CC3)c2C)cc1] | 25b | 4-ethyl-benzyl-amine | 529 | 8.35 | 1E (Hydro) |

-continued

| Ex # | STRUCTURE | Intermediate | Amine | [M + H]+ | HPLC Rt.(min) | Method |
|---|---|---|---|---|---|---|
| 57 | 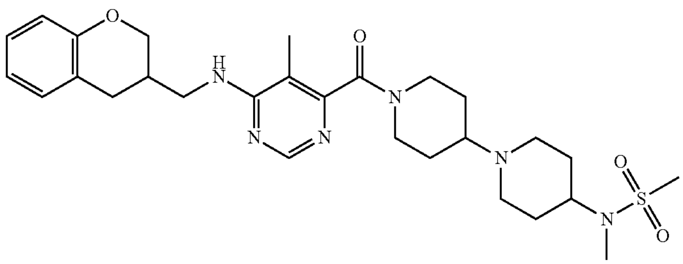 [SMILES: Cc1c(NCC2COc3ccccc3C2)ncnc1C(=O)N1CCC(N2CCC(N(C)S(C)(=O)=O)CC2)CC1] | 25b | chroman-3-yl-methanamine | 557 | 7.62 | 1E (Hydro) |
| 58 | 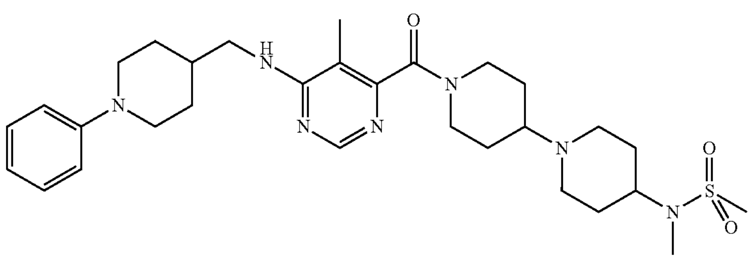 [SMILES: Cc1c(NCC2CCN(c3ccccc3)CC2)ncnc1C(=O)N1CCC(N2CCC(N(C)S(C)(=O)=O)CC2)CC1] | 25b | (1-phenyl-piperidin-4yl)-methanamine | 584 | 8.05 | 1E (Hydro) |
| 59 | 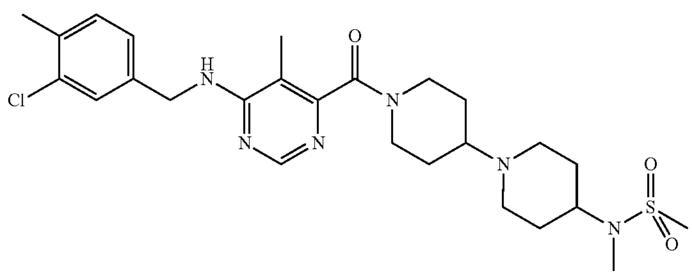 | 25b | 3-chloro-4-methyl-benzyl-amine | 549 | 8.22 | 1E (Hydro) |
| 60 | 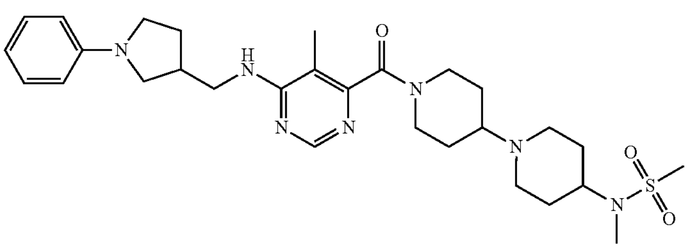 | 25b | (1-phenyl-pyrrolidin-3-yl)-methanamine | 570 | 8.07-8.47 | 1E (Hydro) |
| 61 | 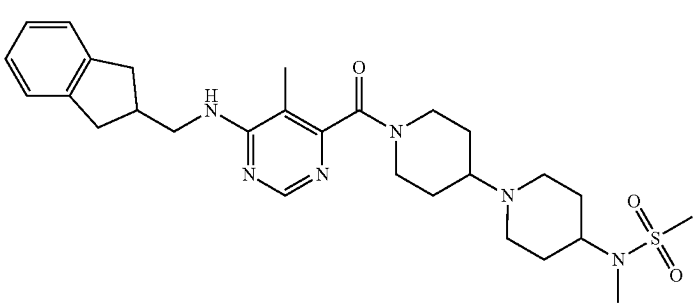 [SMILES: Cc1c(NCC2Cc3ccccc3C2)ncnc1C(=O)N1CCC(N2CCC(N(C)S(C)(=O)=O)CC2)CC1] | 25b | indan-2yl-methanamine | 541 | 8.03 | 1E (Hydro) |

| Ex # | STRUCTURE | Intermediate | Amine | [M + H]+ | HPLC R$_t$(min) | Method |
|---|---|---|---|---|---|---|
| 62 | 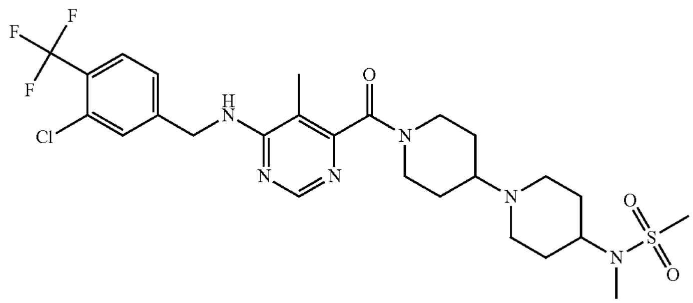 [SMILES: Cc1c(NCc2ccc(C(F)(F)F)c(Cl)c2)ncnc1C(=O)N1CCC(N2CCC(N(C)S(C)(=O)=O)CC2)CC1] | 25b | 3-chloro-4-trifluoromethyl-benzylamine | 603 | 8.68 | 1E (Hydro) |
| 63 | 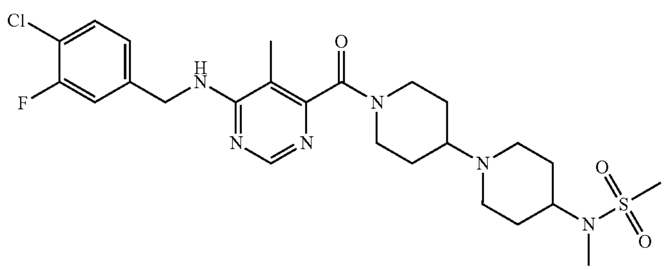 [SMILES: Cc1c(NCc2ccc(Cl)c(F)c2)ncnc1C(=O)N1CCC(N2CCC(N(C)S(C)(=O)=O)CC2)CC1] | 25b | 4-chloro-3-fluoro-benzylamine | 553 | 7.55 | 1E (Hydro) |
| 64 | 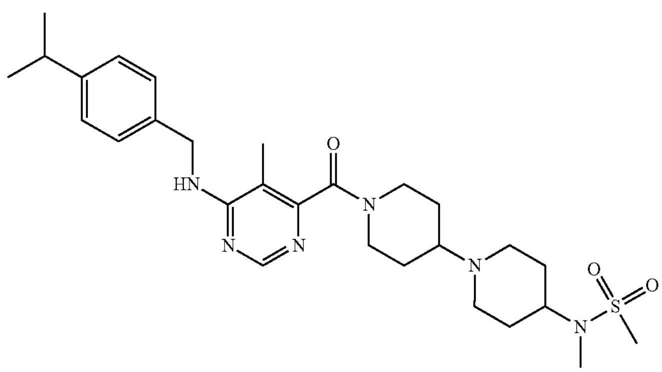 [SMILES: Cc1c(NCc2ccc(C(C)C)cc2)ncnc1C(=O)N1CCC(N2CCC(N(C)S(C)(=O)=O)CC2)CC1] | 25b | 4-isopropyl-benzylamine | 543 | 6.82 | 2F |
| 65 | 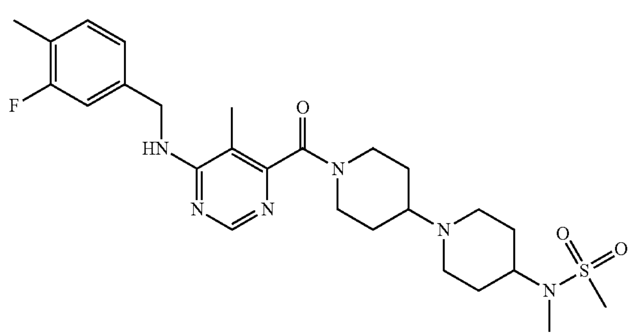 [SMILES: Cc1ccc(CNc2ncnc(C(=O)N3CCC(N4CCC(N(C)S(C)(=O)=O)CC4)CC3)c2C)cc1F] | 25b | 3-fluoro-4-methyl-benzylamine | 533 | 8.57 | 1E (Hydro) |

-continued

| Ex # | STRUCTURE | Intermediate | Amine | [M + H]+ | HPLC Rr.(min) | Method |
|---|---|---|---|---|---|---|
| 66 | 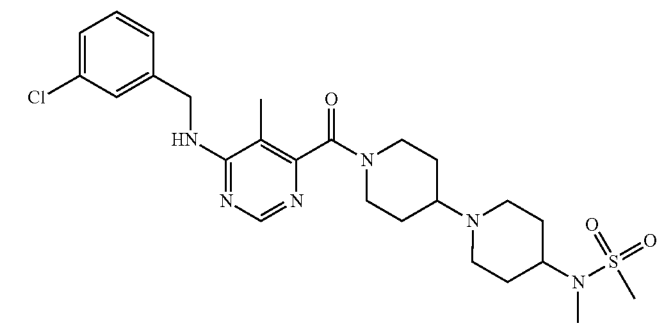 | 25b | 3-chloro-benzyl-amine | 535 | 6.72 | 2F |
| 67 | 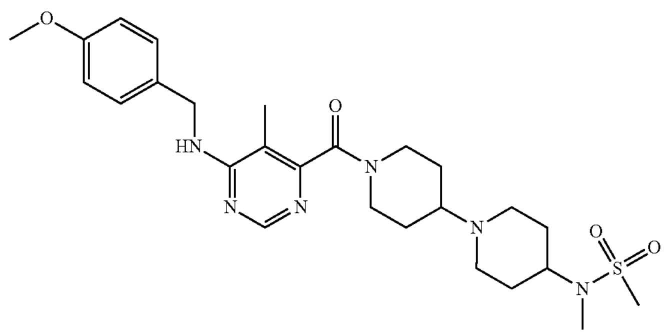 [SMILES: COc1ccc(CNc2ncnc(C(=O)N3CCC(N4CCC(N(C)S(C)(=O)=O)CC4)CC3)c2C)cc1] | 25b | 4-methoxy-benzyl-amine | 531 | 2.39 | 2F |
| 68 | 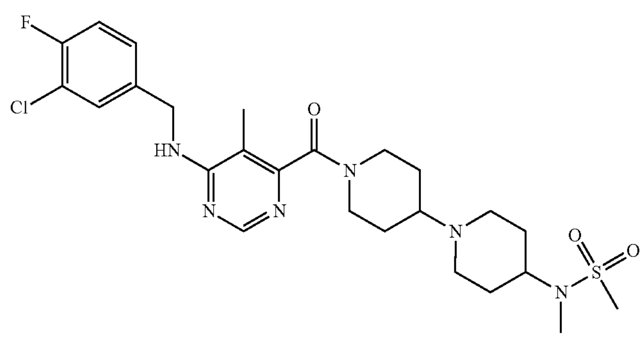 [SMILES: Cc1c(NCc2ccc(F)c(Cl)c2)ncnc1C(=O)N1CCC(N2CCC(N(C)S(C)(=O)=O)CC2)CC1] | 25b | 3-chloro-4-fluoro-benzyl-amine | 553 | 7.57 | 2F |
| 69 | 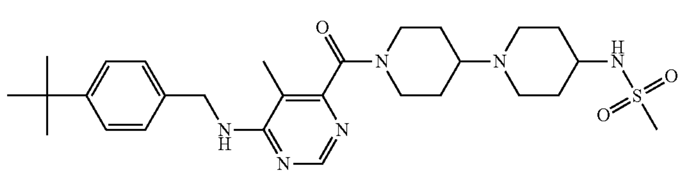 [SMILES: Cc1c(NCc2ccc(C(C)(C)C)cc2)ncnc1C(=O)N1CCC(N2CCC(NS(C)(=O)=O)CC2)CC1] | 25a | 4-tert-butyl-benzyl-amine | 543 | 7.97 | 1E (Hydro) |
| 70 | 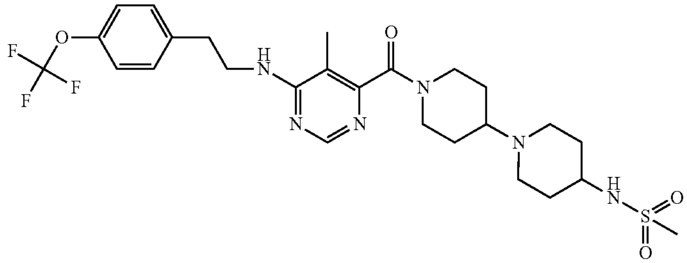 [SMILES: Cc1c(NCCc2ccc(OC(F)(F)F)cc2)ncnc1C(=O)N1CCC(N2CCC(NS(C)(=O)=O)CC2)CC1] | 25a | 4-trifluoro methoxy-benzyl-amine | 585 | 7.63 | 1E (Hydro) |

-continued

| Ex # | STRUCTURE | Intermediate | Amine | [M + H]+ | HPLC R_t(min) | Method |
|---|---|---|---|---|---|---|
| 71 | 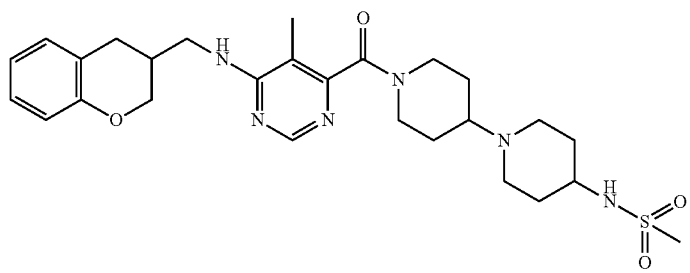 [SMILES: Cc1c(NCC2COc3ccccc3C2)ncnc1C(=O)N1CCC(N2CCC(NS(C)(=O)=O)CC2)CC1] | 25a | chroman-3-yl-methan amine | 543 | 6.75 | 1E (Hydro) |
| 72 | 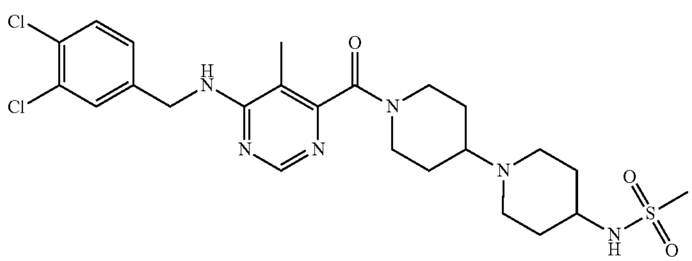 [SMILES: Cc1c(NCc2ccc(Cl)c(Cl)c2)ncnc1C(=O)N1CCC(N2CCC(NS(C)(=O)=O)CC2)CC1] | 25a | 3,4-di-chloro-benzyl-amine | 555 | 7.30 | 1E (Hydro) |
| 73 | 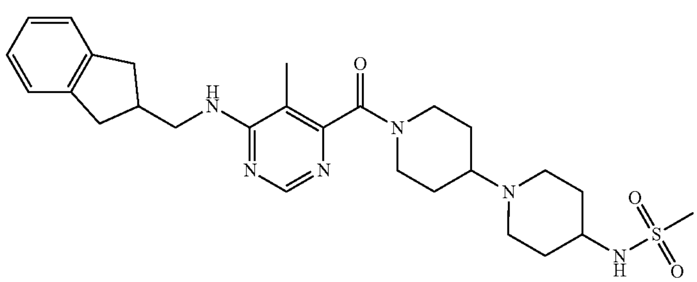 [SMILES: Cc1c(NCC2Cc3ccccc3C2)ncnc1C(=O)N1CCC(N2CCC(NS(C)(=O)=O)CC2)CC1] | 25a | indan-2yl-methan-amine | 527 | 7.35 | 1E (Hydro) |
| 74 | 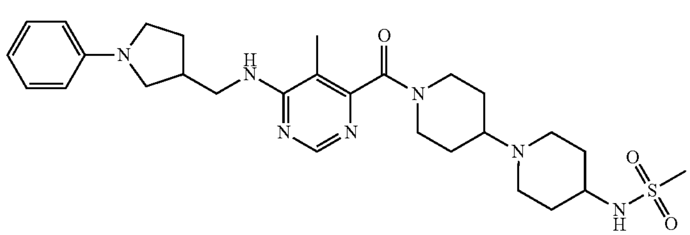 [SMILES: Cc1c(NCC2CCN(c3ccccc3)C2)ncnc1C(=O)N1CCC(N2CCC(NS(C)(=O)=O)CC2)CC1] | 25a | (1-phenyl-pyrrolidin-3-yl)-methan-amine | 555 | 7.43-7.80 | 1E (Hydro) |
| 75 | 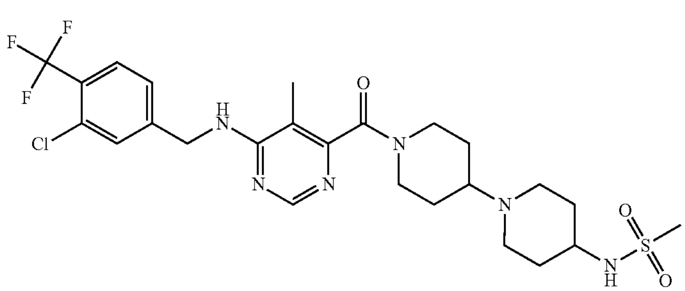 [SMILES: Cc1c(NCc2ccc(C(F)(F)F)c(Cl)c2)ncnc1C(=O)N1CCC(N2CCC(NS(C)(=O)=O)CC2)CC1] | 25a | 3-chloro-4-tri-fluoro methyl-benzyl-amine | 589 | 7.78 | 2F |

-continued

| Ex # | STRUCTURE | Intermediate | Amine | [M + H]+ | HPLC R<sub>t</sub>(min) | Method |
|---|---|---|---|---|---|---|
| 76 | 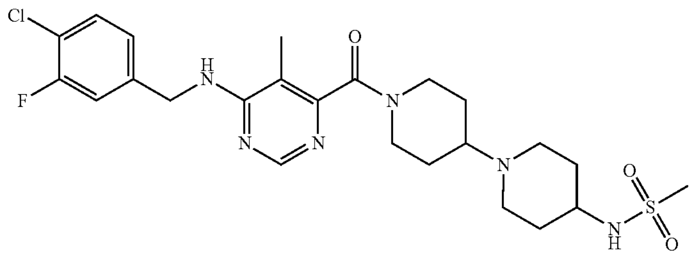 [SMILES: Cc1c(NCc2ccc(Cl)c(F)c2)ncnc1C(=O)N1CCC(N2CCC(NS(C)(=O)=O)CC2)CC1] | 25a | 4-chloro-3-fluoro-benzyl-amine | 539 | 2.07 | 1F |
| 77 | 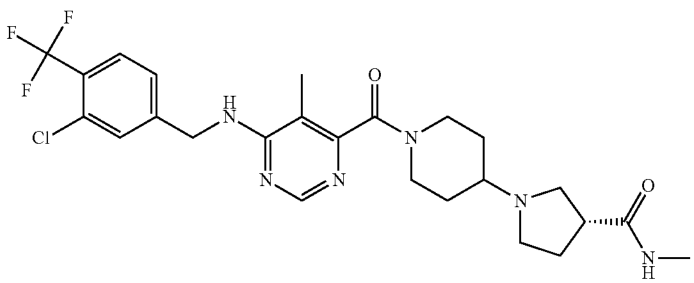 [SMILES: CNC(=O)[C@@H]1CCN(C2CCN(C(=O)c3ncnc(NCc4ccc(C(F)(F)F)c(Cl)c4)c3C)CC2)C1] | 25e | 3-chloro-4-trifluoromethyl-benzyl-amine | 539 | 8.23 | 1E (Hydro) |
| 78 | 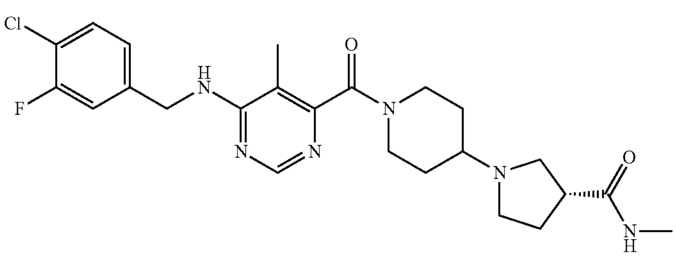 [SMILES: CNC(=O)[C@@H]1CCN(C2CCN(C(=O)c3ncnc(NCc4ccc(Cl)c(F)c4)c3C)CC2)C1] | 25e | 4-chloro-3-fluoro-benzyl-amine | 489 | 7.33 | 1E (Hydro) |
| 79 | 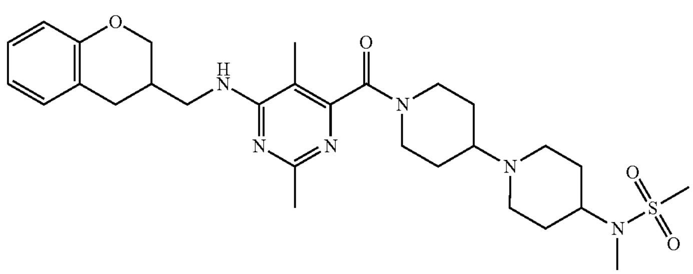 [SMILES: Cc1nc(NCC2COc3ccccc3C2)c(C)c(C(=O)N2CCC(N3CCC(N(C)S(C)(=O)=O)CC3)CC2)n1] | 25l | chroman-3-yl-methanamine | 571 | 8.13 | 1E (Hydro) |
| 80 | 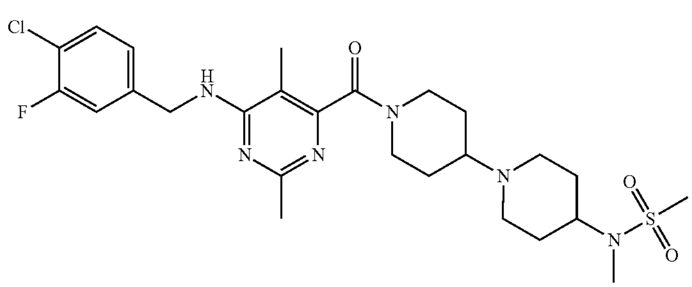 [SMILES: Cc1nc(NCc2ccc(Cl)c(F)c2)c(C)c(C(=O)N2CCC(N3CCC(N(C)S(C)(=O)=O)CC3)CC2)n1] | 25l | 4-chloro-3-fluoro-benzyl-amine | 567 | 8.36 | 1E (Hydro) |

| Ex # | STRUCTURE | Intermediate | Amine | [M + H]+ | HPLC Rt(min) | Method |
|---|---|---|---|---|---|---|
| 81 | 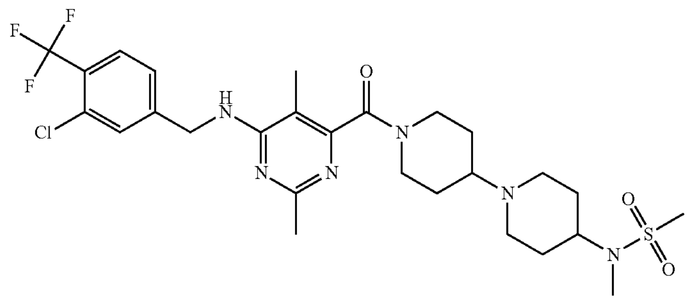 [SMILES: Cc1nc(NCc2ccc(C(F)(F)F)c(Cl)c2)c(C)c(C(=O)N2CCC(N3CCC(N(C)S(C)(=O)=O)CC3)CC2)n1] | 25l | 3-chloro-4-trifluoromethyl-benzyl-amine | 617 | 9.12 | 1E (Hydro) |
| 82 | 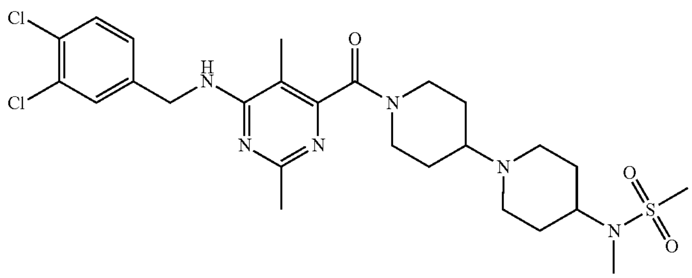 [SMILES: Cc1nc(NCc2ccc(Cl)c(Cl)c2)c(C)c(C(=O)N2CCC(N3CCC(N(C)S(C)(=O)=O)CC3)CC2)n1] | 25l | 3,4-dichloro-benzyl-amine | 583 | 8.83 | 1E (Hydro) |
| 83 | 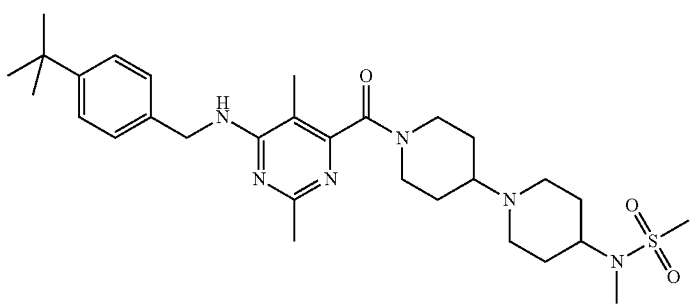 [SMILES: Cc1nc(NCc2ccc(C(C)(C)C)cc2)c(C)c(C(=O)N2CCC(N3CCC(N(C)S(C)(=O)=O)CC3)CC2)n1] | 25l | 4-tert-butyl-benzyl-amine | 571 | 9.73 | 1E (Hydro) |
| 84 | 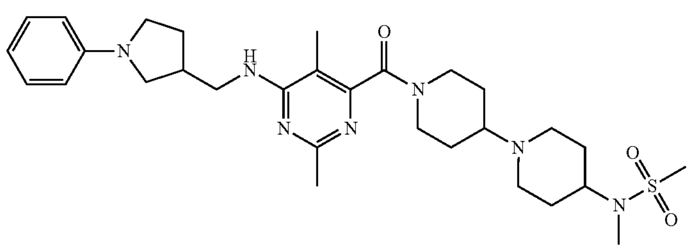 [SMILES: Cc1nc(NCC2CCN(c3ccccc3)C2)c(C)c(C(=O)N2CCC(N3CCC(N(C)S(C)(=O)=O)CC3)CC2)n1] | 25l | (1-phenyl-pyrrolidin-3-yl)-methan-amine | 584 | 8.70–9.02 | 1E (Hydro) |
| 85 | 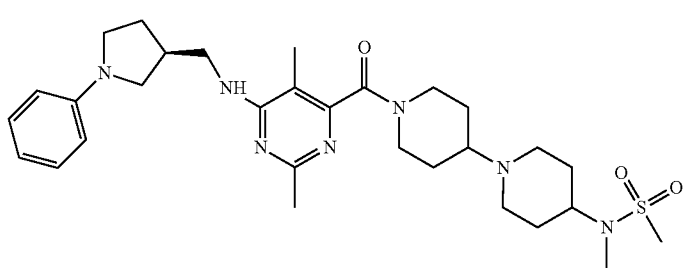 [SMILES: Cc1nc(NC[C@@H]2CCN(c3ccccc3)C2)c(C)c(C(=O)N2CCC(N3CCC(N(C)S(C)(=O)=O)CC3)CC2)n1] | 25l | 9c | 584 | 9.1 | 1E (Hydro) |

-continued

| Ex # | STRUCTURE | Intermediate | Amine | [M + H]+ | HPLC R_t (min) | Method |
|---|---|---|---|---|---|---|
| 86 | 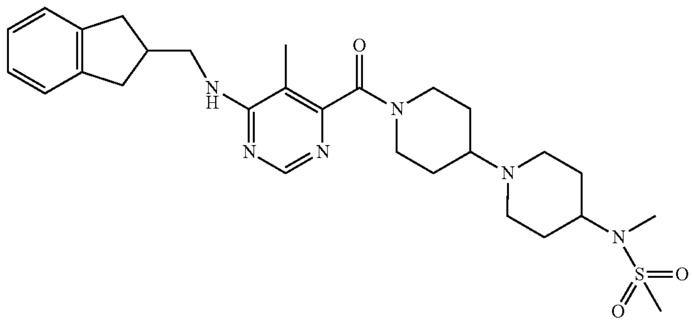 [SMILES: Cc1c(NCC2Cc3ccccc3C2)ncnc1C(=O)N1CCC(N2CCC(N(C)S(C)(=O)=O)CC2)CC1] | 25l | indan-2yl-methan-amine | 555 | 8.80 | 1E (Hydro) |
| 87 | 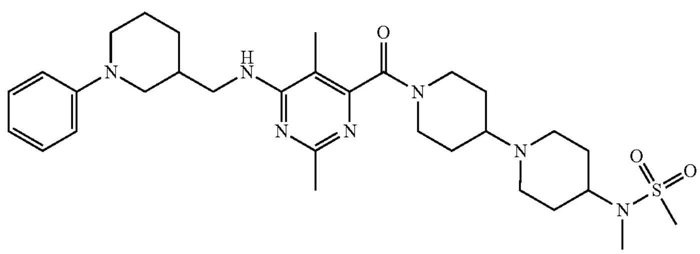 [SMILES: Cc1nc(NCC2CCCN(c3ccccc3)C2)c(C)c(C(=O)N2CCC(N3CCC(N(C)S(C)(=O)=O)CC3)CC2)n1] | 25l | 9a | 598 | 8.97 | 1E (Hydro) |
| 88 | 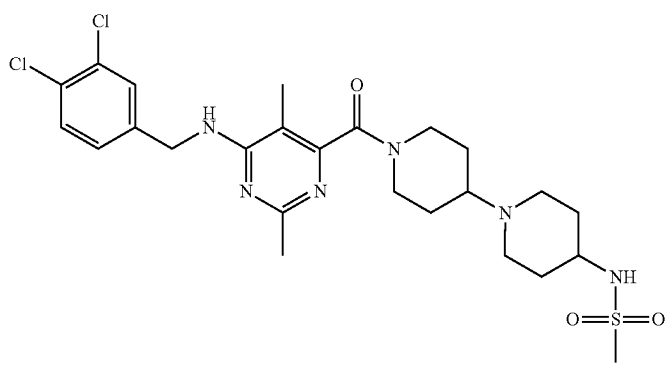 [SMILES: Cc1nc(NCc2ccc(Cl)c(Cl)c2)c(C)c(C(=O)N2CCC(N3CCC(NS(C)(=O)=O)CC3)CC2)n1] | 25k | 3,4-di-chloro-benzyl-amine | 569 | 7.78 | 1E (Hydro) |
| 89 | 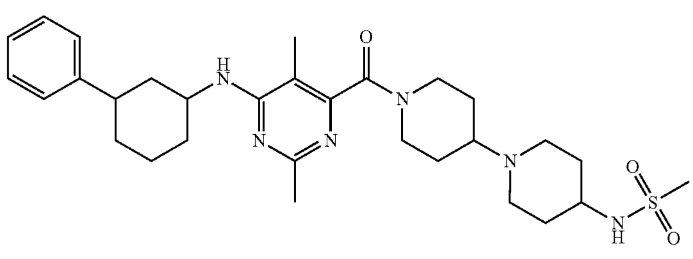 [SMILES: Cc1nc(NC2CCCC(c3ccccc3)C2)c(C)c(C(=O)N2CCC(N3CCC(NS(C)(=O)=O)CC3)CC2)n1] | 25k | 3-phenyl-cyclo-hexyl-amine | 569 | 8.45 | 1E (Hydro) |
| 90 | 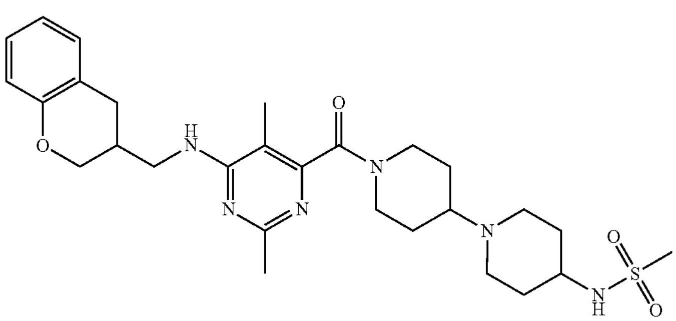 [SMILES: Cc1nc(NCC2COc3ccccc3C2)c(C)c(C(=O)N2CCC(N3CCC(NS(C)(=O)=O)CC3)CC2)n1] | 25k | chroman-3-yl-methan amine | 557 | 7.20 | 1E (Hydro) |

-continued

| Ex # | STRUCTURE | Intermediate | Amine | [M + H]+ | HPLC R<sub>t</sub>(min) | Method |
|---|---|---|---|---|---|---|
| 91 | 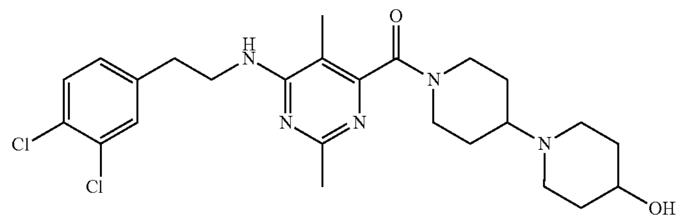 [SMILES: Cc1nc(NCCc2ccc(Cl)c(Cl)c2)c(C)c(C(=O)N2CCC(N3CCC(O)CC3)CC2)n1] | 25m | 2-(3,4-dichlorophenyl)-ethylamine | 506 | 7.87 | 1E |
| 92 | 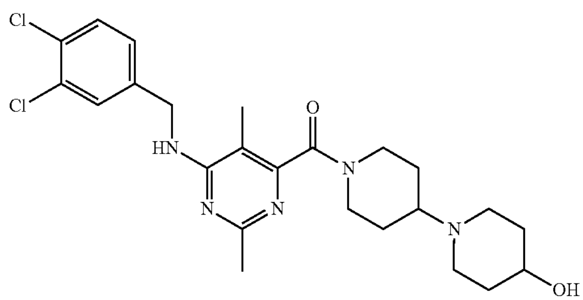 [SMILES: Cc1nc(NCc2ccc(Cl)c(Cl)c2)c(C)c(C(=O)N2CCC(N3CCC(O)CC3)CC2)n1] | 25m | 3,4-dichlorobenzylamine | 492 | 7.62 | 1E |
| 93 | 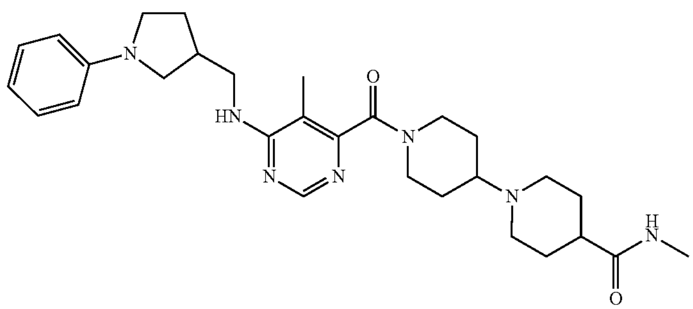 [SMILES: CNC(=O)C1CCN(C2CCN(C(=O)c3ncnc(NCC4CCN(c5ccccc5)C4)c3C)CC2)CC1] | 25d | (1-phenylpyrrolidin-3-yl)-methanamine | 520 | 7.70 | 1E (Hydro) |
| 94 | 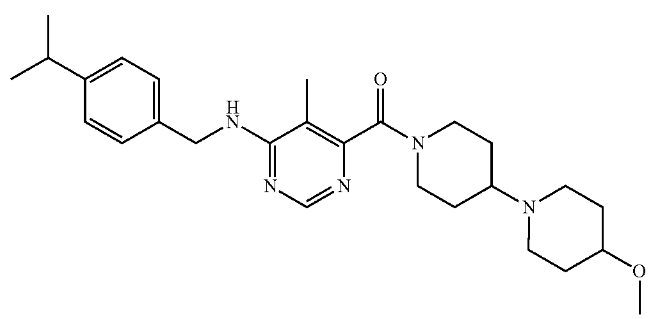 [SMILES: COC1CCN(C2CCN(C(=O)c3ncnc(NCc4ccc(C(C)C)cc4)c3C)CC2)CC1] | 25g | 4-isopropylbenzylamine | 466 | 6.71 | 2F |
| 95 | 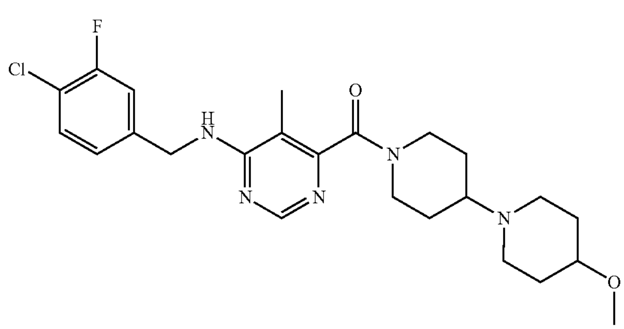 [SMILES: COC1CCN(C2CCN(C(=O)c3ncnc(NCc4ccc(Cl)c(F)c4)c3C)CC2)CC1] | 25g | 4-chloro-3-fluorobenzylamine | 476 | 9.18 | 1E (Hydro) |

| Ex # | STRUCTURE | Intermediate | Amine | [M + H]⁺ | HPLC $R_t$(min) | Method |
|---|---|---|---|---|---|---|
| 96 | 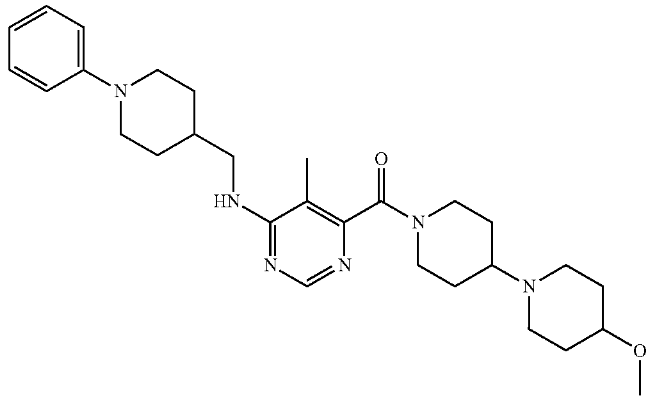 [SMILES: COC1CCN(C2CCN(C(=O)c3ncnc(NCC4CCN(c5ccccc5)CC4)c3C)CC2)CC1] | 25g | (1-phenyl-piperidin-4-yl)-methanamine | 507 | 9.55 | 1E (Hydro) |
| 97 | 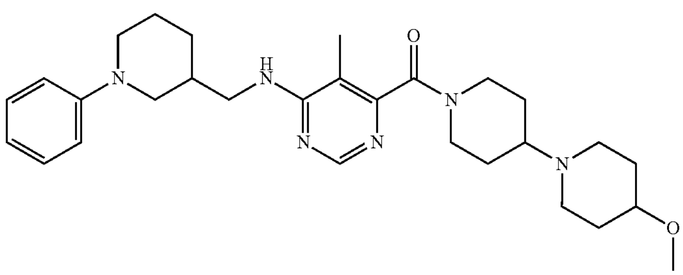 [SMILES: COC1CCN(C2CCN(C(=O)c3ncnc(NCC4CCCN(c5ccccc5)C4)c3C)CC2)CC1] | 25g | 9a | 507 | 1.22 | 2F |
| 98 | 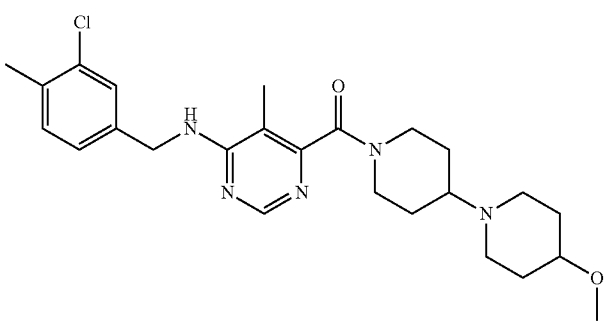 | 25g | 3-chloro-4-methyl-benzyl-amine | 472 | 9.62 | 1E (Hydro) |

Example 99

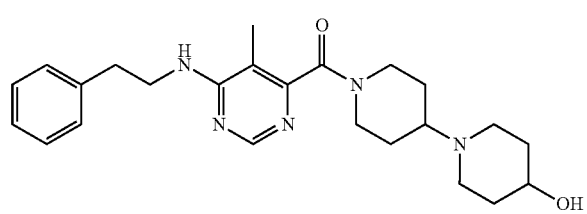 [SMILES: Cc1c(NCCc2ccccc2)ncnc1C(=O)N1CCC(N2CCC(O)CC2)CC1]

Intermediate 2a (200 mg, 1.047 mmol) was dissolved in 30 ml of dichloromethane. [1,4']Bipiperidinyl-4-ol (192 mg, 1.047 mmol) was added and the reaction mixture was stirred at room temperature for 2 h. The reaction mixture was concentrated under vacuum and the crude product was dissolved in 1 ml of DMSO. Phenethylamine (0.6 ml, 4.73 mmol) and N,N-diisopropyl-ethyl amine (0.013 ml, 0.075 mmol) were added and the reaction mixture was stirred at 80° C. overnight. The reaction mixture was concentrated under vacuum. The crude product was purified by reverse phase preparative HPLC. 331 mg (0.616 mmol) of the desired product were obtained.

HPLC (Method C): $R_t$ (min)=1.34

[M+H]⁺=424

The following examples were synthesized in analogy to the preparation of Example 99.

| Ex # | STRUCTURE | Intermediate | Intermediate | Amine | [M + H]⁺ | HPLC $R_t$ (min) | Method |
|---|---|---|---|---|---|---|---|
| 100 | 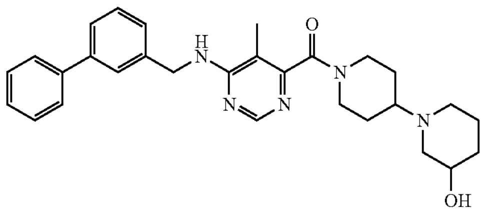 [SMILES: Cc1c(NCc2cccc(-c3ccccc3)c2)ncnc1C(=O)N1CCC(N2CCCC(O)C2)CC1] | 2a | [1,4']-Bipiperidinyl-3-ol | Biphenyl-3-yl-methanamine | 486 | 1.53 | 2C |
| 101 | 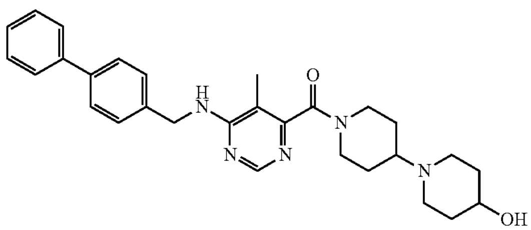 [SMILES: Cc1c(NCc2ccc(-c3ccccc3)cc2)ncnc1C(=O)N1CCC(N2CCC(O)CC2)CC1] | 2a | [1,4']Bipiperidinyl-4-ol | Biphenyl-4-yl-methanamine | 486 | 1.51 | 2C |
| 102 | 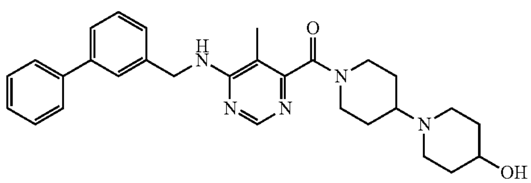 [SMILES: Cc1c(NCc2cccc(-c3ccccc3)c2)ncnc1C(=O)N1CCC(N2CCC(O)CC2)CC1] | 2a | [1,4']Bipiperidinyl-4-ol | Biphenyl-3-yl-methanamine | 486 | 1.52 | 2C |
| 103 | 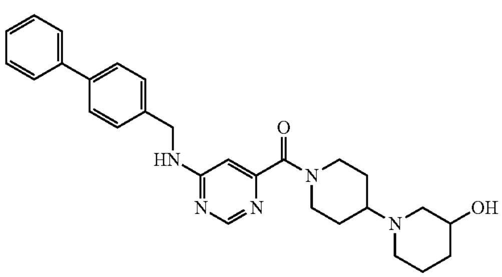 [SMILES: O=C(c1cc(NCc2ccc(-c3ccccc3)cc2)ncn1)N1CCC(N2CCCC(O)C2)CC1] | 6-chloro-pyrimidine-4-carbonyl chloride | [1,4']-Bipiperidin-in-yl-3-ol | Biphenyl-4-yl-methanamine | 472 | 1.59 | 2C |

Example 104

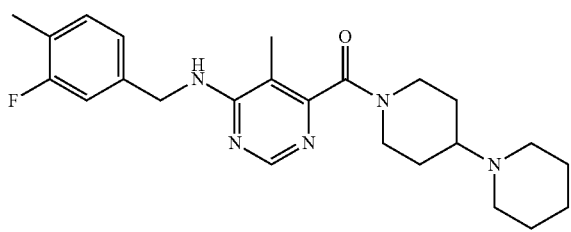 [SMILES: Cc1ccc(CNc2ncnc(C(=O)N3CCC(N4CCCCC4)CC3)c2C)cc1F]

Intermediate 25i (17 mg, 0.05 mmol), 3-fluoro-4-methyl-benzylamine (10 mg, 0.075 mmol) and diisopropyl-ethyl amine (0.013 ml, 0.075 mmol) in 1 ml of dry DMSO were stirred at 80° C. overnight. The reaction mixture was concentrated under vacuum. The crude product was purified by reverse phase preparative HPLC. 20 mg (0.047 mmol) of the desired product were obtained.

HPLC (Method C): $R_t$ (min)=1.45

[M+H]⁺=426

The following examples were synthesized in analogy to the preparation of Example 104.

| Ex # | STRUCTURE | Intermediate | Amine | [M + H]⁺ | HPLC R_t (min) | Method |
|---|---|---|---|---|---|---|
| 105 | 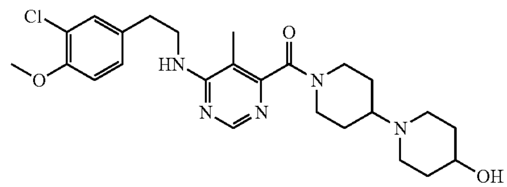 [SMILES: COc1ccc(CCNc2ncnc(C(=O)N3CCC(N4CCC(O)CC4)CC3)c2C)cc1Cl] | 25f | 2-(3-chloro-4-methoxy-phenyl)-ethyl-amine | 488 | 1.43 | 2C |
| 106 | 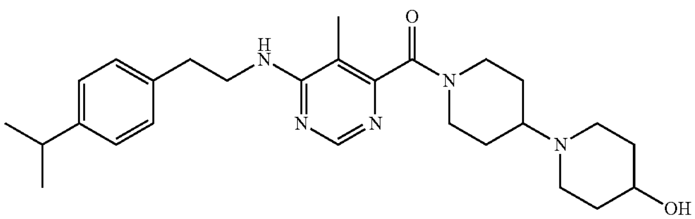 [SMILES: Cc1c(NCCc2ccc(C(C)C)cc2)ncnc1C(=O)N1CCC(N2CCC(O)CC2)CC1] | 25f | 2-(4-isopropyl-phenyl)-ethylamine | 466 | 2.88 | 2B |
| 107 | 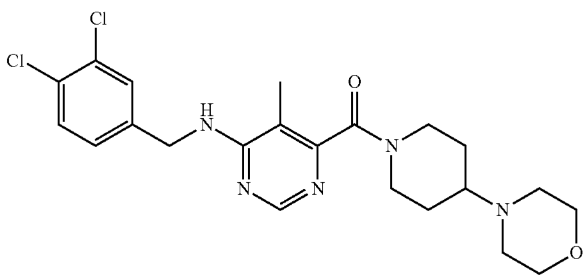 [SMILES: Cc1c(NCc2ccc(Cl)c(Cl)c2)ncnc1C(=O)N1CCC(N2CCOCC2)CC1] | 25h | 3,4-dichloro-benzyl-amine | 464 | 5.6 | 1A |
| 108 | 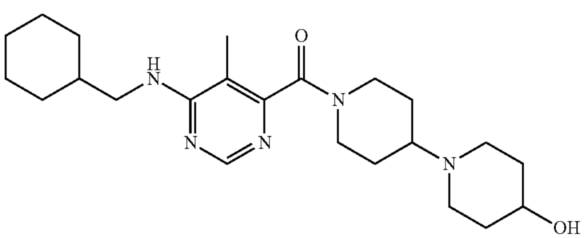 [SMILES: Cc1c(NCC2CCCCC2)ncnc1C(=O)N1CCC(N2CCC(O)CC2)CC1] | 25f | Cyclohexyl-methan-amine | 416 | 2.67 | 2B |
| 109 | 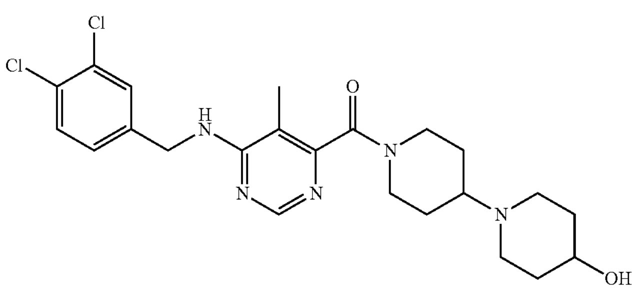 [SMILES: Cc1c(NCc2ccc(Cl)c(Cl)c2)ncnc1C(=O)N1CCC(N2CCC(O)CC2)CC1] | 25f | 3,4-dichloro-benzyl-amine | 478 | 2.81 | 2B |
| 110 | 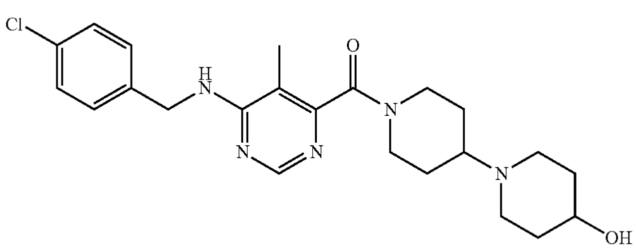 [SMILES: Cc1c(NCc2ccc(Cl)cc2)ncnc1C(=O)N1CCC(N2CCC(O)CC2)CC1] | 25f | 4-chloro-benzyl-amine | 444 | 1.6 | 2A |

| Ex # | STRUCTURE | Intermediate | Amine | [M + H]⁺ | HPLC R_t. (min) | Method |
|---|---|---|---|---|---|---|
| 111 | 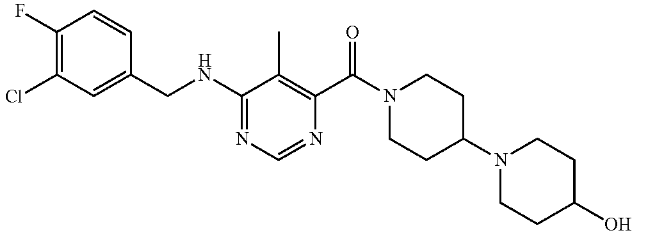 [SMILES: Cc1c(NCc2ccc(F)c(Cl)c2)ncnc1C(=O)N1CCC(N2CCC(O)CC2)CC1] | 25f | 3-chloro-4-fluoro-benzyl-amine | 462 | 1.63 | 2A |
| 112 | 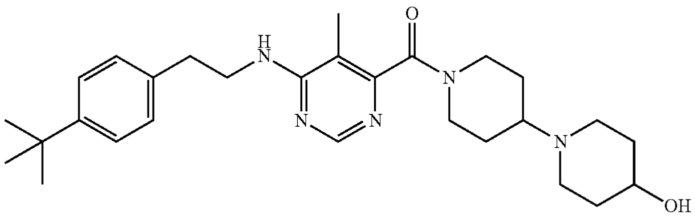 [SMILES: Cc1c(NCCc2ccc(C(C)(C)C)cc2)ncnc1C(=O)N1CCC(N2CCC(O)CC2)CC1] | 25f | 2-(4-tert-butyl-phenyl)-ethylamine | 480 | 1.8 | 2A |
| 113 | 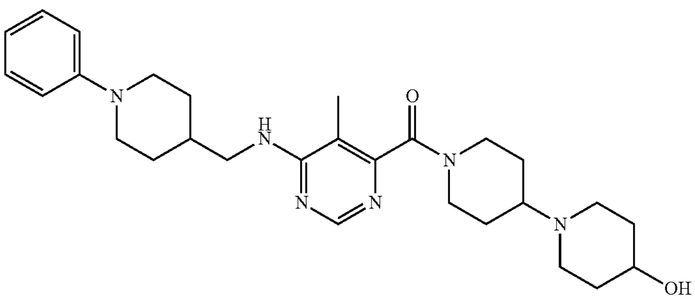 [SMILES: Cc1c(NCC2CCN(c3ccccc3)CC2)ncnc1C(=O)N1CCC(N2CCC(O)CC2)CC1] | 25f | (1-phenyl-piperidin-4-yl)methan-amine | 493 | 1.32 | 2A |
| 114 | 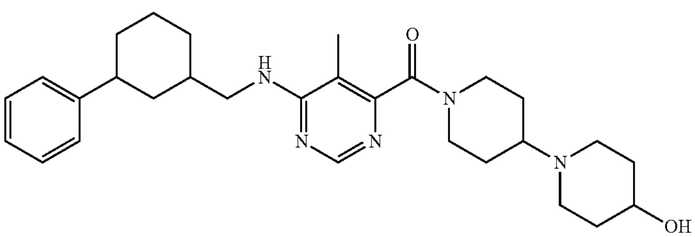 [SMILES: Cc1c(NCC2CCCC(c3ccccc3)C2)ncnc1C(=O)N1CCC(N2CCC(O)CC2)CC1] | 25f | 7a | 492 | 7.42 | 2F |
| 115 | 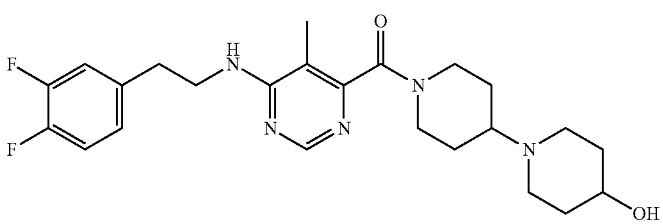 [SMILES: Cc1c(NCCc2ccc(F)c(F)c2)ncnc1C(=O)N1CCC(N2CCC(O)CC2)CC1] | 25f | 2-(3,4-difluoro-phenyl)-ethylamine | 460 | 1.61 | 2A |
| 116 | 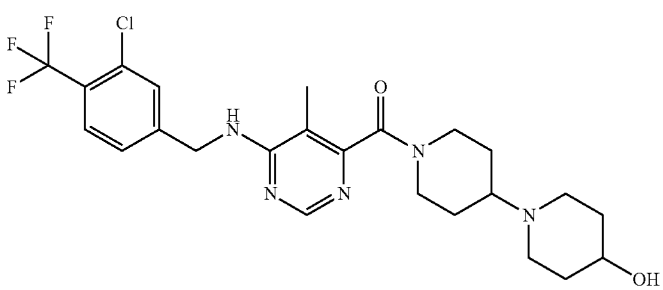 [SMILES: Cc1c(NCc2ccc(C(F)(F)F)c(Cl)c2)ncnc1C(=O)N1CCC(N2CCC(O)CC2)CC1] | 25f | 3-chloro-4-tri-fluoro-methyl-benzyl-amine | 512 | 1.74 | 2A |

| Ex # | STRUCTURE | Intermediate | Amine | [M + H]+ | HPLC R$_t$. (min) | Method |
|---|---|---|---|---|---|---|
| 117 | 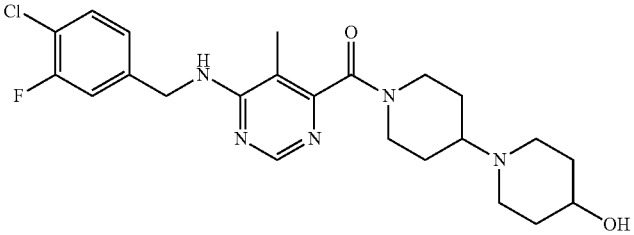 | 25f | 4-chloro-3-fluoro-benzyl-amine | 462 | 1.64 | 2A |
| 118 | 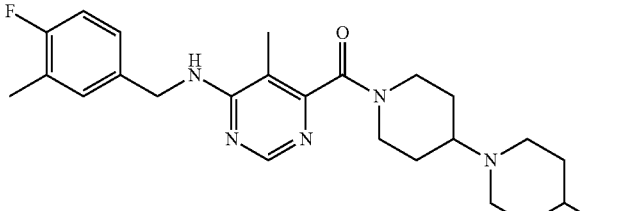 | 25f | 4-fluoro-3-methyl-benzyl-amine | 442 | 1.61 | 2A |
| 119 | 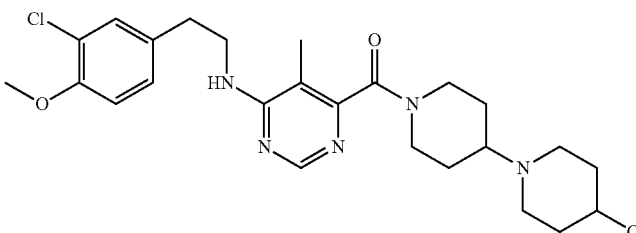 | 25f | 2-(3-chloro-4-methoxy-phenyl)-ethyl-amine | 488 | 1.63 | 2A |
| 120 | 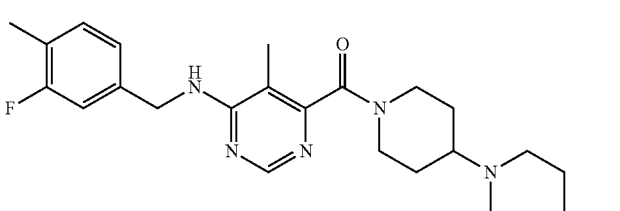 | 25f | 3-fluoro-4-methyl-benzyl-amine | 442 | 1.61 | 2A |
| 121 | 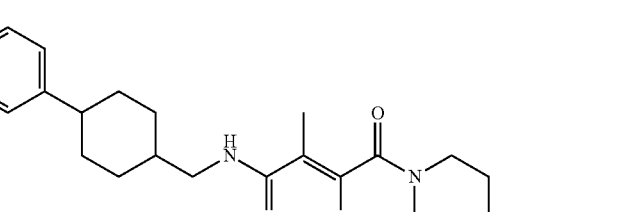 | 25f | (4-phenylcyclo-hexyl)-methan-amine | 492 | 1.78 | 2A |
| 122 | 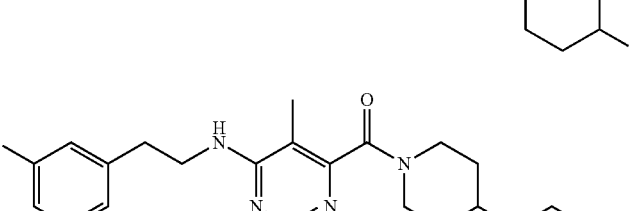 | 25f | 2-(3-chloro-phenyl)-ethylamine | 458 | 1.63 | 2A |

-continued

| Ex # | STRUCTURE | Intermediate | Amine | [M + H]⁺ | HPLC $R_t$ (min) | Method |
|---|---|---|---|---|---|---|
| 123 | 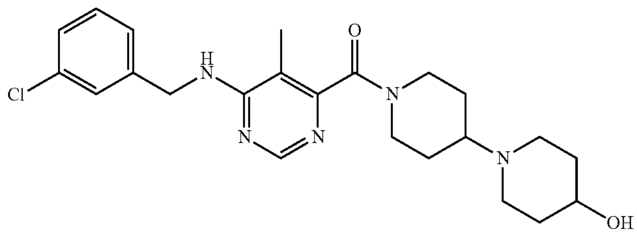 [SMILES: Cc1c(NCc2cccc(Cl)c2)ncnc1C(=O)N1CCC(N2CCC(O)CC2)CC1] | 25f | 3-chloro-benzyl-amine | 444 | 1.6 | 2A |
| 124 | 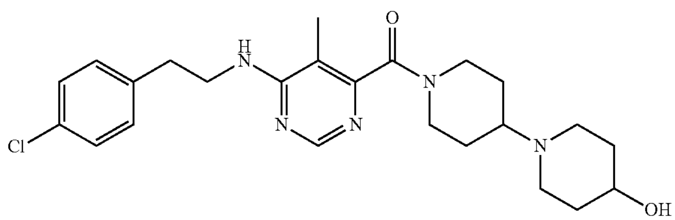 [SMILES: Cc1c(NCCc2ccc(Cl)cc2)ncnc1C(=O)N1CCC(N2CCC(O)CC2)CC1] | 25f | 2-(4-chloro-phenyl)-ethylamine | 458 | 1.65 | 2A |
| 125 | 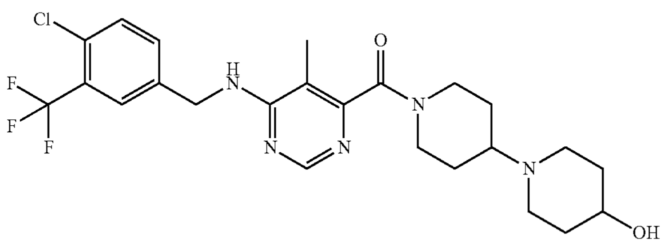 [SMILES: Cc1c(NCc2ccc(Cl)c(C(F)(F)F)c2)ncnc1C(=O)N1CCC(N2CCC(O)CC2)CC1] | 25f | 4-chloro-3-trifluoro-methyl-benzyl-amine | 512 | 1.74 | 2A |
| 126 | 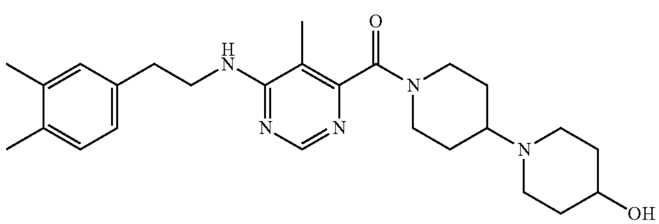 [SMILES: Cc1ccc(CCNc2ncnc(C(=O)N3CCC(N4CCC(O)CC4)CC3)c2C)cc1C] | 25f | 2-(3,4-dimethyl-phenyl)-ethylamine | 452 | 1.68 | 2A |
| 127 | 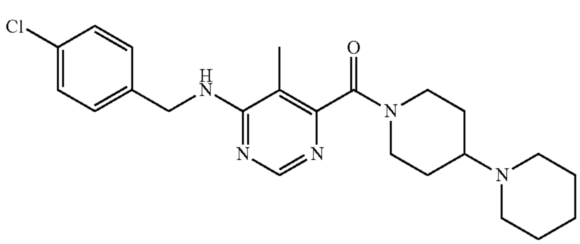 [SMILES: Cc1c(NCc2ccc(Cl)cc2)ncnc1C(=O)N1CCC(N2CCCCC2)CC1] | 25i | 4-chloro-benzyl-amine | 428 | 1.65 | 2A |
| 128 | 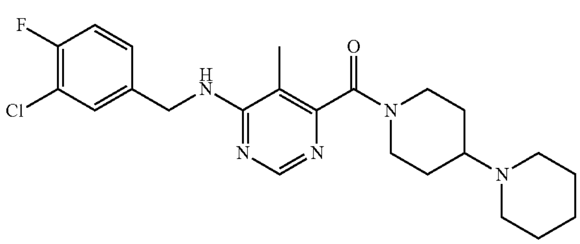 | 25i | 3-chloro-4-fluoro-benzyl-amine | 446 | 1.67 | 2A |

-continued

| Ex # | STRUCTURE | Intermediate | Amine | [M + H]+ | HPLC R_t. (min) | Method |
|---|---|---|---|---|---|---|
| 129 | 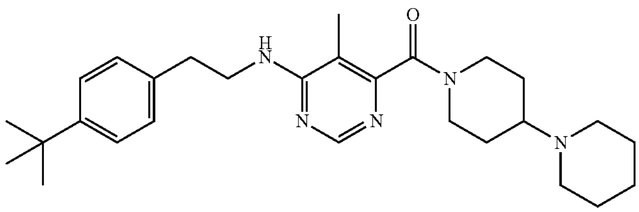 [SMILES: Cc1c(NCCc2ccc(C(C)(C)C)cc2)ncnc1C(=O)N1CCC(N2CCCCC2)CC1] | 25i | 2-(4-tert-butyl-phenyl)-ethylamine | 464 | 1.84 | 2A |
| 130 | 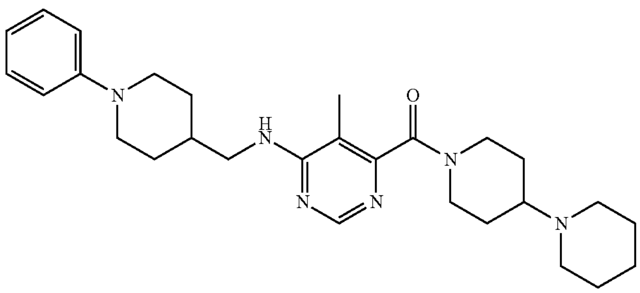 [SMILES: Cc1c(NCC2CCN(c3ccccc3)CC2)ncnc1C(=O)N1CCC(N2CCCCC2)CC1] | 25i | (1-phenyl-piperidin-4-yl)-methan-amine | 477 | 1.37 | 2A |
| 131 | 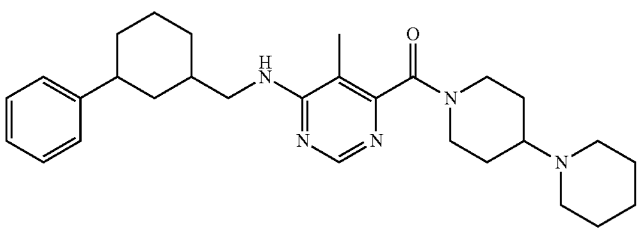 [SMILES: Cc1c(NCC2CCCC(c3ccccc3)C2)ncnc1C(=O)N1CCC(N2CCCCC2)CC1] | 25i | 7a | 476 | 1.84 | 2A |
| 132 | 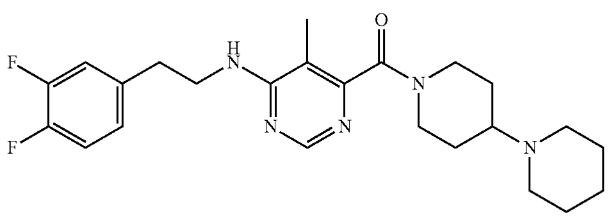 [SMILES: Cc1c(NCCc2ccc(F)c(F)c2)ncnc1C(=O)N1CCC(N2CCCCC2)CC1] | 25i | 2-(3,4-difluoro-phenyl)-ethylamine | 444 | 1.66 | 2A |
| 133 | 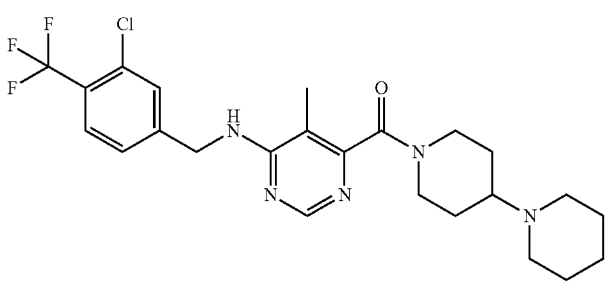 [SMILES: Cc1c(NCc2ccc(C(F)(F)F)c(Cl)c2)ncnc1C(=O)N1CCC(N2CCCCC2)CC1] | 25i | 3-chloro-4-trifluoro-methyl-benzyl-amine | 496 | 1.79 | 2A |
| 134 | 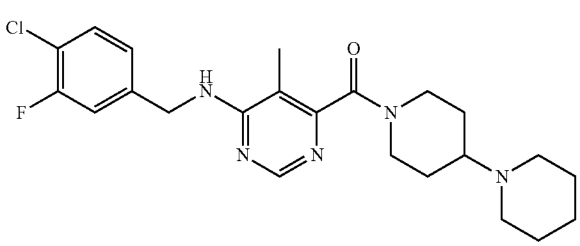 | 25i | 4-chloro-3-fluoro-benzyl-amine | 446 | 1.67 | 2A |

| Ex # | STRUCTURE | Intermediate | Amine | [M + H]+ | HPLC R_t (min) | Method |
|---|---|---|---|---|---|---|
| 135 | 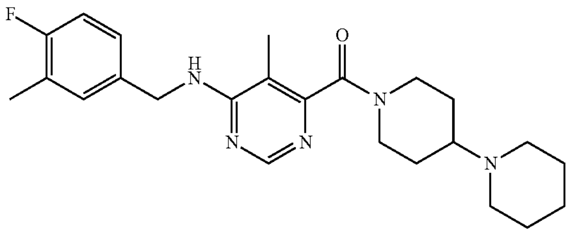 [SMILES: Cc1cc(CNc2ncnc(C(=O)N3CCC(N4CCCCC4)CC3)c2C)ccc1F] | 25i | 4-fluoro-3-methyl-benzyl-amine | 426 | 1.65 | 2A |
| 136 | 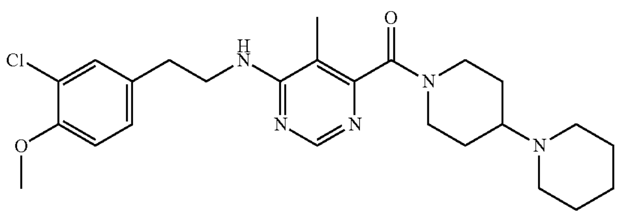 [SMILES: COc1ccc(CCNc2ncnc(C(=O)N3CCC(N4CCCCC4)CC3)c2C)cc1Cl] | 25i | 2-(3-chloro-4-methoxy-phenyl)-ethylamine | 472 | 1.66 | 2A |
| 137 | 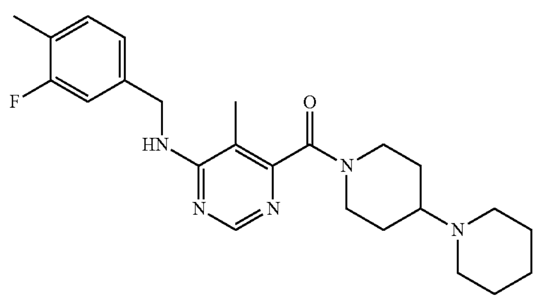 [SMILES: Cc1ccc(CNc2ncnc(C(=O)N3CCC(N4CCCCC4)CC3)c2C)cc1F] | 25i | 3-fluoro-4-methyl-benzyl-amine | 426 | 1.65 | 2A |
| 138 | 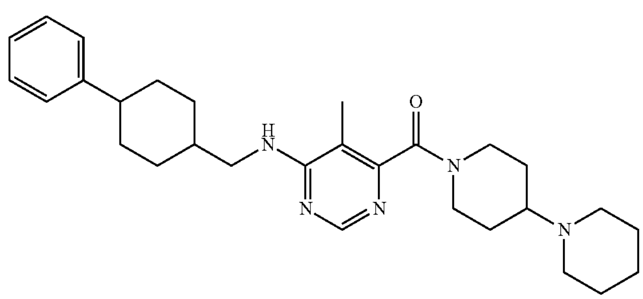 | 25i | (4-phenylcyclohexyl)-methan-amine | 476 | 1.84 | 2A |
| 139 | 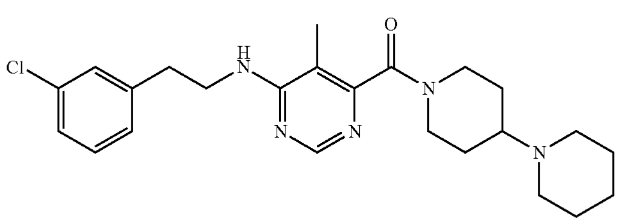 [SMILES: Cc1c(NCCc2cccc(Cl)c2)ncnc1C(=O)N1CCC(N2CCCCC2)CC1] | 25i | 2-(3-chloro-phenyl)-ethylamine | 442 | 1.68 | 2A |
| 140 | 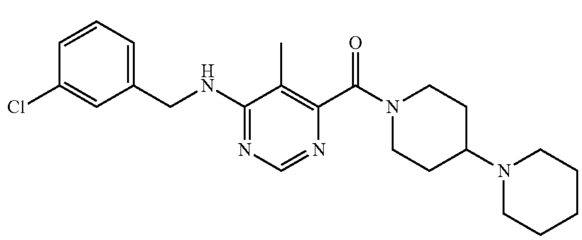 [SMILES: Cc1c(NCc2cccc(Cl)c2)ncnc1C(=O)N1CCC(N2CCCCC2)CC1] | 25i | 3-chloro-benzyl-amine | 428 | 1.64 | 2A |

| Ex # | STRUCTURE | Intermediate | Amine | [M + H]⁺ | HPLC R_t (min) | Method |
|---|---|---|---|---|---|---|
| 141 | 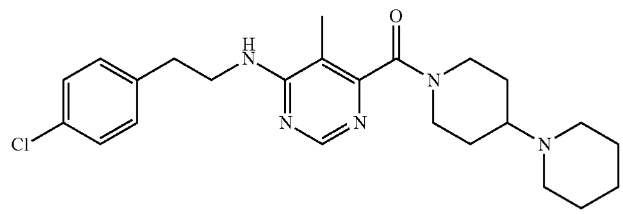 [SMILES: Cc1c(NCCc2ccc(Cl)cc2)ncnc1C(=O)N1CCC(N2CCCCC2)CC1] | 25i | 2-(4-chlorophenyl)-ethylamine | 442 | 1.69 | 2A |
| 142 | 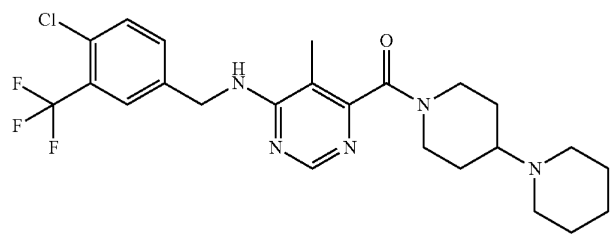 [SMILES: Cc1c(NCc2ccc(Cl)c(C(F)(F)F)c2)ncnc1C(=O)N1CCC(N2CCCCC2)CC1] | 25i | 4-chloro-3-trifluoromethyl-benzyl-amine | 496 | 1.79 | 2A |
| 143 | 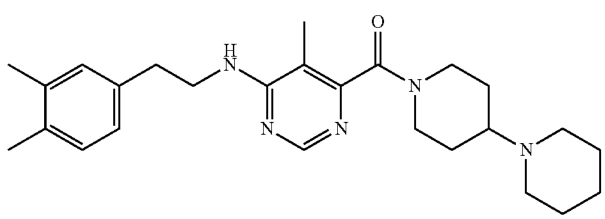 [SMILES: Cc1ccc(CCNc2ncnc(C(=O)N3CCC(N4CCCCC4)CC3)c2C)cc1C] | 25i | 2-(3,4-dimethyl-phenyl)-ethylamine | 436 | 1.72 | 2A |
| 144 | 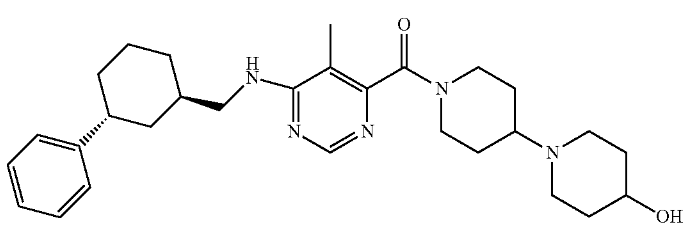 [SMILES: Cc1c(NC[C@@H]2CCC[C@@H](c3ccccc3)C2)ncnc1C(=O)N1CCC(N2CCC(O)CC2)CC1] | 25f | 7a | 492 | 7.7 | 2H (isocratic) |
| 145 | 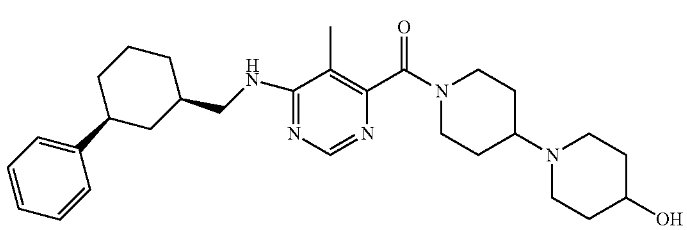 [SMILES: Cc1c(NC[C@@H]2CCC[C@H](c3ccccc3)C2)ncnc1C(=O)N1CCC(N2CCC(O)CC2)CC1] | 25f | 7a | 492 | 10.2 | 2H (isocratic) |

Example 146

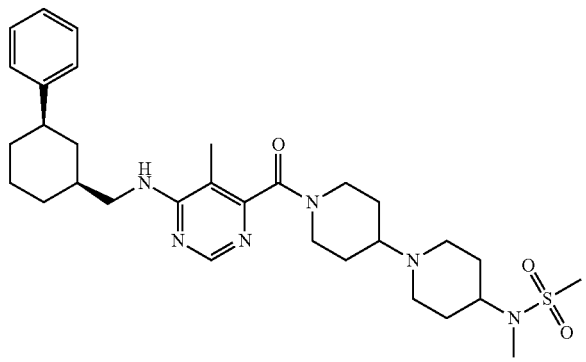 [SMILES: Cc1c(NC[C@H]2CCC[C@@H](c3ccccc3)C2)ncnc1C(=O)N1CCC(N2CCC(N(C)S(C)(=O)=O)CC2)CC1]

Intermediate 25b (80 mg, 0.18 mmol), Intermediate 7c (40 mg, 0.21 mmol) and N,N-diisopropyl-ethyl amine (0.046 ml, 0.26 mmol) in 0.2 ml of dry 1,4-dioxane were mixed in a microwave vial and reacted in the following conditions: Power 100, Ramp 5 min, Hold 2 h, Temperature 150° C., Pression 150° C., Stirring. The reaction mixture was concentrated under vacuum and diluted with dichloromethane. The organic phase was washed with an aqueous saturated sodium bicarbonate solution, dried over sodium sulfate and concentrated under vacuum. The crude product was purified by reverse phase preparative HPLC. 36 mg (0.06 mmol) of the desired product were obtained.

HPLC (Method 1E Hydro): $R_{t.}$ (min)=9.52
$[M+H]^+$=583

The following examples were synthesized in analogy to the preparation of Example 146

| Ex # | STRUCTURE | Intermediate | Amine | $[M + H]^+$ | HPLC $R_{t.}$ (min) | Method |
|---|---|---|---|---|---|---|
| 147 | 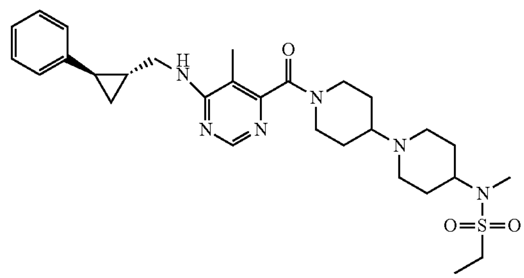 [SMILES: CCS(=O)(=O)N(C)C1CCN(C2CCN(C(=O)c3ncnc(NC[C@@H]4C[C@H]4c4ccccc4)c3C)CC2)CC1] | 25c | (trans-2-phenyl-cyclo-propyl)-methan-amine | 555 | 8.48 | 1E (Hydro) |
| 148 | 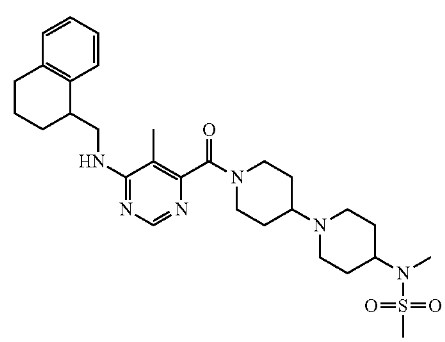 [SMILES: Cc1c(NCC2CCCc3ccccc32)ncnc1C(=O)N1CCC(N2CCC(N(C)S(C)(=O)=O)CC2)CC1] | 25b | (1,2,3,4-tetrahydro-naphthalen-1-yl)-methan-amine | 555 | 8.62 | 1E (Hydro) |
| 149 | 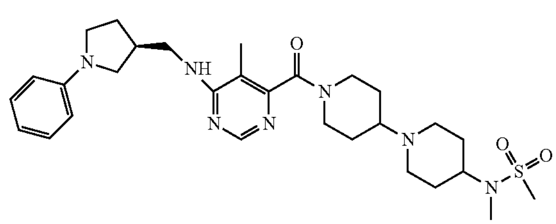 [SMILES: Cc1c(NC[C@@H]2CCN(c3ccccc3)C2)ncnc1C(=O)N1CCC(N2CCC(N(C)S(C)(=O)=O)CC2)CC1] | 25b | 9c | 570 | 8.7 | 1E (Hydro) |

-continued

| Ex # | STRUCTURE | Intermediate | Amine | [M + H]+ | HPLC R_t (min) | Method |
|---|---|---|---|---|---|---|
| 150 | 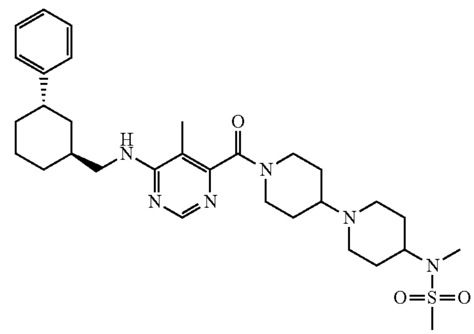 [SMILES: Cc1c(NC[C@H]2CCC[C@H](c3ccccc3)C2)ncnc1C(=O)N1CCC(N2CCC(N(C)S(C)(=O)=O)CC2)CC1] | 25b | 7d | 583 | 9.12 | 1E (Hydro) |
| 151 | 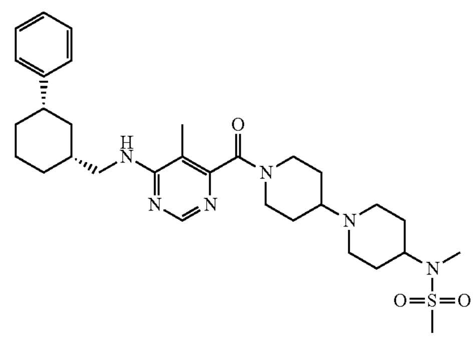 [SMILES: Cc1c(NC[C@@H]2CCC[C@H](c3ccccc3)C2)ncnc1C(=O)N1CCC(N2CCC(N(C)S(C)(=O)=O)CC2)CC1] | 25b | 7e | 583 | 9.22 | 1E (Hydro) |
| 152 | 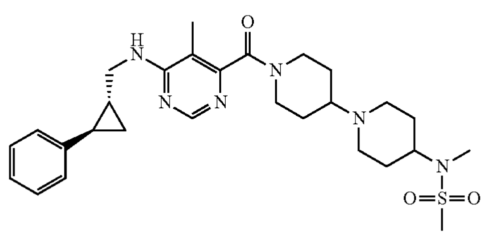 [SMILES: Cc1c(NC[C@@H]2C[C@H]2c2ccccc2)ncnc1C(=O)N1CCC(N2CCC(N(C)S(C)(=O)=O)CC2)CC1] | 25b | (trans-2-phenyl-cyclo-propyl)-methan-amine | 541 | 8.03 | 1E (Hydro) |
| 153 | 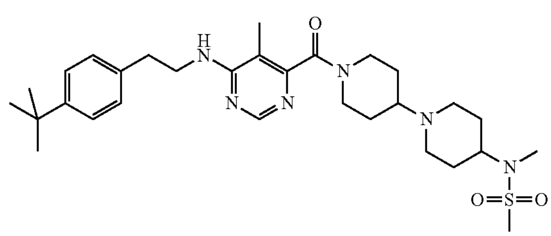 [SMILES: Cc1c(NCCc2ccc(C(C)(C)C)cc2)ncnc1C(=O)N1CCC(N2CCC(N(C)S(C)(=O)=O)CC2)CC1] | 25b | 2-(4-tert-butyl-phenyl)-ethyl-amine | 571 | 9.42 | 1E (Hydro) |
| 154 | 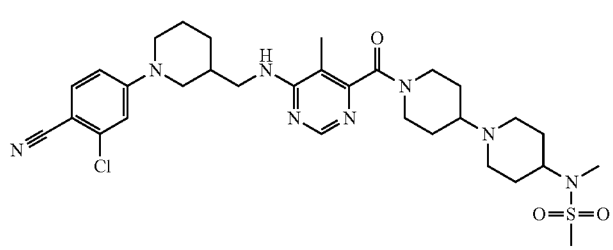 [SMILES: Cc1c(NCC2CCCN(c3ccc(C#N)c(Cl)c3)C2)ncnc1C(=O)N1CCC(N2CCC(N(C)S(C)(=O)=O)CC2)CC1] | 25b | 11 | 643 | 8.65 | 1E (Hydro) |

-continued

| Ex # | STRUCTURE | Intermediate | Amine | [M + H]+ | HPLC R_t (min) | Method |
|---|---|---|---|---|---|---|
| 155 | 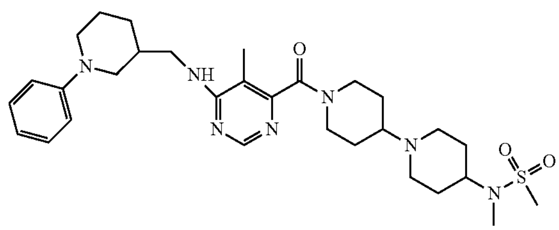 [SMILES: Cc1c(NCC2CCCN(c3ccccc3)C2)ncnc1C(=O)N1CCC(N2CCC(N(C)S(C)(=O)=O)CC2)CC1] | 25b | 9a | 584 | 8.52 | 1E (Hydro) |
| 156 | 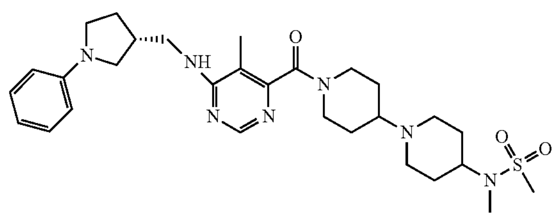 [SMILES: Cc1c(NC[C@H]2CCN(c3ccccc3)C2)ncnc1C(=O)N1CCC(N2CCC(N(C)S(C)(=O)=O)CC2)CC1] | 25b | 9b | 570 | 8.48 | 1E (Hydro) |
| 157 | 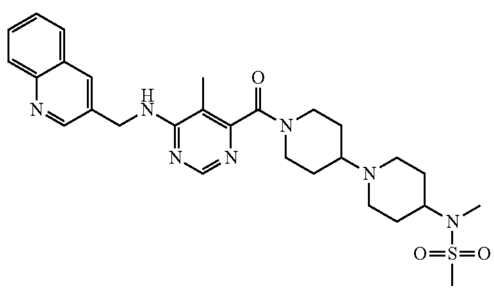 [SMILES: Cc1c(NCc2cnc3ccccc3c2)ncnc1C(=O)N1CCC(N2CCC(N(C)S(C)(=O)=O)CC2)CC1] | 25b | Quinolin-3-ylmethanamine | 552 | 1.28 | 2F |
| 158 | 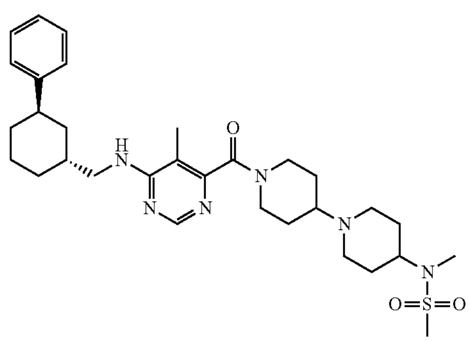 [SMILES: Cc1c(NC[C@@H]2CCC[C@@H](c3ccccc3)C2)ncnc1C(=O)N1CCC(N2CCC(N(C)S(C)(=O)=O)CC2)CC1] | 25b | 7b | 583 | 9.48 | 1E (Hydro) |
| 159 | 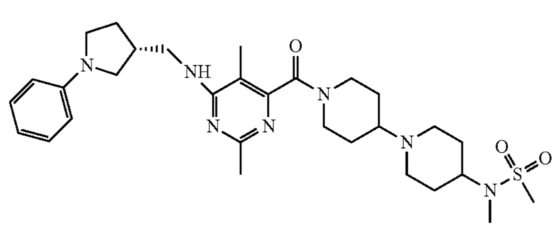 | 25l | 9b | 584 | 8.85 | 1E (Hydro) |

-continued

| Ex # | STRUCTURE | Intermediate | Amine | [M + H]+ | HPLC R_t. (min) | Method |
|---|---|---|---|---|---|---|
| 159a | 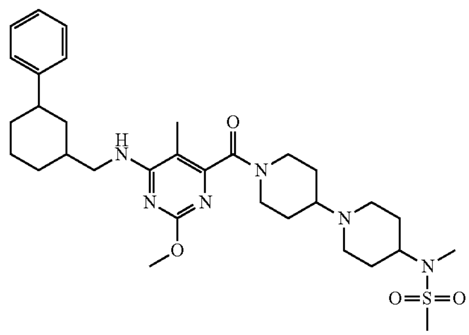 [SMILES: COc1nc(NCC2CCCC(c3ccccc3)C2)c(C)c(C(=O)N2CCC(N3CCC(N(C)S(C)(=O)=O)CC3)CC2)n1] | 25n | 7a | 613 | 2.21 | 2Ca |
| 159b | 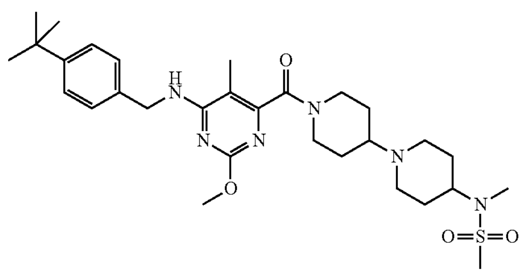 [SMILES: COc1nc(NCc2ccc(C(C)(C)C)cc2)c(C)c(C(=O)N2CCC(N3CCC(N(C)S(C)(=O)=O)CC3)CC2)n1] | 25n | 4-tert-butyl-benzyl-amine | 587 | 1.89 | 2Ca |
| 159c | 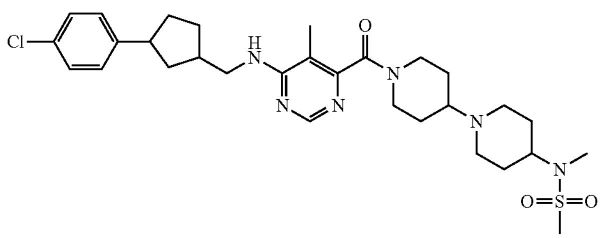 [SMILES: Cc1c(NCC2CCC(c3ccc(Cl)cc3)C2)ncnc1C(=O)N1CCC(N2CCC(N(C)S(C)(=O)=O)CC2)CC1] | 25b | 7m | 603 | 9.88 | 1E (Hydro) |
| 159d | 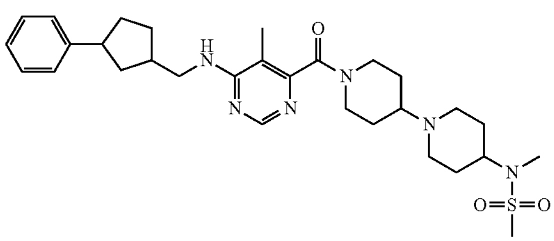 [SMILES: Cc1c(NCC2CCC(c3ccccc3)C2)ncnc1C(=O)N1CCC(N2CCC(N(C)S(C)(=O)=O)CC2)CC1] | 25b | 7l | 569 | 9.62 | 1E (Hydro) |
| 159e | 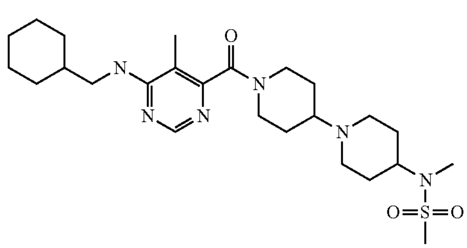 [SMILES: Cc1c(NCC2CCCCC2)ncnc1C(=O)N1CCC(N2CCC(N(C)S(C)(=O)=O)CC2)CC1] | 25b | C-Cyclohexyl-methyl-amine | 507 | 8.37 | 1E (Hydro) |

| Ex # | STRUCTURE | Intermediate | Amine | [M + H]+ | HPLC $R_t$ (min) | Method |
|---|---|---|---|---|---|---|
| 159f | 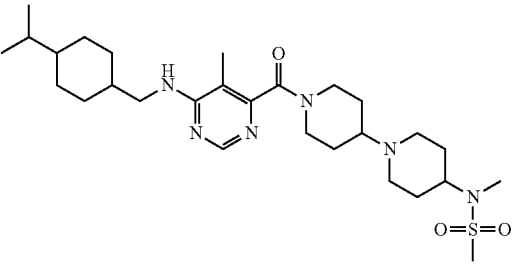 [SMILES: Cc1c(NCC2CCC(C(C)C)CC2)ncnc1C(=O)N1CCC(N2CCC(N(C)S(C)(=O)=O)CC2)CC1] | 25b | C-(4-isopropyl-cyclo-hexyl)-methyl-amine | 549 | 10.12 | 1E (Hydro) |
| 159g | 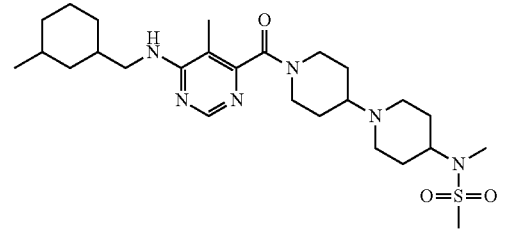 [SMILES: Cc1c(NCC2CCCC(C)C2)ncnc1C(=O)N1CCC(N2CCC(N(C)S(C)(=O)=O)CC2)CC1] | 25b | C-(3-methyl-cyclo-hexyl)-methyl-amine | 521 | 9.25 | 1E (Hydro) |
| 159h | 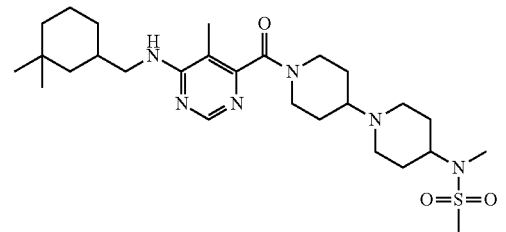 [SMILES: Cc1c(NCC2CCCC(C)(C)C2)ncnc1C(=O)N1CCC(N2CCC(N(C)S(C)(=O)=O)CC2)CC1] | 25b | C-(3,3-dimethyl-cyclo-hexyl)-methyl-amine | 535 | 9.68 | 1E (Hydro) |
| 159i | 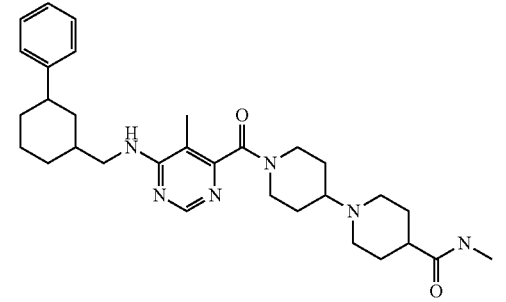 [SMILES: CNC(=O)C1CCN(C2CCN(C(=O)c3ncnc(NCC4CCCC(c5ccccc5)C4)c3C)CC2)CC1] | 25d | 7a | 533 | 9.53 | 1E (Hydro) |
| 159k | 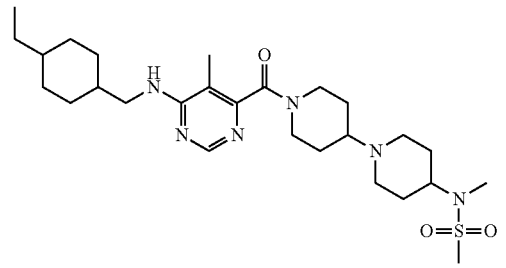 [SMILES: CCC1CCC(CNc2ncnc(C(=O)N3CCC(N4CCC(N(C)S(C)(=O)=O)CC4)CC3)c2C)CC1] | 25b | C-(4-ethyl-cyclo-hexyl)-methyl-amine | 535 | 9.98 | 1E (Hydro) |

| Ex # | STRUCTURE | Intermediate | Amine | [M + H]+ | HPLC R$_t$ (min) | Method |
|---|---|---|---|---|---|---|
| 159l | 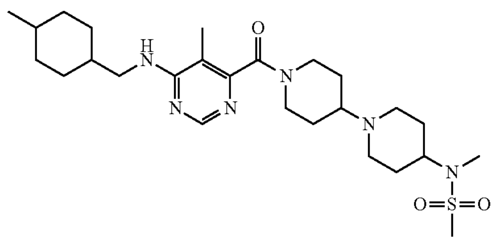 [SMILES: Cc1c(NCC2CCC(C)CC2)ncnc1C(=O)N1CCC(N2CCC(N(C)S(C)(=O)=O)CC2)CC1] | 25b | C-(4-methyl-cyclo-hexyl)-methyl-amine | 521 | 9.28 | 1E (Hydro) |
| 159m | 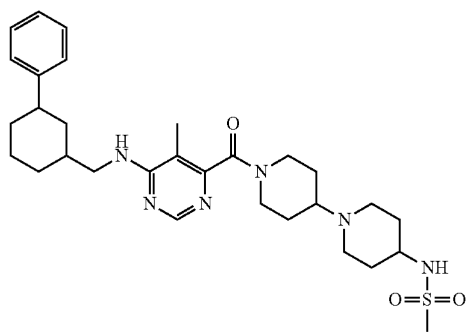 [SMILES: Cc1c(NCC2CCCC(c3ccccc3)C2)ncnc1C(=O)N1CCC(N2CCC(NS(C)(=O)=O)CC2)CC1] | 25a | 7a | 569 | 9.33 | 1E (Hydro) |
| 159n | 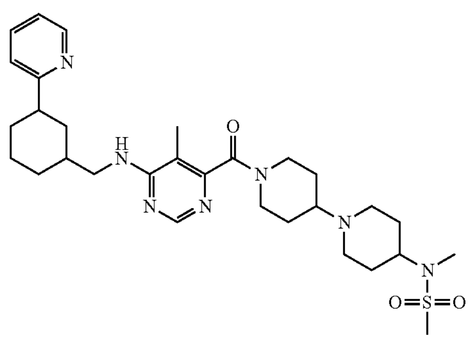 [SMILES: Cc1c(NCC2CCCC(c3ccccn3)C2)ncnc1C(=O)N1CCC(N2CCC(N(C)S(C)(=O)=O)CC2)CC1] | 25b | C-(3-pyridin-2yl-cyclo-hexyl)-methyl-amine | 584 | 7.90 8.05 | 1E (Hydro) |
| 159o | 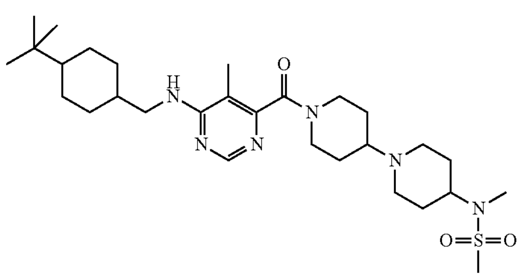 [SMILES: Cc1c(NCC2CCC(C(C)(C)C)CC2)ncnc1C(=O)N1CCC(N2CCC(N(C)S(C)(=O)=O)CC2)CC1] | 25b | C-(4-tert-butyl-cyclo-hexyl)-methyl-amine | 563 | 10.87 | 1E (Hydro) |
| 159p | 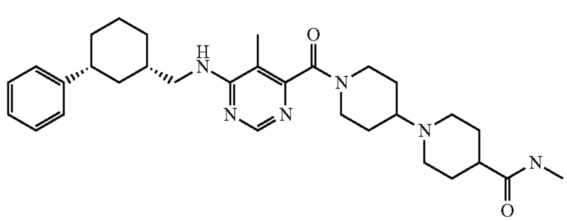 [SMILES: CNC(=O)C1CCN(C2CCN(C(=O)c3ncnc(NC[C@H]4CCC[C@@H](c5ccccc5)C4)c3C)CC2)CC1] | 25d | 7c | 533 | 9.53 | 1E (Hydro) |

-continued

| Ex # | STRUCTURE | Intermediate | Amine | [M + H]⁺ | HPLC R$_t$. (min) | Method |
|---|---|---|---|---|---|---|
| 159q | 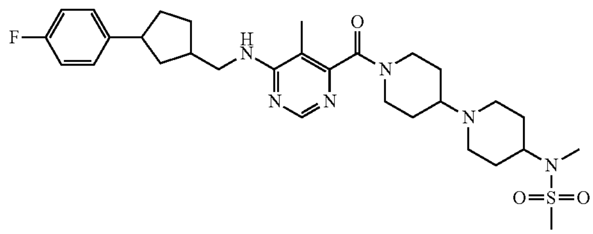 [SMILES: Cc1c(NCC2CCC(c3ccc(F)cc3)C2)ncnc1C(=O)N1CCC(N2CCC(N(C)S(C)(=O)=O)CC2)CC1] | 25b | 7n | 587 | 9.37 | 1E (Hydro) |
| 159r | 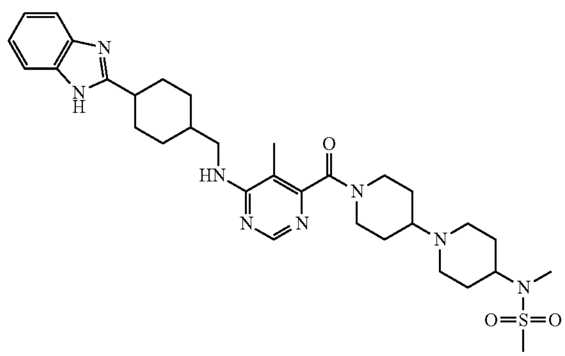 [SMILES: Cc1c(NCC2CCC(c3nc4ccccc4[nH]3)CC2)ncnc1C(=O)N1CCC(N2CCC(N(C)S(C)(=O)=O)CC2)CC1] | 25b | C-[4-(1H-Benzo-imidazol-2-yl)-cyclo-hexyl]-methyl-amine | 623 | 7.17 | 1E (Hydro) |
| 159s | 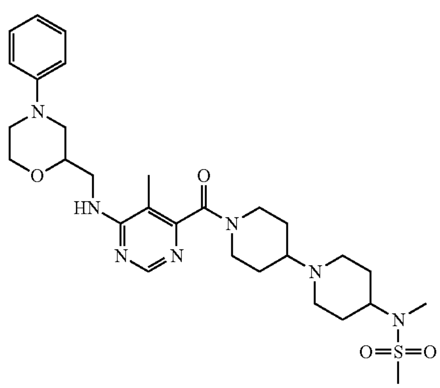 [SMILES: Cc1c(NCC2CN(c3ccccc3)CCO2)ncnc1C(=O)N1CCC(N2CCC(N(C)S(C)(=O)=O)CC2)CC1] | 25b | C-[(4-phenyl-morpholin-2-yl)-methyl-amine | 586 | 7.73 | 1E (Hydro) |
| 159t | 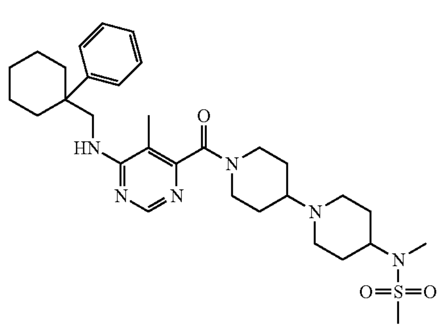 [SMILES: Cc1c(NCC2(c3ccccc3)CCCCC2)ncnc1C(=O)N1CCC(N2CCC(N(C)S(C)(=O)=O)CC2)CC1] | 25b | C-(1-pheny-cyclo-hexyl)-methyl-amine | 583 | 9.5 | 1E (Hydro) |

-continued

| Ex # | STRUCTURE | Intermediate | Amine | [M + H]+ | HPLC R_t. (min) | Method |
|---|---|---|---|---|---|---|
| 159u | 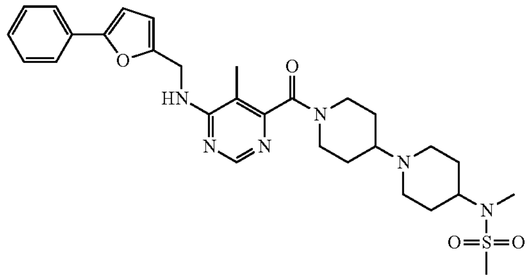 [SMILES: Cc1c(NCc2ccc(-c3ccccc3)o2)ncnc1C(=O)N1CCC(N2CCC(N(C)S(C)(=O)=O)CC2)CC1] | 25b | C-(5-phenyl-furan-2yl)-methyl-amine | 567 | 8.93 | 1E (Hydro) |
| 159w | 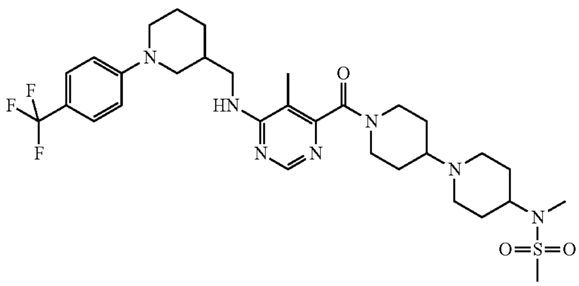 [SMILES: Cc1c(NCC2CCCN(c3ccc(C(F)(F)F)cc3)C2)ncnc1C(=O)N1CCC(N2CCC(N(C)S(C)(=O)=O)CC2)CC1] | 25b | 9d | 652 | 9.57 | 1E (Hydro) |
| 159y | 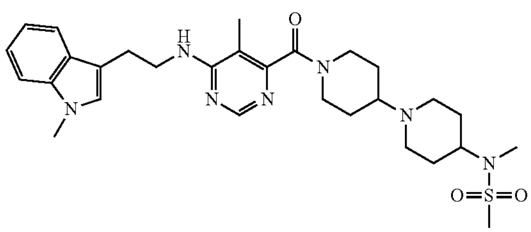 [SMILES: Cc1c(NCCc2cn(C)c3ccccc23)ncnc1C(=O)N1CCC(N2CCC(N(C)S(C)(=O)=O)CC2)CC1] | 25b | 2-(1-methyl-1H-indol-3yl)-ethyl-amine | 568 | 8.2 | 1E (Hydro) |
| 159x | 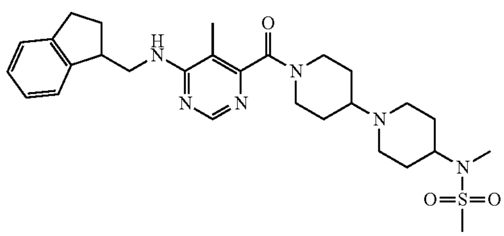 [SMILES: Cc1c(NCC2CCc3ccccc32)ncnc1C(=O)N1CCC(N2CCC(N(C)S(C)(=O)=O)CC2)CC1] | 25b | C-Indan-1-yl-methyl-amine | 541 | 8.27 | 1E (Hydro) |
| 159z | 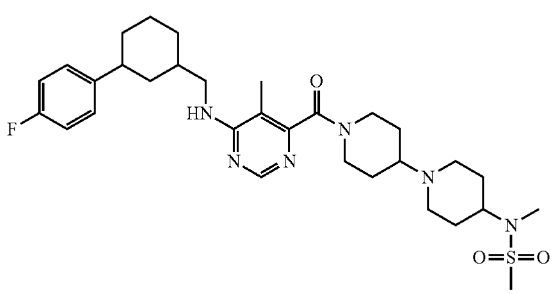 [SMILES: Cc1c(NCC2CCCC(c3ccc(F)cc3)C2)ncnc1C(=O)N1CCC(N2CCC(N(C)S(C)(=O)=O)CC2)CC1] | 25b | 7g | 601 | 9.8 | 1E (Hydro) |
| 159aa | 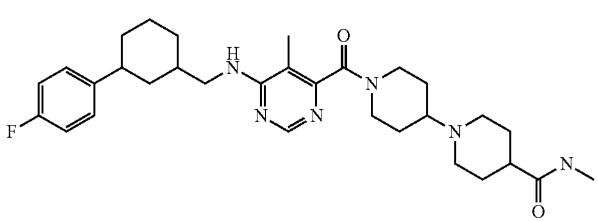 [SMILES: CNC(=O)C1CCN(C2CCN(C(=O)c3ncnc(NCC4CCCC(c5ccc(F)cc5)C4)c3C)CC2)CC1] | 25d | 7g | 551 | 9.47 | 1E (Hydro) |

-continued
| Ex # | STRUCTURE | Intermediate | Amine | [M + H]+ | HPLC R_t. (min) | Method |
|---|---|---|---|---|---|---|
| 159ba | 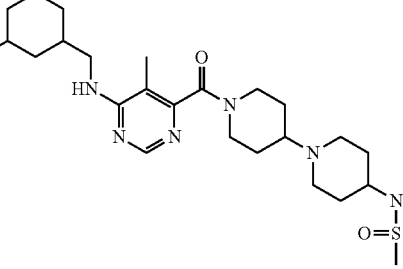 | 25a | 7g | 587 | 9.32 | 1E (Hydro) |
| 159ca | 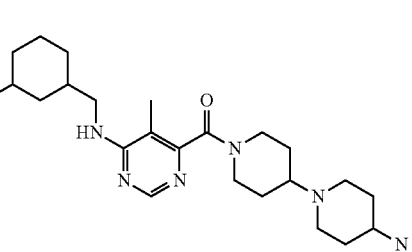 | 25a | 7f | 603 | 9.95 | 1E (Hydro) |
| 159da | 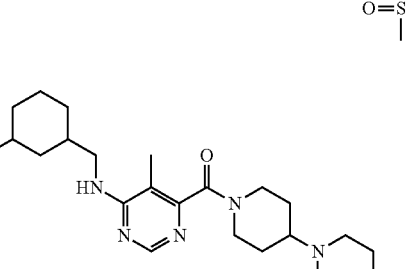 | 25b | 7f | 617 | 10.5 | 1E (Hydro) |
| 159ea | 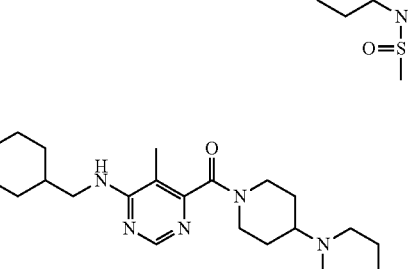 | 25d | 7f | 567 | 7.4 | 2F |
| 159fa | 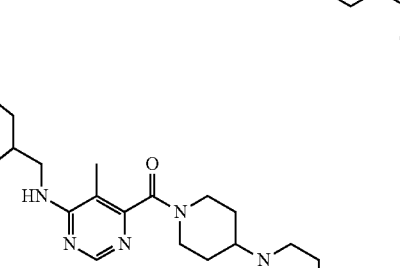 | 25b | C-cyclo-heptyl-methyl-amine | 521 | 8.88 | 1E (Hydro) |

-continued

| Ex # | STRUCTURE | Intermediate | Amine | [M + H]+ | HPLC R$_t$. (min) | Method |
|---|---|---|---|---|---|---|
| 159ga | 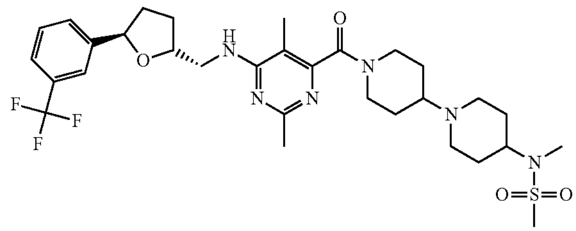 | 25l | 54a | 653 | 5.38 | 2M |
| 159ha | 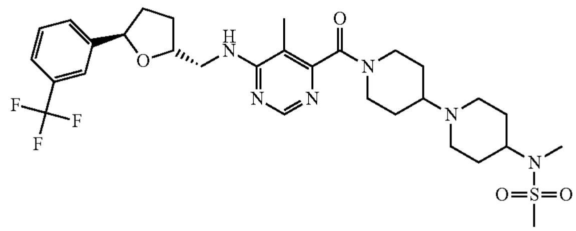 | 25b | 54a | 639 | 5.94 | 2M |
| 159ia | 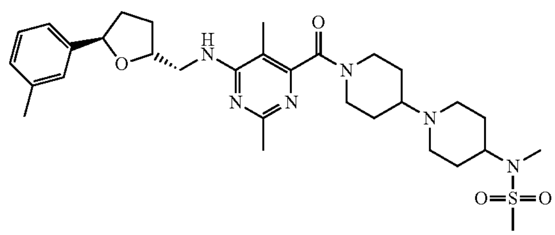 | 25b | 54b | 585 | 5.42 | 2M |
| 159ja | 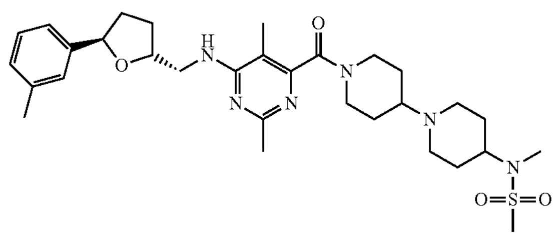 | 25l | 54b | 599 | 4.76 | 2M |
| 159ka | 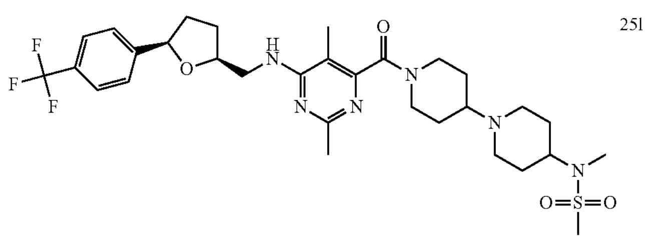 | 25l | 55g | 653 | 9.37 | 1E (Hydro) |
| 159la | 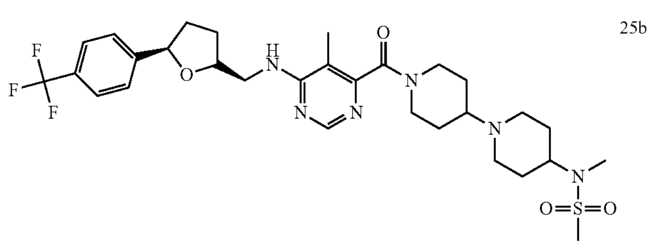 | 25b | 55g | 639 | 9.02 | 1E (Hydro) |

-continued

| Ex # | STRUCTURE | Intermediate | Amine | [M + H]+ | HPLC R_t (min) | Method |
|---|---|---|---|---|---|---|
| 159ma | 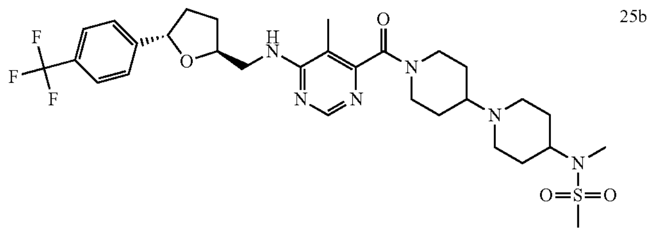 | 25b | 54g | 639 | 9.07 | 1E (Hydro) |
| 159na | 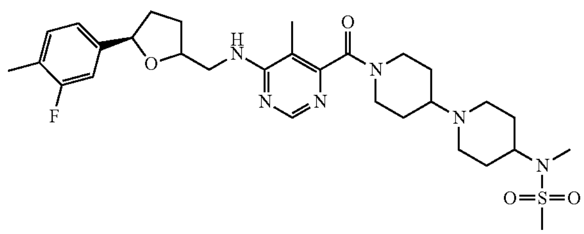 [SMILES: Cc1ccc([C@H]2CCC(CNc3ncnc(C(=O)N4CCC(N5CCC(N(C)S(C)(=O)=O)CC5)CC4)c3C)O2)cc1F] | 25b | 53e | 603 | 8.6 | 1E (Hydro) |
| 159oa | 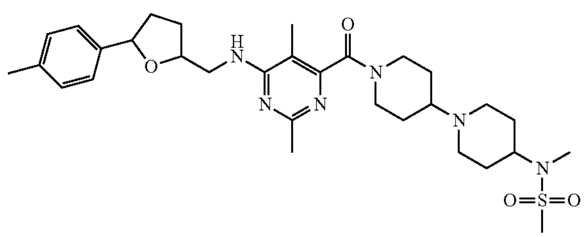 | 25l | 53c | 599 | 9.01 | 1E (Hydro) |
| 159pa | 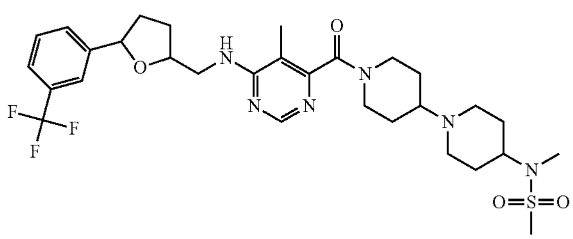 [SMILES: Cc1c(NCC2CCC(c3cccc(C(F)(F)F)c3)O2)ncnc1C(=O)N1CCC(N2CCC(N(C)S(C)(=O)=O)CC2)CC1] | 25b | 53a | 639 | 8.38 | 1E (Hydro) |
| 159qa | 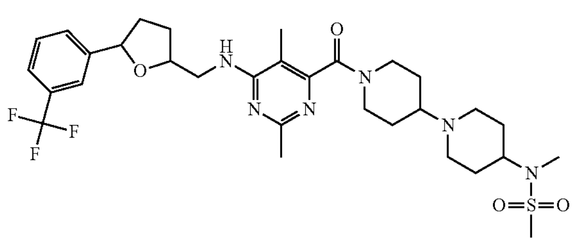 [SMILES: Cc1nc(NCC2CCC(c3cccc(C(F)(F)F)c3)O2)c(C)c(C(=O)N2CCC(N3CCC(N(C)S(C)(=O)=O)CC3)CC2)n1] | 25l | 53a | 653 | 8.85 | 1E (Hydro) |
| 159ra | 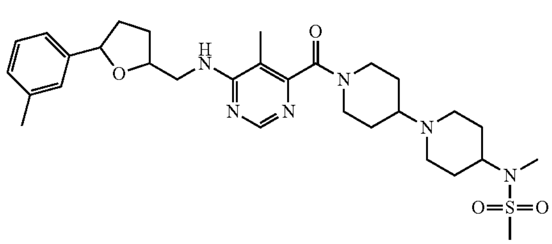 [SMILES: Cc1cccc(C2CCC(CNc3ncnc(C(=O)N4CCC(N5CCC(N(C)S(C)(=O)=O)CC5)CC4)c3C)O2)c1] | 25b | 53b | 585 | 7.86 | 1E (Hydro) |

| Ex # | STRUCTURE | Intermediate | Amine | [M + H]+ | HPLC R_t (min) | Method |
|---|---|---|---|---|---|---|
| 159sa | 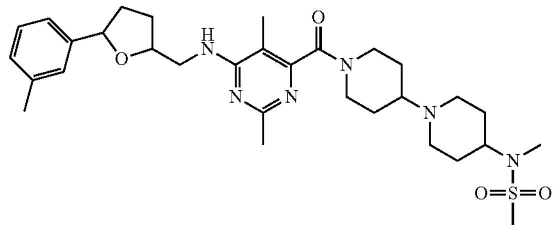 [SMILES: Cc1cccc(C2CCC(CNc3nc(C)nc(C(=O)N4CCC(N5CCC(N(C)S(C)(=O)=O)CC5)CC4)c3C)O2)c1] | 25l | 53b | 599 | 8.36 | 1E (Hydro) |
| 159ta | 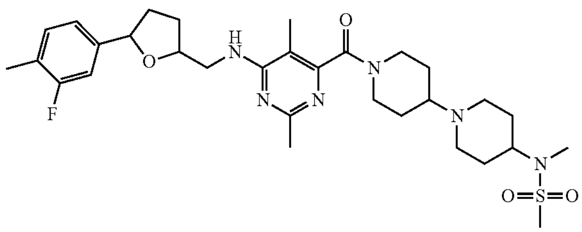 [SMILES: Cc1nc(NCC2CCC(c3ccc(C)c(F)c3)O2)c(C)c(C(=O)N2CCC(N3CCC(N(C)S(C)(=O)=O)CC3)CC2)n1] | 25l | 53e | 617 | 9.03 | 1E (Hydro) |
| 159ua | 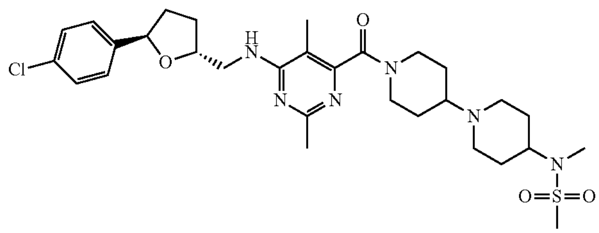 [SMILES: Cc1nc(NC[C@H]2CC[C@H](c3ccc(Cl)cc3)O2)c(C)c(C(=O)N2CCC(N3CCC(N(C)S(C)(=O)=O)CC3)CC2)n1] | 25l | 54f | 619 | 8.63 | 1E (Hydro) |
| 159wa | 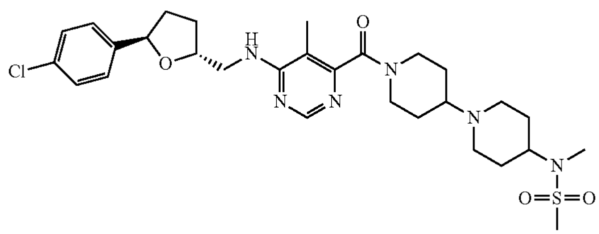 [SMILES: Cc1c(NC[C@H]2CC[C@H](c3ccc(Cl)cc3)O2)ncnc1C(=O)N1CCC(N2CCC(N(C)S(C)(=O)=O)CC2)CC1] | 25b | 54f | 605 | 8.10 | 1E (Hydro) |
| 159ya | 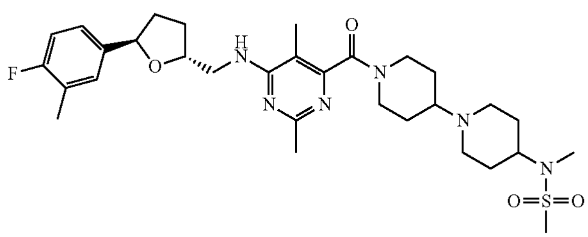 [SMILES: Cc1nc(NC[C@H]2CC[C@H](c3ccc(F)c(C)c3)O2)c(C)c(C(=O)N2CCC(N3CCC(N(C)S(C)(=O)=O)CC3)CC2)n1] | 25l | 54d | 617 | 5.08 | 2M |
| 159xa | 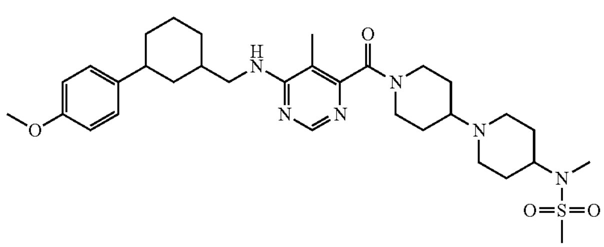 [SMILES: COc1ccc(C2CCCC(CNc3ncnc(C(=O)N4CCC(N5CCC(N(C)S(C)(=O)=O)CC5)CC4)c3C)C2)cc1] | 25b | 7h | 613 | 9.95 | 1E (Hydro) |

-continued

| Ex # | STRUCTURE | Intermediate | Amine | [M + H]⁺ | HPLC R_t. (min) | Method |
|---|---|---|---|---|---|---|
| 159za | 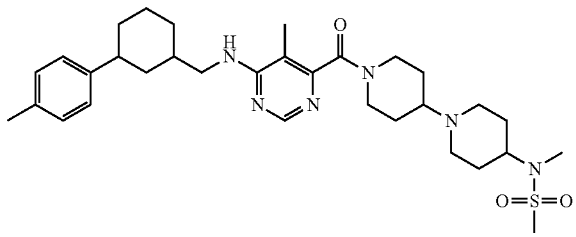 [SMILES: Cc1ccc(C2CCCC(CNc3ncnc(C(=O)N4CCC(N5CCC(N(C)S(C)(=O)=O)CC5)CC4)c3C)C2)cc1] | 25b | 7i | 597 | 10.52 | 1E (Hydro) |
| 159ab | 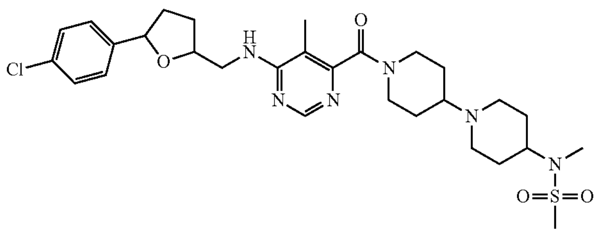 [SMILES: Cc1c(NCC2CCC(c3ccc(Cl)cc3)O2)ncnc1C(=O)N1CCC(N2CCC(N(C)S(C)(=O)=O)CC2)CC1] | 25b | 53f | 605 | 9.0 | 1E (Hydro) |
| 159bb | 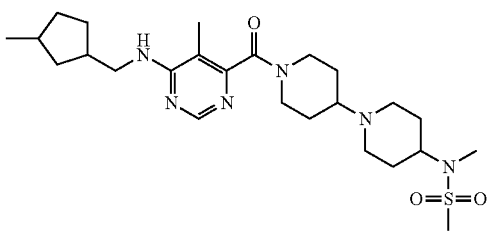 [SMILES: Cc1c(NCC2CCC(C)C2)ncnc1C(=O)N1CCC(N2CCC(N(C)S(C)(=O)=O)CC2)CC1] | 25b | C-(3-methyl-cyclo-pentyl)-methyl-amine | 507 | 8.53 | 1E (Hydro) |
| 159cb | 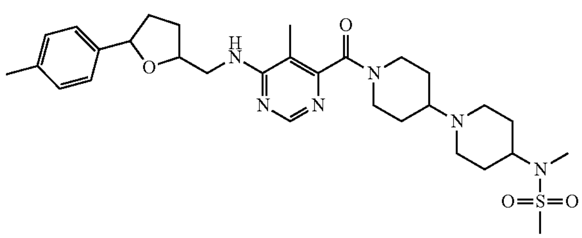 [SMILES: Cc1ccc(C2CCC(CNc3ncnc(C(=O)N4CCC(N5CCC(N(C)S(C)(=O)=O)CC5)CC4)c3C)O2)cc1] | 25b | 53c | 585 | 8.77 | 1E (Hydro) |
| 159db | 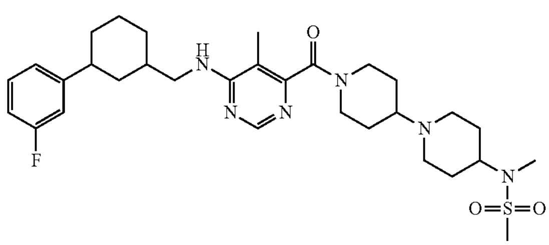 [SMILES: Cc1c(NCC2CCCC(c3cccc(F)c3)C2)ncnc1C(=O)N1CCC(N2CCC(N(C)S(C)(=O)=O)CC2)CC1] | 25b | 7j | 601 | 10 | 1E (Hydro) |
| 159eb | 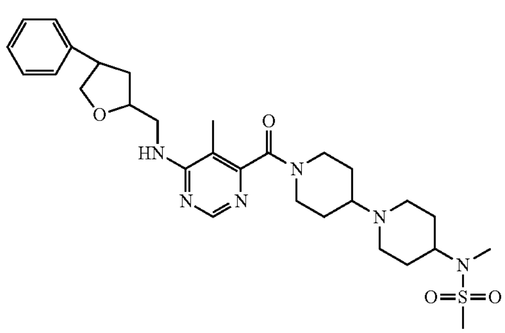 [SMILES: Cc1c(NCC2CC(c3ccccc3)CO2)ncnc1C(=O)N1CCC(N2CCC(N(C)S(C)(=O)=O)CC2)CC1] | 25b | 53h | 571 | 7.93 | 1E (Hydro) |

-continued

| Ex # | STRUCTURE | Intermediate | Amine | [M + H]+ | HPLC R_t (min) | Method |
|---|---|---|---|---|---|---|
| 159fb | 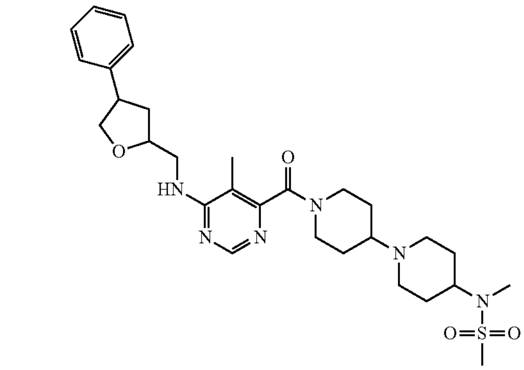 [SMILES: Cc1c(NCC2CC(c3ccccc3)CO2)ncnc1C(=O)N1CCC(N2CCC(N(C)S(C)(=O)=O)CC2)CC1] | 25b | C-(5-phenyl-tetrahydro-furan-3yl)-methyl-amine | 571 | 7.83 | 1E (Hydro) |
| 159gb | 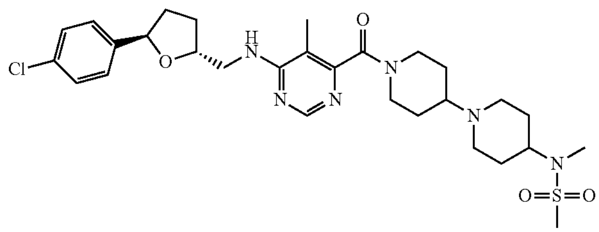 [SMILES: Cc1c(NC[C@H]2CC[C@H](c3ccc(Cl)cc3)O2)ncnc1C(=O)N1CCC(N2CCC(N(C)S(C)(=O)=O)CC2)CC1] | 25b | 54c | 585 | 8.36 | 1E (Hydro) |
| 159hb | 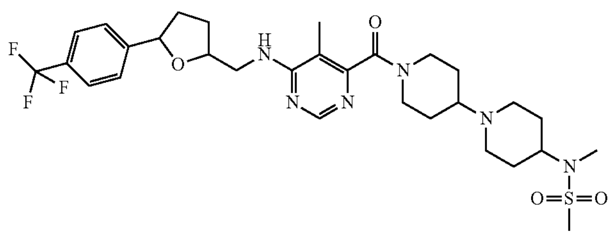 [SMILES: Cc1c(NCC2CCC(c3ccc(C(F)(F)F)cc3)O2)ncnc1C(=O)N1CCC(N2CCC(N(C)S(C)(=O)=O)CC2)CC1] | 25b | 53g | 639 | 8.94 | 1E (Hydro) |
| 159ib | 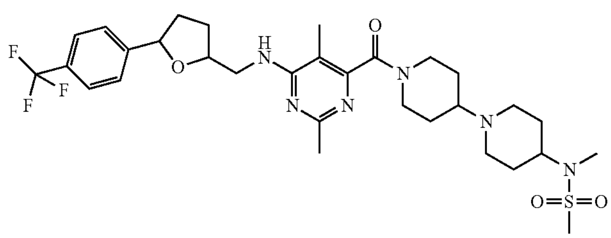 [SMILES: Cc1nc(NCC2CCC(c3ccc(C(F)(F)F)cc3)O2)c(C)c(C(=O)N2CCC(N3CCC(N(C)S(C)(=O)=O)CC3)CC2)n1] | 25l | 53g | 653 | 9.27 | 1E (Hydro) |
| 159jb | 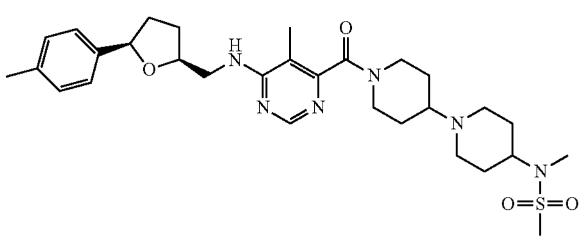 [SMILES: Cc1ccc([C@H]2CC[C@@H](CNc3ncnc(C(=O)N4CCC(N5CCC(N(C)S(C)(=O)=O)CC5)CC4)c3C)O2)cc1] | 25b | 55c | 585 | 8.38 | 1E (Hydro) |
| 159kb | 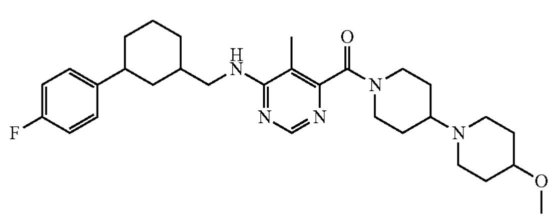 [SMILES: COC1CCN(C2CCN(C(=O)c3ncnc(NCC4CCCC(c5ccc(F)cc5)C4)c3C)CC2)CC1] | 25g | 7g | 524 | 2.87 | 1Fa |

-continued

| Ex # | STRUCTURE | Intermediate | Amine | [M + H]+ | HPLC R<sub>t</sub> (min) | Method |
|---|---|---|---|---|---|---|
| 159lb | 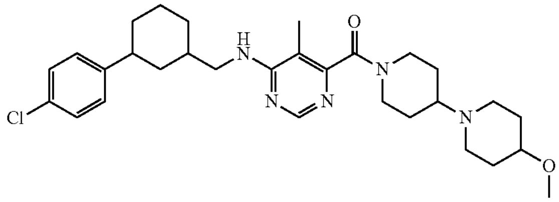 [SMILES: COC1CCN(C2CCN(C(=O)c3ncnc(NCC4CCCC(c5ccc(Cl)cc5)C4)c3C)CC2)CC1] | 25g | 7f | 540 | 3.02 | 1Fa |
| 159mb | 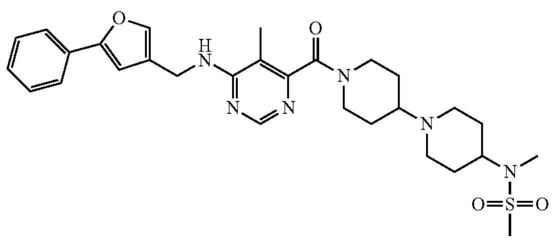 [SMILES: Cc1c(NCc2coc(-c3ccccc3)c2)ncnc1C(=O)N1CCC(N2CCC(N(C)S(C)(=O)=O)CC2)CC1] | 25b | 7r | 567 | 8.85 | 1E (Hydro) |
| 159nb | 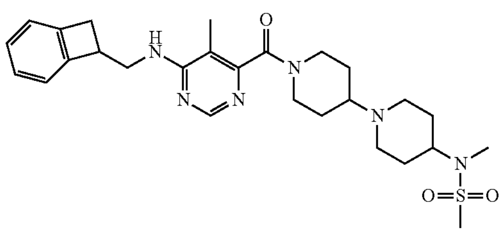 [SMILES: Cc1c(NCC2Cc3ccccc32)ncnc1C(=O)N1CCC(N2CCC(N(C)S(C)(=O)=O)CC2)CC1] | 25b | C-Bicyclo[4.2.0]octa-1(6),2,4-trien-7-yl-methyl-amine | 527 | 7.53 | 1E (Hydro) |
| 159ob | 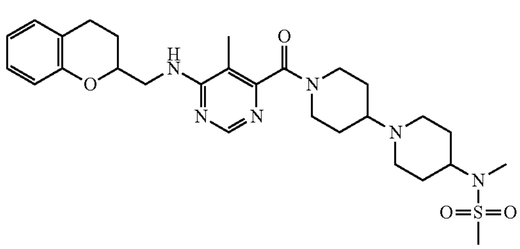 | 25b | C-Chroman-2yl-methyl-amine | 557 | 7.9 | 1E (Hydro) |
| 159pb | 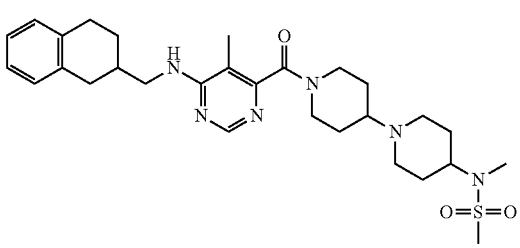 [SMILES: Cc1c(NCC2CCc3ccccc3C2)ncnc1C(=O)N1CCC(N2CCC(N(C)S(C)(=O)=O)CC2)CC1] | 25b | C-(1,2,3,4-Tetra-hydro-naphthalen-2-yl-)-methyl-amine | 555 | 8.47 | 1E (Hydro) |
| 159qb | 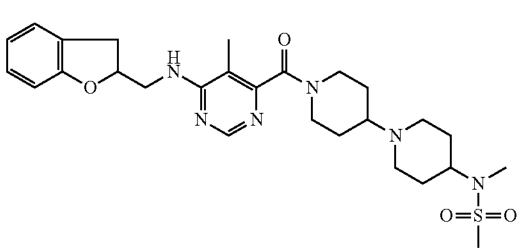 [SMILES: Cc1c(NCC2Cc3ccccc3O2)ncnc1C(=O)N1CCC(N2CCC(N(C)S(C)(=O)=O)CC2)CC1] | 25b | C-(2,3-Dihydro-benzo-furan-2yl)-methyl-amine | 543 | 7.4 | 1E (Hydro) |

-continued

| Ex # | STRUCTURE | Intermediate | Amine | [M + H]+ | HPLC R_t (min) | Method |
|---|---|---|---|---|---|---|
| 159rb | 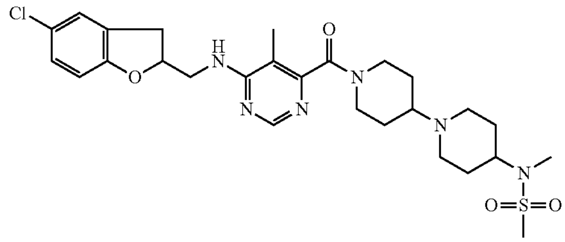 [SMILES: Cc1c(NCC2Cc3cc(Cl)ccc3O2)ncnc1C(=O)N1CCC(N2CCC(N(C)S(C)(=O)=O)CC2)CC1] | 25b | C-(5-Chloro-2,3-Dihydro-benzo-furan-2yl)-methyl-amine | 557 | 6.5 | 2F |
| 159sb | 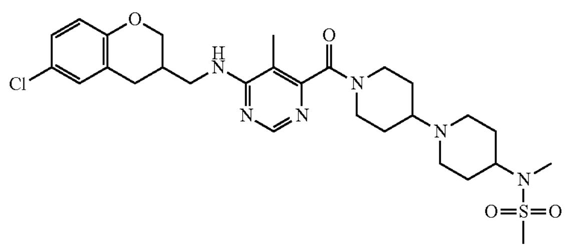 [SMILES: Cc1c(NCC2COc3ccc(Cl)cc3C2)ncnc1C(=O)N1CCC(N2CCC(N(C)S(C)(=O)=O)CC2)CC1] | 25b | C-(6-Chloro-croman-3-yl)-methyl-amine | 591 | 8.09 | 1E (Hydro) |
| 159tb | 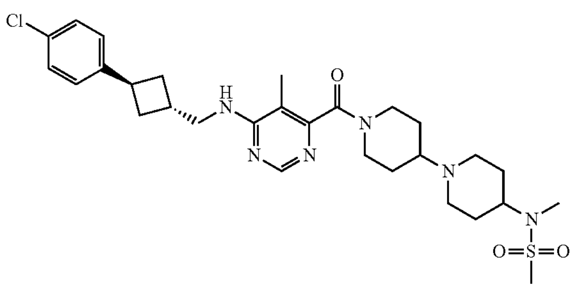 [SMILES: Cc1c(NC[C@H]2C[C@H](c3ccc(Cl)cc3)C2)ncnc1C(=O)N1CCC(N2CCC(N(C)S(C)(=O)=O)CC2)CC1] | 25b | 7s | 589 | 9.8 | 1E (Hydro) |
| 159ub | 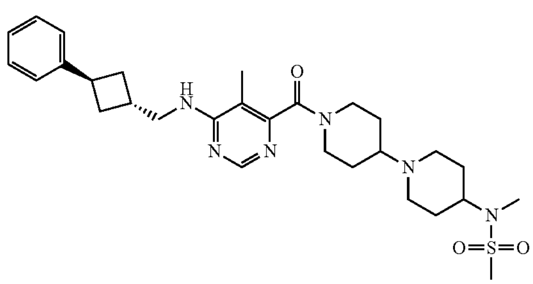 [SMILES: Cc1c(NC[C@H]2C[C@H](c3ccccc3)C2)ncnc1C(=O)N1CCC(N2CCC(N(C)S(C)(=O)=O)CC2)CC1] | 25b | 7t | 555 | 9.07 | 1E (Hydro) |
| 159wb | 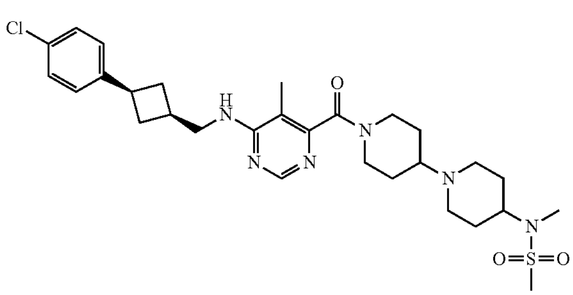 [SMILES: Cc1c(NC[C@H]2C[C@@H](c3ccc(Cl)cc3)C2)ncnc1C(=O)N1CCC(N2CCC(N(C)S(C)(=O)=O)CC2)CC1] | 25b | 7u | 589 | 9.7 | 1E (Hydro) |

-continued

| Ex # | STRUCTURE | Intermediate | Amine | [M + H]+ | HPLC R_t (min) | Method |
|---|---|---|---|---|---|---|
| 159yb | 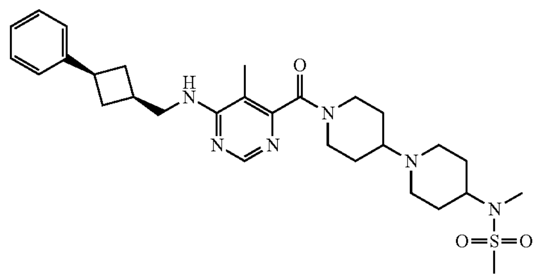 [SMILES: Cc1c(NC[C@H]2C[C@@H](c3ccccc3)C2)ncnc1C(=O)N1CCC(N2CCC(N(C)S(C)(=O)=O)CC2)CC1] | 25b | 7v | 555 | 9.02 | 1E (Hydro) |
| 159xb | 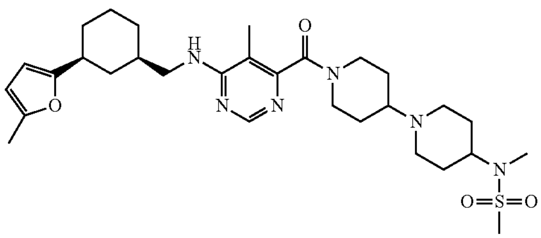 [SMILES: Cc1ccc([C@H]2CCC[C@@H](CNc3ncnc(C(=O)N4CCC(N5CCC(N(C)S(C)(=O)=O)CC5)CC4)c3C)C2)o1] | 25b | 7o | 587 | 9.55 | 1E (Hydro) |
| 159zb | 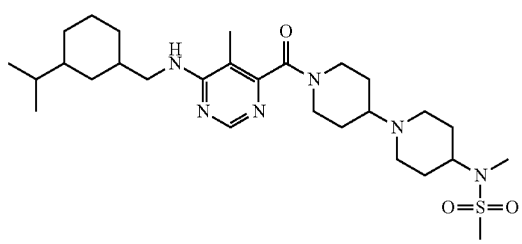 [SMILES: Cc1c(NCC2CCCC(C(C)C)C2)ncnc1C(=O)N1CCC(N2CCC(N(C)S(C)(=O)=O)CC2)CC1] | 25b | 7k | 549 | 10.37 | 1E (Hydro) |
| 159ac | 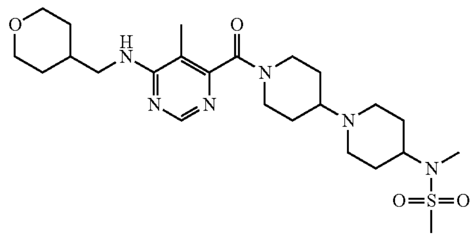 [SMILES: Cc1c(NCC2CCOCC2)ncnc1C(=O)N1CCC(N2CCC(N(C)S(C)(=O)=O)CC2)CC1] | 25b | C-(tetra-hydro-pyran-4-yl)-methyl-amine | 509 | 5.92 | 1E (Hydro) |
| 159bc | 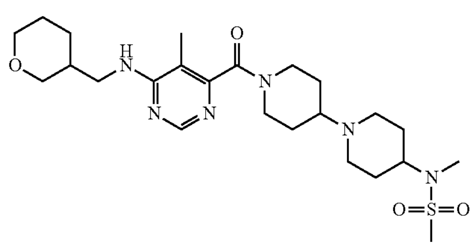 [SMILES: Cc1c(NCC2CCCOC2)ncnc1C(=O)N1CCC(N2CCC(N(C)S(C)(=O)=O)CC2)CC1] | 25b | C-(tetra-hydro-pyran-3-yl)-methyl-amine | 509 | 6.15 | 1E (Hydro) |
| 159cc | 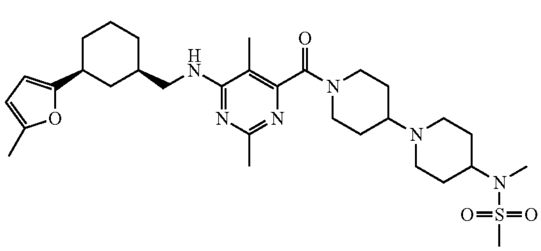 [SMILES: Cc1nc(NC[C@@H]2CCC[C@H](c3ccc(C)o3)C2)c(C)c(C(=O)N2CCC(N3CCC(N(C)S(C)(=O)=O)CC3)CC2)n1] | 25l | 7o | 601 | 5.40 | 2M |

-continued

| Ex # | STRUCTURE | Intermediate | Amine | [M + H]⁺ | HPLC $R_{t}$ (min) | Method |
|---|---|---|---|---|---|---|
| 159dc | 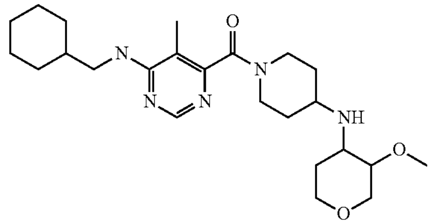 [SMILES: COC1COCCC1NC1CCN(C(=O)c2ncnc(NCC3CCCCC3)c2C)CC1] | 25o | C-cyclohexyl-methyl-amine | 446 | 1.23 | 2Gb |
| 159ec | 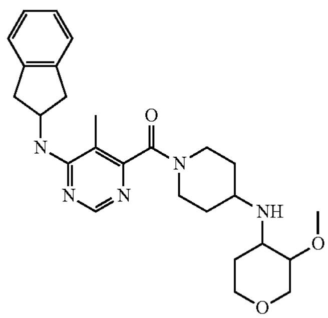 [SMILES: COC1COCCC1NC1CCN(C(=O)c2ncnc(NC3Cc4ccccc4C3)c2C)CC1] | 25o | Indan-2-yl-amine | 466 | 1.24 | 2Gb |
| 159fc | 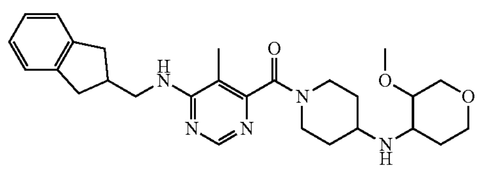 [SMILES: COC1COCCC1NC1CCN(C(=O)c2ncnc(NCC3Cc4ccccc4C3)c2C)CC1] | 25o | C-Indan-2-yl-methyl-amine | 480 | 2.97 | 2Ga |
| 159gc | 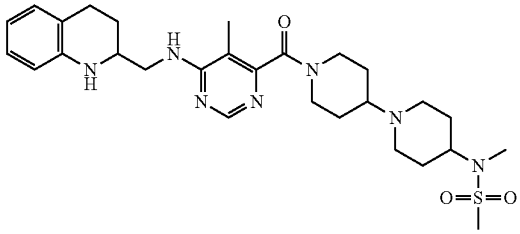 | 25b | C-(1,2,3,4-Tetra-hydro-quinolin-2-yl)-methyl-amine | 556 | 1.35 | 2Ca |

Example 160

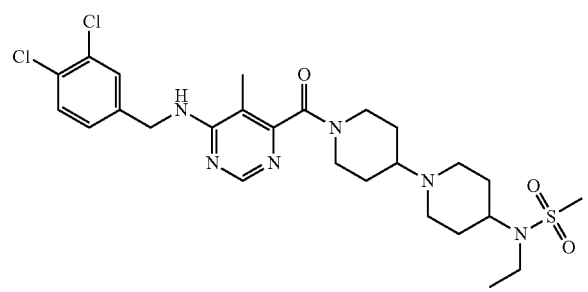 [SMILES: CCN(C1CCN(C2CCN(C(=O)c3ncnc(NCc4ccc(Cl)c(Cl)c4)c3C)CC2)CC1)S(C)(=O)=O]

Intermediate 28b (80 mg, 0.20 mmol), Intermediate 13 (74 mg, 0.30 mmol) and N,N-diisopropyl-ethylamine (0.087 ml, 0.51 mmol) in 2 ml of dichloromethane were stirred at room temperature for 10 min Sodium triacetoxyborohydride (129 mg, 0.61 mmol) was added and the reaction mixture was stirred at room temperature overnight. The organic phase was washed with an aqueous saturated sodium bicarbonate solution, dried over sodium sulfate and concentrated under vacuum. The crude product was purified by reverse phase preparative HPLC. 39 mg (0.06 mmol) of the desired product were obtained.

HPLC (Method 2F): $R_{t}$ (min)=7.25

[M+H]⁺=583

The following examples were synthesized in analogy to the preparation of Example 160.

| Ex # | STRUCTURE | Intermediate | Amine or Ketone | [M + H]⁺ | HPLC R_t (min) | Method |
|---|---|---|---|---|---|---|
| 161 | 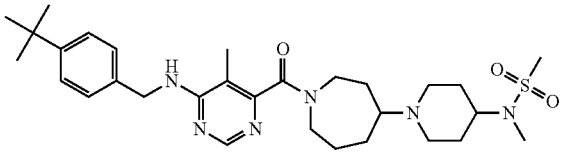 [SMILES: Cc1c(NCc2ccc(C(C)(C)C)cc2)ncnc1C(=O)N1CCCC(N2CCC(N(C)S(C)(=O)=O)CC2)CC1] | 28f | N-Methyl-N-piperidin-4-yl-methane-sulfon-amide | 571 | 7.17 | 2F |
| 162 | 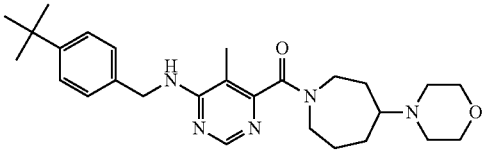 [SMILES: Cc1c(NCc2ccc(C(C)(C)C)cc2)ncnc1C(=O)N1CCCC(N2CCOCC2)CC1] | 28f | Morpho-line | 466 | 9.97-10.27 | 1E |
| 163 | 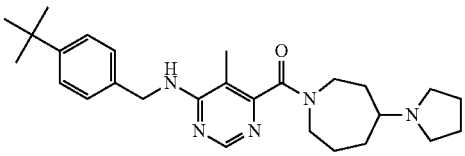 [SMILES: Cc1c(NCc2ccc(C(C)(C)C)cc2)ncnc1C(=O)N1CCCC(N2CCCC2)CC1] | 28f | Pyrroli-dine | 450 | 7.06 | 2F |
| 164 | 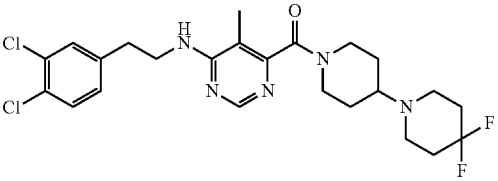 [SMILES: Cc1c(NCCc2ccc(Cl)c(Cl)c2)ncnc1C(=O)N1CCC(N2CCC(F)(F)CC2)CC1] | 28a | 4,4-difluoro-piperidine | 512 | 8.17 | 1E |
| 165 | 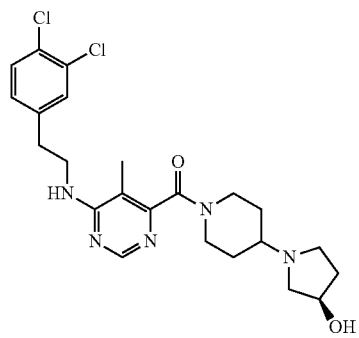 [SMILES: Cc1c(NCCc2ccc(Cl)c(Cl)c2)ncnc1C(=O)N1CCC(N2CC[C@@H](O)C2)CC1] | 28a | (R)-pyrrolidin-3-ol | 478 | 7.62 | 1E |
| 166 | 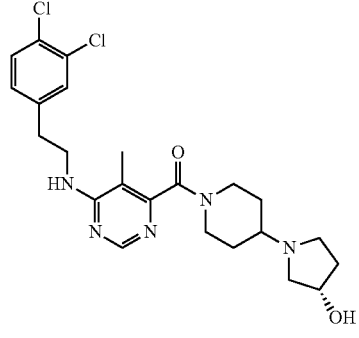 [SMILES: Cc1c(NCCc2ccc(Cl)c(Cl)c2)ncnc1C(=O)N1CCC(N2CC[C@H](O)C2)CC1] | 28a | (S)-pyrrolidin-3-ol | 478 | 7.57 | 1E |

| Ex # | STRUCTURE | Intermediate | Amine or Ketone | [M + H]⁺ | HPLC R_t (min) | Method |
|---|---|---|---|---|---|---|
| 167 | 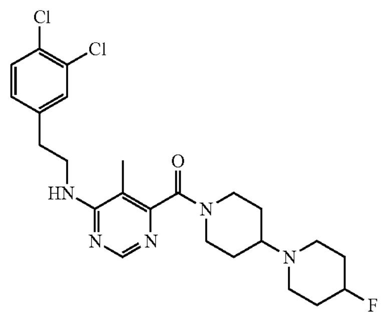 [SMILES: Cc1c(NCCc2ccc(Cl)c(Cl)c2)ncnc1C(=O)N1CCC(N2CCC(F)CC2)CC1] | 28a | 4-fluoro-piperidine | 494 | 7.37 | 2F |
| 168 | 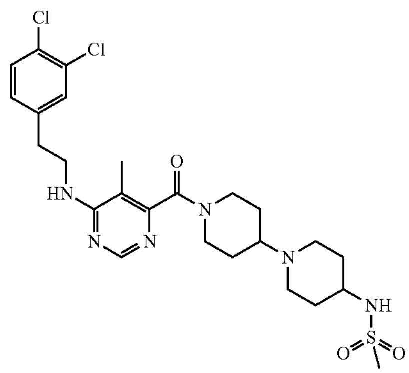 [SMILES: Cc1c(NCCc2ccc(Cl)c(Cl)c2)ncnc1C(=O)N1CCC(N2CCC(NS(C)(=O)=O)CC2)CC1] | 28a | N-piperidin-4yl-methan-sulfon-amide | 569 | 7.28 | 1E (Fusion) |
| 169 | 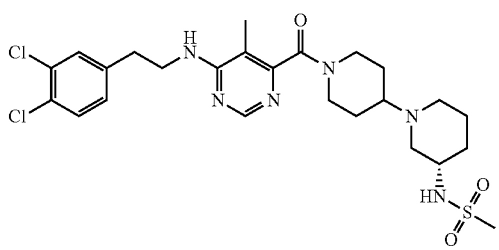 [SMILES: Cc1c(NCCc2ccc(Cl)c(Cl)c2)ncnc1C(=O)N1CCC(N2CCC[C@H](NS(C)(=O)=O)C2)CC1] | 28a | (S)-N-piperidin-3yl-methan-sulfon-amide | 569 | 8.50 | 1E |
| 170 | 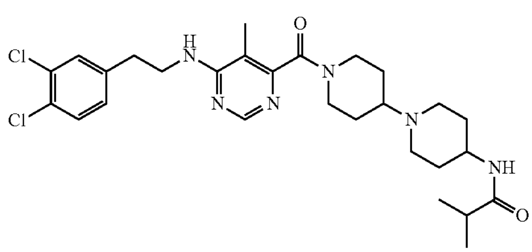 [SMILES: Cc1c(NCCc2ccc(Cl)c(Cl)c2)ncnc1C(=O)N1CCC(N2CCC(NC(=O)C(C)C)CC2)CC1] | 28a | N-piperidin-4yl-isobutyr-amide | 561 | 7.58 | 1E |
| 171 | 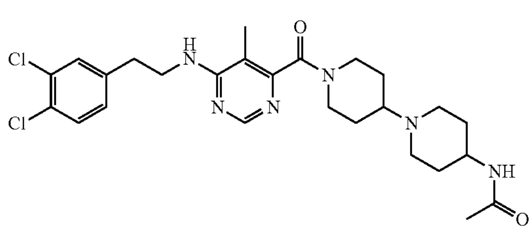 [SMILES: CC(=O)NC1CCN(C2CCN(C(=O)c3ncnc(NCCc4ccc(Cl)c(Cl)c4)c3C)CC2)CC1] | 28a | N-piperidin-4yl-acetamide | 533 | 7.07 | 2F |

-continued

| Ex # | STRUCTURE | Intermediate | Amine or Ketone | [M + H]+ | HPLC $R_t$ (min) | Method |
|---|---|---|---|---|---|---|
| 172 | 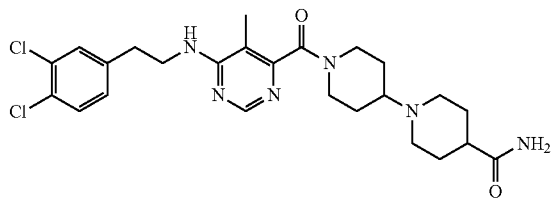 [SMILES: Cc1c(NCCc2ccc(Cl)c(Cl)c2)ncnc1C(=O)N1CCC(N2CCC(C(N)=O)CC2)CC1] | 28a | Piperidin-4-carboxylic acid amide | 519 | 7.07 | 1E (Fusion) |
| 173 | 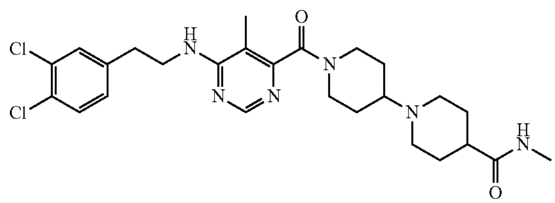 [SMILES: CNC(=O)C1CCN(C2CCN(C(=O)c3ncnc(NCCc4ccc(Cl)c(Cl)c4)c3C)CC2)CC1] | 28a | Piperidin-4-carboxylic acid methyl-amide | 533 | 7.73 | 1E (Fusion) |
| 174 | 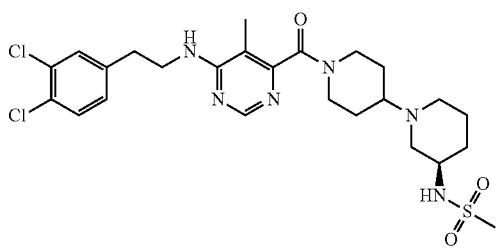 [SMILES: Cc1c(NCCc2ccc(Cl)c(Cl)c2)ncnc1C(=O)N1CCC(N2CCC[C@@H](NS(C)(=O)=O)C2)CC1] | 28a | (R)-N-piperidin-3yl-methan-sulfon-amide | 569 | 8.48 | 1E (Fusion) |
| 175 | 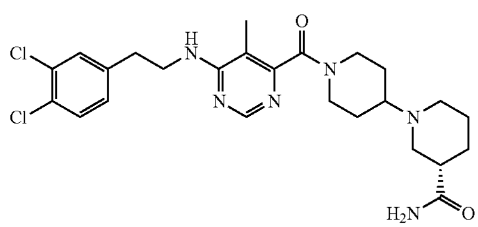 [SMILES: Cc1c(NCCc2ccc(Cl)c(Cl)c2)ncnc1C(=O)N1CCC(N2CCC[C@H](C(N)=O)C2)CC1] | 28a | (S)-piperidine-3-carboxylic acid amide | 519 | 8.70 | 1E (Fusion) |
| 176 | 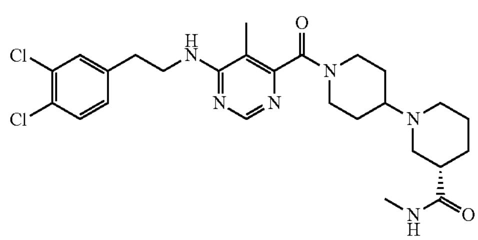 [SMILES: CNC(=O)[C@H]1CCCN(C2CCN(C(=O)c3ncnc(NCCc4ccc(Cl)c(Cl)c4)c3C)CC2)C1] | 28a | (S)-piperidine-3-carboxylic acid methyl amide | 533 | 7.03 | 2F |
| 177 | 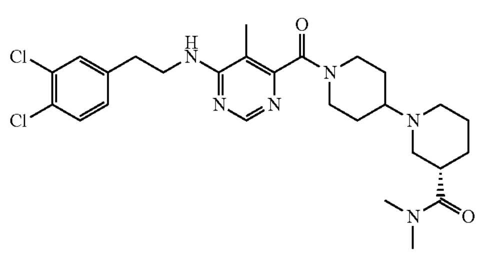 [SMILES: Cc1c(NCCc2ccc(Cl)c(Cl)c2)ncnc1C(=O)N1CCC(N2CCC[C@H](C(=O)N(C)C)C2)CC1] | 28a | (S)-piperidine-3-carboxylic acid dimethyl amide | 547 | 7.15 | 2F |
| 178 | 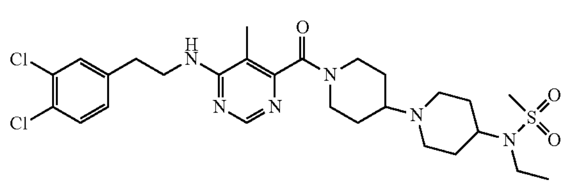 [SMILES: CCN(C1CCN(C2CCN(C(=O)c3ncnc(NCCc4ccc(Cl)c(Cl)c4)c3C)CC2)CC1)S(C)(=O)=O] | 28a | N-Ethyl-N-piperidin-4-yl-methane-sulfon-amide | 597 | 9.62 | 1E (Hydro) |

-continued
| Ex # | STRUCTURE | Intermediate | Amine or Ketone | [M + H]+ | HPLC R_t (min) | Method |
|---|---|---|---|---|---|---|
| 179 | 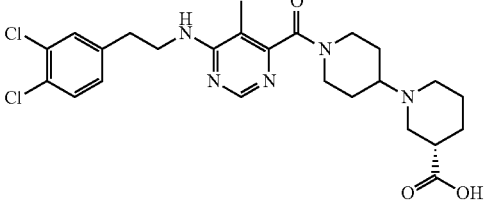 | 28a | (S)-piperidine-3-carboxylic acid | 520 | 6.60 | 1E (Fusion) |
| 180 | 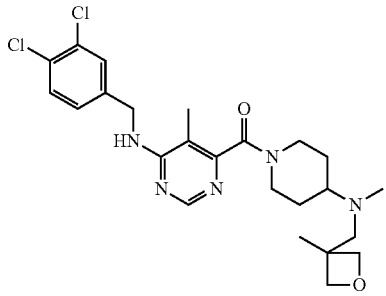 [SMILES: Cc1c(NCc2ccc(Cl)c(Cl)c2)ncnc1C(=O)N1CCC(N(C)CC2(C)COC2)CC1] | 28b | Methyl-(3-methyl-oxetan-3yl-methyl)-amine | 492 | 8.05 | 1E (Hydro) |
| 181 | 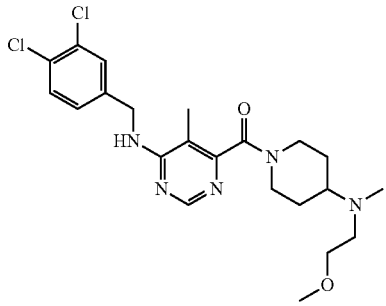 [SMILES: COCCN(C)C1CCN(C(=O)c2ncnc(NCc3ccc(Cl)c(Cl)c3)c2C)CC1] | 28b | 2-(methoxy-ethyl)-methyl-amine | 466 | 7.72 | 1E (Hydro) |
| 182 | 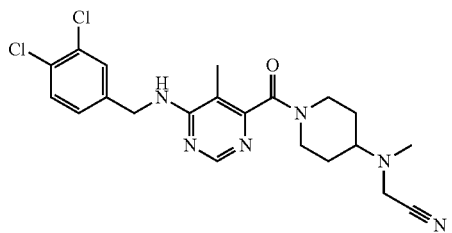 [SMILES: Cc1c(NCc2ccc(Cl)c(Cl)c2)ncnc1C(=O)N1CCC(N(C)CC#N)CC1] | 28b | Methyl-amino-aceto-nitrile | 447 | 8.00 | 1E (Hydro) |
| 183 | 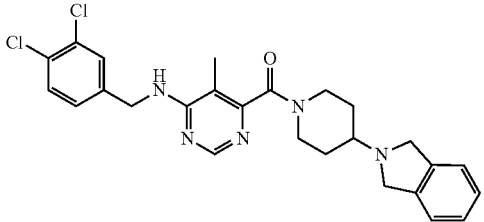 [SMILES: Cc1c(NCc2ccc(Cl)c(Cl)c2)ncnc1C(=O)N1CCC(N2Cc3ccccc3C2)CC1] | 28b | 2,3-dihyro-1H-isoindole | 496 | 9.52 | 1E (Hydro) |

-continued

| Ex # | STRUCTURE | Intermediate | Amine or Ketone | [M + H]+ | HPLC R_t (min) | Method |
|---|---|---|---|---|---|---|
| 184 | 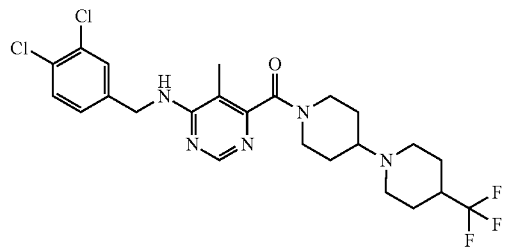 [SMILES: Cc1c(NCc2ccc(Cl)c(Cl)c2)ncnc1C(=O)N1CCC(N2CCC(C(F)(F)F)CC2)CC1] | 28b | 4-trifluoromethyl-piperidine | 530 | 9.60 | 1E (Hydro) |
| 185 | 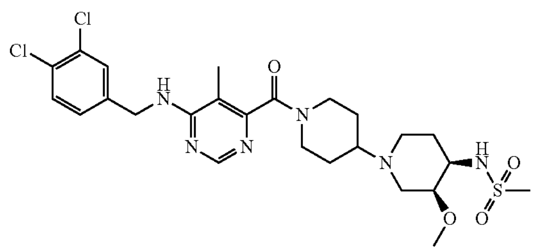 [SMILES: CO[C@H]1CN(C2CCN(C(=O)c3ncnc(NCc4ccc(Cl)c(Cl)c4)c3C)CC2)CC[C@H]1NS(C)(=O)=O] | 28b | 18 | 585 | 7.33 | 1E (Hydro) |
| 186 | 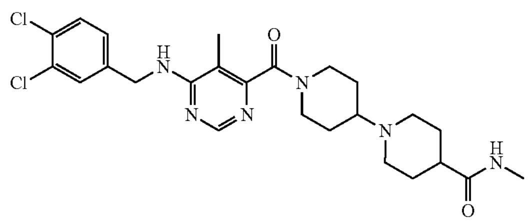 [SMILES: CNC(=O)C1CCN(C2CCN(C(=O)c3ncnc(NCc4ccc(Cl)c(Cl)c4)c3C)CC2)CC1] | 28b | Piperidin-4-carboxylic acid methylamide | 519 | 7.42 | 1E (Hydro) |
| 187 | 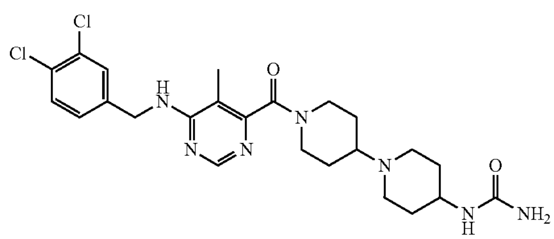 [SMILES: Cc1c(NCc2ccc(Cl)c(Cl)c2)ncnc1C(=O)N1CCC(N2CCC(NC(N)=O)CC2)CC1] | 28b | Piperidin-4yl-urea | 520 | 7.05 | 2F |
| 188 | 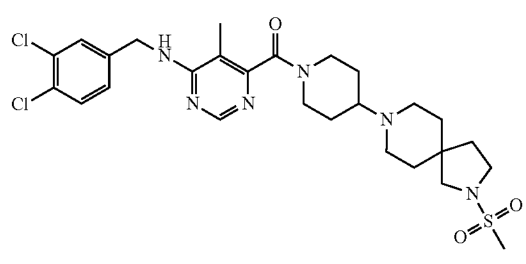 [SMILES: Cc1c(NCc2ccc(Cl)c(Cl)c2)ncnc1C(=O)N1CCC(N2CCC3(CC2)CCN(S(C)(=O)=O)C3)CC1] | 28b | 2-methansulfonyl-2,8-diaza-spiro[4.5]-decane | 595 | 8.32 | 1E (Hydro) |
| 189 | 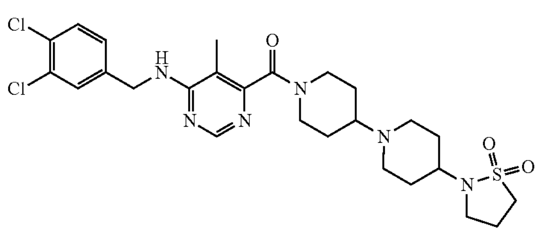 [SMILES: Cc1c(NCc2ccc(Cl)c(Cl)c2)ncnc1C(=O)N1CCC(N2CCC(N3CCCS3(=O)=O)CC2)CC1] | 28b | 4-(1,1-dioxo-isothiazolidin-2-yl)-piperidine | 581 | 8.23 | 1E (Hydro) |

-continued

| Ex # | STRUCTURE | Inter-mediate | Amine or Ketone | [M + H]+ | HPLC R_t. (min) | Method |
|---|---|---|---|---|---|---|
| 190 | 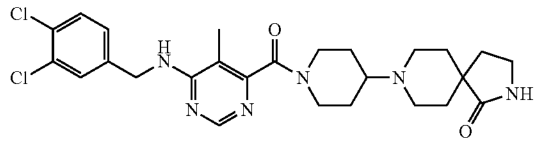 [SMILES: Cc1c(NCc2ccc(Cl)c(Cl)c2)ncnc1C(=O)N1CCC(N2CCC3(CCNC3=O)CC2)CC1] | 28b | 2,8-diazaspiro[4.5]decan-1-one | 531 | 7.58 | 1E (Hydro) |
| 191 | 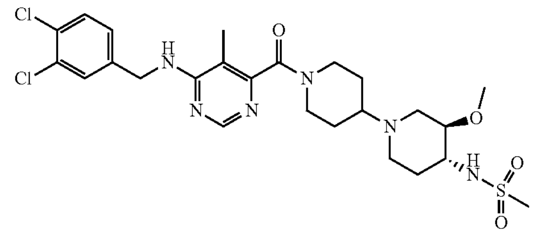 [SMILES: CO[C@@H]1CN(C2CCN(C(=O)c3ncnc(NCc4ccc(Cl)c(Cl)c4)c3C)CC2)CC[C@H]1NS(C)(=O)=O] | 28b | 16a | 585 | 7.65 | 1E (Hydro) |
| 192 | 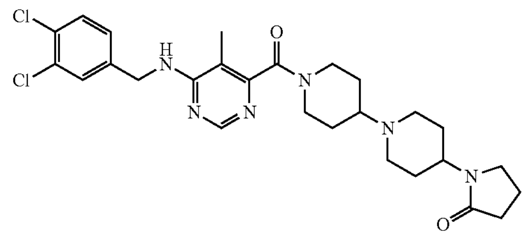 [SMILES: Cc1c(NCc2ccc(Cl)c(Cl)c2)ncnc1C(=O)N1CCC(N2CCC(N3CCCC3=O)CC2)CC1] | 28b | 1-piperidin-4-yl-pyrrolidin-2-one | 545 | 8.08 | 1E (Hydro) |
| 193 | 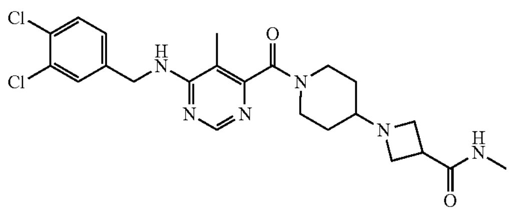 [SMILES: CNC(=O)C1CN(C2CCN(C(=O)c3ncnc(NCc4ccc(Cl)c(Cl)c4)c3C)CC2)C1] | 28b | Azetidin-3-carboxylic acid methyl-amide | 491 | 7.55 | 1E (Hydro) |
| 194 | 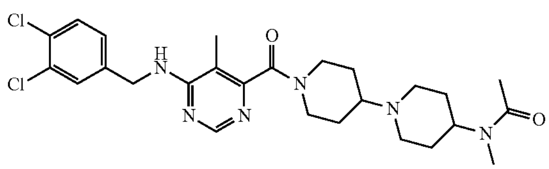 [SMILES: CC(=O)N(C)C1CCN(C2CCN(C(=O)c3ncnc(NCc4ccc(Cl)c(Cl)c4)c3C)CC2)CC1] | 28b | N-methyl-N-piperidin-4yl-acetamide | 533 | 7.87 | 1E (Hydro) |
| 195 | 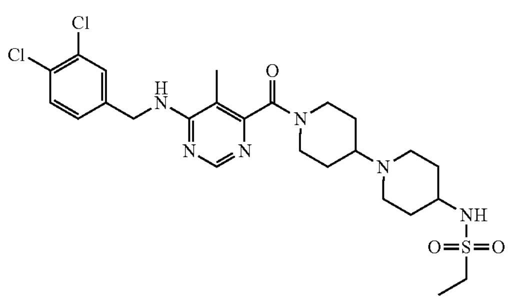 [SMILES: CCS(=O)(=O)NC1CCN(C2CCN(C(=O)c3ncnc(NCc4ccc(Cl)c(Cl)c4)c3C)CC2)CC1] | 28b | Ethan-sulfonic acid-piperidin-4-yl-amide | 569 | 8.15 | 1E (Hydro) |
| 196 | 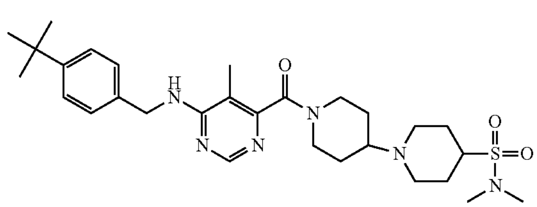 [SMILES: Cc1c(NCc2ccc(C(C)(C)C)cc2)ncnc1C(=O)N1CCC(N2CCC(S(=O)(=O)N(C)C)CC2)CC1] | 28c | Piperidine-4-sulfonic acid dimethyl-amide | 557 | 9.11 | 1E (Hydro) |

-continued

| Ex # | STRUCTURE | Inter-mediate | Amine or Ketone | [M + H]+ | HPLC $R_t$ (min) | Method |
|---|---|---|---|---|---|---|
| 197 | 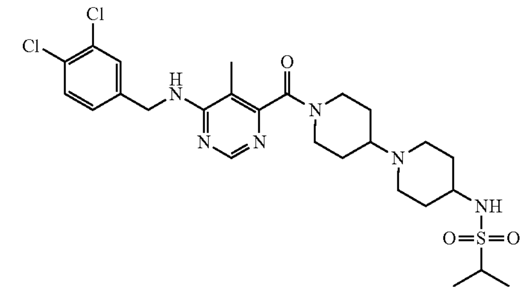 [SMILES: Cc1c(NCc2ccc(Cl)c(Cl)c2)ncnc1C(=O)N1CCC(N2CCC(NS(=O)(=O)C(C)C)CC2)CC1] | 28b | Propan-2-sulfonic acid-piperidin-4-yl-amide | 583 | 8.37 | 1E (Hydro) |
| 198 | 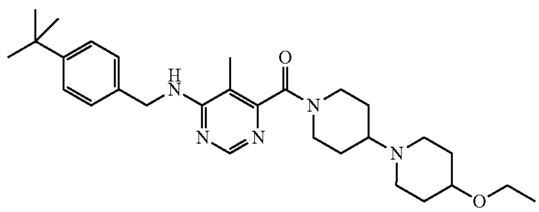 [SMILES: CCOC1CCN(C2CCN(C(=O)c3ncnc(NCc4ccc(C(C)(C)C)cc4)c3C)CC2)CC1] | 28c | 4-ethoxy-piperidine | 494 | 10.75 | 1E (Hydro) |
| 199 | 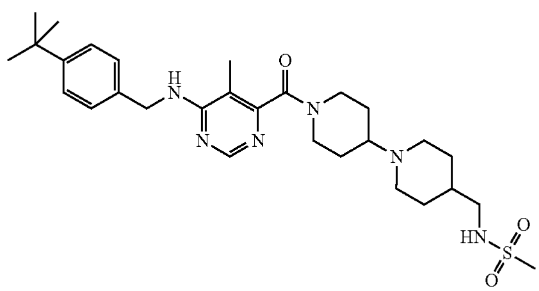 [SMILES: Cc1c(NCc2ccc(C(C)(C)C)cc2)ncnc1C(=O)N1CCC(N2CCC(CNS(C)(=O)=O)CC2)CC1] | 28c | N-piperidin-4-methyl-methan-sulfon-amide | 557 | 9.45 | 1E (Hydro) |
| 200 | 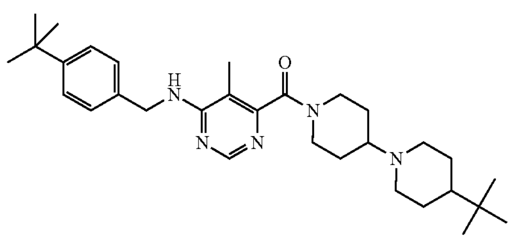 [SMILES: Cc1c(NCc2ccc(C(C)(C)C)cc2)ncnc1C(=O)N1CCC(N2CCC(C(C)(C)C)CC2)CC1] | 28c | 4-tert-butyl-piperidine | 506 | 7.86 | 2F |
| 201 | 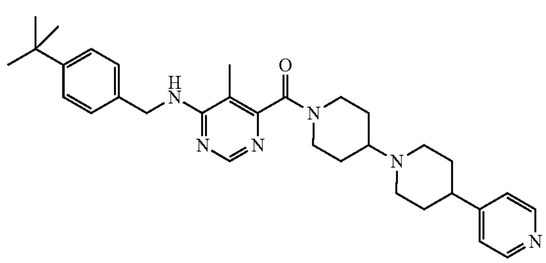 [SMILES: Cc1c(NCc2ccc(C(C)(C)C)cc2)ncnc1C(=O)N1CCC(N2CCC(c3ccncc3)CC2)CC1] | 28c | 4-(piperidin-4-yl)-pyridine | 527 | 10.88 | 1E (Hydro) |
| 202 | 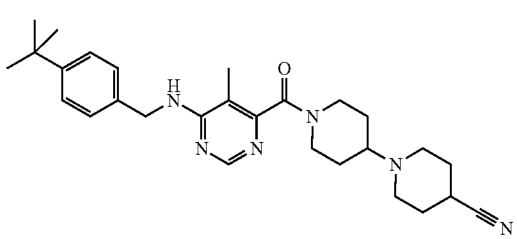 [SMILES: Cc1c(NCc2ccc(C(C)(C)C)cc2)ncnc1C(=O)N1CCC(N2CCC(C#N)CC2)CC1] | 28c | Piperidine-4-carbo-nitrile | 475 | 9.77 | 1E (Hydro) |

| Ex # | STRUCTURE | Inter-mediate | Amine or Ketone | [M + H]⁺ | HPLC R_t (min) | Method |
|---|---|---|---|---|---|---|
| 203 | 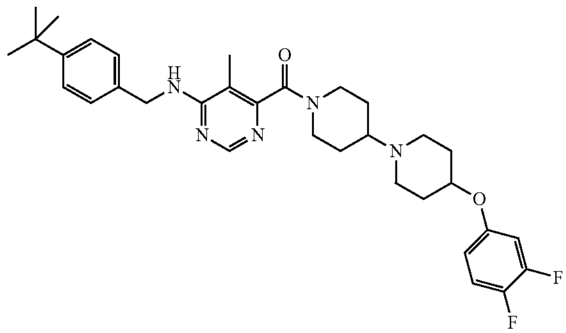 [SMILES: Cc1c(NCc2ccc(C(C)(C)C)cc2)ncnc1C(=O)N1CCC(N2CCC(Oc3ccc(F)c(F)c3)CC2)CC1] | 28c | 4-(3,4-difluoro-phenoxy)-piperidine | 578 | 11.05 | 1E (Hydro) |
| 204 | 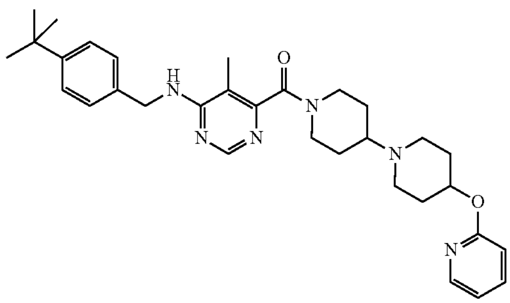 [SMILES: Cc1c(NCc2ccc(C(C)(C)C)cc2)ncnc1C(=O)N1CCC(N2CCC(Oc3ccccn3)CC2)CC1] | 28c | 2-(piperidin-4-yloxy)-pyridine | 543 | 10.38 | 1E (Hydro) |
| 205 | 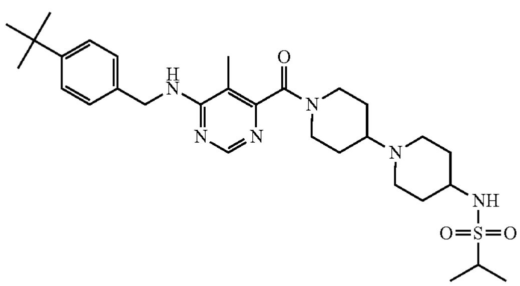 [SMILES: Cc1c(NCc2ccc(C(C)(C)C)cc2)ncnc1C(=O)N1CCC(N2CCC(NS(=O)(=O)C(C)C)CC2)CC1] | 28c | Propan-2-sulfonic-acid-piperidin-4-yl-amide | 571 | 9.12 | 1E (Hydro) |
| 206 | 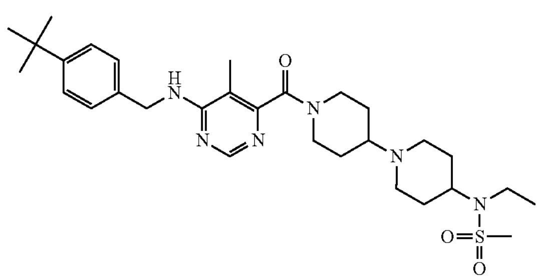 [SMILES: CCN(C1CCN(C2CCN(C(=O)c3ncnc(NCc4ccc(C(C)(C)C)cc4)c3C)CC2)CC1)S(C)(=O)=O] | 28 | N-Ethyl-N-piperidin-4-yl-methane-sulfon-amide | 571 | 10.18 | 1E (Hydro) |
| 207 | 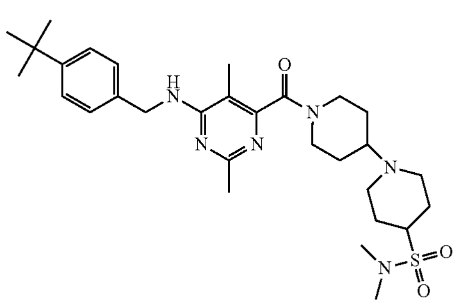 [SMILES: Cc1nc(NCc2ccc(C(C)(C)C)cc2)c(C)c(C(=O)N2CCC(N3CCC(S(=O)(=O)N(C)C)CC3)CC2)n1] | 28g | Piperidine-4-sulfonic acid dimethyl-amide | 571 | 9.67 | 1E (Hydro) |

| Ex # | STRUCTURE | Intermediate | Amine or Ketone | [M + H]+ | HPLC R$_t$ (min) | Method |
|---|---|---|---|---|---|---|
| 208 | 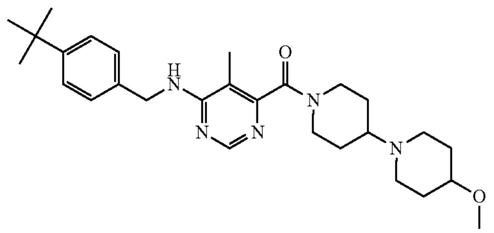 [SMILES: COC1CCN(C2CCN(C(=O)c3ncnc(NCc4ccc(C(C)(C)C)cc4)c3C)CC2)CC1] | 28c | 4-methoxy-piperidine | 480 | 2.21 | 2G |
| 209 | 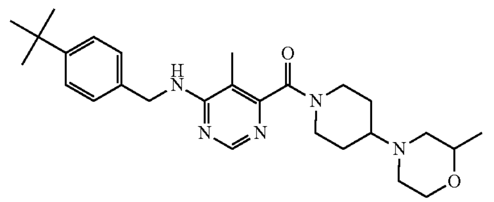 [SMILES: Cc1c(NCc2ccc(C(C)(C)C)cc2)ncnc1C(=O)N1CCC(N2CCOC(C)C2)CC1] | 28c | 2-methyl-morpholine | 466 | 3.46 | 2F |
| 210 | 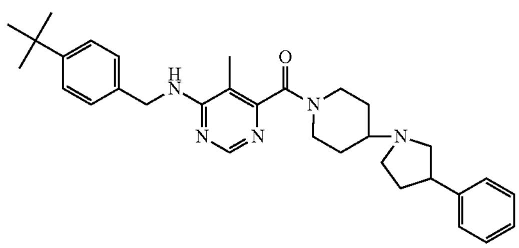 [SMILES: Cc1c(NCc2ccc(C(C)(C)C)cc2)ncnc1C(=O)N1CCC(N2CCC(c3ccccc3)C2)CC1] | 28c | 3-Phenyl-pyrrolidine | 512 | 9.68 | 2F |
| 211 | 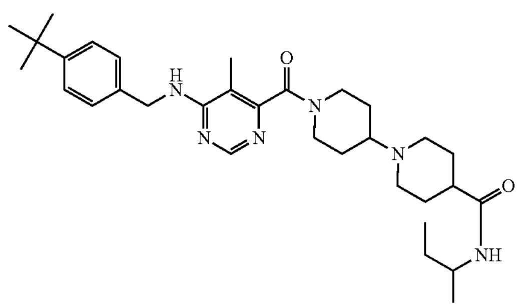 [SMILES: CCC(C)NC(=O)C1CCN(C2CCN(C(=O)c3ncnc(NCc4ccc(C(C)(C)C)cc4)c3C)CC2)CC1] | 28c | Piperidin-4-carboxylic acid sec-butyl amide | 549 | 9.53 | 1E (Hydro) |
| 212 | 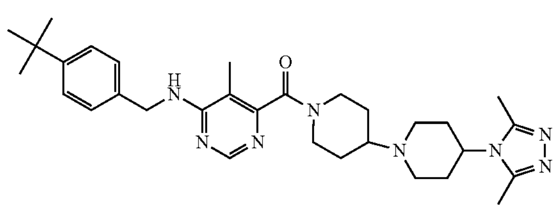 [SMILES: Cc1c(NCc2ccc(C(C)(C)C)cc2)ncnc1C(=O)N1CCC(N2CCC(n3c(C)nnc3C)CC2)CC1] | 28c | 4-(3,5-dimethyl-[1,2,4]-triazol-4-yl)-piperidine | 545 | 8.93 | 1E (Hydro) |
| 213 | 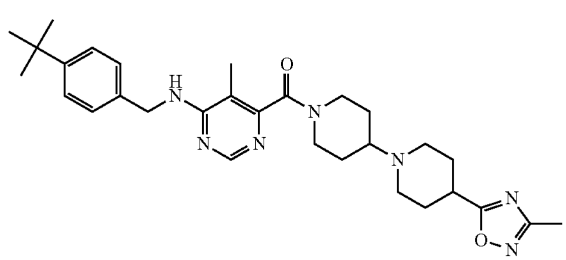 [SMILES: Cc1noc(C2CCN(C3CCN(C(=O)c4ncnc(NCc5ccc(C(C)(C)C)cc5)c4C)CC3)CC2)n1] | 28c | 4-(3-methyl-[1,2,4]-oxadiazol-5-yl)-piperidine | 532 | 8.21 | 2F |

-continued

| Ex # | STRUCTURE | Inter-mediate | Amine or Ketone | [M + H]+ | HPLC R_t. (min) | Method |
|---|---|---|---|---|---|---|
| 214 | 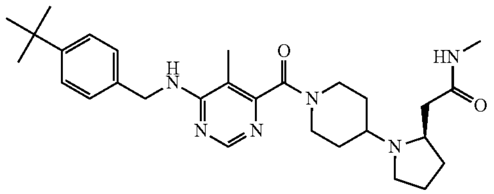 [SMILES: CNC(=O)C[C@H]1CCCN1C1CCN(C(=O)c2ncnc(NCc3ccc(C(C)(C)C)cc3)c2C)CC1] | 28c | N-methyl-2-(R)-(pyrrolidin-2-yl)acetamide | 507 | 9.35 | 1E (Hydro) |
| 215 | 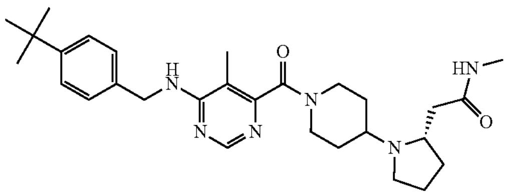 [SMILES: CNC(=O)C[C@@H]1CCCN1C1CCN(C(=O)c2ncnc(NCc3ccc(C(C)(C)C)cc3)c2C)CC1] | 28c | N-methyl-2-(S)-(pyrrolidin-2-yl)acetamide | 507 | 9.24 | 1E (Hydro) |
| 216 | 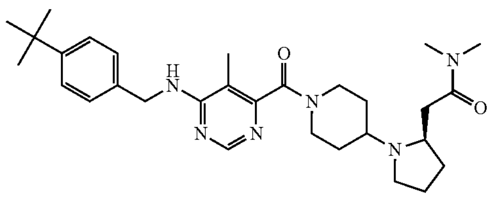 [SMILES: Cc1c(NCc2ccc(C(C)(C)C)cc2)ncnc1C(=O)N1CCC(N2CCC[C@@H]2CC(=O)N(C)C)CC1] | 28c | N,N-dimethyl-2-(R)-(pyrrolidin-2-yl)acetamide | 521 | 9.71 | 1E (Hydro) |
| 217 | 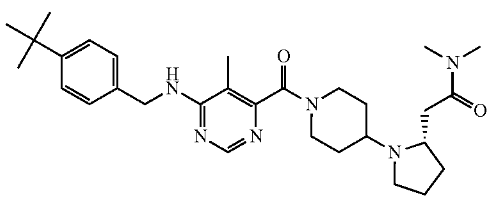 [SMILES: Cc1c(NCc2ccc(C(C)(C)C)cc2)ncnc1C(=O)N1CCC(N2CCC[C@H]2CC(=O)N(C)C)CC1] | 28c | N,N-dimethyl-2-(S)-(pyrrolidin-2-yl)acetamide | 521 | 9.72 | 1E (Hydro) |
| 218 | 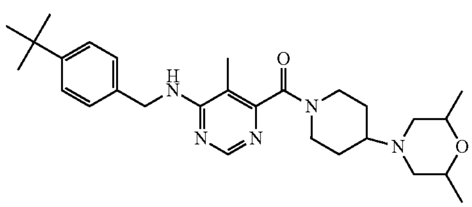 [SMILES: Cc1c(NCc2ccc(C(C)(C)C)cc2)ncnc1C(=O)N1CCC(N2CC(C)OC(C)C2)CC1] | 28c | 2,6-dimethyl-morpholine | 480 | 8.92 | 2F |
| 219 | 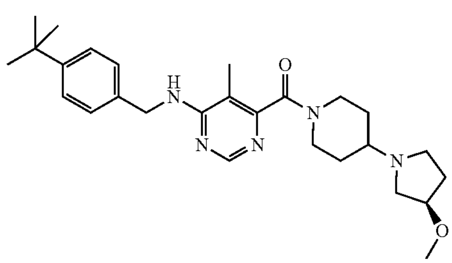 [SMILES: CO[C@@H]1CCN(C2CCN(C(=O)c3ncnc(NCc4ccc(C(C)(C)C)cc4)c3C)CC2)C1] | 28c | (R)-3-methoxy-pyrrolidine | 466 | 7.23 | 2F |
| 220 | 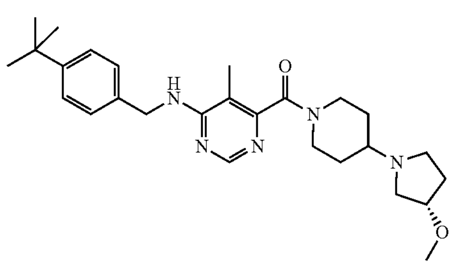 [SMILES: CO[C@H]1CCN(C2CCN(C(=O)c3ncnc(NCc4ccc(C(C)(C)C)cc4)c3C)CC2)C1] | 28c | (S)-3-methoxy-pyrrolidine | 466 | 7.23 | 2F |

-continued

| Ex # | STRUCTURE | Intermediate | Amine or Ketone | [M + H]+ | HPLC R$_{t*}$ (min) | Method |
|---|---|---|---|---|---|---|
| 221 | 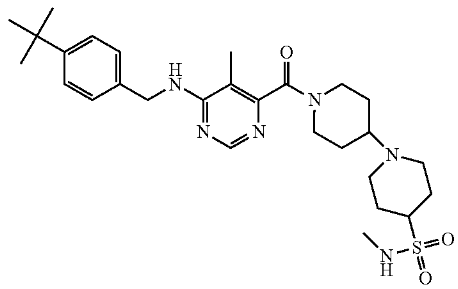 [SMILES: CNS(=O)(=O)C1CCN(C2CCN(C(=O)c3ncnc(NCc4ccc(C(C)(C)C)cc4)c3C)CC2)CC1] | 28c | Piperidine-4-sulfonic acid methyl-amide | 543 | 8.50 | 1E (Hydro) |
| 222 | 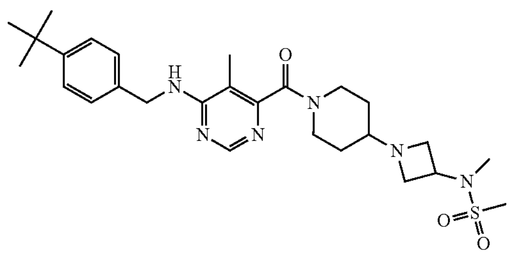 [SMILES: Cc1c(NCc2ccc(C(C)(C)C)cc2)ncnc1C(=O)N1CCC(N2CC(N(C)S(C)(=O)=O)C2)CC1] | 28c | N-azetidin-3-yl-N-methyl-methane-sulfon-amide | 529 | 8.65 | 1E (Hydro) |
| 223 | 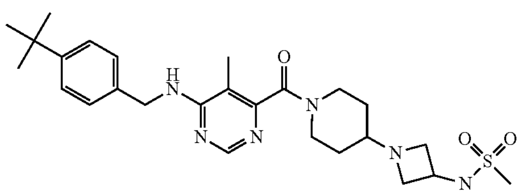 [SMILES: Cc1c(NCc2ccc(C(C)(C)C)cc2)ncnc1C(=O)N1CCC(N2CC(NS(C)(=O)=O)C2)CC1] | 28c | N-azetidin-3-yl-methane-sulfon-amide | 515 | 8.02 | 1E (Hydro) |
| 224 | 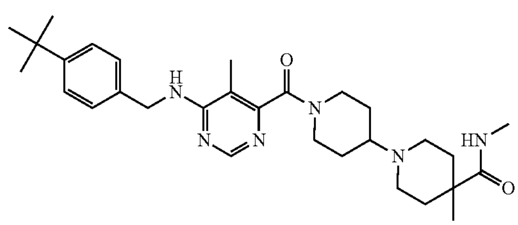 [SMILES: CNC(=O)C1(C)CCN(C2CCN(C(=O)c3ncnc(NCc4ccc(C(C)(C)C)cc4)c3C)CC2)CC1] | 28c | 4-methyl-piperidine-4-carboxylic acid methyl-amide | 521 | 9.00 | 1E (Hydro) |
| 225 | 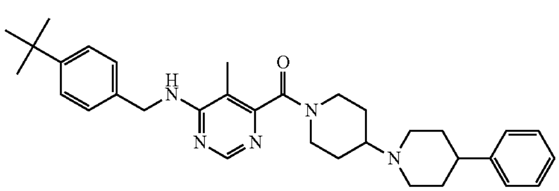 [SMILES: Cc1c(NCc2ccc(C(C)(C)C)cc2)ncnc1C(=O)N1CCC(N2CCC(c3ccccc3)CC2)CC1] | 28c | 4-phenyl-piperidine | 526 | 10.83 | 1E (Hydro) |
| 226 | 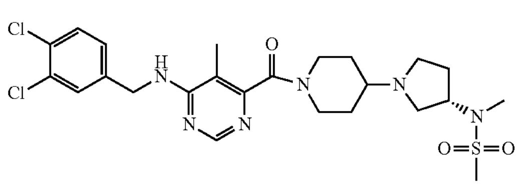 [SMILES: Cc1c(NCc2ccc(Cl)c(Cl)c2)ncnc1C(=O)N1CCC(N2CC[C@H](N(C)S(C)(=O)=O)C2)CC1] | 28b | N-methyl-N-(S)-(pyrrolidin-3yl)-methane-sulfon-amide | 555 | 8.04 | 1E (Hydro) |

-continued

| Ex # | STRUCTURE | Intermediate | Amine or Ketone | [M + H]+ | HPLC R_t. (min) | Method |
|---|---|---|---|---|---|---|
| 227 | 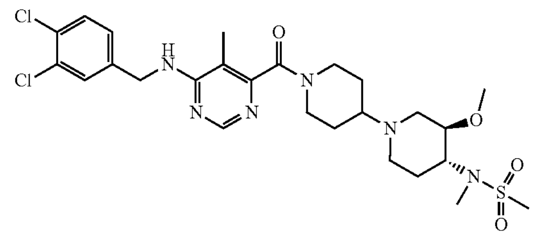 [SMILES: CO[C@@H]1CN(C2CCN(C(=O)c3ncnc(NCc4ccc(Cl)c(Cl)c4)c3C)CC2)CC[C@H]1N(C)S(C)(=O)=O] | 28b | 16b | 599 | 8.13 | 1E (Hydro) |
| 228 | 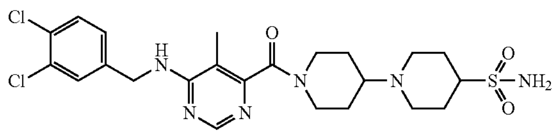 [SMILES: Cc1c(NCc2ccc(Cl)c(Cl)c2)ncnc1C(=O)N1CCC(N2CCC(S(N)(=O)=O)CC2)CC1] | 28b | Piperidine-4-sulfonic acid amide | 541 | 7.12 | 1E (Hydro) |
| 228a | 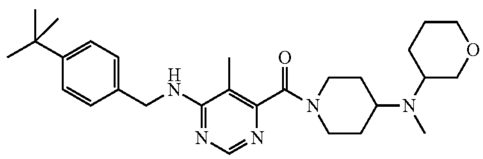 [SMILES: Cc1c(NCc2ccc(C(C)(C)C)cc2)ncnc1C(=O)N1CCC(N(C)C2CCCOC2)CC1] | 28c | Methyl-(tetra-hydro-pyran-3-yl)-amine | 480 | 10.05 | 1E (Hydro) |
| 228b | 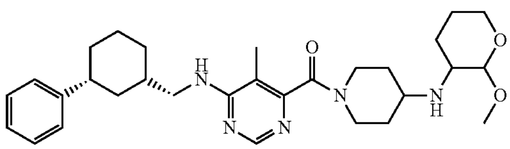 | 41b | 3-methoxy-tetrahydro-pyran-4-one | 522 | 9.25 | 1E (Hydro) |
| 228c | 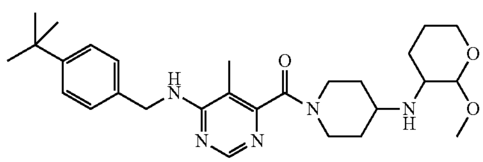 [SMILES: COC1OCCCC1NC1CCN(C(=O)c2ncnc(NCc3ccc(C(C)(C)C)cc3)c2C)CC1] | 41a | 3-methoxy-tetrahydro-pyran-4-one | 496 | 8.87 | 1E (Hydro) |
| 228d | 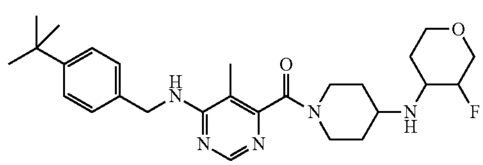 [SMILES: Cc1c(NCc2ccc(C(C)(C)C)cc2)ncnc1C(=O)N1CCC(NC2CCOCC2F)CC1] | 41a | 3-fluoro-tetrahydro-pyran-4-one | 484 | | 1E (Hydro) |
| 228e | 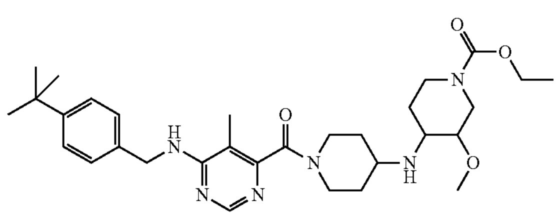 [SMILES: CCOC(=O)N1CCC(NC2CCN(C(=O)c3ncnc(NCc4ccc(C(C)(C)C)cc4)c3C)CC2)C(OC)C1] | 41a | N-carb-ethoxy-3-methoxy-4-piperidone | 567 | 7.42 | 2F |
| 228f | 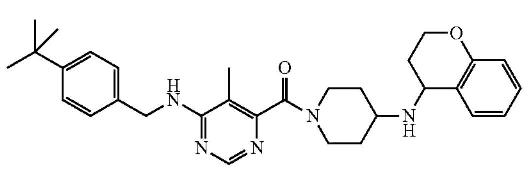 [SMILES: Cc1c(NCc2ccc(C(C)(C)C)cc2)ncnc1C(=O)N1CCC(NC2CCOc3ccccc32)CC1] | 41a | 4-chromanone | 514 | 10.31 | 1E (Hydro) |

| Ex # | STRUCTURE | Intermediate | Amine or Ketone | [M + H]+ | HPLC R$_t$ (min) | Method |
|---|---|---|---|---|---|---|
| 228g | 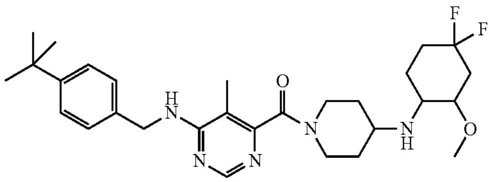 [SMILES: COC1CC(F)(F)CCC1NC1CCN(C(=O)c2ncnc(NCc3ccc(C(C)(C)C)cc3)c2C)CC1] | 41a | 43 | 530 | 9.76 | 1E (Hydro) |
| 228ga | 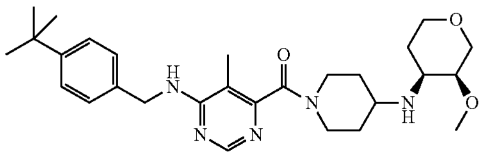 [SMILES: CO[C@@H]1COCC[C@@H]1NC1CCN(C(=O)c2ncnc(NCc3ccc(C(C)(C)C)cc3)c2C)CC1] | 28c | 47a | 496 | 5.77 | 2M |
| 228gb | 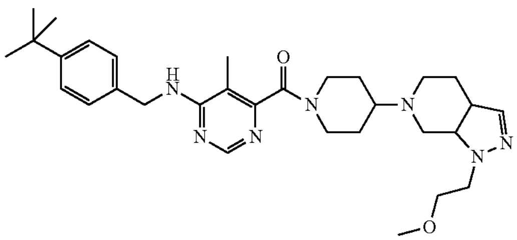 [SMILES: COCCN1N=CC2CCN(C3CCN(C(=O)c4ncnc(NCc5ccc(C(C)(C)C)cc5)c4C)CC3)CC21] | 28c | 1-(2-Methoxy-ethyl)-3a,4,5,6,7,7a-hexahydro-1H-pyrazolo-[3,4-c]pyridine | 546 | 9.55 | 1E (Hydro) |
| 228gc | 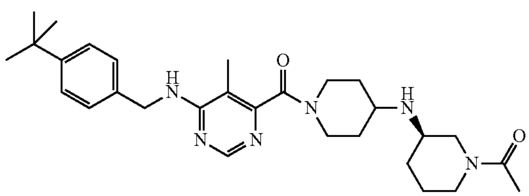 [SMILES: CC(=O)N1CCC[C@@H](NC2CCN(C(=O)c3ncnc(NCc4ccc(C(C)(C)C)cc4)c3C)CC2)C1] | 28c | 1-((R)-3-Amino-piperidin-1-yl)-ethanone | 507 | 8.85 | 1E (Hydro) |
| 228gd | 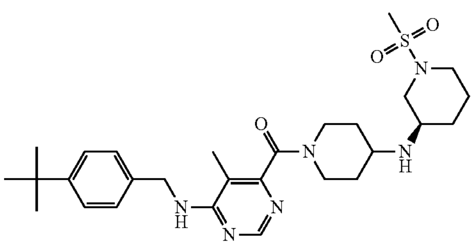 [SMILES: Cc1c(NCc2ccc(C(C)(C)C)cc2)ncnc1C(=O)N1CCC(N[C@@H]2CCCN(S(C)(=O)=O)C2)CC1] | 28c | (R)-1-Methane-sulfonyl-piperidin-3-yllamine | 543 | 9.11 | 1E (Hydro) |
| 228ge | 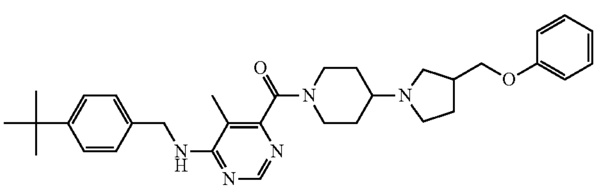 [SMILES: Cc1c(NCc2ccc(C(C)(C)C)cc2)ncnc1C(=O)N1CCC(N2CCC(COc3ccccc3)C2)CC1] | 28c | 3-Phenoxy-methyl-pyrrolidine | 542 | 10.92 | 1E (Hydro) |
| 228gf | 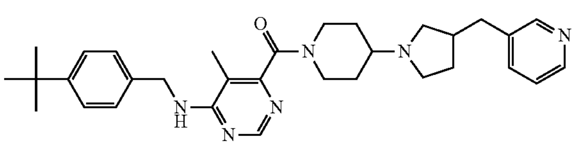 [SMILES: Cc1c(NCc2ccc(C(C)(C)C)cc2)ncnc1C(=O)N1CCC(N2CCC(Cc3cccnc3)C2)CC1] | 28c | 3-Pyrrolidin-3-yl-pyridine | 527 | 10.00 | 1E (Hydro) |
| 228gg | 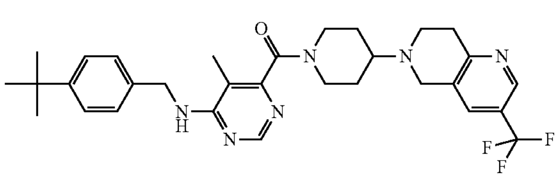 [SMILES: Cc1c(NCc2ccc(C(C)(C)C)cc2)ncnc1C(=O)N1CCC(N2CCc3ncc(C(F)(F)F)cc3C2)CC1] | 28c | 3-Trifluoro-methyl-5,6,7,8-tetrahydro-[1,6]naph-thyridine | 567 | 7.69 | 2F |

-continued

| Ex # | STRUCTURE | Intermediate | Amine or Ketone | [M + H]+ | HPLC R$_t$ (min) | Method |
|---|---|---|---|---|---|---|
| 228gh | 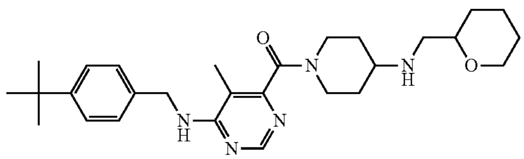 [SMILES: Cc1c(NCc2ccc(C(C)(C)C)cc2)ncnc1C(=O)N1CCC(NCC2CCCCO2)CC1] | 28 | C-(Tetrahydro-pyran-2-yl)methyl-amine | 480 | 2.09 | 2Cb |
| 228gi | 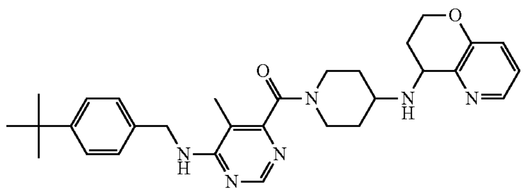 [SMILES: Cc1c(NCc2ccc(C(C)(C)C)cc2)ncnc1C(=O)N1CCC(NC2CCOc3cccnc32)CC1] | 28c | 56 | 515 | 2.18 | 2Cb |
| 228gj | 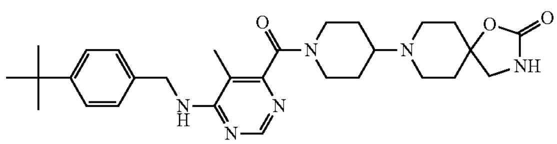 [SMILES: Cc1c(NCc2ccc(C(C)(C)C)cc2)ncnc1C(=O)N1CCC(N2CCC3(CC2)CNC(=O)O3)CC1] | 28c | 1-Oxa-3,8-diaza-spiro[4,5]decan-2-one | 521 | 8.30 | 1E (Hydro) |
| 228gk | 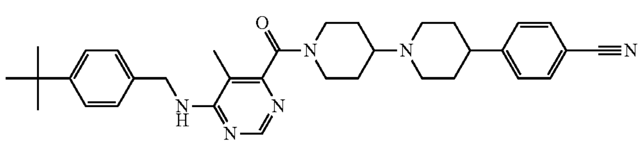 [SMILES: Cc1c(NCc2ccc(C(C)(C)C)cc2)ncnc1C(=O)N1CCC(N2CCC(c3ccc(C#N)cc3)CC2)CC1] | 28c | 4-Piperidin-4-yl-benzonitrile | 551 | 10.35 | 1E (Hydro) |
| 228gl | 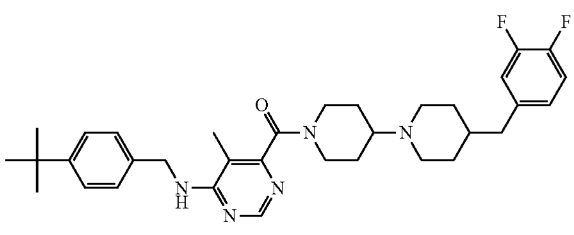 [SMILES: Cc1c(NCc2ccc(C(C)(C)C)cc2)ncnc1C(=O)N1CCC(N2CCC(Cc3ccc(F)c(F)c3)CC2)CC1] | 28c | 4-(3,4-Difluoro-benzyl)-piperidine | 576 | 11.42 | 1E (Hydro) |
| 228gm | 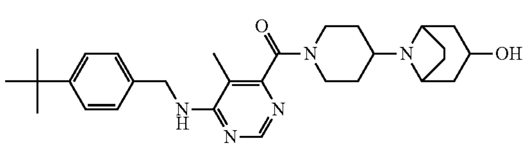 [SMILES: Cc1c(NCc2ccc(C(C)(C)C)cc2)ncnc1C(=O)N1CCC(N2C3CCC2CC(O)C3)CC1] | 28c | 8-Aza-bicyclo[3.2.1]octan-3-ol | 492 | 9.30 | 1E (Hydro) |

-continued

| Ex # | STRUCTURE | Intermediate | Amine or Ketone | [M + H]+ | HPLC R$_t$. (min) | Method |
|---|---|---|---|---|---|---|
| 228gn | 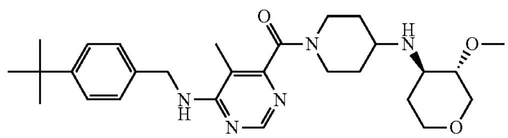 [SMILES: CO[C@@H]1COCC[C@H]1NC1CCN(C(=O)c2ncnc(NCc3ccc(C(C)(C)C)cc3)c2C)CC1] | 28c | 45 | 496 | 5.96 | 2M |
| 228go | 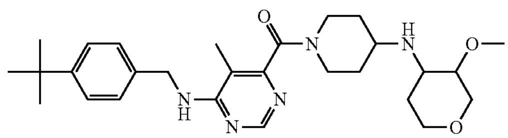 [SMILES: COC1COCCC1NC1CCN(C(=O)c2ncnc(NCc3ccc(C(C)(C)C)cc3)c2C)CC1] | 41a | 3-Methoxy-tetrahydro-pyran-4-one | 508 | 5.77 | 2M |
| 228gp | 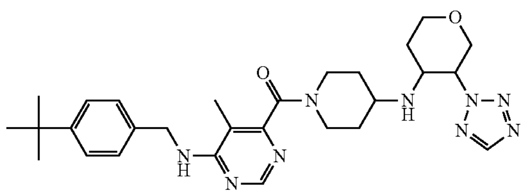 [SMILES: Cc1c(NCc2ccc(C(C)(C)C)cc2)ncnc1C(=O)N1CCC(NC2CCOCC2n2ncnn2)CC1] | 41a | 3-Tetrazol-2-yl-tetrahydro-pyran-4-one | 534 | 7.09 | 2F |

Example 228h

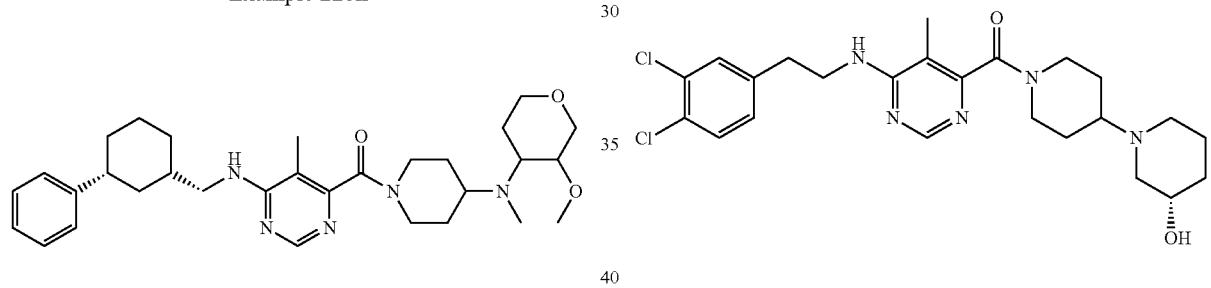

Example 228b (22 mg, 0.032 mmol), formaldehyde (0.003 ml, 0.096 mmol), N,N-diisopropyl-ethylamine (0.008 ml, 0.048 mmol) and trifluoroacetic acid (0.005 ml) in 1.5 ml of methanol were stirred at room temperature for 5 min. Sodium cyanoborohydride (10 mg, 0.160 mmol) was added and the reaction mixture was stirred at room temperature overnight. The organic phase was concentrated under vacuum. The crude product was purified by flash chromatography (Isolute silica gel cartridge 5 g, eluent: ethyl acetate/methanol=7:3%). 8.4 mg (0.016 mmol) of the desired product were obtained.

The following examples were synthesized in analogy to the preparation of Example 228h.

Example 229

Intermediate 28a (100 mg, 0.25 mmol), (S)-3-hydroxypiperidine (67 mg, 0.49 mmol) and trimethylorthoformate (1.07 ml, 9.82 mmol) in 5 ml of methanol were stirred at 60° C. for 1 h. 2-picoline borane complex (26 mg, 0.25 mmol) was added and the reaction mixture was stirred at 60° C. overnight. The reaction mixture was concentrated under vacuum. The crude product was purified by reverse phase preparative HPLC. 64 mg (0.13 mmol) of the desired product were obtained.

| Ex # | STRUCTURE | Starting example | [M + H]+ | HPLC R$_t$. (min) | Method |
|---|---|---|---|---|---|
| 228 ha | 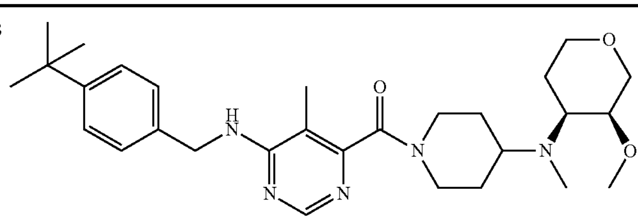 | 228ga | 510 | 5.72 | 2M |

HPLC (Method 1E): R$_t$. (min)=7.18
[M+H]$^+$=492

The following examples were synthesized in analogy to the preparation of Example 229.

| Ex # | STRUCTURE | Intermediate | Amine | [M + H]$^+$ | HPLC R$_t$. (min) | Method |
|---|---|---|---|---|---|---|
| 230 | 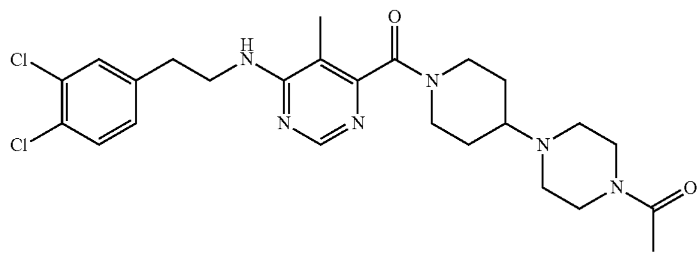 [SMILES: CC(=O)N1CCN(C2CCN(C(=O)c3ncnc(NCCc4ccc(Cl)c(Cl)c4)c3C)CC2)CC1] | 28a | 1-piperazin-1-yl-ethanone | 519 | 7.13 | 2F |
| 231 | 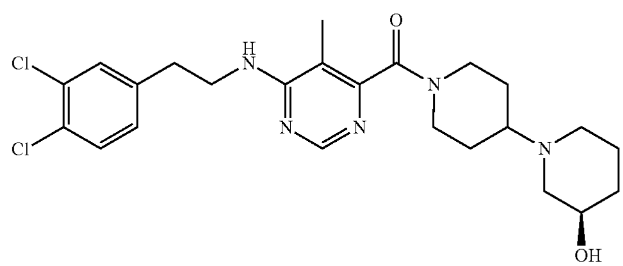 [SMILES: Cc1c(NCCc2ccc(Cl)c(Cl)c2)ncnc1C(=O)N1CCC(N2CCC[C@@H](O)C2)CC1] | 28a | (R)-piperidin-3-ol | 492 | 7.35 | 1E (Fusion) |
| 232 | 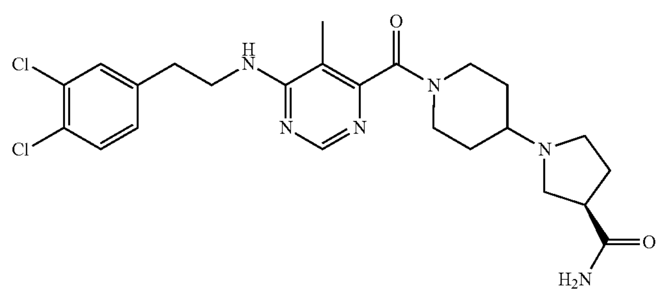 [SMILES: Cc1c(NCCc2ccc(Cl)c(Cl)c2)ncnc1C(=O)N1CCC(N2CC[C@@H](C(N)=O)C2)CC1] | 28a | (R)-pyrrolidin-3-carboxylic acid amide | 505 | 7.83 | 1E (Fusion) |
| 233 | 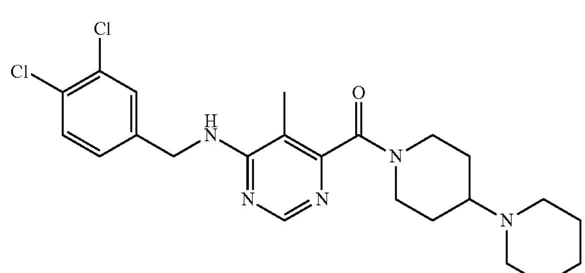 | 28b | 3-fluoro-piperidine | 480 | 8.32 | 1E (Hydro) |

Example 234

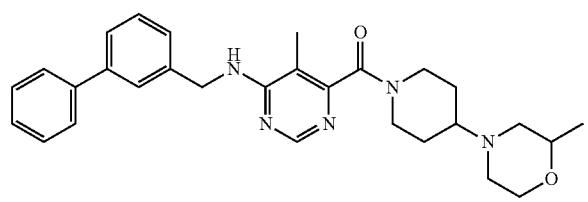 [SMILES: Cc1c(NCc2cccc(-c3ccccc3)c2)ncnc1C(=O)N1CCC(N2CCOC(C)C2)CC1]

Intermediate 28d (20 mg, 0.05 mmol), 2-methyl-morpholine (0.012 ml, 0.10 mmol), sodium triacetoxyborohydride (43 mg, 0.20 mmol), acetic acid (0.05 ml) and trimethylorthoformate (0.05 ml) in 0.9 ml of DMA were stirred at room temperature for 3 h. The reaction mixture was concentrated under vacuum. The crude product was purified by reverse phase preparative HPLC. 3 mg (0.006 mmol) of the desired product were obtained.

HPLC (Method A): $R_t$ (min)=1.74

$[M+H]^+$=486

The following examples were synthesized in analogy to the preparation of Example 234.

| Ex # | STRUCTURE | Intermediate | Amine | $[M+H]^+$ | HPLC $R_t$ (min) | Method |
|---|---|---|---|---|---|---|
| 235 | 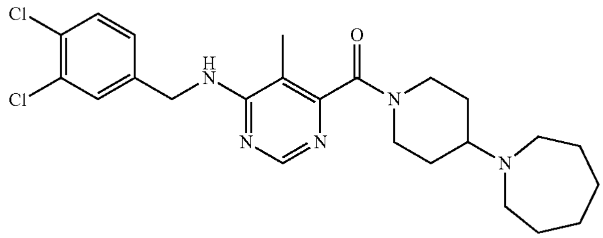 [SMILES: Cc1c(NCc2ccc(Cl)c(Cl)c2)ncnc1C(=O)N1CCC(N2CCCCCC2)CC1] | 28b | Azepane | 476 | 1.72 | 2A |
| 236 | 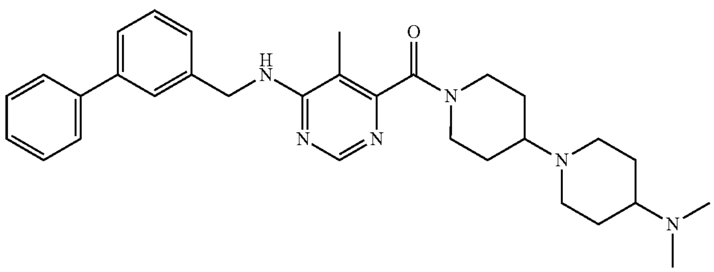 [SMILES: Cc1c(NCc2cccc(-c3ccccc3)c2)ncnc1C(=O)N1CCC(N2CCC(N(C)C)CC2)CC1] | 28d | Dimethyl-piperidin-4yl-amine | 513 | 1.64 | 2A |
| 237 | 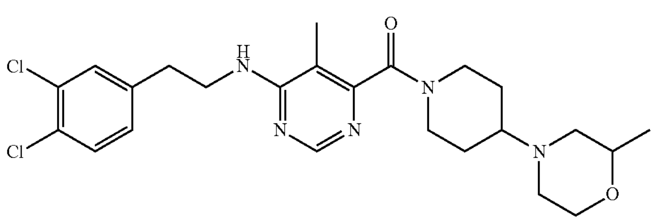 [SMILES: Cc1c(NCCc2ccc(Cl)c(Cl)c2)ncnc1C(=O)N1CCC(N2CCOC(C)C2)CC1] | 28a | 2-methyl-morpholine | 492 | 1.72 | 2A |
| 238 | 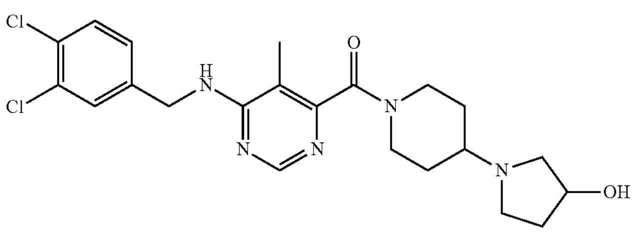 [SMILES: Cc1c(NCc2ccc(Cl)c(Cl)c2)ncnc1C(=O)N1CCC(N2CCC(O)C2)CC1] | 28b | Pyrrolidin-3-ol | 464 | 1.65 | 2A |
| 239 | 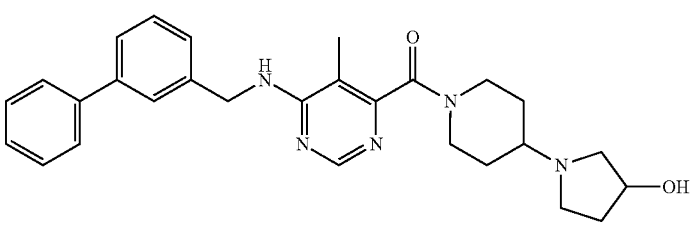 [SMILES: Cc1c(NCc2cccc(-c3ccccc3)c2)ncnc1C(=O)N1CCC(N2CCC(O)C2)CC1] | 28d | Pyrrolidin-3-ol | 472 | 1.71 | 2A |

-continued

| Ex # | STRUCTURE | Intermediate | Amine | [M + H]+ | HPLC R$_t$ (min) | Method |
|---|---|---|---|---|---|---|
| 240 | 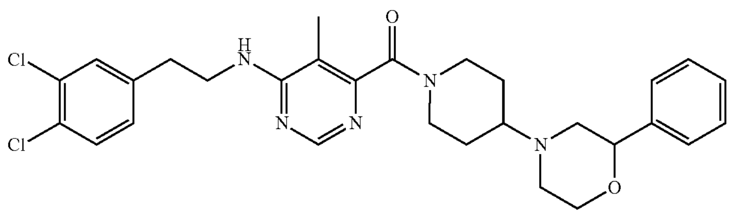 [SMILES: Cc1c(NCCc2ccc(Cl)c(Cl)c2)ncnc1C(=O)N1CCC(N2CCOC(c3ccccc3)C2)CC1] | 28a | 2-phenyl-morpholine | 554 | 1.84 | 2A |
| 241 | 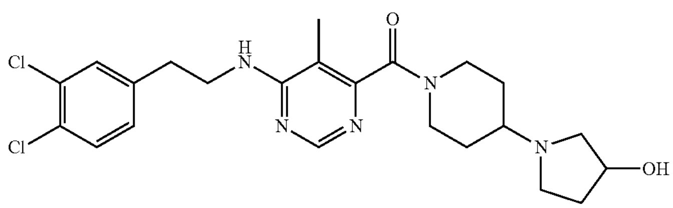 [SMILES: Cc1c(NCCc2ccc(Cl)c(Cl)c2)ncnc1C(=O)N1CCC(N2CCC(O)C2)CC1] | 28a | Pyrrolidin-3-ol | 478 | 1.68 | 2A |
| 242 | 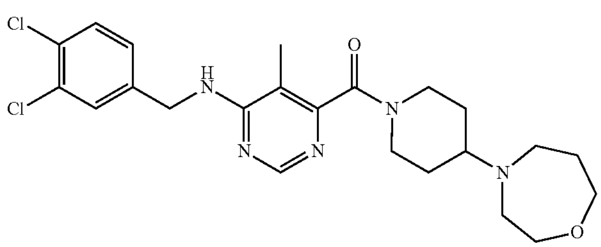 | 28b | [1,4]-oxazepane | 478 | 1.66 | 2A |
| 243 | 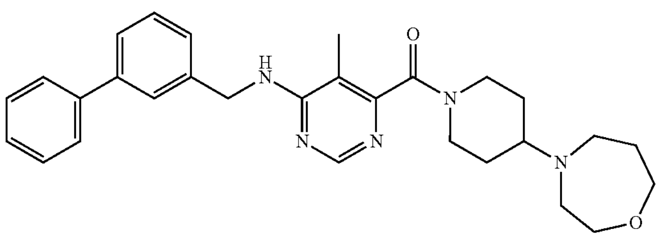 [SMILES: Cc1c(NCc2cccc(-c3ccccc3)c2)ncnc1C(=O)N1CCC(N2CCCOCC2)CC1] | 28d | [1,4]-oxazepane | 486 | 1.72 | 2A |
| 244 | 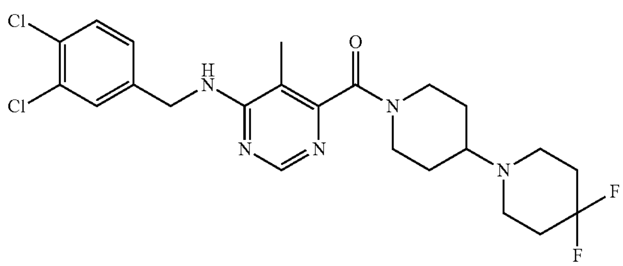 [SMILES: Cc1c(NCc2ccc(Cl)c(Cl)c2)ncnc1C(=O)N1CCC(N2CCC(F)(F)CC2)CC1] | 28b | 4,4-difluoro-piperidine | 498 | 1.72 | 2A |
| 245 | 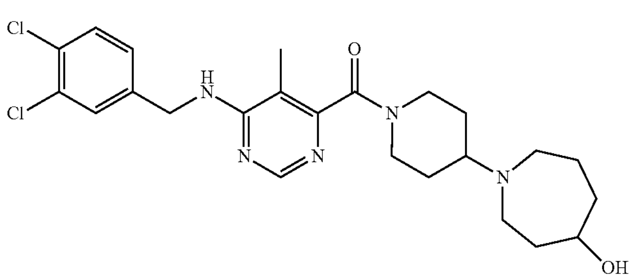 [SMILES: Cc1c(NCc2ccc(Cl)c(Cl)c2)ncnc1C(=O)N1CCC(N2CCCC(O)CC2)CC1] | 28b | Azepan-4-ol | 492 | 1.65 | 2A |

| Ex # | STRUCTURE | Intermediate | Amine | [M + H]+ | HPLC R_t (min) | Method |
|---|---|---|---|---|---|---|
| 246 | ![structure] | 28a | (3S,4R)-piperidine-3,4-diol | 508 | 1.66 | 2A |
| 247 | ![structure] | 28a | Azepan-4-ol | 506 | 1.68 | 2A |

Example 248

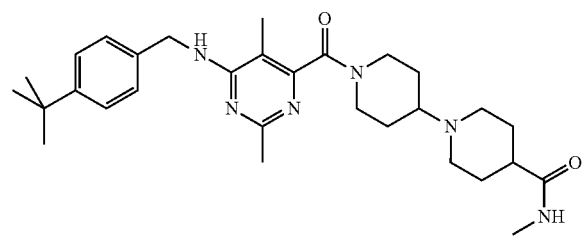 [SMILES: CNC(=O)C1CCN(C2CCN(C(=O)c3nc(C)nc(NCc4ccc(C(C)(C)C)cc4)c3C)CC2)CC1]

Intermediate 27e (105 mg, 0.33 mmol), TBTU (215 mg, 0.67 mmol) and N,N-diisopropyl-ethylamine (0.12 ml, 0.67 mmol) in 2 ml DMF were stirred at room temperature for 5 min Intermediate 20f (100 mg, 0.33 mmol) was added and the reaction mixture was stirred at room temperature overnight. The reaction mixture was concentrated under vacuum and the crude product was dissolved in dichloromethane. The organic phase was washed with an aqueous saturated sodium bicarbonate solution, dried over sodium sulfate and concentrated under vacuum. The crude product was purified by flash chromatography (Si Isolute cartridge (5 g); eluent: ethyl acetate/methanol=90/10%). 30 mg (0.057 mmol) of the desired product were obtained.

HPLC (Method 1E Hydro): R_t. (min)=9.2

[M+H]+=521

The following examples were synthesized in analogy to the preparation of Example 248.

| Ex # | STRUCTURE | Intermediate | Amine | [M + H]+ | HPLC R_t (min) | Method |
|---|---|---|---|---|---|---|
| 249 | ![structure] | 27i | 20a | 568 | 10.07 | 1E (Hydro) |

-continued

| Ex # | STRUCTURE | Intermediate | Amine | [M + H]+ | HPLC R<sub>t</sub>. (min) | Method |
|---|---|---|---|---|---|---|
| 250 | 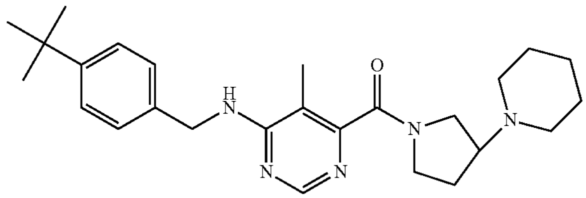 [SMILES: Cc1c(NCc2ccc(C(C)(C)C)cc2)ncnc1C(=O)N1CCC(N2CCCCC2)C1] | 27c | 1-pyrrolidin-3-yl-piperidine | 436 | 1.5 | 1E (Hydro) |
| 251 | 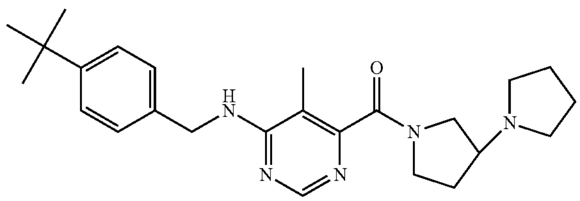 [SMILES: Cc1c(NCc2ccc(C(C)(C)C)cc2)ncnc1C(=O)N1CCC(N2CCCC2)C1] | 27c | [1,3']-Bipyrrolidinyl | 422 | 10.35 | 1E (Hydro) |
| 252 | 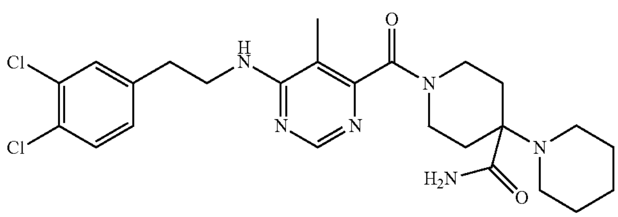 [SMILES: Cc1c(NCCc2ccc(Cl)c(Cl)c2)ncnc1C(=O)N1CCC(C(N)=O)(N2CCCCC2)CC1] | 27a | [1,4']-Bipiperidinyl-4' carboxylic-acid amide | 519 | 8.60 | 1E (Fusion) |
| 253 | 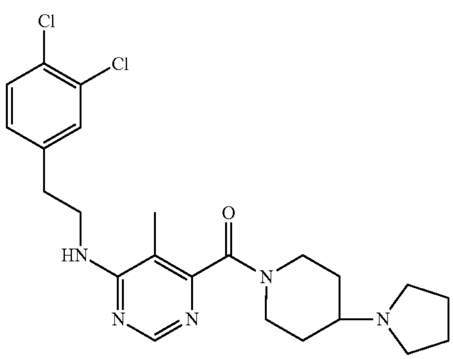 [SMILES: Cc1c(NCCc2ccc(Cl)c(Cl)c2)ncnc1C(=O)N1CCC(N2CCCC2)CC1] | 27a | 4-pyrrolidin-1yl-piperidine | 462 | 7.07 | 2F |
| 254 | 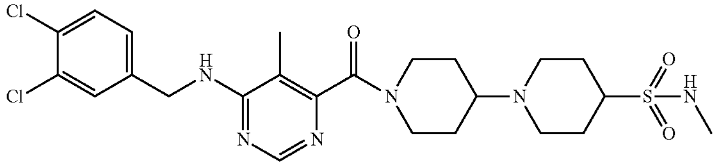 [SMILES: CNS(=O)(=O)C1CCN(C2CCN(C(=O)c3ncnc(NCc4ccc(Cl)c(Cl)c4)c3C)CC2)CC1] | 27b | 20g | 555 | 7.50 | 1E (Hydro) |
| 255 | 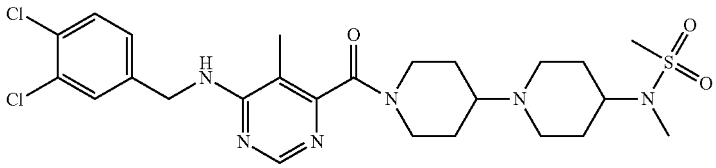 [SMILES: Cc1c(NCc2ccc(Cl)c(Cl)c2)ncnc1C(=O)N1CCC(N2CCC(N(C)S(C)(=O)=O)CC2)CC1] | 27b | 20a | 569 | 8.15 | 1E (Hydro) |
| 256 | 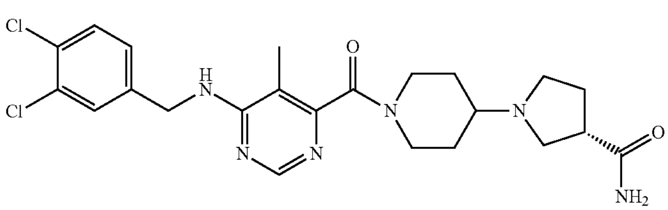 [SMILES: Cc1c(NCc2ccc(Cl)c(Cl)c2)ncnc1C(=O)N1CCC(N2CC[C@H](C(N)=O)C2)CC1] | 27b | 20j | 491 | 7.03 | 1E (Hydro) |

-continued

| Ex # | STRUCTURE | Intermediate | Amine | [M + H]⁺ | HPLC R$_t$ (min) | Method |
|---|---|---|---|---|---|---|
| 257 | 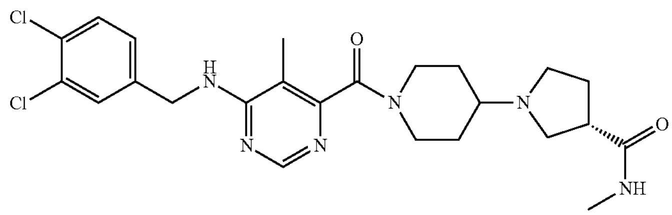 [SMILES: CNC(=O)[C@H]1CCN(C2CCN(C(=O)c3ncnc(NCc4ccc(Cl)c(Cl)c4)c3C)CC2)C1] | 27b | 20i | 505 | 7.43 | 1E (Hydro) |
| 258 | 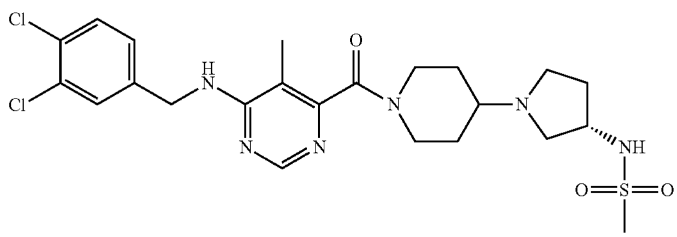 [SMILES: Cc1c(NCc2ccc(Cl)c(Cl)c2)ncnc1C(=O)N1CCC(N2CC[C@H](NS(C)(=O)=O)C2)CC1] | 27b | 20d | 541 | 7.50 | 1E (Hydro) |
| 259 | 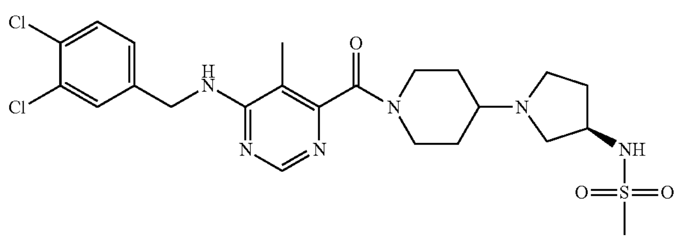 [SMILES: Cc1c(NCc2ccc(Cl)c(Cl)c2)ncnc1C(=O)N1CCC(N2CC[C@@H](NS(C)(=O)=O)C2)CC1] | 27b | 20c | 541 | 7.48 | 1E (Hydro) |
| 260 | 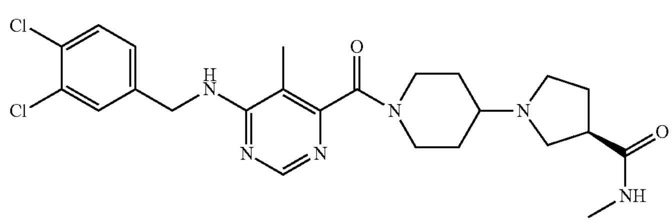 [SMILES: CNC(=O)[C@@H]1CCN(C2CCN(C(=O)c3ncnc(NCc4ccc(Cl)c(Cl)c4)c3C)CC2)C1] | 27b | 20h | 505 | 7.85 | 1E (Hydro) |
| 261 | 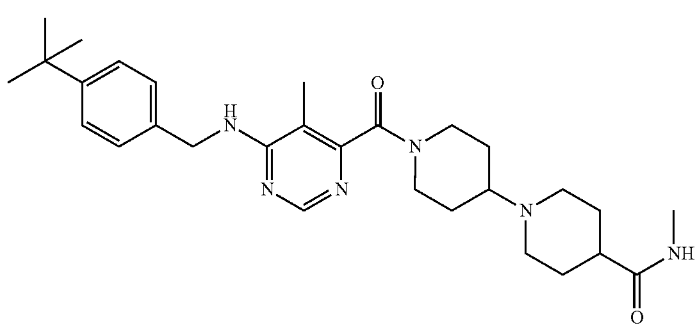 [SMILES: CNC(=O)C1CCN(C2CCN(C(=O)c3ncnc(NCc4ccc(C(C)(C)C)cc4)c3C)CC2)CC1] | 27c | 20f | 507 | 8.70 | 1E (Hydro) |

-continued

| Ex # | STRUCTURE | Intermediate | Amine | [M + H]+ | HPLC R<sub>t</sub> (min) | Method |
|---|---|---|---|---|---|---|
| 262 | 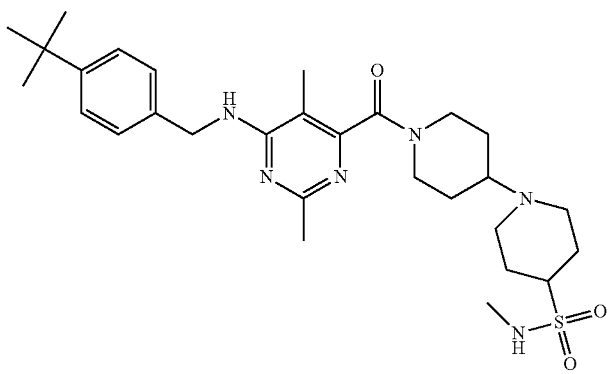 [SMILES: CNS(=O)(=O)C1CCN(C2CCN(C(=O)c3nc(C)nc(NCc4ccc(C(C)(C)C)cc4)c3C)CC2)CC1] | 27e | 20g | 557 | 9.11 | 1E (Hydro) |
| 263 | 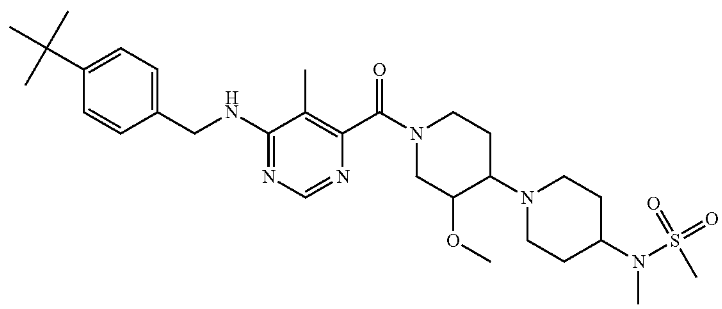 [SMILES: COC1CN(C(=O)c2ncnc(NCc3ccc(C(C)(C)C)cc3)c2C)CCC1N1CCC(N(C)S(C)(=O)=O)CC1] | 27c | 20m | 587 | 8.79 | 2F |
| 264 | 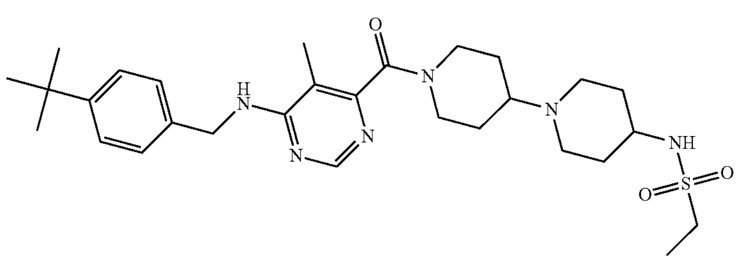 [SMILES: CCS(=O)(=O)NC1CCN(C2CCN(C(=O)c3ncnc(NCc4ccc(C(C)(C)C)cc4)c3C)CC2)CC1] | 27c | 20e | 557 | 8.85 | 1E (Hydro) |
| 265 | 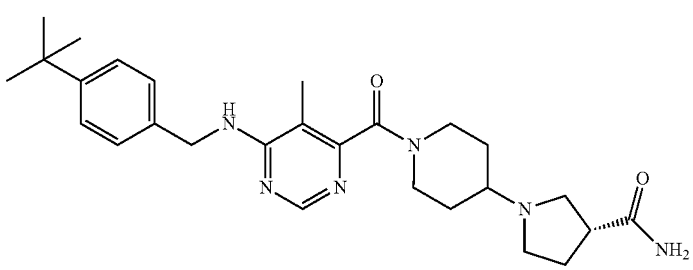 [SMILES: Cc1c(NCc2ccc(C(C)(C)C)cc2)ncnc1C(=O)N1CCC(N2CC[C@@H](C(N)=O)C2)CC1] | 27c | 20l | 479 | 8.37 | 1E (Hydro) |
| 266 | 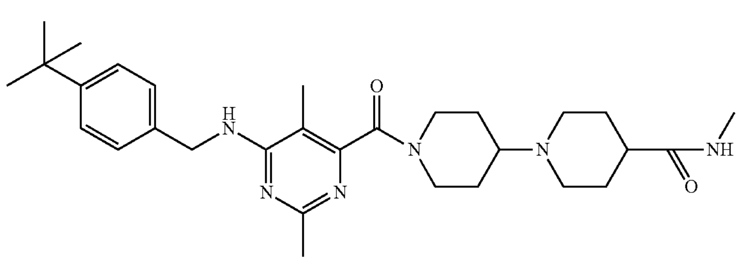 [SMILES: CNC(=O)C1CCN(C2CCN(C(=O)c3nc(C)nc(NCc4ccc(C(C)(C)C)cc4)c3C)CC2)CC1] | 27e | 20f | 521 | 9.2 | 1E (Hydro) |

-continued

| Ex # | STRUCTURE | Intermediate | Amine | [M + H]+ | HPLC R_t (min) | Method |
|---|---|---|---|---|---|---|
| 267 | 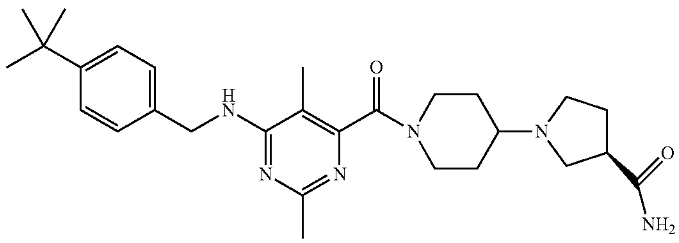 [SMILES: Cc1nc(NCc2ccc(C(C)(C)C)cc2)c(C)c(C(=O)N2CCC(N3CC[C@@H](C(N)=O)C3)CC2)n1] | 27e | 20l | 493 | 8.93 | 1E (Hydro) |
| 268 | 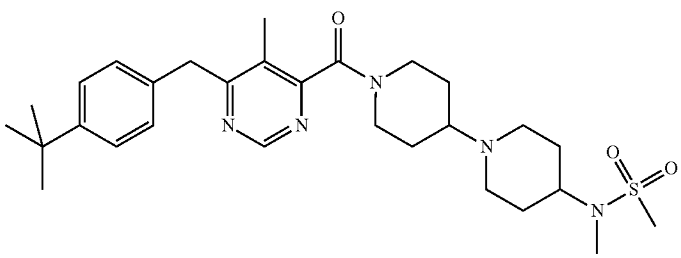 | 39b | 20a | 542 | 3.54 | 2F |
| 269 | 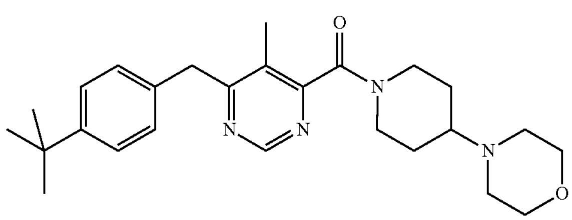 [SMILES: Cc1c(Cc2ccc(C(C)(C)C)cc2)ncnc1C(=O)N1CCC(N2CCOCC2)CC1] | 39b | 4-piperidin-4-yl-morpholine | 436 | 7.43 | 2F |
| 270 | 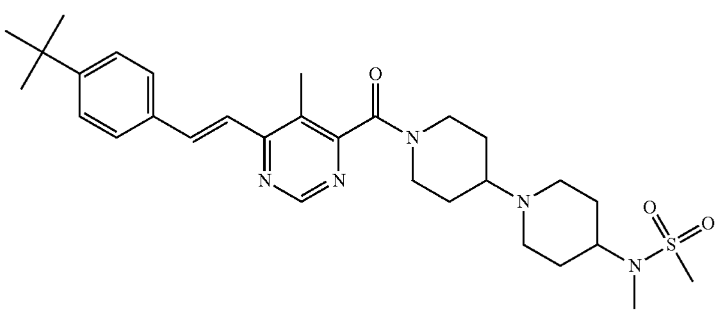 [SMILES: Cc1c(/C=C/c2ccc(C(C)(C)C)cc2)ncnc1C(=O)N1CCC(N2CCC(N(C)S(C)(=O)=O)CC2)CC1] | 39a | 20a | 553 | 8.28 | 2F |
| 271 | 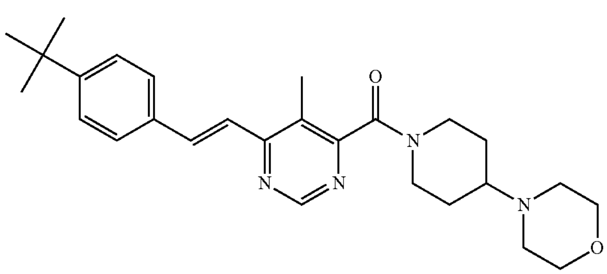 [SMILES: Cc1c(/C=C/c2ccc(C(C)(C)C)cc2)ncnc1C(=O)N1CCC(N2CCOCC2)CC1] | 39a | 4-piperidin-4-yl-morpholine | 449 | 7.60 | 2F |

| Ex # | STRUCTURE | Intermediate | Amine | [M + H]⁺ | HPLC R_t (min) | Method |
|---|---|---|---|---|---|---|
| 272 | 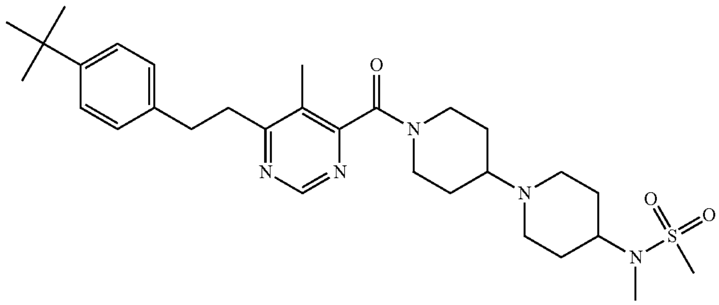 [SMILES: Cc1c(CCc2ccc(C(C)(C)C)cc2)ncnc1C(=O)N1CCC(N2CCC(N(C)S(C)(=O)=O)CC2)CC1] | 39c | 20a | 556 | 7.98 | 2F |
| 273 | 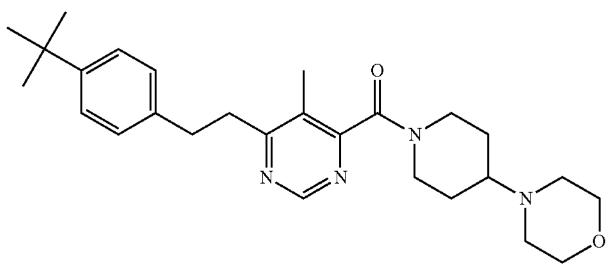 [SMILES: Cc1c(CCc2ccc(C(C)(C)C)cc2)ncnc1C(=O)N1CCC(N2CCOCC2)CC1] | 39c | 4-piperidin-4-yl-morpholine | 450 | 7.29 | 2F |
| 274 | 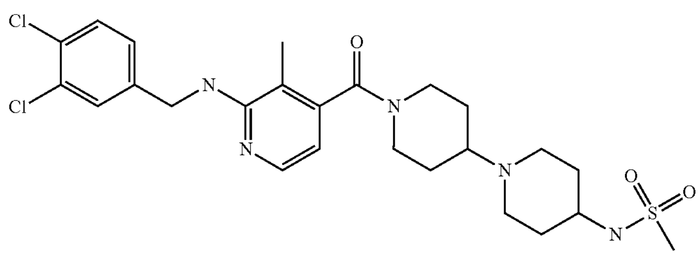 [SMILES: Cc1c(C(=O)N2CCC(N3CCC(NS(C)(=O)=O)CC3)CC2)ccnc1NCc1ccc(Cl)c(Cl)c1] | 39d | 24 | 554 | 8.28 | 1E (Hydro) |
| 275 | 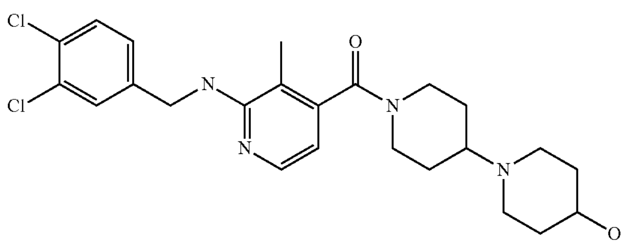 [SMILES: Cc1c(C(=O)N2CCC(N3CCC(O)CC3)CC2)ccnc1NCc1ccc(Cl)c(Cl)c1] | 39d | [1,4']-bipiperidinyl-4-ol | 477 | 7.77 | 1E (Hydro) |
| 275a | 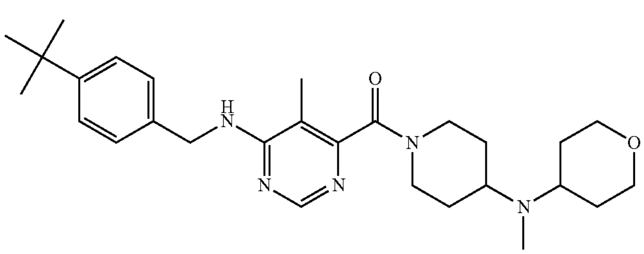 [SMILES: Cc1c(NCc2ccc(C(C)(C)C)cc2)ncnc1C(=O)N1CCC(N(C)C2CCOCC2)CC1] | 27c | 20la | 480 | 10.03 | 1E (Hydro) |

-continued

| Ex # | STRUCTURE | Intermediate | Amine | [M + H]+ | HPLC R_t. (min) | Method |
|---|---|---|---|---|---|---|
| 275b | 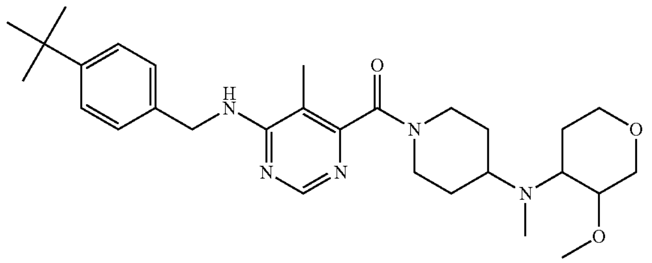 [SMILES: COC1COCCC1N(C)C1CCN(C(=O)c2ncnc(NCc3ccc(C(C)(C)C)cc3)c2C)CC1] | 27c | 20lb | 510 | 9.48 | 1E (Hydro) |
| 275c | 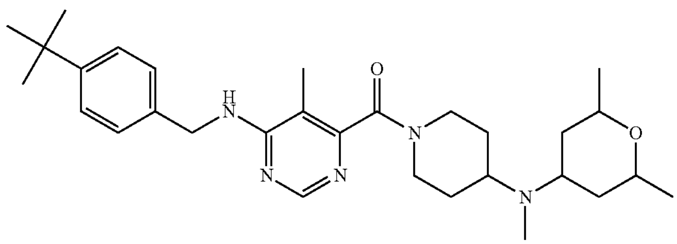 [SMILES: Cc1c(NCc2ccc(C(C)(C)C)cc2)ncnc1C(=O)N1CCC(N(C)C2CC(C)OC(C)C2)CC1] | 27c | 20lc | 508 | 10.27 | 1E (Hydro) |
| 275d | 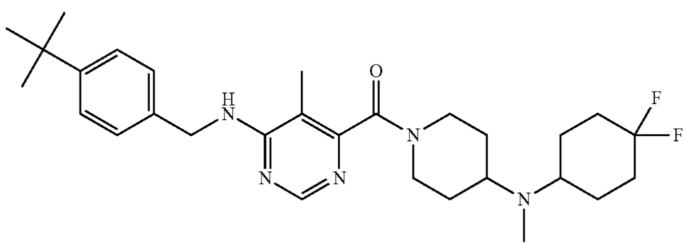 [SMILES: Cc1c(NCc2ccc(C(C)(C)C)cc2)ncnc1C(=O)N1CCC(N(C)C2CCC(F)(F)CC2)CC1] | 27c | 20ld | 514 | 10.13 | 1E (Hydro) |
| 275da | 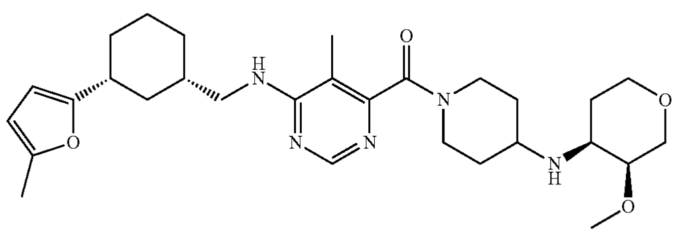 [SMILES: CO[C@@H]1COCC[C@@H]1NC1CCN(C(=O)c2ncnc(NC[C@H]3CCC[C@@H](c4ccc(C)o4)C3)c2C)CC1] | 27hc | 20lg | 526 | 9.16 | 1E (Hydro) |
| 275db | 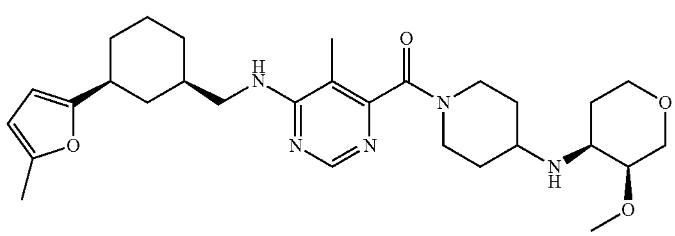 [SMILES: CO[C@@H]1COCC[C@@H]1NC1CCN(C(=O)c2ncnc(NC[C@@H]3CCC[C@H](c4ccc(C)o4)C3)c2C)CC1] | 27hd | 20lg | 526 | 9.18 | 1E (Hydro) |
| 275dc | 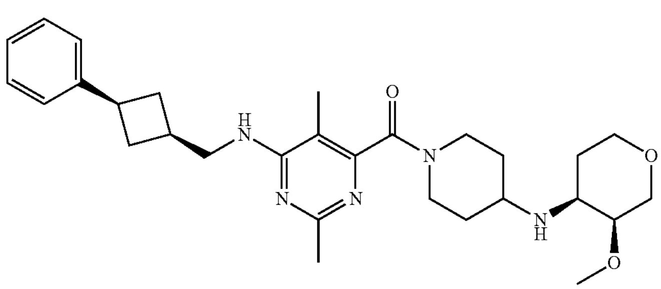 [SMILES: CO[C@@H]1COCC[C@@H]1NC1CCN(C(=O)c2nc(C)nc(NC[C@H]3C[C@@H](c4ccccc4)C3)c2C)CC1] | 27hs | 20lg | 508 | 7.25 | 1F |

-continued

| Ex # | STRUCTURE | Intermediate | Amine | [M + H]⁺ | HPLC R$_t$ (min) | Method |
|---|---|---|---|---|---|---|
| 275dd | 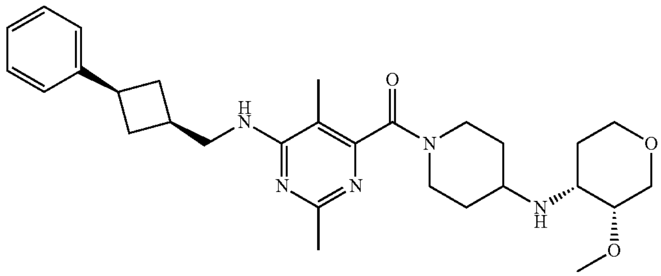 [SMILES: CO[C@H]1COCC[C@H]1NC1CCN(C(=O)c2nc(C)nc(NC[C@H]3C[C@@H](c4ccccc4)C3)c2C)CC1] | 27hf | 20lf | 494 | 6.53 | 2F |
| 275de | 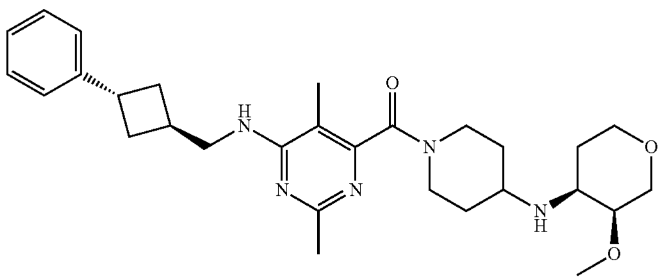 [SMILES: CO[C@@H]1COCC[C@@H]1NC1CCN(C(=O)c2nc(C)nc(NC[C@H]3C[C@H](c4ccccc4)C3)c2C)CC1] | 27hr | 20lg | 508 | 8.55 | 1E (Hydro) |
| 275df | 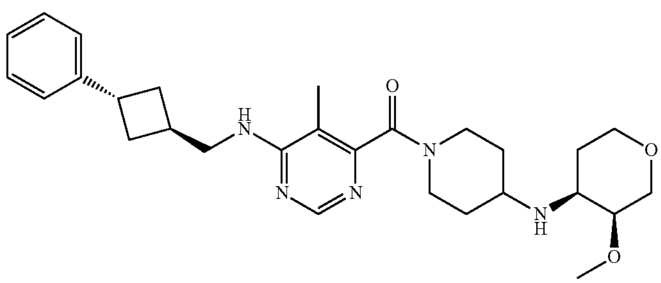 [SMILES: CO[C@@H]1COCC[C@@H]1NC1CCN(C(=O)c2ncnc(NC[C@H]3C[C@H](c4ccccc4)C3)c2C)CC1] | 27he | 20lg | 494 | 8.07 | 1E (Hydro) |
| 275dg | 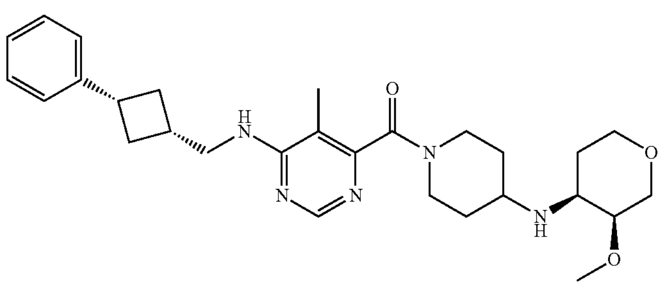 [SMILES: CO[C@@H]1COCC[C@@H]1NC1CCN(C(=O)c2ncnc(NC[C@H]3C[C@@H](c4ccccc4)C3)c2C)CC1] | 27hf | 20lg | 494 | 8.10 | 1E (Hydro) |
| 275dh | 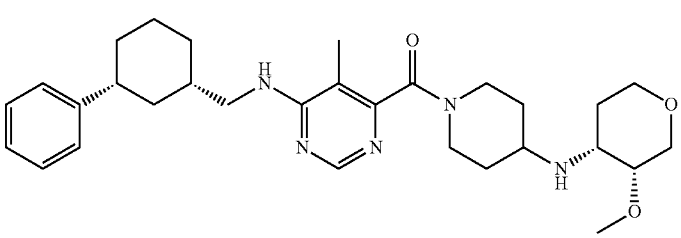 [SMILES: CO[C@H]1COCC[C@H]1NC1CCN(C(=O)c2ncnc(NC[C@H]3CCC[C@@H](c4ccccc4)C3)c2C)CC1] | 27ha | 20lf | 522 | 9.03 | 1E (Hydro) |

| Ex # | STRUCTURE | Intermediate | Amine | [M + H]+ | HPLC Rt. (min) | Method |
|---|---|---|---|---|---|---|
| 275di | 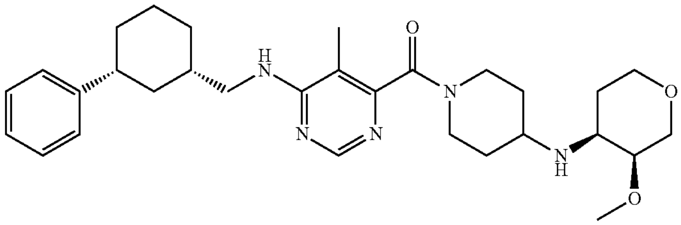 [SMILES: CO[C@@H]1COCC[C@@H]1NC1CCN(C(=O)c2ncnc(NC[C@H]3CCC[C@@H](c4ccccc4)C3)c2C)CC1] | 27ha | 20lg | 522 | 9.00 | 1E (Hydro) |
| 275dj | 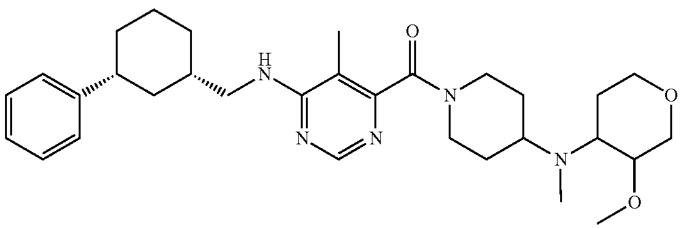 [SMILES: COC1COCCC1N(C)C1CCN(C(=O)c2ncnc(NC[C@H]3CCC[C@@H](c4ccccc4)C3)c2C)CC1] | 27ha | 20la | 536 | 9.76 | 1E (Hydro) |
| 275dk | 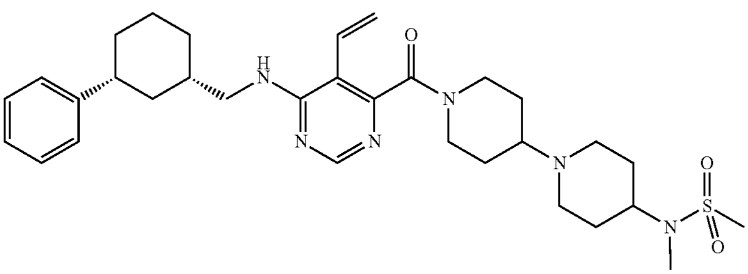 [SMILES: C=Cc1c(NC[C@H]2CCC[C@@H](c3ccccc3)C2)ncnc1C(=O)N1CCC(N2CCC(N(C)S(C)(=O)=O)CC2)CC1] | 27ib | 20a | 595 | 2.16 | 2Cb |
| 275dl | 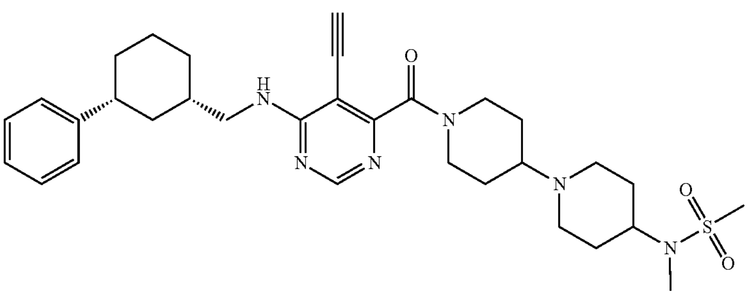 [SMILES: C#Cc1c(NC[C@H]2CCC[C@@H](c3ccccc3)C2)ncnc1C(=O)N1CCC(N2CCC(N(C)S(C)(=O)=O)CC2)CC1] | 27ic | 20a | 593 | 2.20 | 2Cb |

Example 276

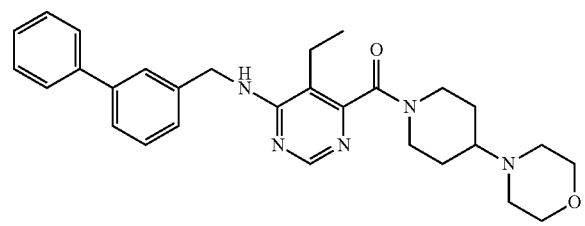 [SMILES: CCc1c(NCc2cccc(-c3ccccc3)c2)ncnc1C(=O)N1CCC(N2CCOCC2)CC1]

Intermediate 27g (50 mg, 0.14 mmol), HATU (55 mg, 0.14 mmol) and N,N-diisopropyl-ethylamine (0.05 ml, 0.28 mmol) in 2 ml DMF were stirred at room temperature for 5 min 4-piperidin-4-yl-morpholine (24 mg, 0.14 mmol) was added and the reaction mixture was stirred at room temperature 3 h. The reaction mixture was concentrated under vacuum and the crude product was dissolved in dichloromethane. The organic phase was washed with an aqueous saturated sodium bicarbonate solution, dried over sodium sulfate and concentrated under vacuum. The crude product was purified by reverse phase preparative HPLC. 80 mg (0.13 mmol) of the desired product were obtained.

HPLC (Method C): $R_t$ (min)=1.57

[M+H]+=486

The following examples were synthesized in analogy to the preparation of Example 276.

| Ex # | STRUCTURE | Intermediate | Amine | [M + H]+ | HPLC R<sub>t</sub> (min) | Method |
|---|---|---|---|---|---|---|
| 277 | 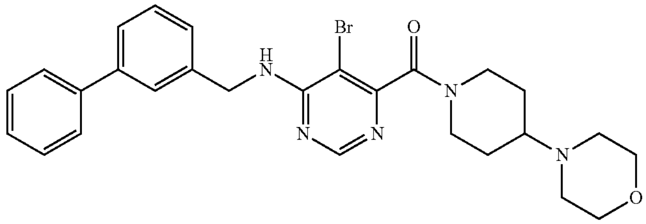 [SMILES: O=C(c1ncnc(NCc2cccc(-c3ccccc3)c2)c1Br)N1CCC(N2CCOCC2)CC1] | 27h | 4-piperidin-4-yl-morpholine | 536 | 1.69 | 2C |
| 278 | 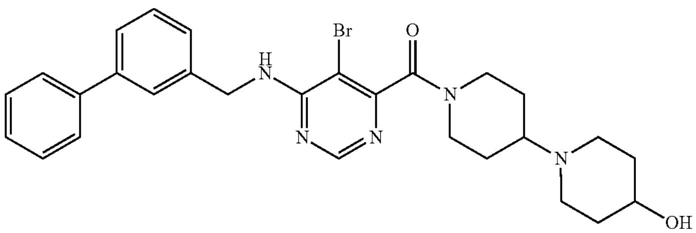 [SMILES: O=C(c1ncnc(NCc2cccc(-c3ccccc3)c2)c1Br)N1CCC(N2CCC(O)CC2)CC1] | 27h | [1,4']-Bipiperidinyl-4-ol | 550 | 1.65 | 2C |
| 279 | 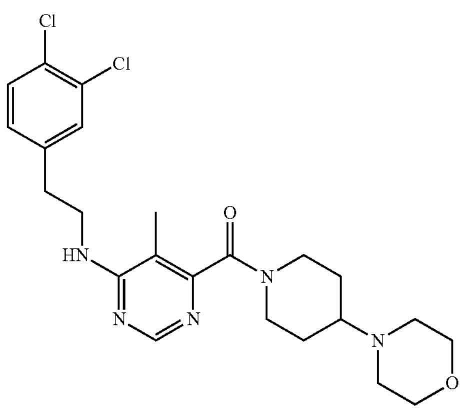 [SMILES: Cc1c(NCCc2ccc(Cl)c(Cl)c2)ncnc1C(=O)N1CCC(N2CCOCC2)CC1] | 27a | 4-piperidin-4-yl-morpholine | 478 | 1.52 | 2C |
| 280 | 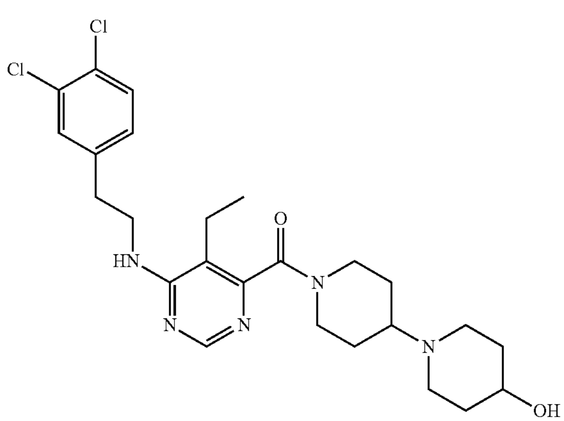 [SMILES: CCc1c(NCCc2ccc(Cl)c(Cl)c2)ncnc1C(=O)N1CCC(N2CCC(O)CC2)CC1] | 27f | [1,4']-Bipiperidinyl-4-ol | 506 | 1.52 | 2C |

| Ex # | STRUCTURE | Intermediate | Amine | [M + H]+ | HPLC $R_t$ (min) | Method |
|---|---|---|---|---|---|---|
| 281 | 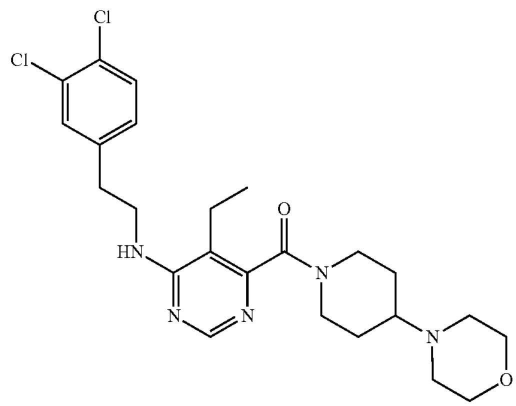 [SMILES: CCc1c(NCCc2ccc(Cl)c(Cl)c2)ncnc1C(=O)N1CCC(N2CCOCC2)CC1] | 27f | 4-piperidin-4-yl-morpholine | 492 | 1.53 | 2C |
| 282 | 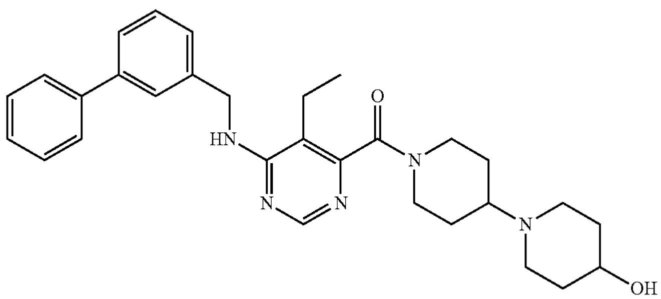 [SMILES: CCc1c(NCc2cccc(-c3ccccc3)c2)ncnc1C(=O)N1CCC(N2CCC(O)CC2)CC1] | 27g | [1,4']-Bipiperidinyl-4-ol | 500 | 1.55 | 2C |
| 283 | 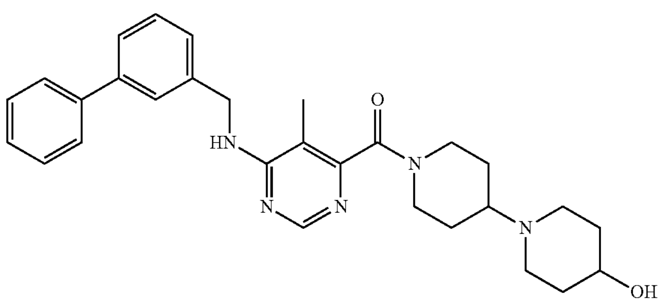 [SMILES: Cc1c(NCc2cccc(-c3ccccc3)c2)ncnc1C(=O)N1CCC(N2CCC(O)CC2)CC1] | 39e | [1,4']-Bipiperidinyl-4-ol | 484 | 1.66 | 2C |

Example 284

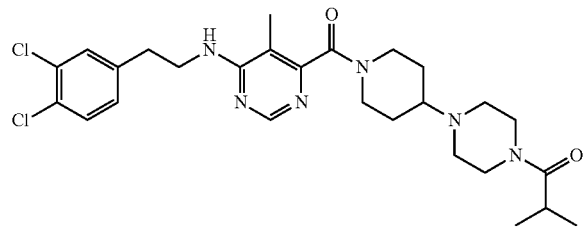 [SMILES: Cc1c(NCCc2ccc(Cl)c(Cl)c2)ncnc1C(=O)N1CCC(N2CCN(C(=O)C(C)C)CC2)CC1]

Intermediate 30 (45 mg, 0.088 mmol) and N,N-diisopropylethylamine (0.05 ml, 0.27 mmol were dissolved in 5 ml of dichloromethane. The reaction mixture was stirred at 0° C. and isobutyrylchloride (0.01 ml, 0.09 mmol) was added. The reaction mixture was stirred at 0° C. for 20 min, then it was washed with an aqueous saturated sodium bicarbonate solution, dried over sodium sulfate and concentrated under vacuum. The crude product was suspended and stirred in diisopropyl ether, the solid filtered off to obtain 30 mg (0.05 mmol) of the desired compound.

HPLC (Method 1E): $R_t$ (min)=7.02

[M+H]+=547

The following examples were synthesized in analogy to the preparation of Example 284.

| Ex # | STRUCTURE | Intermediate | Chloride | [M + H]⁺ | HPLC R$_t$ (min) | Method |
|---|---|---|---|---|---|---|
| 285 | 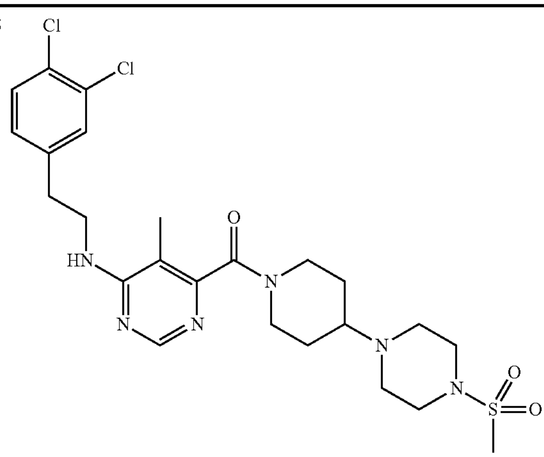 | 30 | Methanesulfonyl chloride | 555 | 6.91 | 2F |

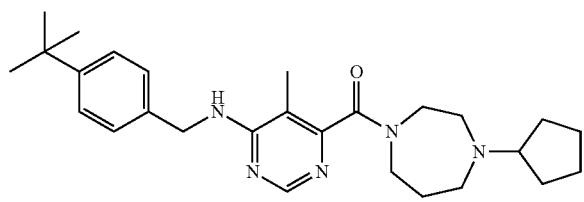 [SMILES: Cc1c(NCc2ccc(C(C)(C)C)cc2)ncnc1C(=O)N1CCCN(C2CCCC2)CC1]

Example 286

Intermediate 32 (100 mg, 0.26 mmol) and cyclopentanone (0.02 ml, 0.26 mmol) in 2 ml of dichloromethane were stirred at room temperature for 10 min Sodium triacetoxyborohydride (132 mg, 0.62 mmol) was added and the reaction mixture was stirred at room temperature overnight. The reaction mixture was washed with an aqueous saturated sodium bicarbonate solution, dried over sodium sulfate and concentrated under vacuum. The crude product was purified by reverse phase preparative HPLC. 31 mg (0.07 mmol) of the desired product were obtained.

HPLC (Method 2F): R$_t$ (min)=7.52

[M+H]⁺=450

The following examples were synthesized in analogy to the preparation of Example 286.

| Ex # | STRUCTURE | Intermediate | Ketone | [M + H]⁺ | HPLC R$_t$ (min) | Method |
|---|---|---|---|---|---|---|
| 287 | 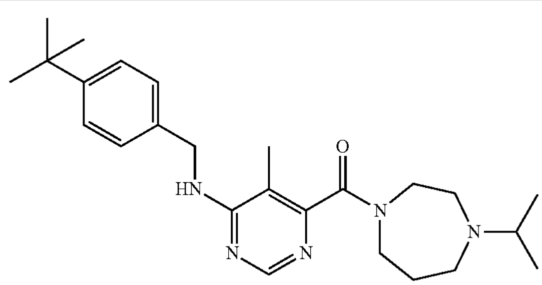 [SMILES: Cc1c(NCc2ccc(C(C)(C)C)cc2)ncnc1C(=O)N1CCCN(C(C)C)CC1] | 32 | Acetone | 424 | 7.24 | 2F |
| 288 | 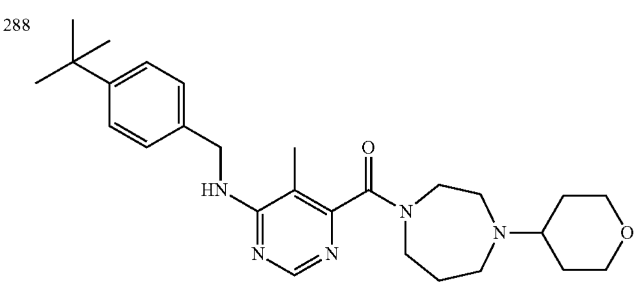 | 33 | Tetrahydropyran-4-one | 466 | 7.18 | 2F |

Example 289

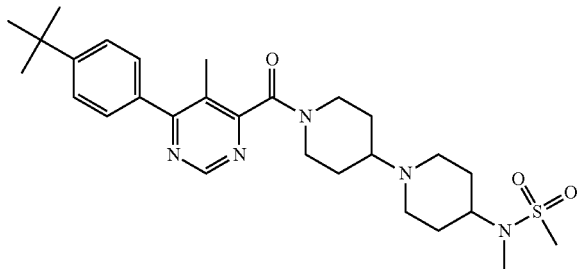 [SMILES: Cc1c(C(=O)N2CCC(N3CCC(N(C)S(C)(=O)=O)CC3)CC2)ncnc1-c1ccc(C(C)(C)C)cc1]

Intermediate 25b (200 mg, 0.46 mmol) 4-tert-butylphenyl-boronic acid (99 mg, 0.56 mmol), tetrakis(triphenylphosphine)palladium (53 mg, 0.05 mmol) and 0.56 ml of a 2M aqueous solution of sodium carbonate in 2 ml of 1,2-dimethoxyethane were stirred at 80° C. overnight. After cooling to room temperature, water was added and the reaction mixture was extracted with dichloromethane. The organic phase was washed with an aqueous saturated sodium bicarbonate solution, dried over sodium sulfate and concentrated under vacuum. The crude product was purified by flash chromatography (Si Isolute cartridge (5 g); eluent: ethyl acetate/methanol=95/5%). 41 mg (0.08 mmol) of the desired product were obtained.

HPLC (Method 1E Hydro): $R_t$ (min)=9.93

$[M+H]^+=528$

Example 290

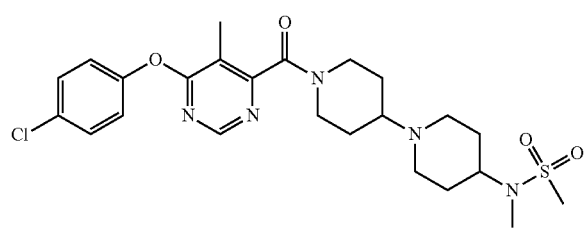 [SMILES: Cc1c(Oc2ccc(Cl)cc2)ncnc1C(=O)N1CCC(N2CCC(N(C)S(C)(=O)=O)CC2)CC1]

Intermediate 25b (60 mg, 0.14 mmol) and 4-chlorophenol (0.014 ml, 0.14 mmol) were dissolved in 2 ml of DMF. Cesium carbonate (45 mg, 0.14 mmol) was added and the reaction mixture was stirred at room temperature overnight. The solvent was concentrated under vacuum, the crude product was dissolved in dichloromethane and the organic phase was washed with water, dried over sodium sulfate and concentrated under vacuum. The crude product was purified by flash chromatography (Si Isolute cartridge (5 g); eluent: dichloromethane/ethyl acetate=90/1%). 50 mg (0.09 mmol) of the desired product were obtained.

HPLC (Method 1E Hydro): $R_t$ (min)=8.9

$[M+H]^+=522$

The following example was synthesized in analogy to the preparation of Example 290.

| Ex # | STRUCTURE | Intermediate | Phenol | $[M + H]^+$ | HPLC $R_t$ (min) | Method |
|---|---|---|---|---|---|---|
| 291 | 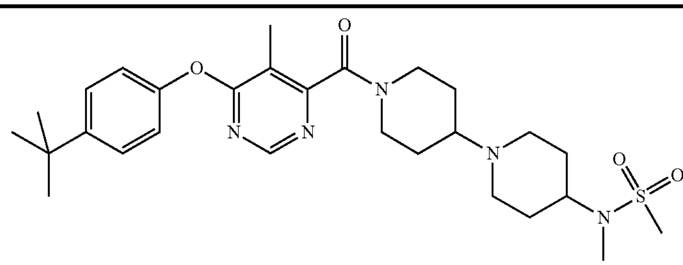 | 25b | 4-tertbutyl-phenol | 544 | 7.64 | 2F |

Example 292

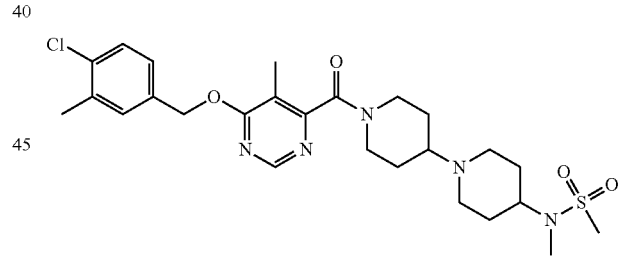

Sodium hydride (19 mg, 0.46 mmol) and 4-chloro-3-methylbenzylalcohol (44 mg, 0.28 mmol) were suspended in 5 ml of dry tetrahydrofuran. The reaction mixture was stirred at room temperature for 10 min, then Intermediate 25b (100 mg, 0.23 mmol) was added. The reaction mixture was stirred at 50° C. overnight. The solvent was concentrated under vacuum, the crude product was dissolved in dichloromethane and the organic phase was washed with water, dried over sodium sulfate and concentrated under vacuum. The crude product was purified by flash chromatography (Si Isolute cartridge (5 g); eluent: dichloromethane/methanol=95/5%). 40 mg (0.07 mmol) of the desired product were obtained.

HPLC (Method 1E Hydro): $R_t$ (min)=9.95

$[M+H]^+=550$

The following examples were synthesized in analogy to the preparation of Example 292.

| Ex # | STRUCTURE | Intermediate | Phenol | [M + H]+ | HPLC R$_t$ (min) | Method |
|---|---|---|---|---|---|---|
| 293 | 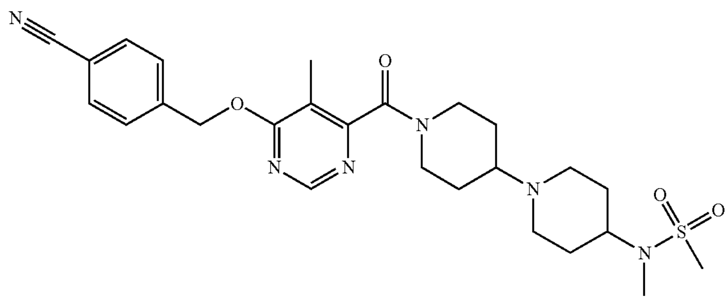 [SMILES: Cc1c(OCc2ccc(C#N)cc2)ncnc1C(=O)N1CCC(N2CCC(N(C)S(C)(=O)=O)CC2)CC1] | 25b | 4-hydroxymethylbenzonitrile | 527 | 8.17 | 1E (Hydro) |
| 294 | 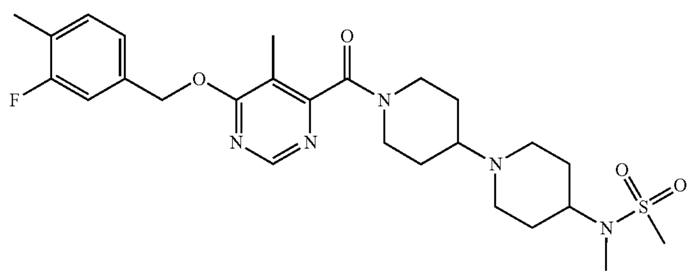 [SMILES: Cc1ccc(COc2ncnc(C(=O)N3CCC(N4CCC(N(C)S(C)(=O)=O)CC4)CC3)c2C)cc1F] | 25b | (3-fluoro-4-methylphenyl)-methanol | 534 | 9.12 | 1E (Hydro) |
| 295 | 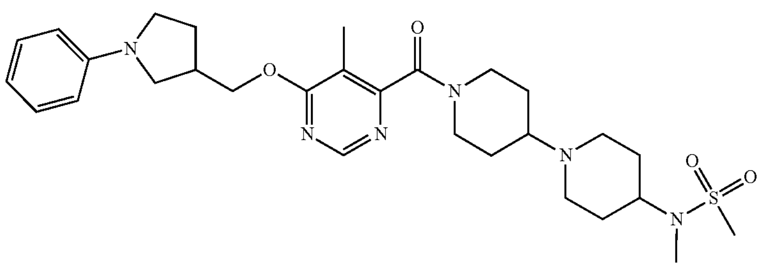 [SMILES: Cc1c(OCC2CCN(c3ccccc3)C2)ncnc1C(=O)N1CCC(N2CCC(N(C)S(C)(=O)=O)CC2)CC1] | 25b | (1-phenylpyrrolydin-3-yl)-methanol | 571 | 10.2 | 1E (Hydro) |
| 296 | 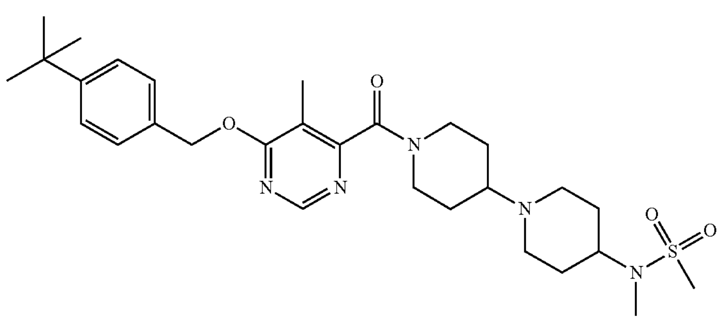 [SMILES: Cc1c(OCc2ccc(C(C)(C)C)cc2)ncnc1C(=O)N1CCC(N2CCC(N(C)S(C)(=O)=O)CC2)CC1] | 25b | (4-tert-butylphenyl)-methanol | 558 | 2.71 | 1F |
| 297 | 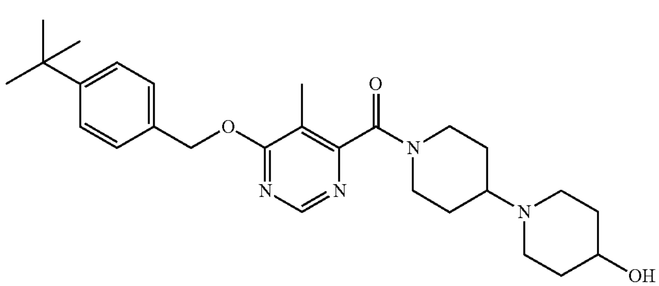 [SMILES: Cc1c(OCc2ccc(C(C)(C)C)cc2)ncnc1C(=O)N1CCC(N2CCC(O)CC2)CC1] | 25f | (4-tert-butylphenyl)-methanol | 466 | 9.50 | 1E (Hydro) |

| Ex # | STRUCTURE | Intermediate | Phenol | [M + H]+ | HPLC $R_t$ (min) | Method |
|---|---|---|---|---|---|---|
| 298 | 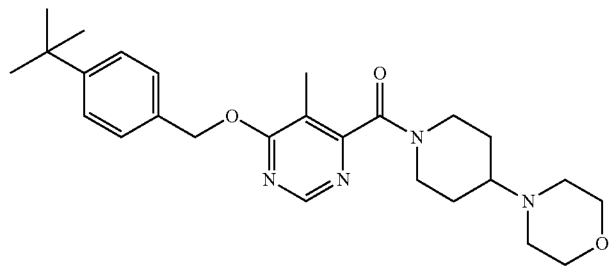 [SMILES: Cc1c(OCc2ccc(C(C)(C)C)cc2)ncnc1C(=O)N1CCC(N2CCOCC2)CC1] | 25h | (4-tert-butyl-phenyl)-methanol | 453 | 8.01 | 2F |
| 299 | 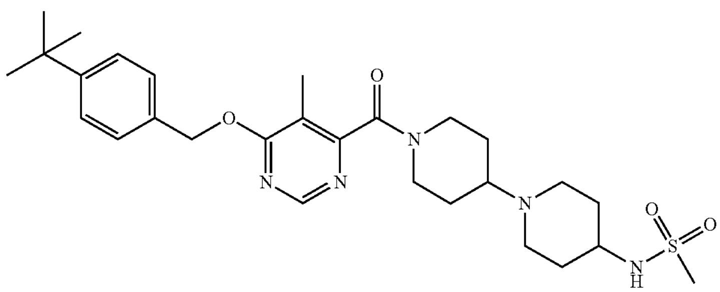 [SMILES: Cc1c(OCc2ccc(C(C)(C)C)cc2)ncnc1C(=O)N1CCC(N2CCC(NS(C)(=O)=O)CC2)CC1] | 25a | (4-tert-butyl-phenyl)-methanol | 544 | 9.68 | 1E (Hydro) |
| 300 | 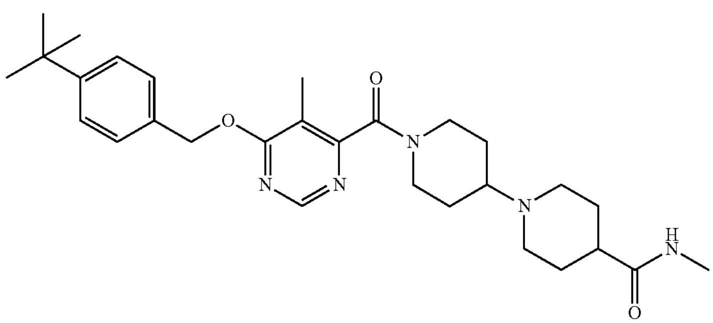 [SMILES: CNC(=O)C1CCN(C2CCN(C(=O)c3ncnc(OCc4ccc(C(C)(C)C)cc4)c3C)CC2)CC1] | 25d | (4-tert-butyl-phenyl)-methanol | 508 | 10.25 | 1E (Hydro) |
| 301 | 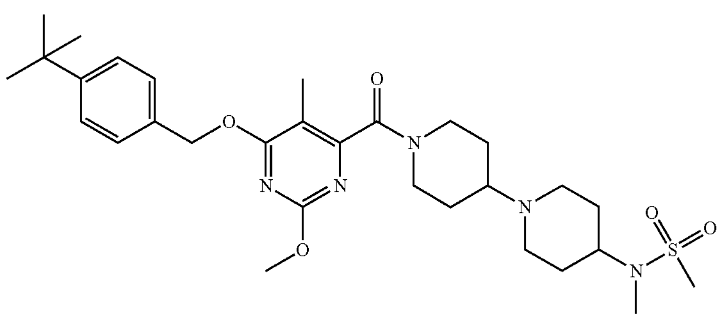 [SMILES: COc1nc(OCc2ccc(C(C)(C)C)cc2)c(C)c(C(=O)N2CCC(N3CCC(N(C)S(C)(=O)=O)CC3)CC2)n1] | 25n | (4-tert-butyl-phenyl)-methanol | 588 | 2.20 | 2Ca |
| 302 | 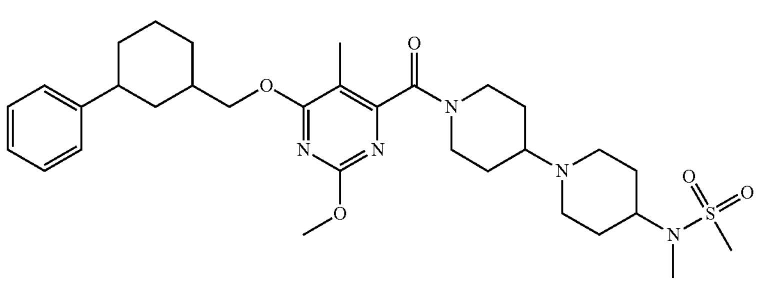 [SMILES: COc1nc(OCC2CCCC(c3ccccc3)C2)c(C)c(C(=O)N2CCC(N3CCC(N(C)S(C)(=O)=O)CC3)CC2)n1] | 25n | (3-Phenyl-cyclo-hexyl)-methanol | 614 | 2.18 | 2Ca |

The invention claimed is:
1. A process for the production of a compound of formula (I),
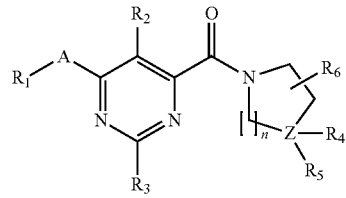
wherein
R₁ is selected from the group consisting of
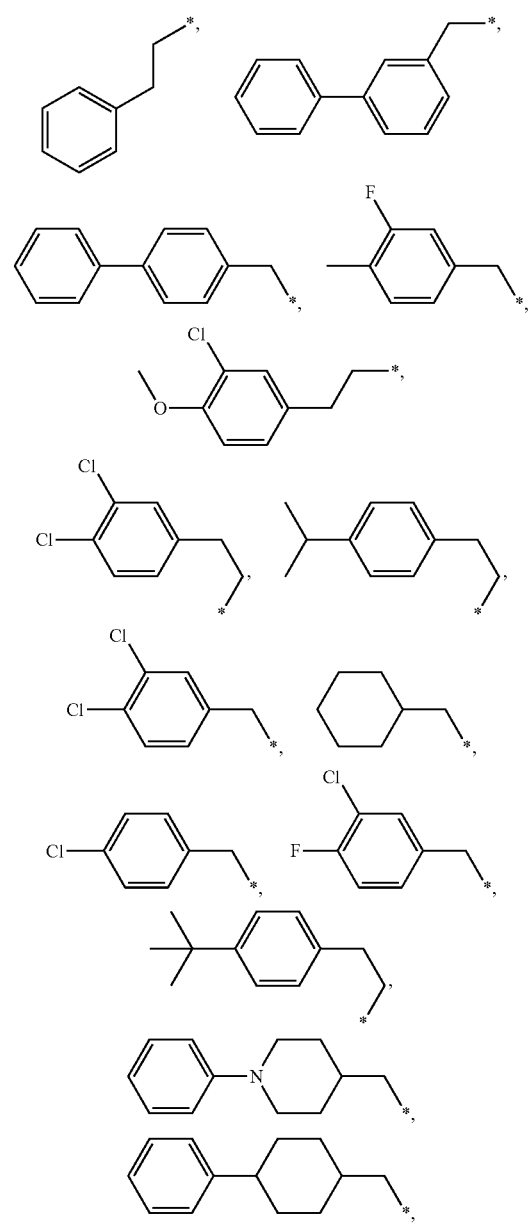
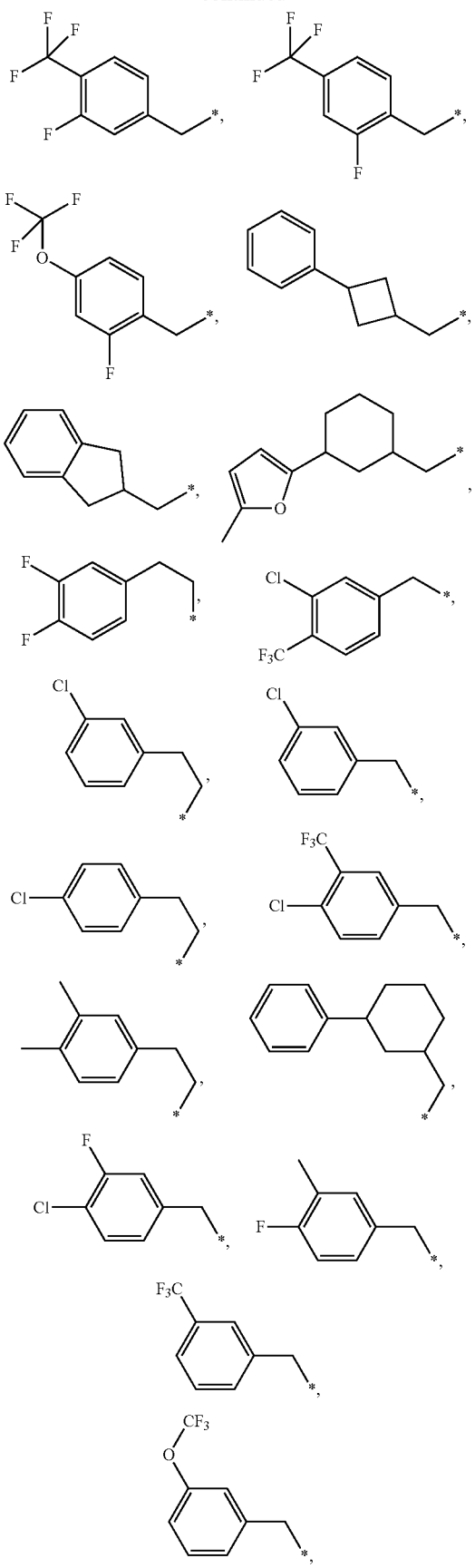

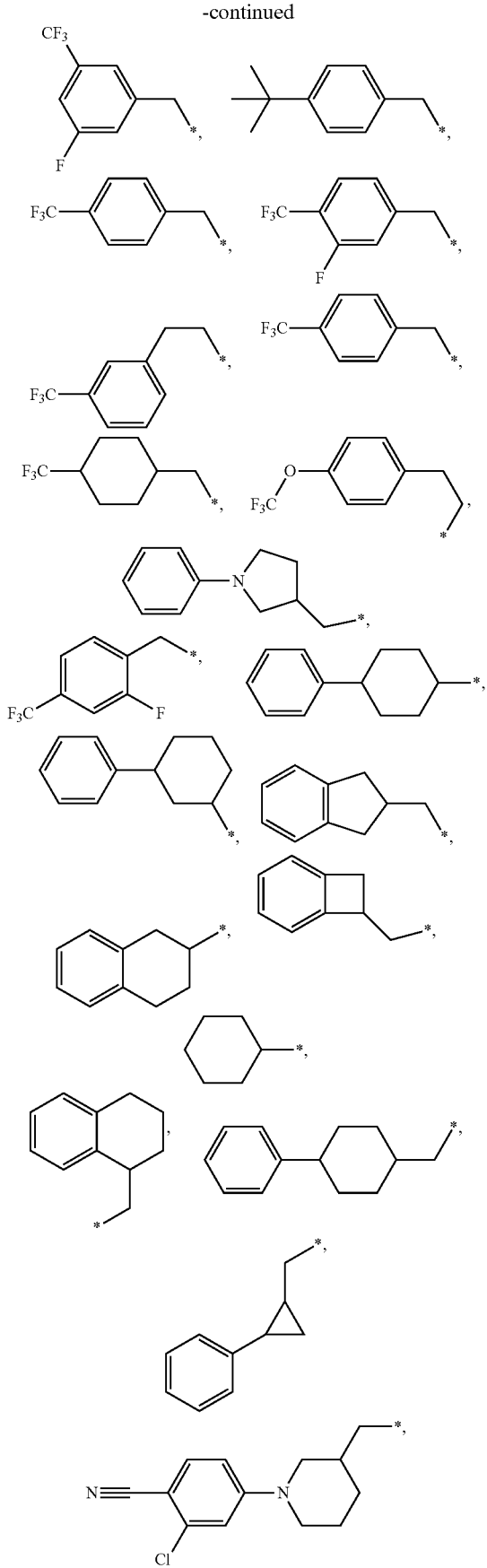
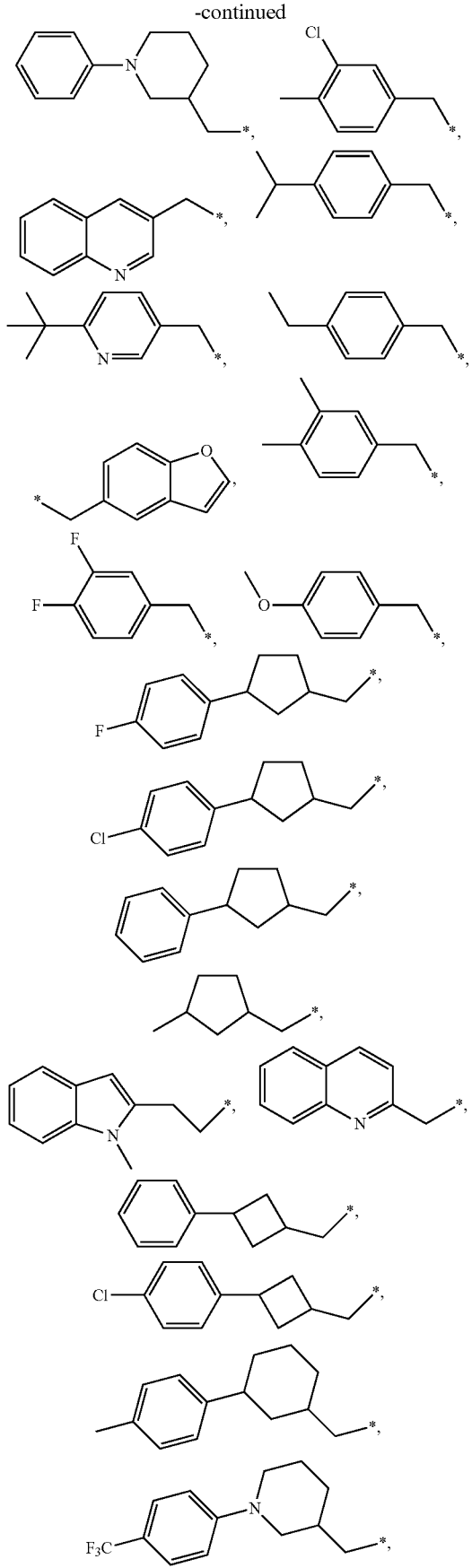

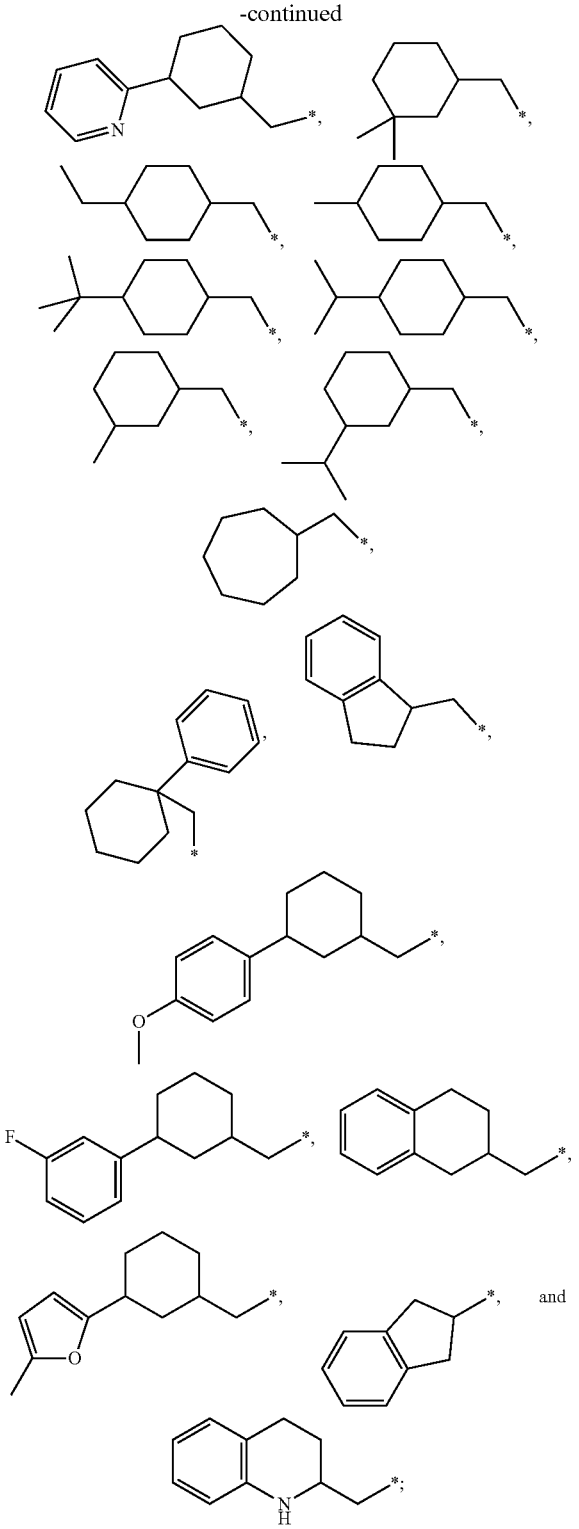

$R_2$ is selected from the group consisting of —H, -halogen, —CN, —O—$C_1$-$C_4$-alkyl, —$C_1$-$C_4$-alkyl, —CH=$CH_2$, —C≡CH, —$CF_3$, —$OCF_3$, —$OCF_2H$, and —$OCFH_2$;

$R_3$ is selected from the group consisting of —H, -methyl, -ethyl, -propyl, -i-propyl, -cyclopropyl, —$OCH_3$, and —CN;

$R_4$ and $R_5$ are independently selected from the group consisting of an electron pair, —H, —$C_1$-$C_6$-alkyl, —$NH_2$, —$C_3$-$C_8$-cycloalkyl, —$C_3$-$C_8$-heterocyclyl, —$C_5$-$C_{10}$-aryl, —$C_5$-$C_{10}$-heteroaryl, and —C(O)—N($R_8$,$R_{8'}$), with $R_8$ and $R_{8'}$ independently being selected from the group consisting of —H, and —$C_1$-$C_6$-alkyl, and wherein $R_4$ and $R_5$ if different from an electron pair or —H are optionally independently substituted with one or more groups selected from the group consisting of -halogen, —OH, —$CF_3$, —CN, —$C_1$-$C_6$-alkyl, —O—$C_1$-$C_6$-alkyl, —O—$C_3$-$C_8$-cycloalkyl, —O—$C_3$-$C_8$-heterocyclyl, —O—$C_5$-$C_{10}$-aryl, —O—$C_5$-$C_{10}$-heteroaryl, —$C_0$-$C_6$-alkylene-CN, —$C_0$-$C_4$-alkylene-O—$C_1$-$C_4$-alkyl, —$C_0$-$C_4$-alkylene-O—$C_3$-$C_8$-cycloalkyl, —$C_0$-$C_4$-alkylene-O—$C_3$-$C_8$-heterocyclyl, —$C_0$-$C_4$-alkylene-O—$C_5$-$C_{10}$-aryl, —$C_0$-$C_4$-alkylene-O—$C_5$-$C_{10}$-heteroaryl, —$C_0$-$C_4$-alkylene-Q-$C_0$-$C_4$-alkyl-N($R_9$,$R_{9'}$), —$C_0$-$C_4$-alkylene-N($R_{10}$)-Q-$C_1$-$C_4$-alkyl, —$C_0$-$C_4$-alkylene-N($R_{10}$)-Q-$C_3$-$C_8$-cycloalkyl, —$C_0$-$C_4$-alkylene-N($R_{10}$)-Q-$C_3$-$C_8$-heterocyclyl, —$C_0$-$C_4$-alkylene-N($R_{10}$)-Q-$C_5$-$C_{10}$-aryl, —$C_0$-$C_4$-alkylene-N($R_{10}$)-Q-$C_5$-$C_{10}$-heteroaryl, —$C_0$-$C_4$-alkylene-Q-N($R_{11}$,$R_{11'}$), —$C_0$-$C_4$-alkylen-N($R_{12}$)-Q-N($R_{13}$,$R_{13'}$), —$C_0$-$C_4$-alkylen-$R_{14}$, —$C_0$-$C_4$-alkylene-Q-$C_1$-$C_6$-alkyl, —$C_0$-$C_4$-alkylene-Q-$C_3$-$C_8$-cycloalkyl, —$C_0$-$C_4$-alkylene-Q-$C_3$-$C_8$-heterocyclyl, —$C_0$-$C_4$-alkylene-Q-$C_5$-$C_{10}$-aryl, —$C_0$-$C_4$-alkylene-Q-$C_5$-$C_{10}$-heteroaryl, —$C_0$-$C_4$-alkylene-O-Q-N($R_{15}$,$R_{15'}$), and —$C_0$-$C_4$-alkylene-N($R_{16}$)-Q-O—($R_{17}$), wherein Q is —C(O)— or —$SO_2$—, wherein $R_{12}$, $R_{16}$, are independently selected from the group consisting of —H, —$C_1$-$C_6$-alkyl, and —$C_3$-$C_6$-cycloalkyl, wherein $R_9$, $R_{9'}$, $R_{10}$, $R_{11}$, $R_{11'}$, $R_{13}$, $R_{13'}$, $R_{15}$, $R_{15'}$, are independently selected from the group consisting of —H, —$C_1$-$C_6$-alkyl, and —$C_3$-$C_6$-cycloalkyl, or wherein $R_9$ and $R_{9'}$, $R_{11}$ and $R_{11'}$, $R_{13}$ and $R_{13'}$, $R_{15}$ and $R_{15'}$ together form a —$C_2$-$C_6$-alkylene group, wherein $R_{14}$ and $R_{17}$ are independently selected from the group consisting of —H, —$C_1$-$C_6$-alkyl, —$C_5$-$C_{10}$-aryl, —$C_5$-$C_{10}$-heteroaryl, —$C_3$-$C_8$-cycloalkyl, and —$C_3$-$C_8$-heterocyclyl, wherein said —$C_3$-$C_8$-heterocyclyl optionally comprises nitrogen and/or —$SO_2$— in the ring, and wherein $R_{14}$ and $R_{17}$ are optionally substituted with one or more groups selected from the group consisting of —OH, —$OCH_3$, —$CF_3$, —$OCF_3$, —CN, -halogen, —$C_1$-$C_4$-alkyl, =O, and —$SO_2$—$C_1$-$C_4$-alkyl, or $R_4$ and/or $R_5$ are independently a group of the structure -$L_2$-$R_{18}$, wherein $L_2$ is —NH— and/or N($C_1$-$C_4$-alkyl)-, wherein $R_{18}$ is —$C_5$-$C_{10}$-aryl, —$C_5$-$C_{10}$-heteroaryl, —$C_3$-$C_8$-cycloalkyl or —$C_3$-$C_8$-heterocyclyl, wherein $R_{18}$ is optionally substituted by one or more groups selected from the group consisting of halogen, —$CF_3$, —$OCF_3$, —CN, —OH, —O—$C_1$-$C_4$-alkyl, —$C_1$-$C_6$-alkyl, —NH—C(O)—$C_1$-$C_6$-alkyl, —N($C_1$-$C_4$-alkyl)-C(O)—$C_1$-$C_6$-alkyl, —C(O)—$C_1$-$C_6$-alkyl, —S(O)$_2$—$C_1$-$C_6$-alkyl, —NH—S(O)$_2$—$C_1$-$C_6$-alkyl, —N($C_1$-$C_4$-alkyl)-S(O)$_2$—$C_1$-$C_6$-alkyl, and —C(O)—O—$C_1$-$C_6$-alkyl;

$R_6$ is selected from the group consisting of —H, —$C_1$-$C_4$-alkyl, —OH, —O—$C_1$-$C_4$-alkyl, -halogen, —CN, —$CF_3$, and —$OCF_3$;

A is —NH—;

n is 1, 2 or 3;

Z is C or N, characterized in that a compound of formula II
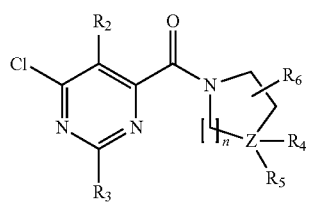
(II)
in which $R_2$, $R_3$, $R_4$, $R_5$, $R_6$, Z, and n have the meaning as in formula I, is coupled with a primary amine selected from the group consisting of
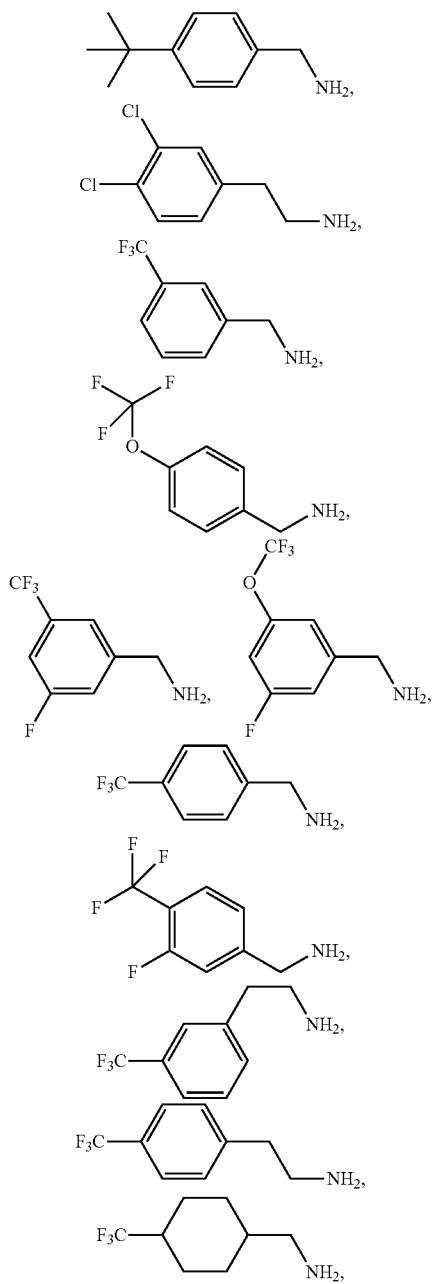
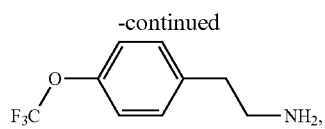
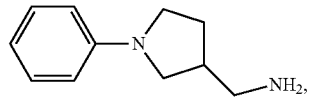
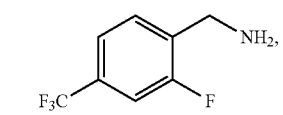
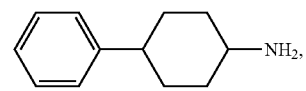
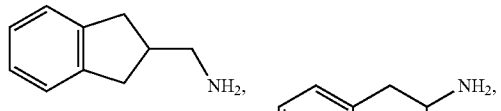
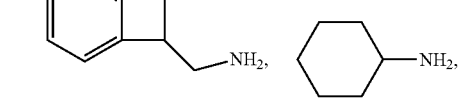
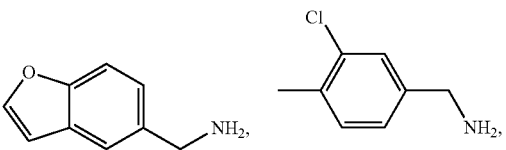
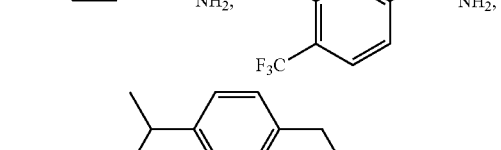
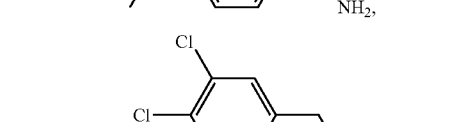
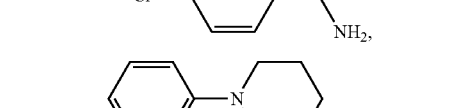
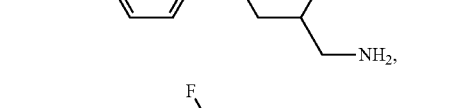
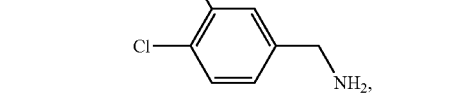
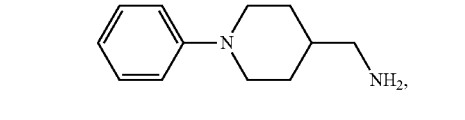

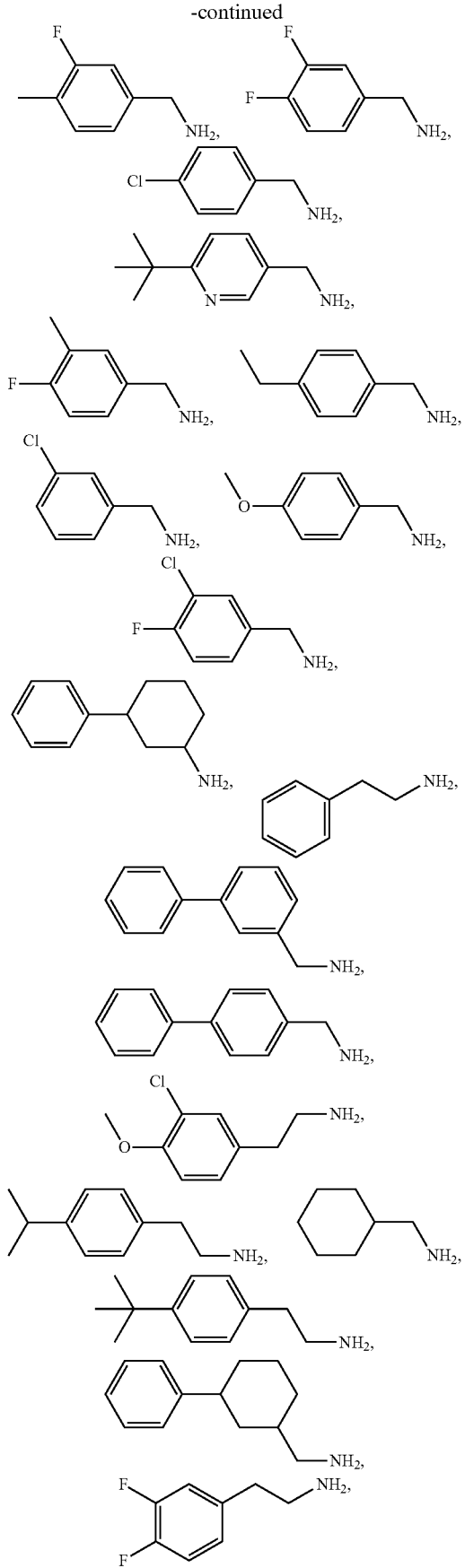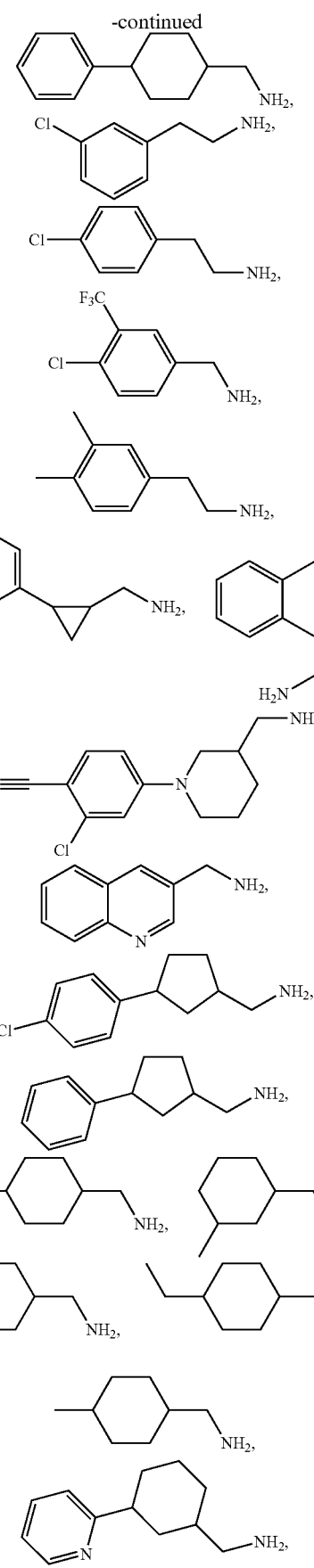

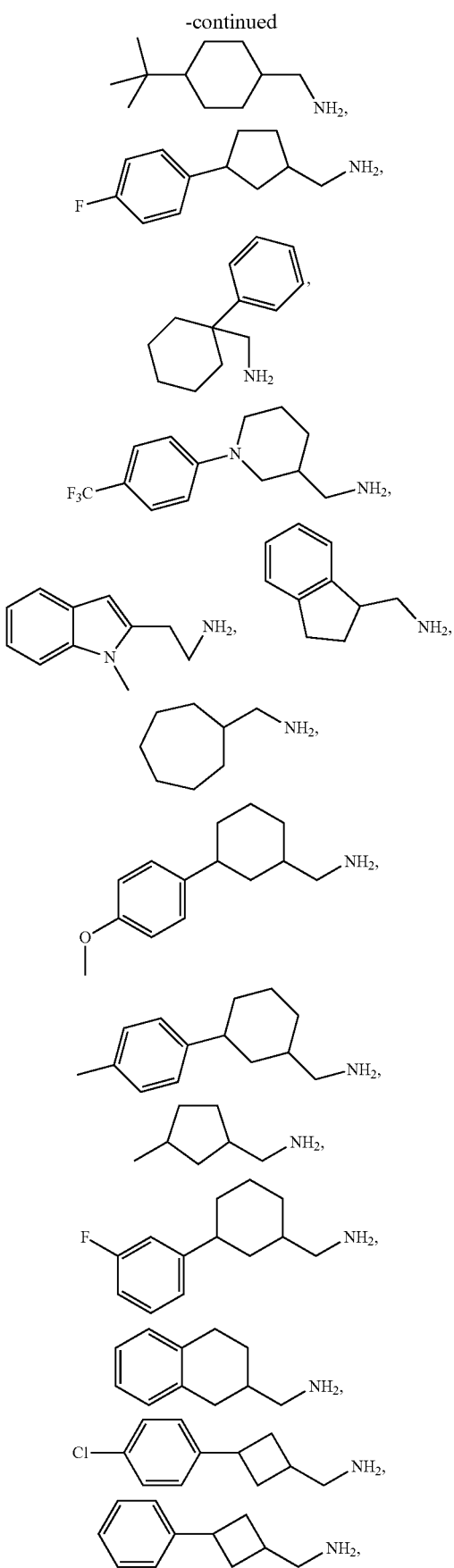
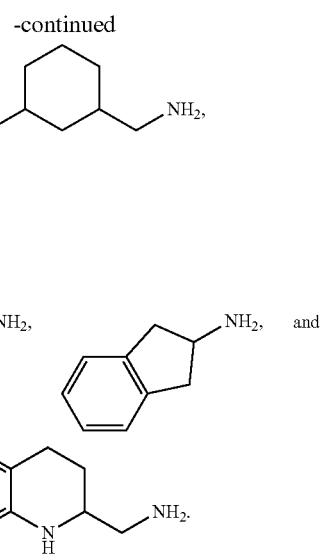
2. The process for the production of the compound of formula (I) according to claim 1,
wherein
$R_2$ is selected from the group consisting of —H, -methyl, -ethyl, -propyl, -i-propyl, -cyclopropyl, -butyl, -i-butyl, -t-butyl, —F, —Cl, —Br, —I, —CN, —CH=CH$_2$, —CCH, and —OCH$_3$;
$R_3$ is —H, -methyl, and/or —OCH$_3$;
$R_4$ is selected from the group consisting of
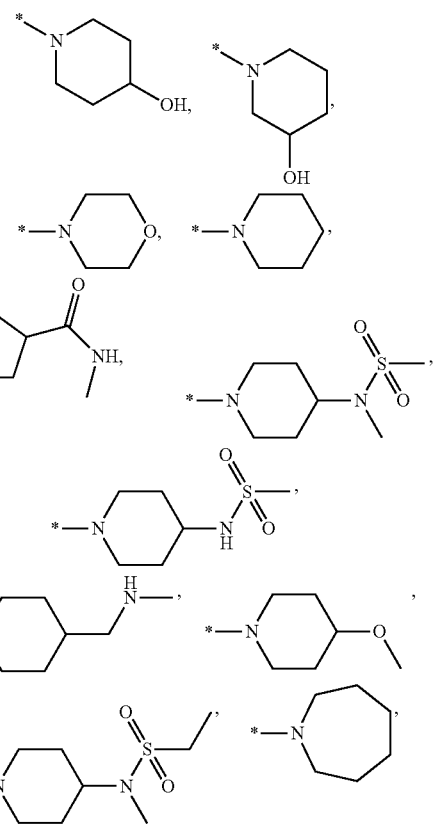

297
-continued
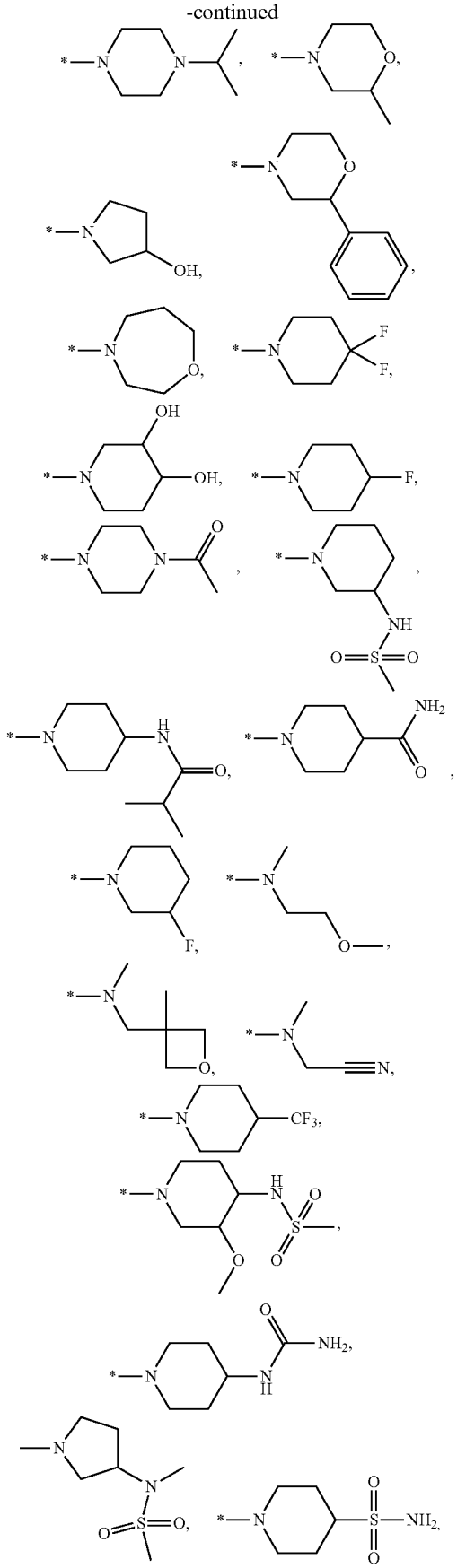
298
-continued
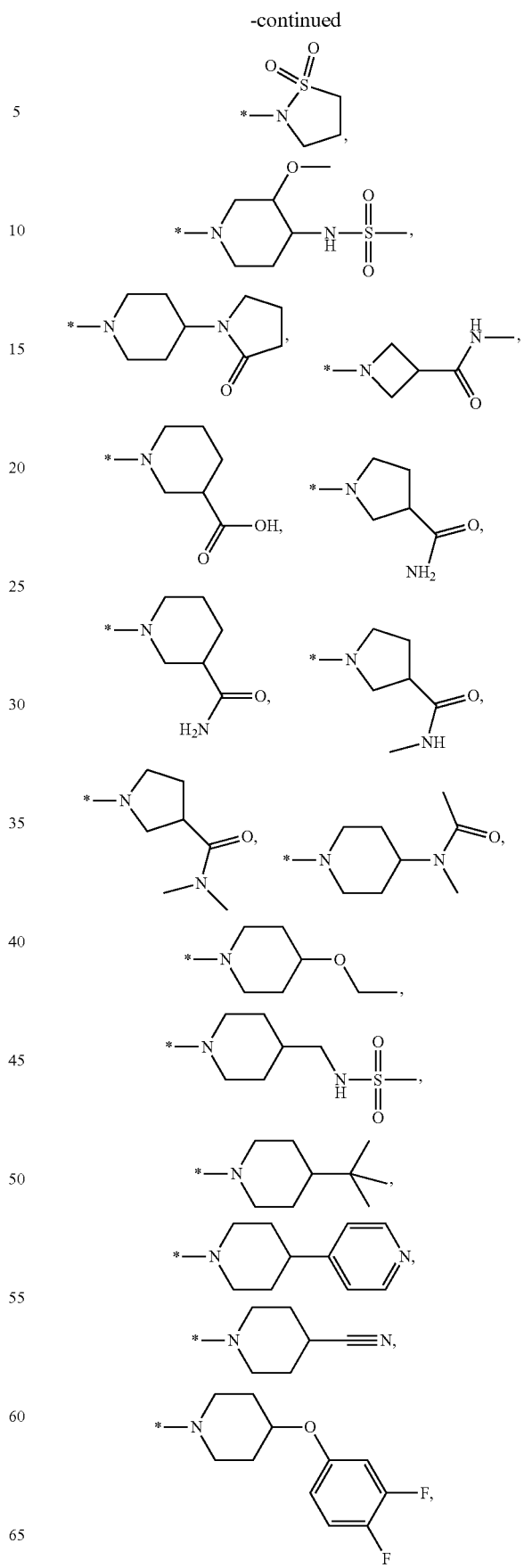

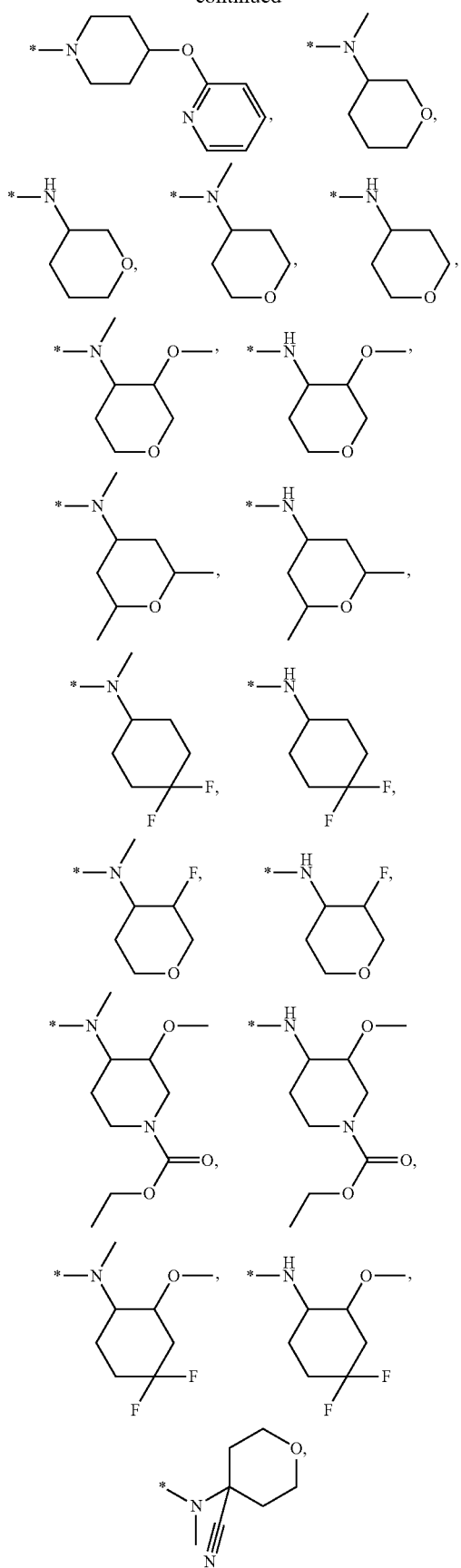
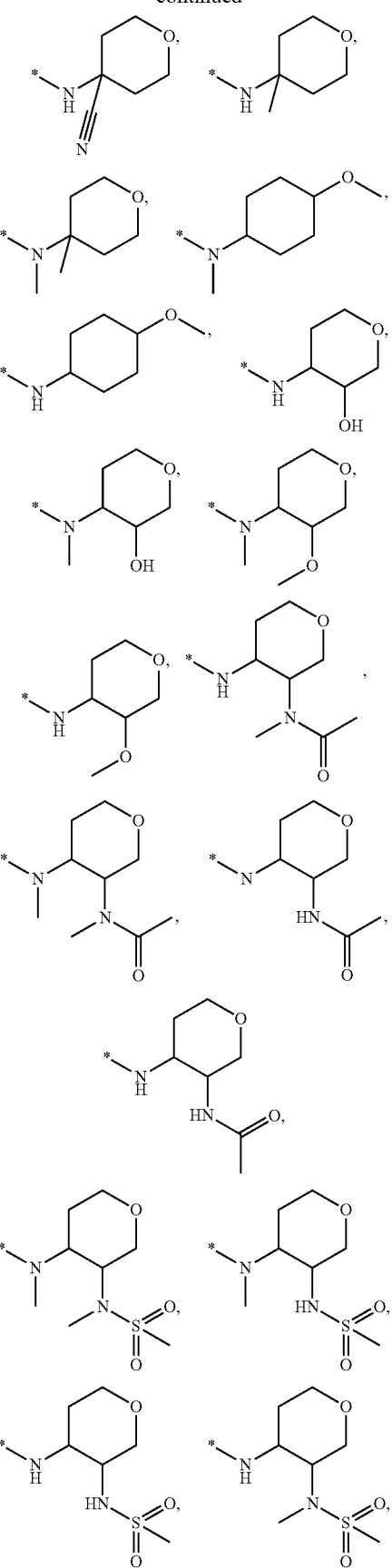

301
-continued
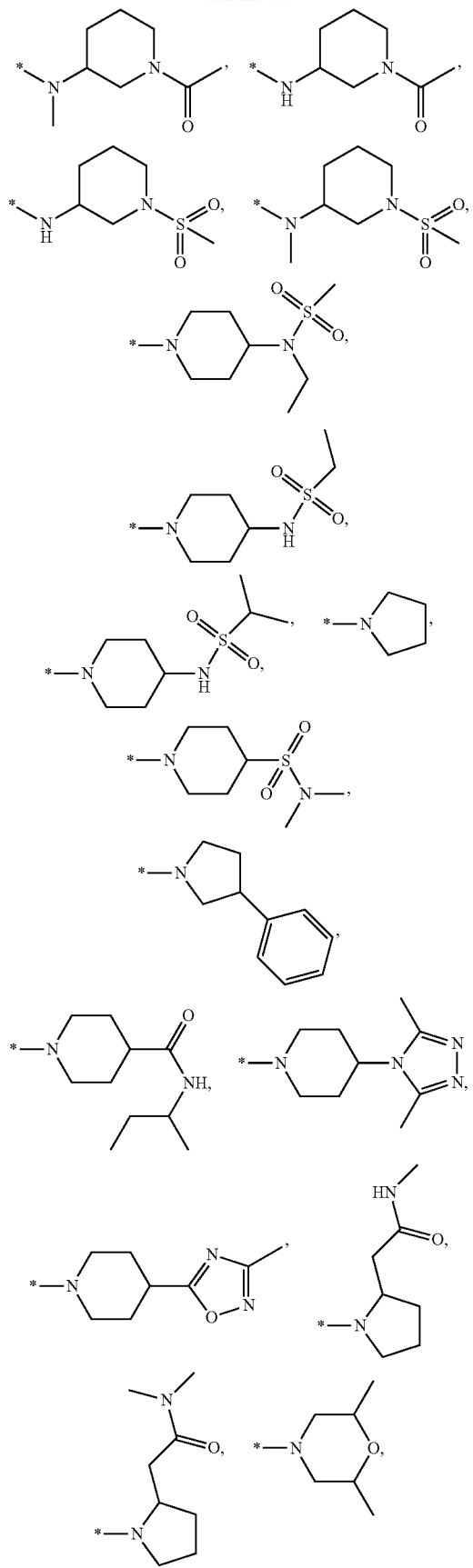
302
-continued
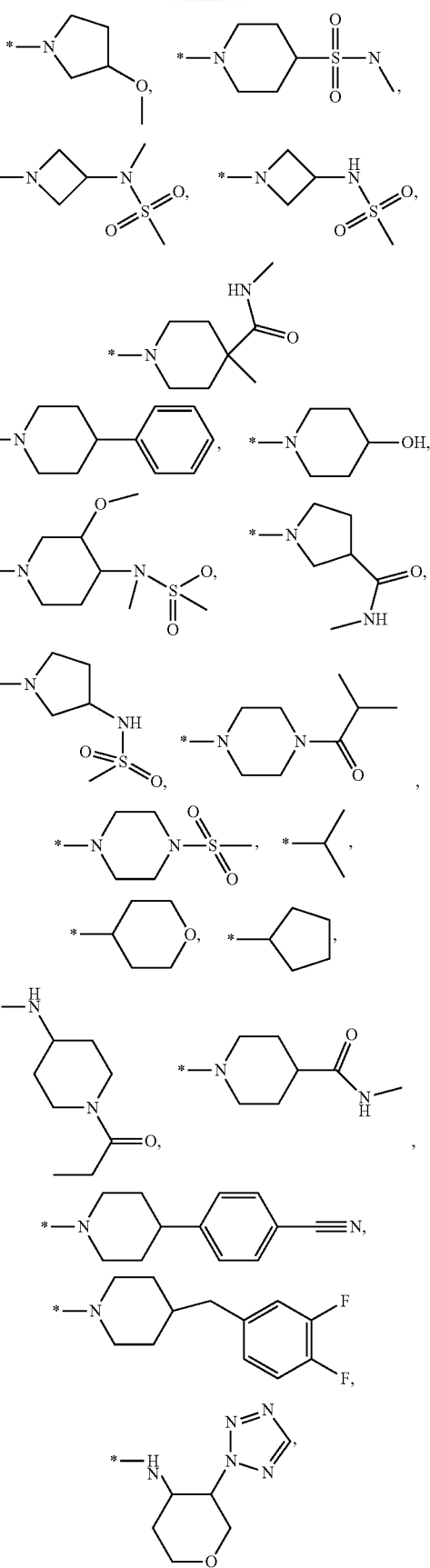

303
-continued
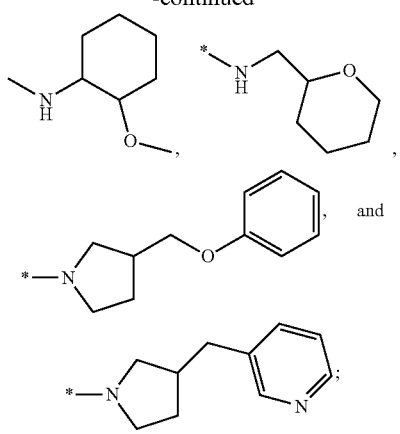
and
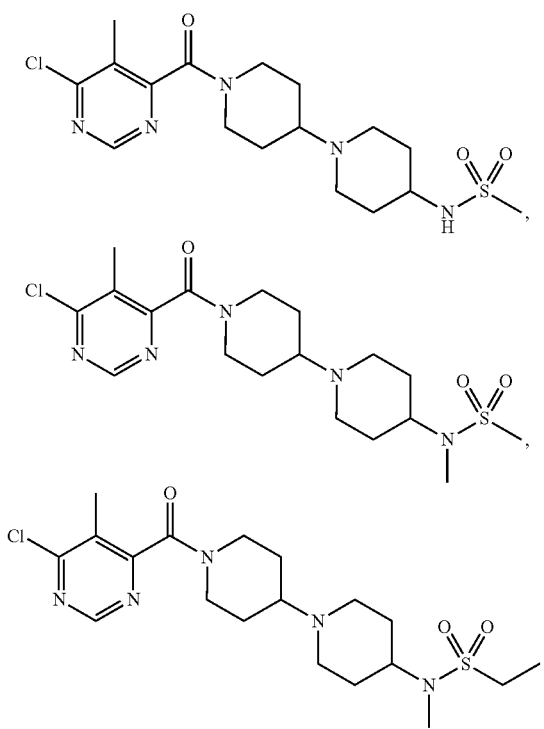
$R_5$ is —H or —C(O)—$NH_2$;
$R_6$ is selected from the group consisting of —H, —$CH_3$, —$C_2H_5$, —O—$CH_3$, —O—$C_2H_5$, —F, —$CF_3$, and —$OCF_3$; and
Z is C.
3. An intermediate compound selected from the group consisting of
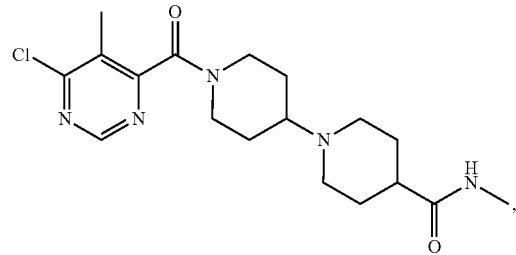
304
-continued
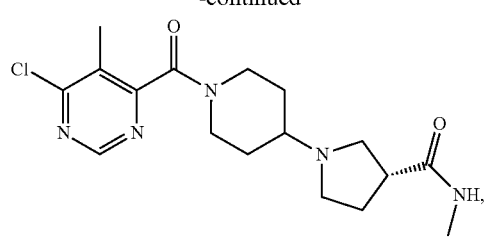
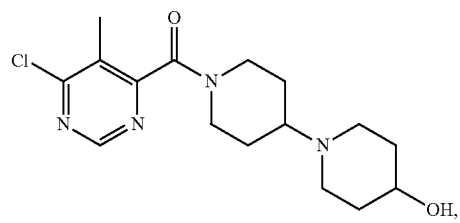
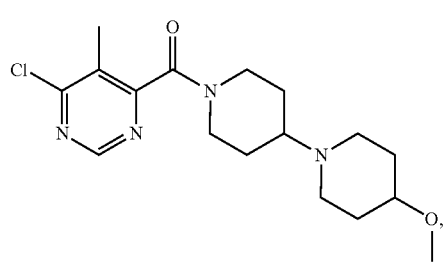
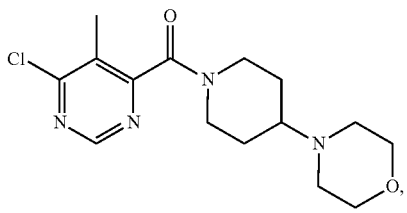
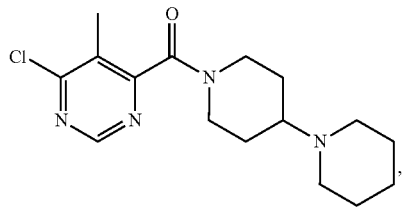
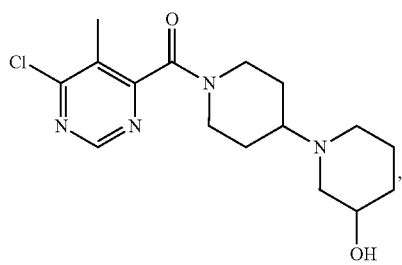
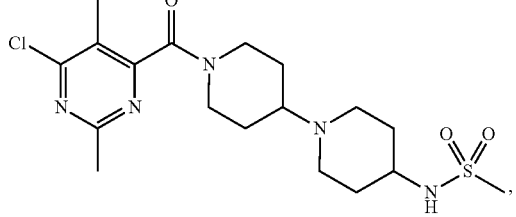

-continued

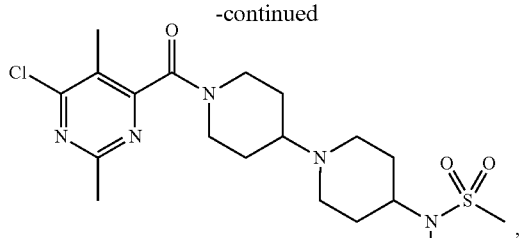

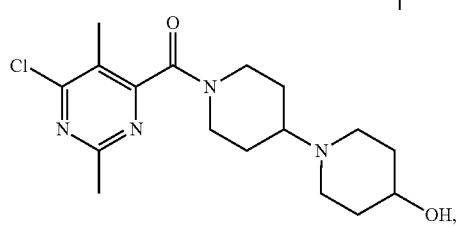

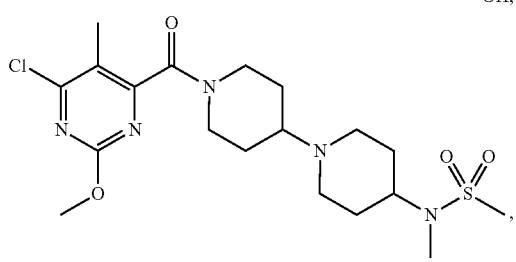, and

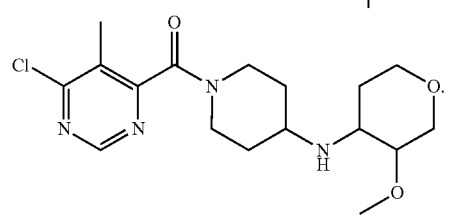

4. The intermediate according to claim 3, wherein the intermediate is

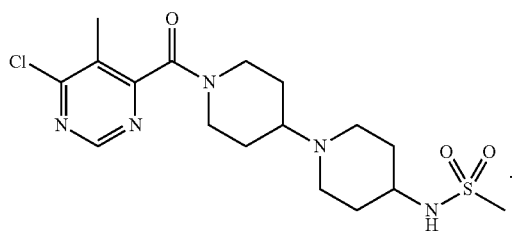 [SMILES: Cc1c(Cl)ncnc1C(=O)N1CCC(N2CCC(NS(C)(=O)=O)CC2)CC1]

5. The intermediate according to claim 3, wherein the intermediate is

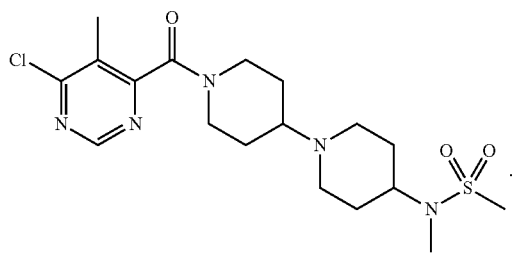 [SMILES: Cc1c(Cl)ncnc1C(=O)N1CCC(N2CCC(N(C)S(C)(=O)=O)CC2)CC1]

6. The intermediate according to claim 3, wherein the intermediate is

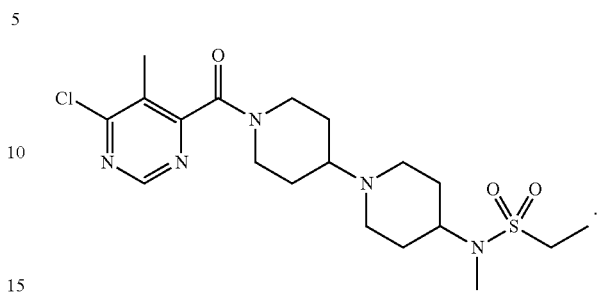

7. The intermediate according to claim 3, wherein the intermediate is

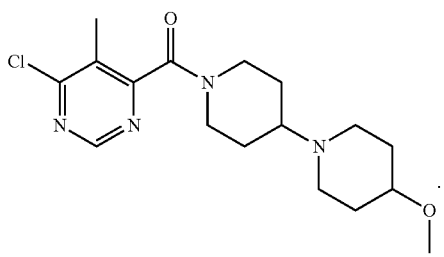 [SMILES: COC1CCN(C2CCN(C(=O)c3ncnc(Cl)c3C)CC2)CC1]

8. The intermediate according to claim 3, wherein the intermediate is

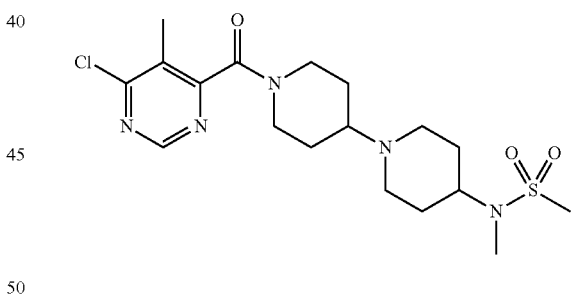

9. The intermediate according to claim 3, wherein the intermediate is

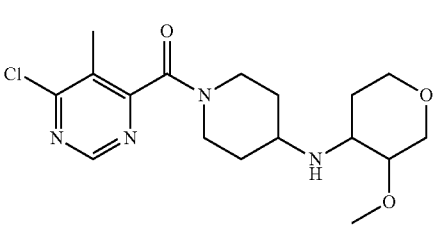

* * * * *